(12) United States Patent
Zhao et al.

(10) Patent No.: US 11,608,335 B2
(45) Date of Patent: Mar. 21, 2023

(54) SOMATOSTATIN MODULATORS AND USES THEREOF

(71) Applicant: CRINETICS PHARMACEUTICALS, INC., San Diego, CA (US)

(72) Inventors: Jian Zhao, San Diego, CA (US); Shimiao Wang, San Diego, CA (US); Yunfei Zhu, San Diego, CA (US)

(73) Assignee: CRINETICS PHARMACEUTICALS, INC., San Diego, CA (US)

( * ) Notice: Subject to any disclaimer, the term of this patent is extended or adjusted under 35 U.S.C. 154(b) by 93 days.

(21) Appl. No.: 16/968,533

(22) PCT Filed: Feb. 11, 2019

(86) PCT No.: PCT/US2019/017529
§ 371 (c)(1),
(2) Date: Aug. 7, 2020

(87) PCT Pub. No.: WO2019/157458
PCT Pub. Date: Aug. 15, 2019

(65) Prior Publication Data
US 2021/0040087 A1    Feb. 11, 2021

Related U.S. Application Data

(60) Provisional application No. 62/724,421, filed on Aug. 29, 2018, provisional application No. 62/673,042, filed on May 17, 2018, provisional application No. 62/629,377, filed on Feb. 12, 2018.

(51) Int. Cl.
*C07D 471/04* (2006.01)
*A61P 3/08* (2006.01)
*C07D 401/14* (2006.01)

(52) U.S. Cl.
CPC ............. *C07D 471/04* (2013.01); *A61P 3/08* (2018.01); *C07D 401/14* (2013.01)

(58) Field of Classification Search
CPC ........ A61P 3/08; C07D 471/04; C07D 401/14
USPC .................................................. 514/210.21
See application file for complete search history.

(56) References Cited

U.S. PATENT DOCUMENTS

| | | | |
|---|---|---|---|
| 6,025,372 A | 2/2000 | Yang et al. |
| 6,127,343 A | 10/2000 | Ankersen et al. |
| 7,754,744 B2 | 7/2010 | Binggeli et al. |
| 8,110,574 B2 | 2/2012 | Thurieau et al. |
| 8,778,925 B2 | 7/2014 | McDonald et al. |
| 9,630,976 B2 | 4/2017 | Ishida et al. |
| 9,643,951 B2 | 5/2017 | Ishida et al. |
| 10,214,540 B2 | 2/2019 | Ishida et al. |
| 10,696,689 B2 | 6/2020 | Han et al. |
| 2006/0281764 A1 | 12/2006 | Gaul et al. |
| 2011/0059971 A1 | 3/2011 | Thurieau et al. |
| 2013/0040978 A1 | 2/2013 | Duffy et al. |
| 2015/0232478 A1 | 8/2015 | Ishida et al. |
| 2016/0311794 A1 | 10/2016 | Ishida et al. |
| 2020/0000816 A1 | 1/2020 | Ishida et al. |
| 2020/0010453 A1 | 1/2020 | Han et al. |
| 2020/0283453 A1 | 9/2020 | Han et al. |
| 2021/0047287 A1 | 2/2021 | Zhao et al. |
| 2022/0048924 A1 | 2/2022 | Han et al. |
| 2022/0144802 A1 | 5/2022 | Zhao et al. |

FOREIGN PATENT DOCUMENTS

| | | |
|---|---|---|
| CA | 2925651 A1 | 4/2015 |
| CN | 105593221 A | 5/2016 |
| CN | 110300749 A | 10/2019 |
| EP | 2871179 A1 | 5/2015 |
| EP | 3053916 A1 | 8/2016 |
| EP | 3053961 A1 | 8/2016 |
| EP | 3053916 B1 | 1/2019 |
| EP | 3581569 A1 | 12/2019 |
| JP | 2008543760 A | 12/2008 |
| WO | WO-2008051272 A2 | 5/2008 |
| WO | WO-2009051705 A1 | 4/2009 |
| WO | WO-2009158467 A2 | 12/2009 |
| WO | WO-2010041054 A1 | 4/2010 |
| WO | WO-2011027249 A2 | 3/2011 |
| WO | WO-2011144891 A1 | 11/2011 |
| WO | WO-2014007228 A1 | 1/2014 |
| WO | WO-2015046482 A1 | 4/2015 |
| WO | WO-2018013676 A1 | 1/2018 |
| WO | WO-2018147300 A1 | 8/2018 |
| WO | WO-2018170284 A1 | 9/2018 |
| WO | WO-2019023278 A1 | 1/2019 |
| WO | WO-2019157458 A1 | 8/2019 |
| WO | WO-2020061046 A1 | 3/2020 |
| WO | WO-2021030262 A1 | 2/2021 |

OTHER PUBLICATIONS

Ishida et al. Discovery and SAR Studies of Orally Active Somatostatin Receptor Subtype-2 (SSTR2) Agonists for the Treatment of Acromegaly. ACS Chem Neurosci 11(10):1482-1494 (2020).
Liu et al. Nonpeptide somatostatin agonists with sst4 selectivity: synthesis and structure-activity relationships of thioureas. J Med Chem 41(24):4693-705 (1998).
Zhao et al. Discovery of nonpeptide 3,4-dihydroquinazoline-4-carboxamides as potent and selective sst2 agonists. Bioorg Med Chem Lett 30(17):127391 (2020).
Zhao et al. Discovery of substituted 3H-pyrido[2,3-d]pyrimidin-4-ones as potent, biased, and orally bioavailable sst2 agonist. Bioorg Med Chem Lett 30(21):127496 (2020).
Abbott et al. MiRP1 forms IKr potassium channels with HERG and is associated with cardiac arrhythmia. Cell 97:175-187 (1999).

(Continued)

*Primary Examiner* — Kahsay Habte
(74) *Attorney, Agent, or Firm* — Wilson Sonsini Goodrich & Rosati

(57) ABSTRACT

Described herein are compounds that are somatostatin modulators, methods of making such compounds, pharmaceutical compositions and medicaments comprising such compounds, and methods of using such compounds in the treatment of conditions, diseases, or disorders that would benefit from modulation of somatostatin activity.

21 Claims, No Drawings

(56) References Cited

OTHER PUBLICATIONS

Berge et al. Pharmaceutical Salts. Journal of Pharmaceutical Sciences 66(1):1-19 (Jan. 1977).

Brazeau et al. Hypothalamic polypeptide that inhibits the secretion of immunoreactive pituitary growth hormone. Science 179:77-79 (1973).

Bundgaard. Design and Application of Prodrugs. Textbook of Drug Design and Development. Krosgaard-Larsen and Bundgaard. Chapter 5. pp. 113-191 (1991).

Bundgaard. Means to Enhance Penetration: Prodrugs as a Means to Improve the Delivery of Peptide Drugs. Advanced Drug Delivery Review 8:1-38 (1992).

Crider. Somatostatin receptor agonists and antagonists. Expert Opinion on Therapeutic Patents 13(9):1427-1441 (2003).

Esch et al. Primary structure of ovine hypothalamic somatostatin-28 and somatostatin-25. PNAS USA 77:6827-6831 (1980).

Khlebnikov et al. A Novel Strategy for the Synthesis of 3-(N-Heteryl)pyrrole Derivatives. Org Lett 14(14):3768-71 (2012).

Mallinger et al. Discovery of Potent, Orally Bioavailable, Small-Molecule Inhibitors of WNT Signaling from a Cell-Based Pathway Screen. J Med Chem 58(4):1717-35 (2015).

Ortiz-Marciales et al. Catalytic enantioselective borane reduction of benzyl oximes: preparation of (S)-1-Pyridin-3-YL-Ethylamine Bis Hydrochloride. Organic Synth. 87:36-52 (2010).

Patel et al. Somatostatin receptors. Trends Endocrinol Metab 8:398-405 (1997).

PCT/US2019/017529 International Search Report and Written Opinion dated Jun. 3, 2019.

Pradayrol et al. N-terminally extended somatostatin: the primary structure of somatostatin-28. FEBS Letters 109:55-58 (1980).

Reisine et al. Molecular biology of somatostatin receptors. Endocr Rev 16:427-442 (1995).

Sanguinetti et al. hERG potassium channels and cardiac arrhythmia. Nature 440(7083):463-469 (2006).

Science IP Report. Chemical Structure Search (May 24, 2016) (311 pgs.).

Stella. Prodrugs: Some Thoughts and Current Issues. J Pharm Sci 99(12):4755-4765 (2010).

Weckbecker et al. Opportunities in somatostatin research: biological, chemical and therapeutic aspects. Nat Rev Drug Discov 2(12):999-1017 (2003).

Widder et al. Section III: Prodrugs Kinetics. Method in Enzymology. 112:309-396 (1985).

Wolf et al. Cytochrome P450 CYP2D6. IARC Sci Publ 148:209-229 (1999).

Wolkenberg et al. Design, synthesis, and evaluation of novel 3,6-diaryl-4-aminoalkoxyquinolines as selective agonists of somatostatin receptor subtype 2. J Med Chem 54:2351-2358 (2011).

SOMATOSTATIN MODULATORS AND USES THEREOF

STATEMENT AS TO FEDERALLY SPONSORED RESEARCH

This invention was made with government support under grant number DK115290 awarded by the National Institutes of Health. The government has certain rights in the invention.

RELATED APPLICATIONS

This application is a U.S. National Stage of PCT International Application No. PCT/US2019/017529, filed on Feb. 11, 2019, which claims the benefit of U.S. Provisional Patent Application No. 62/629,377 filed on Feb. 12, 2018; U.S. Provisional Patent Application No. 62/673,042 filed on May 17, 2018; and U.S. Provisional Patent Application No. 62/724,421 filed on Aug. 29, 2018; all of which are herein incorporated by reference in their entireties.

FIELD OF THE INVENTION

Described herein are compounds that are somatostatin modulators, methods of making such compounds, pharmaceutical compositions and medicaments comprising such compounds, and methods of using such compounds in the treatment of conditions, diseases, or disorders that would benefit from modulating somatostatin activity.

BACKGROUND OF THE INVENTION

Somatostatin is a peptide hormone that regulates the endocrine system and affects neurotransmission and cell proliferation via interaction with G-protein-coupled somatostatin receptors and inhibition of the release of numerous secondary hormones. Six subtype somatostatin receptor proteins have been identified (SSTR1, SSTR2a, SSTR2b, SSTR3, SSTR4, SSTR5) and are encoded by five different somatostatin receptor genes. Modulation of a particular subtype somatostatin receptor or combination thereof, is attractive for the treatment of conditions, diseases, or disorders that would benefit from modulating somatostatin activity.

SUMMARY OF THE INVENTION

Compounds described herein are somatostatin modulator compounds. In some embodiments, compounds described herein modulate one or more of the subtype somatostatin receptor proteins. In some embodiments, compounds described herein modulate one subtype somatostatin receptor. In some embodiments, compounds described herein modulate SST5 receptor. Somatostatin peptide analogs, such as octreotide, lanreotide and pasireotide, formulated as depot injections, are routinely used to normalize hormone levels for the treatment of Growth Hormone (GH) secreting adenomas, pancreatic neuroendocrine tumors, and carcinoid tumors. Octreotide is also reported to be used as a treatment for congenital hyperinsulinism (CHI, sometimes referred to as congenital hyperinsulinism of infancy, or persistent hyperinsulinemic hypoglycemia of infancy), a condition that causes individuals to have abnormally high levels of insulin, which in turn to lead to frequent episodes of low blood sugar (hypoglycemia). The depot preparations of these peptide drugs are extremely expensive and require frequent doctor's office visits for painful injections that can lead to injection site reactions. Compounds described herein are molecules that are structurally different from peptide analogs. The compounds described herein are somatostatin modulators that selectively activate somatostatin receptor subtype 5 (SSTR5) that in turn inhibits insulin secretion and promotes glucose release and also inhibits GH secretion.

In one aspect, described herein is a compound of Formula (I), or a pharmaceutically acceptable salt, pharmaceutically acceptable solvate, diastereomeric mixture, enantiomer or prodrug thereof:

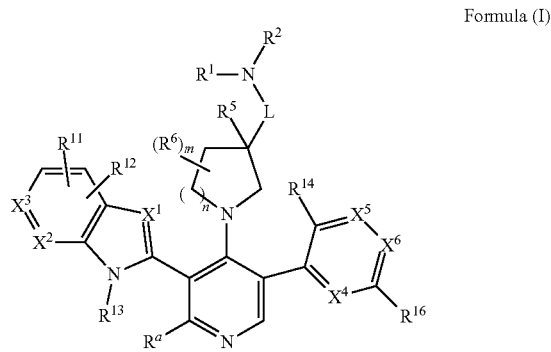

Formula (I)

wherein:
$R^1$ and $R^2$ are independently H, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_6$cycloalkyl, or substituted or unsubstituted $C_3$-$C_5$heterocycloalkyl that has 1 O atom;

L is absent or —$C(R^3)(R^4)$—;

$R^3$ and $R^4$ are independently H or substituted or unsubstituted $C_1$-$C_6$alkyl;

$R^5$ is H, —OH, substituted or unsubstituted $C_1$-$C_6$alkyl, substituted or unsubstituted $C_1$-$C_6$alkoxy, or substituted or unsubstituted $C_i$$C_6$heteroalkyl;

each $R^6$ is independently H, halogen, —$OR^{17}$, —$N(R^{17})_2$, —CN, —$CO_2R^{17}$, —$C(=O)N(R^{17})_2$, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted monocyclic carbocycle, or substituted or unsubstituted monocyclic heterocycle;

$R^a$ is H or —$NR^7R^8$;

$R^7$ is H, substituted or unsubstituted $C_1$-$C_4$alkyl, substituted or unsubstituted $C_1$-$C_4$fluoroalkyl, substituted or unsubstituted $C_1$-$C_4$heteroalkyl, or substituted or unsubstituted $C_3$-$C_6$cycloalkyl;

$R^8$ is H, substituted or unsubstituted $C_1$-$C_4$alkyl, substituted or unsubstituted $C_1$-$C_4$fluoroalkyl, substituted or unsubstituted $C_1$-$C_4$heteroalkyl, or substituted or unsubstituted $C_3$-$C_6$cycloalkyl;

$X^1$ is N or C—$R^9$;

$R^9$ is H, F, Cl, Br, —CN, —$N(R^{17})_2$, substituted or unsubstituted $C_1$-$C_4$alkyl, substituted or unsubstituted $C_1$-$C_4$alkoxy, substituted or unsubstituted $C_1$-$C_4$fluoroalkyl, substituted or unsubstituted $C_1$-$C_4$fluoroalkoxy, substituted or unsubstituted $C_1$-$C_4$heteroalkyl, or substituted $C_3$-$C_6$cycloalkyl;

$X^2$ is C—$R^{10}$ or N;

$X^3$ is C—$R^{11}$ or N;

$R^{10}$, each $R^{11}$ and $R^{12}$ are each independently H, halogen, substituted or unsubstituted $C_1$-$C_4$alkyl, substituted or unsubstituted $C_1$-$C_4$alkenyl, substituted or unsubstituted $C_1$-$C_4$alkynyl, substituted or unsubstituted $C_1$-$C_4$fluoroalkyl, substituted or unsubstituted $C_1$-$C_6$heteroalkyl, substituted or unsubstituted monocyclic carbocycle, substituted or unsubstituted monocyclic heterocycle, —CN, —$OR^{17}$, —$CO_2R^{17}$, —C(=O)N($R^{17}$)$_2$, —N($R^{17}$)$_2$, —$NR^{17}$C(=O)$R^{18}$, —$NR^{17}$C(=O)$OR^{18}$, —$NR^{17}$C(=O)N($R^{17}$)$_2$, —C($R^{17}$)=N—$OR^{17}$, —$SR^{17}$, —S(=O)$R^{17}$, —$SO_2R^{17}$, or —$SO_2$N($R^{17}$)$_2$;

$R^{13}$ is H, substituted or unsubstituted $C_1$-$C_4$alkyl, substituted or unsubstituted $C_1$-$C_4$fluoroalkyl, substituted or unsubstituted $C_1$-$C_4$heteroalkyl, or substituted or unsubstituted $C_3$-$C_6$cycloalkyl;

$X^4$ and $X^6$ are independently $CR^{14}$ or N;

each $R^{14}$ is independently H, halogen, substituted or unsubstituted $C_1$-$C_4$alkyl, substituted or unsubstituted $C_1$-$C_4$fluoroalkyl, substituted or unsubstituted $C_1$-$C_6$heteroalkyl, substituted or unsubstituted monocyclic carbocycle, substituted or unsubstituted monocyclic heterocycle, —CN, —$OR^{17}$, —$CO_2R^{17}$, —C(=O)N($R^{17}$)$_2$, —N($R^{17}$)$_2$, —$NR^{17}$C(=O)$R^{18}$, —$NR^{17}$C(=O)$OR^{18}$, —$NR^{17}$C(=O)N($R^{17}$)$_2$, —C($R^{17}$)=N—$OR^{17}$, —$SR^{17}$, —S(=O)$R^{17}$, —$SO_2R^{17}$, or —$SO_2$N($R^{17}$)$_2$;

$X^5$ is $CR^{15}$ or N;

$R^{15}$ and $R^{16}$ are independently H, halogen, substituted or unsubstituted $C_1$-$C_4$alkyl, substituted or unsubstituted $C_1$-$C_4$fluoroalkyl, substituted or unsubstituted $C_1$-$C_6$heteroalkyl, substituted or unsubstituted monocyclic carbocycle, substituted or unsubstituted monocyclic heterocycle, —CN, —$OR^{17}$, —$CO_2R^{17}$, —C(=O)N($R^{17}$)$_2$, —N($R^{17}$)$_2$, —$NR^{17}$C(=O)$R^{18}$, —$NR^{17}$C(=O)$OR^{18}$, —$NR^{17}$C(=O)N($R^{17}$)$_2$, —C($R^{17}$)=N—$OR^{17}$, —$SR^{17}$, —S(=O)$R^{17}$, —$SO_2R^{17}$, or —$SO_2$N($R^{17}$)$_2$;

each $R^{17}$ is independently selected from H, substituted or unsubstituted $C_1$-$C_6$alkyl, substituted or unsubstituted $C_1$-$C_6$heteroalkyl, substituted or unsubstituted $C_3$-$C_7$cycloalkyl, substituted or unsubstituted monocyclic $C_2$-$C_6$heterocycloalkyl, substituted or unsubstituted phenyl, and substituted or unsubstituted monocyclic heteroaryl;

or two $R^{17}$ on the same N atom are taken together with the N atom to which they are attached to form a substituted or unsubstituted N-containing heterocycle;

each $R^{18}$ is independently selected from substituted or unsubstituted $C_1$-$C_6$alkyl, substituted or unsubstituted $C_1$-$C_6$heteroalkyl, substituted or unsubstituted $C_3$-$C_7$cycloalkyl, substituted or unsubstituted monocyclic $C_2$-$C_6$heterocycloalkyl, substituted or unsubstituted phenyl, and substituted or unsubstituted monocyclic heteroaryl;

m is 0, 1, or 2; and n is 0 or 1.

Any combination of the groups described above for the various variables is contemplated herein. Throughout the specification, groups and substituents thereof are chosen by one skilled in the field to provide stable moieties and compounds.

Also described herein is a pharmaceutical composition comprising a compound described herein, or a pharmaceutically acceptable salt, or solvate thereof, and at least one pharmaceutically acceptable excipient. In some embodiments, the pharmaceutical composition is formulated for administration to a mammal by intravenous administration, subcutaneous administration, oral administration, inhalation, nasal administration, dermal administration, or ophthalmic administration. In some embodiments, the pharmaceutical composition is formulated for administration to a mammal by oral administration. In some embodiments, the pharmaceutical composition is in the form of a tablet, a pill, a capsule, a liquid, a suspension, a gel, a dispersion, a solution, an emulsion, an ointment, or a lotion. In some embodiments, the pharmaceutical composition is in the form of a tablet, a pill, or a capsule.

Also described herein is a method of treating a disease or condition in a mammal that would benefit from the modulation of somatostatin receptor activity comprising administering a small molecule non-peptidyl compound, or pharmaceutically acceptable salt, or solvate thereof, to the mammal in need thereof. In some embodiments, the small molecule non-peptidyl compound is orally administered. In some embodiments, the small molecule non-peptidyl compound is a compound as described herein, or a pharmaceutically acceptable salt or solvate thereof. In some embodiments, the small molecule non-peptidyl compound is a SSTR5 modulator as described herein, or a pharmaceutically acceptable salt or solvate thereof. In some embodiments, the disease or condition is persistent or recurring hyperinsulinemia, hypoglycemia, acromegaly, a neuroendocrine tumor, an insulinoma, Cushing's disease, an ophthalmic disease or condition, cancer, pain, a neurodegenerative disease or condition, an inflammatory disease or condition, a psychiatric disease or condition, or combinations thereof In any of the aforementioned aspects are further embodiments in which the effective amount of the compound of Formula (I), or a pharmaceutically acceptable salt thereof, is: (a) systemically administered to the mammal; and/or (b) administered orally to the mammal; and/or (c) intravenously administered to the mammal; and/or (d) administered by inhalation; and/or (e) administered by nasal administration; or and/or (f) administered by injection to the mammal; and/or (g) administered topically to the mammal; and/or (h) administered by ophthalmic administration; and/or (i) administered rectally to the mammal; and/or (j) administered non- systemically or locally to the mammal.

In any of the aforementioned aspects are further embodiments comprising single administrations of the effective amount of the compound, including further embodiments in which the compound is administered once a day to the mammal or the compound is administered to the mammal multiple times over the span of one day. In some embodiments, the compound is administered on a continuous dosing schedule. In some embodiments, the compound is administered on a continuous daily dosing schedule.

In any of the embodiments disclosed herein, the mammal is a human.

In some embodiments, compounds provided herein are orally administered to a human.

Articles of manufacture, which include packaging material, a compound of Formula (I), or a pharmaceutically acceptable salt thereof, within the packaging material, and a label that indicates that the compound or composition, or pharmaceutically acceptable salt, tautomers, pharmaceutically acceptable N-oxide, pharmaceutically active metabolite, pharmaceutically acceptable prodrug, or pharmaceutically acceptable solvate thereof, is used for modulating one or more subtype somatostatin receptor proteins, or for the treatment, prevention or amelioration of one or more symptoms of a disease or condition that would benefit from modulating one or more subtype somatostatin receptor proteins, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Somatostatin (SST), also known as somatotropin release inhibiting factor (SRIF) was initially isolated as a 14-amino acid peptide from ovine hypothalami (Brazeau et al., *Science* 179, 77-79, 1973). An N-terminal extended 28-amino acid peptide with similar biological activity to 14-amino acid somatostatin was subsequently isolated (Pradayrol et, al., *FEBS Letters,* 109, 55-58, 1980; Esch et al., *Proc. Natl. Acad. Sci. USA,* 77, 6827-6831, 1980). SST is a regulatory peptide produced by several cell types in response to other neuropeptides, neurotransmitters, hormones, cytokines, and growth factors. SST acts through both endocrine and paracrine pathways to affect its target cells. Many of these effects are related to the inhibition of secretion of other hormones, most notably growth hormone (GH). They are produced by a wide variety of cell types in the central nervous system (CNS) and gut and have multiple functions including modulation of secretion of growth hormone (GH), insulin, glucagon, as well as many other hormones that are anti-proliferative.

These pleotropic actions of somatostatins are mediated by six somatostatin receptor proteins (SSTR1, SSTR2a, SSTR2b, SSTR3, SSTR4, SSTR5). The six somatostatin receptor proteins are encoded by five different somatostatin receptor genes (Reisine and Bell, *Endocr Rev.* 16, 427-442, 1995; Patel and Srikant, *Trends Endocrinol Metab* 8, 398-405, 1997). All the receptors are members of the class-A subgroup of the GPCR superfamily.

It is possible to selectively modulate any one of the somatostatin receptor subtypes, or combination thereof. In some embodiments, selectively modulating any one of the somatostatin receptor subtypes relative to the other somatostatin receptor subtypes reduces unwanted side effects in a variety of clinical applications.

In one aspect, compounds described herein are modulators of SSTR5. In some embodiments, compounds described herein selectively modulate the activity of SSTR5 relative to the other somatostatin receptors.

In some embodiments, compounds described here are amenable to oral administration to a mammal in need of treatment with a somatostatin modulator.

In some embodiments, somatostatin receptor modulators described herein have utility over a wide range of therapeutic applications. In some embodiments, somatostatin receptor modulators described herein are used in the treatment of a variety of diseases or conditions such as, but not limited to acromegaly, neuroendocrine tumors and hyperinsulinism. In some embodiments, somatostatin receptor modulators described herein are used in the treatment of hyperinsulinism in a mammal.

In some embodiments, somatostatin receptor modulators described herein inhibit the secretion of various hormones and trophic factors in mammals. In some embodiments, the compounds are used to suppress certain endocrine secretions, such as, but not limited to GH, IGF-1 and insulin. The suppression of certain endocrine secretions is useful in the treatment of disorders such as acromegaly, hyperinsulinism, endocrine tumors such as carcinoids, VIPomas, insulinomas and glucagonomas. In some embodiments, somatostatin receptor modulators described herein are used to suppress exocrine secretions in the pancreas, stomach and intestines, for the treatment of disorders such as pancreatitis, fistulas, bleeding ulcers and diarrhea associated with such diseases as AIDS or cholera. Disorders involving autocrine or paracrine secretions of trophic factors such as IGF-1 (as well as some endocrine factors) which may be treated by administration of the compounds described herein include cancers of the breast, prostate, and lung (both small cell and non-small cell epidermoids), as well as hepatomas, neuroblastomas, insulinomas, colon and pancreatic adenocarcinomas (ductal type), chondrosarcomas, and melanomas, and atherosclerosis associated with vascular grafts and restenosis following angioplasty.

In some embodiments, somatostatin receptor modulators described herein are used to suppress the mediators of neurogenic inflammation (e.g. substance P or the tachykinins), and may be used in the treatment of rheumatoid arthritis; psoriasis; topical inflammation such as is associated with sunburn, eczema, or other sources of itching; inflammatory bowel disease; irritable bowel syndrome; allergies, including asthma and other respiratory diseases In some other embodiments, the somatostatin receptor modulators described herein function as neuromodulators in the central nervous system and are useful in the treatment of Alzheimer's disease and other forms of dementia, pain, and headaches. In some embodiments, somatostatin receptor modulators described herein provide cytoprotection in disorders involving the splanchnic blood flow, including cirrhosis and oesophagal varices.

In some embodiments, somatostatin receptor modulators described herein are used to treat hyperinsulinemia in a mammal. Hyperinsulinemia leads to several conditions, such as but not limited to, hypoglycemia or low blood sugar, diabetes or uncontrolled blood sugar that fluctuates between a low and high level, increased risk of Polycystic Ovarian Syndrome (PCOS), increased production of very low-density lipoproteins (VLDLs) (referred to as hypertriglyceridemia), increased risk of cardiovascular or heart disease, coronary artery disease (the high insulin level damages the endothelial cells that line the coronary arteries), hypertension or high blood pressure, underactive thyroid gland, weight gain and lethargy.

Hyperinsulinism refers to an above normal level of insulin in the blood of a person or animal. Normal insulin secretion and blood levels are closely related to the level of glucose in the blood, so that a given level of insulin can be normal for one blood glucose level but low or high for another. Hyperinsulinism can be associated with several types of medical problems, which can be roughly divided into two broad and largely non-overlapping categories: those tending toward reduced sensitivity to insulin and high blood glucose levels (hyperglycemia), and those tending toward excessive insulin secretion and low glucose levels (hypoglycemia).

Hyperinsulinemic hypoglycemia (HH) is one of the most frequent causes of persistent hypoglycemia in infants. It is a heterogeneous condition caused by increased insulin secretion from pancreatic β-cells. HH can result in apneas, seizures, developmental delays, learning disabilities, epilepsy, and even death. The most severe form of HH is inherited and referred to as congenital hyperinsulinism (CHI). As with many rare diseases, there are no current drugs specifically tailored for patients with CHI, though some drugs have been adapted for use, including but not limited to diazoxide and octreotide.

The pancreas is a principal site of somatostatin action, and there it inhibits the synthesis and secretion of the two major hormones that control glucose homeostasis: glucagon and insulin. Different somatostatin receptor subtypes control these vital processes: sst2 receptors suppress glucagon, while both sst2 and sst5 are responsible for the suppression of insulin.

Hypoglycemia due to excessive endogenous insulin can be congenital or acquired, apparent in the newborn period, or many years later. The hypoglycemia can be severe and life-threatening or a minor, occasional nuisance. By far the most common type of severe but transient hyperinsulinemic hypoglycemia occurs accidentally in persons with type 1 diabetes who take insulin.

Hypoglycemia due to endogenous insulin includes, but is not limited to, congenital hyperinsulinism, transient neonatal hyperinsulinism, focal hyperinsulinism (KATP channel disorders), diffuse hyperinsulinism, acquired forms of hyperinsulinism, insulinomas (insulin-secreting tumors), adult nesidioblastosis, autoimmune insulin syndrome, non-insulinoma pancreatogenous hypoglycemia, reactive hypoglycemia, a side effect of gastric bypass surgery or gastric dumping syndrome.

Drug induced hyperinsulinism results from exposure to certain drugs such as, but not limited to, sulfonylureas, aspirin, pentamidine, quinine, disopyramide, bordetella pertussis vaccine or infection, D-chiro-inositol and myo-inositol.

Hypoglycemia due to exogenous (injected) insulin includes but is not limited to, insulin self-injected for treatment of diabetes (i.e., diabetic hypoglycemia), insulin self-injected surreptitiously (e.g., Munchausen syndrome), insulin self-injected in a suicide attempt or successful suicide, insulin potentiation therapy, and insulin-induced coma for depression treatment.

Compounds

Compounds of Formula (I), including pharmaceutically acceptable salts, prodrugs, active metabolites and pharmaceutically acceptable solvates thereof, are somatostatin receptor modulators. In some embodiments, the compounds of Formula (I), including pharmaceutically acceptable salts, prodrugs, active metabolites and pharmaceutically acceptable solvates thereof, are SST5 receptor modulators.

In some embodiments, compounds described herein are at least 10 times, at least 15 times, at least 20 times, at least 30 times, at least 40 times, at least 50 times, at least 100 times, at least 200 times, at least 300 times, at least 400 times, or greater than 500 times more selective at modulating SST5 receptor activity than SST2 receptor activity.

In one aspect, provided herein is a compound of Formula (I), or a pharmaceutically acceptable salt, pharmaceutically acceptable solvate, diastereomeric mixture, individual enantiomers or prodrug thereof:

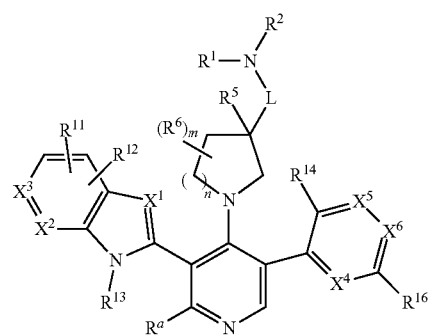

Formula (I)

wherein:
$R^1$ and $R^2$ are independently H, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_6$cycloalkyl, or substituted or unsubstituted $C_3$-$C_5$heterocycloalkyl that has 1 O atom;

L is absent or —C($R^3$)($R^4$)—;

$R^3$ and $R^4$ are independently H or substituted or unsubstituted $C_1$-$C_6$alkyl;

$R^5$ is H, —OH, substituted or unsubstituted $C_1$-$C_6$alkyl, substituted or unsubstituted $C_1$-$C_6$alkoxy, or substituted or unsubstituted $C_1$-$C_6$heteroalkyl;

each $R^6$ is independently H, halogen, —O$R^{17}$, —N($R^{17}$)$_2$, —CN, —CO$_2R^{17}$, —C(=O)N($R^{17}$)$_2$, substituted or unsubstituted $C_1$-$C_6$alkyl, and substituted or unsubstituted $C_1$-$C_6$fluoroalkyl, substituted or unsubstituted $C_1$-$C_6$heteroalkyl, substituted or unsubstituted monocyclic carbocycle, or substituted or unsubstituted monocyclic heterocycle;

$R^a$ is H or —N$R^7R^8$;

$R^7$ is H, substituted or unsubstituted $C_1$-$C_4$alkyl, substituted or unsubstituted $C_1$-$C_4$fluoroalkyl, substituted or unsubstituted $C_1$-$C_4$heteroalkyl, or substituted or unsubstituted $C_3$-$C_6$cycloalkyl;

$R^8$ is H, substituted or unsubstituted $C_1$-$C_4$alkyl, substituted or unsubstituted $C_1$-$C_4$fluoroalkyl, substituted or unsubstituted $C_1$-$C_4$heteroalkyl, or substituted or unsubstituted $C_3$-$C_6$cycloalkyl;

$X^1$ is N or C—$R^9$;

$R^9$ is H, F, Cl, Br, —CN, —N($R^{17}$)$_2$, substituted or unsubstituted $C_1$-$C_4$alkyl, substituted or unsubstituted $C_1$-$C_4$alkoxy, substituted or unsubstituted $C_1$-$C_4$fluoroalkyl, substituted or unsubstituted $C_1$-$C_4$fluoroalkoxy, substituted or unsubstituted $C_1$-$C_4$heteroalkyl, or substituted $C_3$-$C_6$cycloalkyl;

$X^2$ is C—$R^{19}$ or N;

$X^3$ is C—$R^{11}$ or N;

$R^{10}$, each $R^{11}$ and $R^{12}$ are each independently H, halogen, substituted or unsubstituted $C_1$-$C_4$alkyl, substituted or unsubstituted $C_1$-$C_4$alkenyl, substituted or unsubstituted $C_1$-$C_4$alkynyl, substituted or unsubstituted $C_1$-$C_4$fluoroalkyl, substituted or unsubstituted $C_1$-$C_6$heteroalkyl, substituted or unsubstituted monocyclic carbocycle, substituted or unsubstituted monocyclic heterocycle, —CN, —O$R^{17}$, —CO$_2R^{17}$, —C(=O)N($R^{17}$)$_2$, —N($R^{17}$)$_2$, —N$R^{17}$C(=O)$R^{18}$, —N$R^{17}$C(=O)O$R^{18}$, —N$R^{17}$C(=O)N($R^{17}$)$_2$, —C($R^{17}$)=N—O$R^{17}$, —S$R^{17}$, —S(=O)$R^{17}$, —SO$_2R^{17}$, or —SO$_2$N($R^{17}$)$_2$;

R¹³ is H, substituted or unsubstituted $C_1$-$C_4$alkyl, substituted or unsubstituted $C_1$-$C_4$fluoroalkyl, substituted or unsubstituted $C_1$-$C_4$heteroalkyl, or substituted or unsubstituted $C_3$-$C_6$cycloalkyl;

$X^4$ and $X^6$ are independently $CR^{14}$ or N;

each $R^{14}$ is independently H, halogen, substituted or unsubstituted $C_1$-$C_4$alkyl, substituted or unsubstituted $C_1$-$C_4$fluoroalkyl, substituted or unsubstituted $C_1$-$C_6$heteroalkyl, substituted or unsubstituted monocyclic carbocycle, substituted or unsubstituted monocyclic heterocycle, —CN, —$OR^{17}$, —$CO_2R^{17}$, —C(=O)N($R^{17}$)$_2$, —N($R^{17}$)$_2$, —$NR^{17}$C(=O)$R^{18}$, —$NR^{17}$C(=O)$OR^{18}$, —$NR^{17}$C(=O)N($R^{17}$)$_2$, —C($R^{17}$)=N—$OR^{17}$, —$SR^{17}$, —S(=O)$R^{17}$, —$SO_2R^{17}$, or —$SO_2$N($R^{17}$)$_2$;

$X^5$ is $CR^{15}$ or N;

$R^{15}$ and $R^{16}$ are independently H, halogen, substituted or unsubstituted $C_1$-$C_4$alkyl, substituted or unsubstituted $C_1$-$C_4$fluoroalkyl, substituted or unsubstituted $C_1$-$C_6$heteroalkyl, substituted or unsubstituted monocyclic carbocycle, substituted or unsubstituted monocyclic heterocycle, —CN, —$OR^{17}$, —$CO_2R^{17}$, —C(=O)N($R^{17}$)$_2$, —N($R^{17}$)$_2$, —$NR^{17}$C(=O)$R^{18}$, —$NR^{17}$C(=O)$OR^{18}$, —$NR^{17}$C(=O)N($R^{17}$)$_2$, —C($R^{17}$)=N—$OR^{17}$, —$SR^{17}$, —S(=O)$R^{17}$, —$SO_2R^{17}$, or —$SO_2$N($R^{17}$)$_2$;

each $R^{17}$ is independently selected from H, substituted or unsubstituted $C_1$-$C_6$alkyl, substituted or unsubstituted $C_1$-$C_6$heteroalkyl, substituted or unsubstituted $C_3$-$C_7$cycloalkyl, substituted or unsubstituted monocyclic $C_2$-$C_6$heterocycloalkyl, substituted or unsubstituted phenyl, and substituted or unsubstituted monocyclic heteroaryl;

or two $R^{17}$ on the same N atom are taken together with the N atom to which they are attached to form a substituted or unsubstituted N-containing heterocycle;

each $R^{18}$ is independently selected from substituted or unsubstituted $C_1$-$C_6$alkyl, substituted or unsubstituted $C_1$-$C_6$heteroalkyl, substituted or unsubstituted $C_3$-$C_7$cycloalkyl, substituted or unsubstituted monocyclic $C_2$-$C_6$heterocycloalkyl, substituted or unsubstituted phenyl, and substituted or unsubstituted monocyclic heteroaryl;

m is 0, 1, or 2; and n is 0 or 1.

For any and all of the embodiments, substituents are selected from among a subset of the listed alternatives. For example, in some embodiments, L is absent or —C($R^3$)($R^4$)—. In other embodiments, L is absent. In some other embodiments, L is absent or —$CH_2$—.

In some embodiments, L is absent when n is 1; and L is —C($R^3$)($R^4$)— when n is 0 or 1. In some embodiments, L is absent when n is 1; and L is —C($R^3$)($R^4$)— when n is 0. In some embodiments, L is absent when n is 1. In some embodiments, L is —C($R^3$)($R^4$)— when n is 0.

In some embodiments, $R^1$ H; $R^2$ is H, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_6$cycloalkyl or substituted or unsubstituted $C_3$-$C_5$heterocycloalkyl that has 1 O atom; L is absent or —C($R^3$)($R^4$)—; $R^3$ and $R^4$ are independently H, —$CH_3$, or —$CH_2CH_3$.

In some embodiments, $R^1$ is H; $R^2$ is H, —$CH_3$, —$CH_2CH_3$, —$CH_2CH_2F$, —$CH_2CHF_2$, —$CH_2CF_3$, —$CH_2CH_2OCH_3$, —$CH_2CH_2NH_2$, —$CH_2CH_2NHCH_3$, —$CH_2CH_2N(CH_3)_2$, —$CH_2CH_2CH_3$, —CH($CH_3$)$_2$, cyclopropyl, $CH_2CH_2CH_2OCH_3$, —$CH_2CH_2CH_2CH_3$, —$CH_2CH(CH_3)_2$, —CH($CH_3$)($CH_2CH_3$), —C($CH_3$)$_3$, cyclobutyl, cyclopentyl, cyclohexyl, oxetanyl, tetrahydrofuranyl, or tetrahydropyranyl; L is absent or —C($R^3$)($R^4$)—; $R^3$ and $R^4$ are independently H or —$CH_3$.

In some embodiments, $R^1$ is H; $R^2$ is H; L is absent.

In some embodiments, $R^a$ is H or —$NR^7R^8$; $R^7$ is H, $C_1$-$C_4$alkyl, $C_1$-$C_4$fluoroalkyl, $C_1$-$C_4$heteroalkyl, or $C_3$-$C_6$cycloalkyl; $R^8$ is H, $C_1$-$C_4$alkyl, $C_1$-$C_4$fluoroalkyl, $C_1$-$C_4$heteroalkyl, or $C_3$-$C_6$cycloalkyl.

In some embodiments, $R^a$ is H or —$NR^7R^8$; $R^7$ is H, —$CH_3$, —$CH_2CH_3$, —$CH_2CH_2CH_3$, —CH($CH_3$)$_2$, —$CH_2CH_2CH_2CH_3$, —$CH_2CH(CH_3)_2$, —CH($CH_3$)($CH_2CH_3$), —C($CH_3$)$_3$, —$CH_2CH_2OH$, —$CH_2CH_2OCH_3$, —$CH_2CN$; $R^8$ is H, —$CH_3$, —$CH_2CH_3$, —$CH_2CH_2CH_3$, —CH($CH_3$)$_2$, —$CH_2CH_2CH_2CH_3$, —$CH_2CH(CH_3)_2$, —CH($CH_3$)($CH_2CH_3$), —C($CH_3$)$_3$, —$CH_2CH_2OH$, —$CH_2CH_2OCH_3$, —$CH_2CN$, or —$CH_2CF_3$. In some embodiments, $R^a$ is H or —$NR^7R^8$; $R^7$ is H, —$CH_3$, or —$CH_2CH_3$; $R^8$ is H, —$CH_3$, or —$CH_2CH_3$.

In some embodiments, $R^8$ is H.

In some embodiments, $R^a$ is H.

In some embodiments, $R^5$ is H, —OH, or $C_1$-$C_4$alkyl. In some embodiments, $R^5$ is H, —OH, —$CH_3$ or —$CH_2CH_3$.

In some embodiments, the compound has the structure of Formula (II), or a pharmaceutically acceptable salt, pharmaceutically acceptable solvate, diastereomeric mixture, or individual enantiomers thereof:

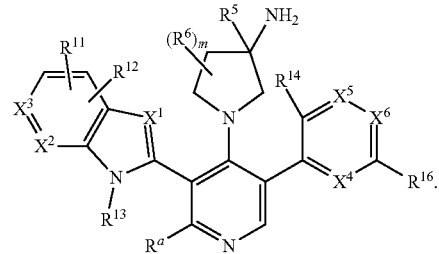

Formula (II)

In some embodiments, the compound has the structure of Formula (IIa), or a pharmaceutically acceptable salt, pharmaceutically acceptable solvate, diastereomeric mixture, or individual enantiomers thereof:

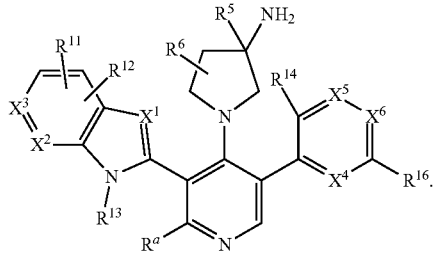

Formula (IIa)

In some embodiments, each $R^6$ is independently H, halogen, —$OR^{17}$, —N($R^{17}$)$_2$, —CN, —$CO_2R^{17}$, —C(=O)N($R^{17}$)$_2$, substituted or unsubstituted $C_1$-$C_6$alkyl, and substituted or unsubstituted $C_1$-$C_6$fluoroalkyl, substituted or unsubstituted $C_1$-$C_6$heteroalkyl, substituted or unsubstituted phenyl, or substituted or unsubstituted monocyclic 5-membered or 6-membered heterocycle.

In some embodiments, each $R^6$ is independently H, F, Cl, —OH, —OCH$_3$, —OCH$_2$CH$_3$, —OCF$_3$, —NH$_2$, —NHCH$_3$, —N(CH$_3$)$_2$, —CN, —C(=O)OCH$_3$, —C(=O)NH$_2$, —C(=O)NHCH$_3$, —C(=O)N(CH$_3$)$_2$, —CH$_3$, —CH$_2$CH$_3$, —CH$_2$OH, —CH$_2$OCH$_3$, —CH$_2$NH$_2$, —CH$_2$NHCH$_3$, —CH$_2$N(CH$_3$)$_2$, —CH$_2$CN, —CH$_2$F, —CHF$_2$, —CF$_3$, or —CH$_2$CF$_3$.

In some embodiments, each $R^6$ is independently H, F, —OH, —OCH$_3$, —OCH$_2$CH$_3$, —OCF$_3$, —NH$_2$, —NHCH$_3$, —N(CH$_3$)$_2$, —CN, —C(=O)OCH$_3$, —C(=O)NH$_2$, —C(=O)NHCH$_3$, —C(=O)N(CH$_3$)$_2$, —CH$_3$, —CH$_2$CH$_3$, —CH$_2$OH, —CH$_2$OCH$_3$, —CH$_2$CN, or —CF$_3$. In some embodiments, each $R^6$ is independently H, F, —OH, —OCH$_3$, —OCH$_2$CH$_3$, —OCF$_3$, —CH$_3$, —CH$_2$CH$_3$, —CH$_2$OH, or —CH$_2$OCH$_3$. In some embodiments, each $R^6$ is H or —OH. In some embodiments, each $R^6$ is H.

In some embodiments, the compound has the structure of Formula (III), or a pharmaceutically acceptable salt, pharmaceutically acceptable solvate, diastereomeric mixture, or individual enantiomers thereof:

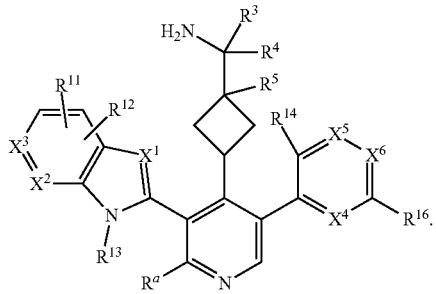

Formula (III)

In some embodiments, $R^{13}$ is H, or $C_1$-$C_4$alkyl; $X^1$ is N or C—$R^9$; $R^9$ is H, F, Cl, Br, —CN, —N($R^{17}$)$_2$, $C_1$-$C_4$alkyl, $C_1$-$C_4$alkoxy, $C_1$-$C_4$fluoroalkyl, or $C_1$-$C_4$fluoroalkoxy.

In some embodiments, $R^{13}$ is H, —CH$_3$, —CH$_2$CH$_3$, —CH$_2$CH$_2$CH$_3$, —CH(CH$_3$)$_2$, —CH$_2$CH$_2$CH$_2$CH$_3$, or —CH$_2$CH(CH$_3$)$_2$.

In some embodiments, $R^9$ is H, F, Cl, Br, —CN, —CH$_3$, —OCH$_3$, —NH$_2$, —NHCH$_3$, —N(CH$_3$)$_2$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$), or —C(CH$_3$)$_3$. In some embodiments, $R^9$ is H, F, Cl, —CH$_3$, —CH$_2$CH$_3$, or —CH$_2$CH$_2$CH$_3$.

In some embodiments, $X^1$ is C—$R^9$.

In some embodiments, $X^1$ is N.

In some embodiments,

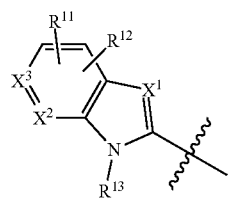

is

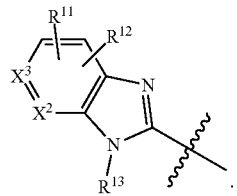

In some embodiments, $X^2$ is C—$R^{10}$; and $X^3$ is C—$R^{11}$.

In some embodiments, $X^2$ is N; and $X^3$ is C—$R^{11}$.

In some embodiments, $X^2$ is C—$R^{10}$; and $X^3$ is N.

In some embodiments,

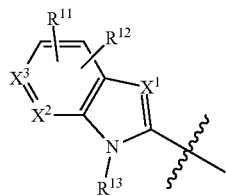

is

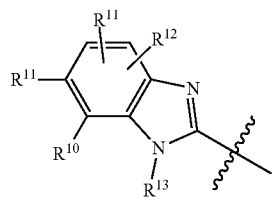

In some embodiments,

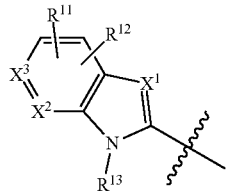

is

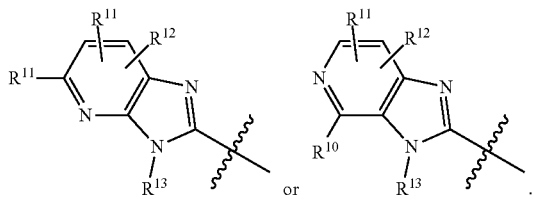

In some embodiments,
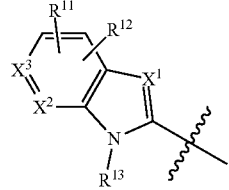
is
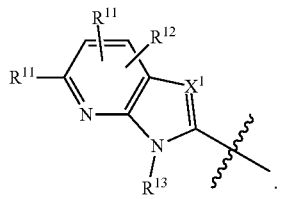
In some embodiments,
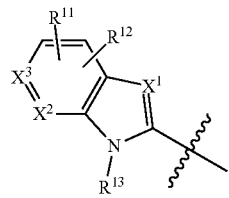
is
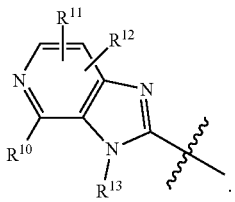
In some embodiments,
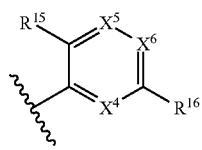
is
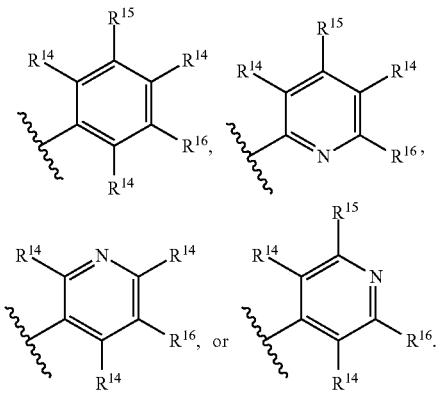
In some embodiments,
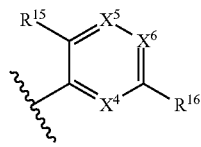
is
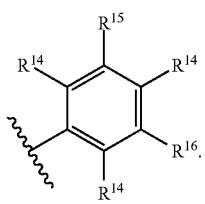
In some embodiments,
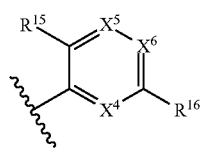
is
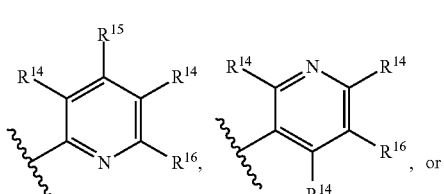
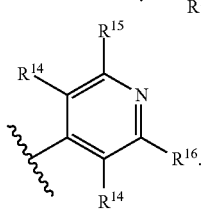

In some embodiments,
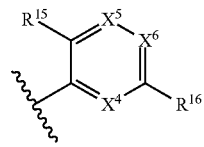
is
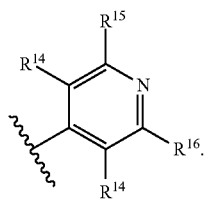
In some embodiments,
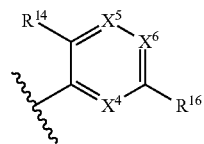
is
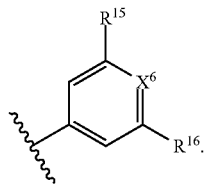
In some embodiments,
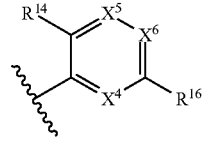
is
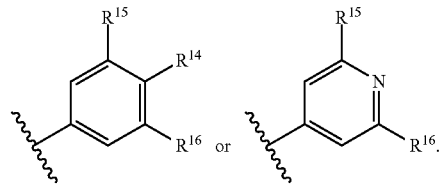
In some embodiments,
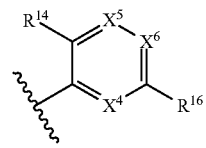
is
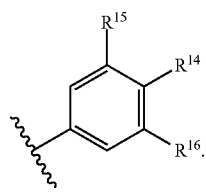
In some embodiments,
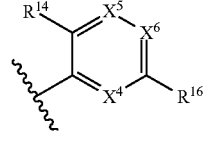
is
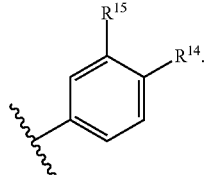
In some embodiments,
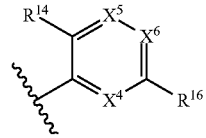
is
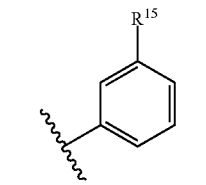

In some embodiments,

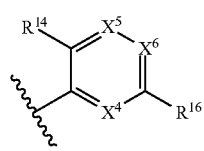

is

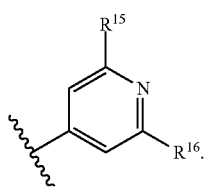

In some embodiments,

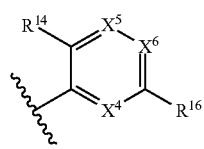

is

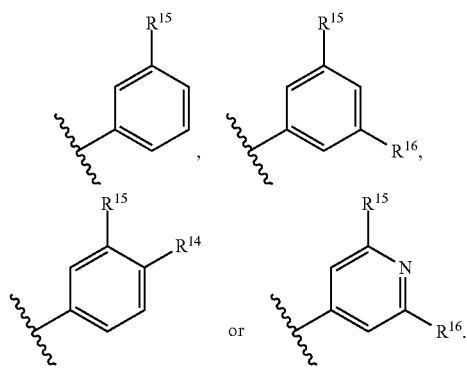

In some embodiments, the structure of Formula (IV), or a pharmaceutically acceptable salt, pharmaceutically acceptable solvate, diastereomeric mixture, or individual enantiomers thereof:

Formula (IV)

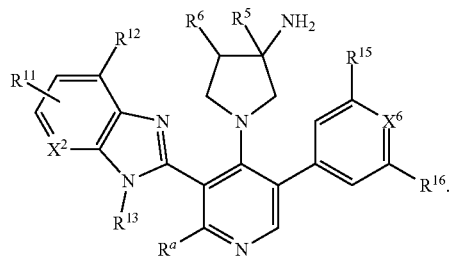

In some embodiments, the compound has the structure of Formula (IVa) or Formula (IVb), or a pharmaceutically acceptable salt, pharmaceutically acceptable solvate, diastereomeric mixture, or individual enantiomers thereof:

Formula (IVa)

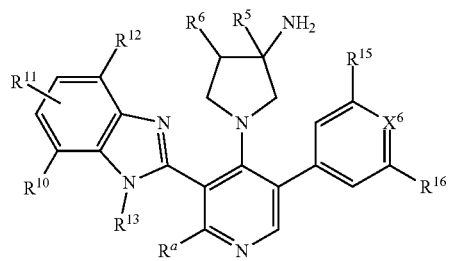

Formula (IVb)

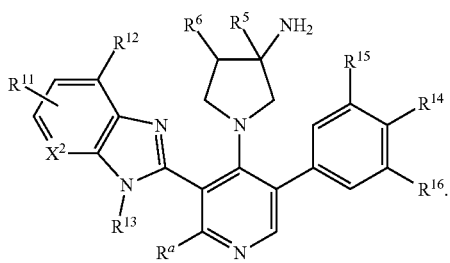

In some embodiments, the compound has the structure of Formula (IVa), or a pharmaceutically acceptable salt, pharmaceutically acceptable solvate, diastereomeric mixture, or individual enantiomers thereof:

Formula (IVa)

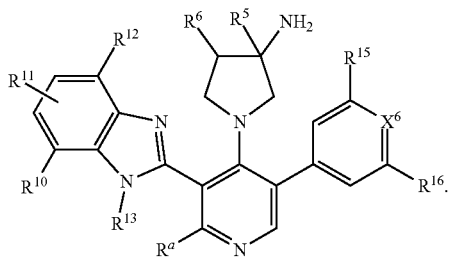

In some embodiments, the compound has the structure of Formula (IVb), or a pharmaceutically acceptable salt, pharmaceutically acceptable solvate, diastereomeric mixture, or individual enantiomers thereof:

Formula (IVb)

In some embodiments, the compound has the structure of Formula (IVc), or a pharmaceutically acceptable salt, pharmaceutically acceptable solvate, diastereomeric mixture, or individual enantiomers thereof:

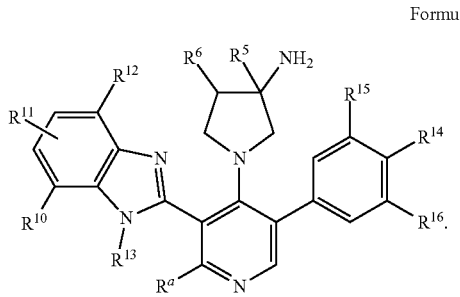

Formula (IVc)

In some embodiments, the compound has the structure of Formula (IVd), or Formula (IVe), or a pharmaceutically acceptable salt, pharmaceutically acceptable solvate, diastereomeric mixture, or individual enantiomers thereof:

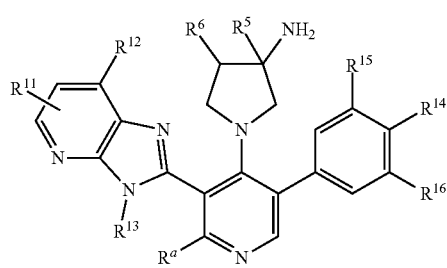

Formula (IVd)

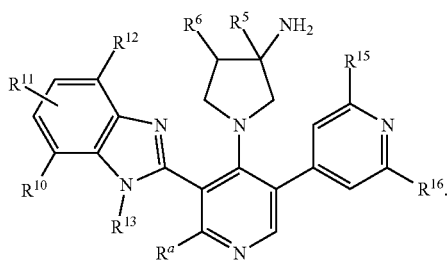

Formula (IVe)

In some embodiments, the compound has the structure of Formula (IVd), or a pharmaceutically acceptable salt, pharmaceutically acceptable solvate, diastereomeric mixture, or individual enantiomers thereof:

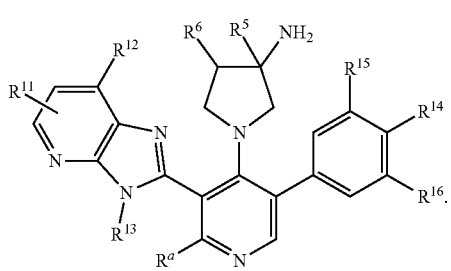

Formula (IVd)

In some embodiments, the compound has the structure of Formula (IVe), or a pharmaceutically acceptable salt, pharmaceutically acceptable solvate, diastereomeric mixture, or individual enantiomers thereof:

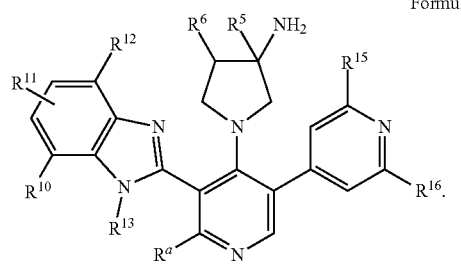

Formula (IVe)

In some embodiments, the compound has the structure of Formula (IVf), or a pharmaceutically acceptable salt, pharmaceutically acceptable solvate, diastereomeric mixture, or individual enantiomers thereof:

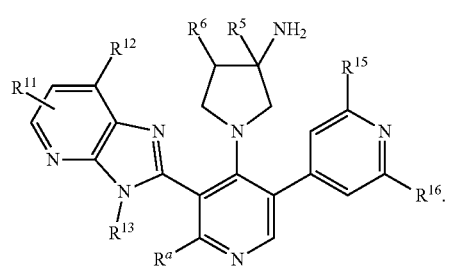

Formula (IVf)

In some embodiments, $R^5$ is H, —OH, or $C_1$-$C_4$alkyl. In some embodiments, $R^5$ is H or $C_1$-$C_4$alkyl. In some embodiments, $R^5$ is H, —CH$_3$ or —CH$_2$CH$_3$. In some embodiments, $R^5$ is H.

In some embodiments, $R^a$ is H or —NR$^7$R$^8$; $R^7$ is H, $C_1$-$C_4$alkyl, $C_1$-$C_4$fluoroalkyl, $C_1$-$C_4$heteroalkyl, or $C_3$-$C_6$cycloalkyl; $R^8$ is H, $C_1$-$C_4$alkyl, $C_1$-$C_4$fluoroalkyl, $C_1$-$C_4$heteroalkyl, or $C_3$-$C_6$cycloalkyl.

In some embodiments, $R^7$ is H, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$), —C(CH$_3$)$_3$, —CH$_2$CH$_2$OH, —CH$_2$CH$_2$OCH$_3$, or —CH$_2$CN; $R^8$ is H, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$), —C(CH$_3$)$_3$, —CH$_2$CH$_2$OH, —CH$_2$CH$_2$OCH$_3$, —CH$_2$CN, or —CH$_2$CF$_3$.

In some embodiments, $R^8$ is H.

In some embodiments, $R^a$ is H; $R^5$ is H, —OH, —CH$_3$ or —CH$_2$CH$_3$.

In some embodiments, each $R^6$ is independently H, halogen, —OR$^{17}$, —N(R$^{17}$)$_2$, —CN, —CO$_2$R$^{17}$, —C(=O)N(R$^{17}$)$_2$, substituted or unsubstituted $C_1$-$C_6$alkyl, and substituted or unsubstituted $C_1$-$C_6$fluoroalkyl, substituted or unsubstituted $C_1$-$C_6$heteroalkyl, substituted or unsubstituted phenyl, or substituted or unsubstituted monocyclic 5-membered or 6-membered heterocycle.

In some embodiments, each $R^6$ is independently H, F, Cl, —OH, —OCH$_3$, —OCH$_2$CH$_3$, —OCF$_3$, —NH$_2$, —NHCH$_3$, —N(CH$_3$)$_2$, —CN, —C(=O)OCH$_3$, —C(=O)NH$_2$, —C(=O)NHCH$_3$, —C(=O)N(CH$_3$)$_2$, —CH$_3$, —CH$_2$CH$_3$, —CH$_2$OH, —CH$_2$OCH$_3$, —CH$_2$NH$_2$, —CH$_2$NHCH$_3$, —CH$_2$N(CH$_3$)$_2$, —CH$_2$CN, —CH$_2$F, —CHF$_2$, —CF$_3$, or —CH$_2$CF$_3$.

In some embodiments, each R$^6$ is independently H, F, —OH, —OCH$_3$, —OCH$_2$CH$_3$, —OCF$_3$, —NH$_2$, —NHCH$_3$, —N(CH$_3$)$_2$, —CN, —C(=O)OCH$_3$, —C(=O)NH$_2$, —C(=O)NHCH$_3$, —C(=O)N(CH$_3$)$_2$, —CH$_3$, —CH$_2$CH$_3$, —CH$_2$OH, —CH$_2$OCH$_3$, —CH$_2$CN, or —CF$_3$.

In some embodiments, the compound has the structure of Formula (V), or a pharmaceutically acceptable salt, pharmaceutically acceptable solvate, diastereomeric mixture, or individual enantiomers thereof:

Formula (V)

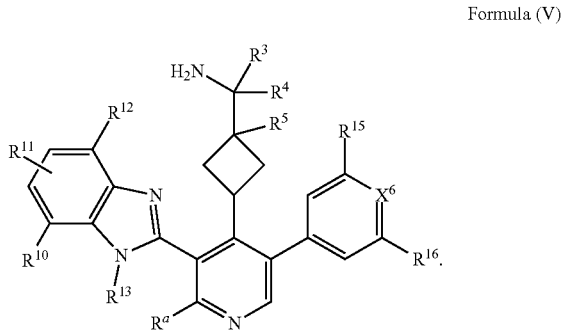

In some embodiments, R$^3$ and R$^4$ are independently H, —CH$_3$, or —CH$_2$CH$_3$; R$^5$ is H, —OH, or C$_1$-C$_4$alkyl; R$^a$ is H or —NR$^7$R$^8$; R$^7$ is H, C$_1$-C$_4$alkyl, C$_1$-C$_4$fluoroalkyl, C$_1$-C$_4$heteroalkyl, or C$_3$-C$_6$cycloalkyl; R$^8$ is H, C$_1$-C$_4$alkyl, C$_1$-C$_4$fluoroalkyl, C$_1$-C$_4$heteroalkyl, or C$_3$-C$_6$cycloalkyl.

In some embodiments, R$^7$ is H, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$), —C(CH$_3$)$_3$, —CH$_2$CH$_2$OH, —CH$_2$CH$_2$OCH$_3$, or —CH$_2$CN; R$^8$ is H, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$), —C(CH$_3$)$_3$, —CH$_2$CH$_2$OH, —CH$_2$CH$_2$OCH$_3$, —CH$_2$CN, or —CH$_2$CF$_3$.

In some embodiments, R$^8$ is H.

In some embodiments, R$^a$ is H; R$^3$ and R$^4$ are H; R$^5$ is H, —OH, or —CH$_3$.

In some embodiments, R$^{10}$, each R$^{11}$ and R$^{12}$ are each independently H, halogen, substituted or unsubstituted C$_1$-C$_4$alkyl, substituted or unsubstituted C$_1$-C$_4$alkenyl, substituted or unsubstituted C$_1$-C$_4$alkynyl, substituted or unsubstituted C$_1$-C$_4$fluoroalkyl, substituted or unsubstituted C$_1$-C$_6$heteroalkyl, substituted or unsubstituted phenyl, substituted or unsubstituted C$_3$-C$_6$cycloalkyl, substituted or unsubstituted monocyclic C$_3$-C$_5$heterocycloalkyl, substituted or unsubstituted monocyclic C$_1$-C$_5$heteroaryl, —CN, —OR$^{17}$, —CO$_2$R$^{17}$, —C(=O)N(R$^{17}$)$_2$, —N(R$^{17}$)$_2$, —NR$^{17}$C(=O)R$^{18}$, —C(R$^{17}$)=N—OR$^{17}$, —SR$^{17}$, —S(=O)R$^{17}$, —SO$_2$R$^{17}$, or —SO$_2$N(R$^{17}$)$_2$.

In some embodiments, when more than one R$^{11}$ is present then each R$^{11}$ is individually and independently selected from the recited list of groups.

In some embodiments, R$^{10}$ and R$^{12}$ are each independently H, halogen, substituted or unsubstituted C$_1$-C$_4$alkyl, substituted or unsubstituted C$_1$-C$_4$fluoroalkyl, substituted or unsubstituted C$_2$-C$_4$alkenyl, substituted or unsubstituted C$_2$-C$_4$alkynyl, substituted or unsubstituted C$_1$-C$_6$heteroalkyl, substituted or unsubstituted monocyclic C$_3$-C$_5$heterocycloalkyl, substituted or unsubstituted monocyclic C$_1$-C$_5$heteroaryl, —CN, —OR$^{17}$, —CO$_2$R$^{17}$, —C(=O)N(R$^{17}$)$_2$, —N(R$^{17}$)$_2$, —NR$^{17}$C(=O)R$^{17}$, —C(R$^{17}$)=N—OR$^{17}$, —SR$^{17}$, —S(=O)R$^{17}$, —SO$_2$R$^{17}$, or —SO$_2$N(R$^{17}$)$_2$.

In some embodiments, each R$^{11}$ is independently H, halogen, substituted or unsubstituted C$_1$-C$_4$alkyl, substituted or unsubstituted C$_1$-C$_4$fluoroalkyl, substituted or unsubstituted C$_2$-C$_4$alkenyl, substituted or unsubstituted C$_2$-C$_4$alkynyl, substituted or unsubstituted C$_1$-C$_6$heteroalkyl, —CN, —OH, —O-(substituted or unsubstituted C$_1$-C$_4$alkyl), or —O-(substituted or unsubstituted C$_1$-C$_4$fluoroalkyl).

In some embodiments, R$^{11}$ is H, halogen, substituted or unsubstituted C$_1$-C$_4$alkyl, substituted or unsubstituted C$_1$-C$_4$fluoroalkyl, substituted or unsubstituted C$_2$-C$_4$alkenyl, substituted or unsubstituted C$_2$-C$_4$alkynyl, substituted or unsubstituted C$_1$-C$_6$heteroalkyl, —CN, —OH, —O-(substituted or unsubstituted C$_1$-C$_4$alkyl), or —O-(substituted or unsubstituted C$_1$-C$_4$fluoroalkyl).

In some embodiments, R$^{10}$ and R$^{12}$ are each independently H, F, Cl, Br, —CH$_3$, —CH$_2$CH$_3$, —CH$_2$OH, —CH$_2$CH$_2$OH, —CH$_2$CN, —CH$_2$CO$_2$H, —CH$_2$CO$_2$CH$_3$, —CH$_2$CO$_2$CH$_2$CH$_3$, —CH$_2$C(=O)NH$_2$, —CH$_2$C(=O)NHCH$_3$, —CH$_2$C(=O)N(CH$_3$)$_2$, —CH$_2$NH$_2$, —CH$_2$NHCH$_3$, —CH$_2$N(CH$_3$)$_2$, —CH$_2$F, —CHF$_2$, —CF$_3$, —CH=CH$_2$, —C≡CH, —CN, —OH, -OCH$_3$, —OCH$_2$CH$_3$, —OCF$_3$, cyclopropyloxy, cyclobutyloxy, cyclopentyloxy, oxetanyloxy, tetrahydrofuranyloxy, tetrahydropyranyloxy, azetidinyl, pyrrolidinyl, tetrazolyl, —CN, —OH, —OCH$_3$, —OCH$_2$CH$_3$, —OCH$_2$CH$_2$OH, —OCH$_2$CN, —OCF$_3$, —CO$_2$H, —CO$_2$CH$_3$, —CO$_2$CH$_2$CH$_3$, —C(=O)NH$_2$, —C(=O)NHCH$_3$, —C(=O)N(CH$_3$)$_2$, —NH$_2$, —NHCH$_3$, —N(CH$_3$)$_2$, —NHC(=O)CH$_3$, —NCH$_3$C(=O)CH$_3$, —CH=N—OH, —CH=N—OCH$_3$, —SO$_2$CH$_3$, —SO$_2$NH$_2$, —SO$_2$NHCH$_3$, or —SO$_2$N(CH$_3$)$_2$; R$^{11}$ is H, F, Cl, Br, —CN, —CH$_3$, —CH$_2$CH$_3$, —CF$_3$, —CH=CH$_2$, —C≡CH, —CN, —OH, —OCH$_3$, —OCH$_2$CH$_3$, or —OCF$_3$.

In some embodiments, R$^{10}$ and R$^{12}$ are each independently H, F, Cl, —CH$_3$, —CF$_3$, —C≡CH, —CN, —OH, —OCH$_3$, —OCF$_3$, azetidinyl, pyrrolidinyl, —CN, —OH, —OCH$_3$, —OCH$_2$CH$_3$, —OCH$_2$CH$_2$OH, —OCH$_2$CN, —OCF$_3$, —CO$_2$H, —CO$_2$CH$_3$, —C(=O)NH$_2$, —C(=O)NHCH$_3$, —C(=O)N(CH$_3$)$_2$, —NH$_2$, —NHCH$_3$, —N(CH$_3$)$_2$, —NHC(=O)CH$_3$, —NCH$_3$C(=O)CH$_3$, —CH=N—OH, —CH=N—OCH$_3$, —SO$_2$CH$_3$, or —SO$_2$NH$_2$; is H, F, Cl, Br, —CN, —CH$_3$, —CF$_3$, —CN, —OH, —OCH$_3$, or —OCF$_3$.

In some embodiments, each R$^H$ is independently H, halogen, substituted or unsubstituted C$_1$-C$_4$alkyl, substituted or unsubstituted C$_1$-C$_4$fluoroalkyl, substituted or unsubstituted C$_1$-C$_4$heteroalkyl, —CN, —OH, —O-(substituted or unsubstituted C$_1$-C$_4$alkyl), or —O-(substituted or unsubstituted C$_1$-C$_4$fluoroalkyl); R$^{15}$ is H, halogen, substituted or unsubstituted C$_1$-C$_4$alkyl, substituted or unsubstituted C$_1$-C$_4$fluoroalkyl, substituted or unsubstituted C$_1$-C$_4$heteroalkyl, —CN, —OH, —O-(substituted or unsubstituted C$_1$-C$_4$alkyl), or —O-(substituted or unsubstituted C$_1$-C$_4$fluoroalkyl); R$^{16}$ is H, halogen, substituted or unsubstituted C$_1$-C$_4$alkyl, substituted or unsubstituted C$_1$-C$_4$fluoroalkyl, substituted or unsubstituted C$_1$-C$_4$heteroalkyl, substituted or unsubstituted phenyl, substituted or unsubstituted C$_3$-C$_6$cycloalkyl, substituted or unsubstituted monocyclic C$_3$-C$_5$heterocycloalkyl, substituted or unsubstituted monocyclic C$_1$-C$_5$heteroaryl, —CN, —OR$^{17}$, —CO$_2$R$^{17}$, —C(=O)N(R$^{17}$)$_2$, —N(R$^{17}$)$_2$, —NR$^{17}$C(=O)R$^{18}$, —NR$^{17}$C(=O)OR$^{18}$, —NR$^{17}$C(=O)N $(R^{17})_2$, $-C(R^{17})=N-OR^{17}$, $-SR^{17}$, $-S(=O)R^{17}$, $-SO_2R^{17}$, or $-SO_2N(R^{17})_2$.

In some embodiments, each $R^{14}$ is independently H, F, Cl, Br, $-CH_3$, $-CH_2CH_3$, $-CH_2CH_2CH_3$, $-CH(CH_3)_2$, $-CH_2CH_2CH_2CH_3$, $-CH_2CH(CH_3)_2$, $-CH(CH_3)(CH_2CH_3)$, $-C(CH_3)_3$, $-CH_2OH$, $-CH_2CN$, $-CH_2F$, $-CHF_2$, $-CF_3$, $-CN$, $-NH_2$, $-NHCH_3$, $-N(CH_3)_2$, $-OH$, $-OCH_3$, $-OCH_2CH_3$, $-OCH_2CN$, or $-OCF_3$; $R^{15}$ is H, F, Cl, Br, $-CH_3$, $-CH_2CH_3$, $-CH_2CH_2CH_3$, $-CH(CH_3)_2$, $-CH_2CH_2CH_2CH_3$, $-CH_2CH(CH_3)_2$, $-CH(CH_3)(CH_2CH_3)$, $-C(CH_3)_3$, $-CH_2OH$, $-CH_2CN$, $-CH_2F$, $-CHF_2$, $-CF_3$, $-CN$, $-NH_2$, $-NHCH_3$, $-N(CH_3)_2$, $-OH$, $-OCH_3$, $-OCH_2CH_3$, $-OCH_2CN$, or $-OCF_3$; $R^{16}$ is H, F, Cl, Br, $-CH_3$, $-CH_2CH_3$, $-CH_2CH_2CH_3$, $-CH(CH_3)_2$, $-CH_2CH_2CH_2CH_3$, $-CH_2CH(CH_3)_2$, $-CH(CH_3)(CH_2CH_3)$, $-C(CH_3)_3$, $-CH_2OH$, $-CH_2CN$, $-CH_2F$, $-CHF_2$, $-CF_3$, $-CN$, $-OH$, $-OCH_3$, $-OCH_2CH_3$, $-OCH_2CN$, $-OCF_3$, $-CO_2H$, $-CO_2CH_3$, $-CO_2CH_2CH_3$, $-CH_2CO_2H$, $-CH_2CO_2CH_3$, $-CH_2CO_2CH_2CH_3$, $-C(=O)NH_2$, $-C(=O)NHCH_3$, $-C(=O)N(CH_3)_2$, $-CH_2C(=O)NH_2$, $-CH_2C(=O)NHCH_3$, $-CH_2C(=O)N(CH_3)_2$, $-NH_2$, $-NHCH_3$, $-N(CH_3)_2$, $-CH_2NH_2$, $-CH_2NHCH_3$, $-CH_2N(CH_3)_2$.

In some embodiments, each $R^{14}$ is independently H, F, Cl, Br, $-CH_3$, $-CF_3$, $-CN$, $-OH$, $-OCH_3$, or $-OCF_3$; $R^{15}$ is H, F, Cl, Br, $-CH_3$, $-CF_3$, $-CN$, $-OH$, $-OCH_3$, or $-OCF_3$; $R^{16}$ is H, F, Cl, Br, $-CH_3$, $-CF_3$, $-CN$, $-OH$, $-OCH_3$, $-OCF_3$, or $-NH_2$.

In some embodiments, compounds described herein have the following structure:

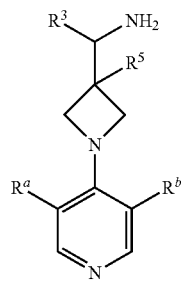

wherein,
$R^a$ is as described in Table 1;
$R^3$ is as described in Table 1;
$R^4$ is as described in Table 1; and
$R^b$ is as described in Table 1.

In some embodiments, compounds described herein have the following structure:

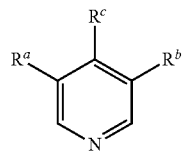

wherein,
$R^a$ is as described in Table 2;
$R^b$ is as described in Table 2; and
$R^c$ is as described in Table 2.

In some embodiments, compounds described herein have the following structure:

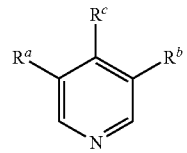

wherein,
$R^a$ is

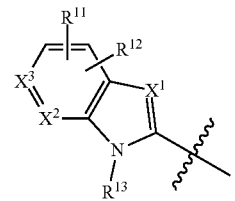

as described herein;
$R^b$ is

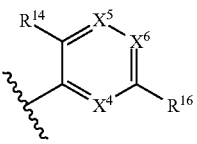

as described herein; and
$R^c$ is

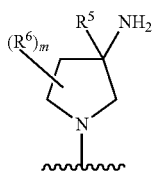

as described herein.

In some embodiments,

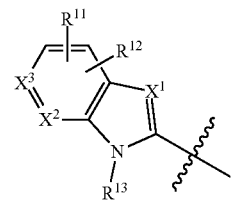

is $R^a$ as described in Table 1 or Table 2.

In some embodiments,
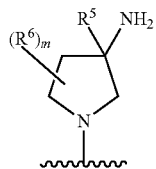
is $R^c$ as described in Table 2. In some embodiments,
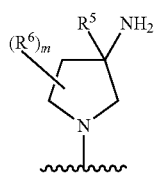
is
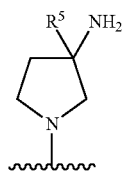
In some embodiments,
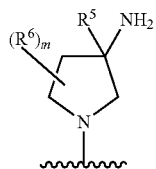
is
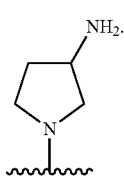
In some embodiments,
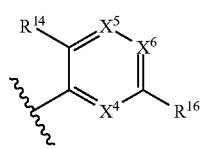
is $R^b$ as described in Table 1 or Table 2.
In some embodiments,
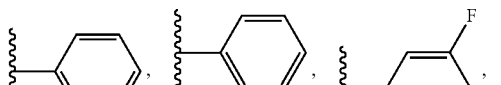
is
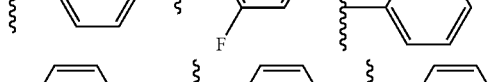
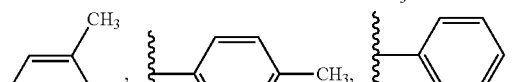
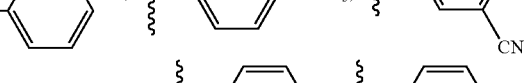
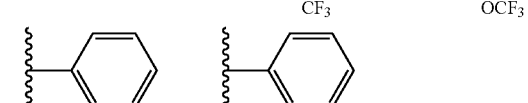
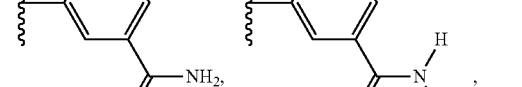
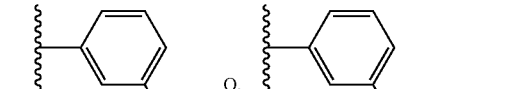
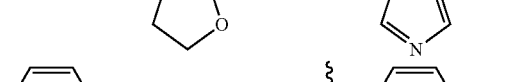
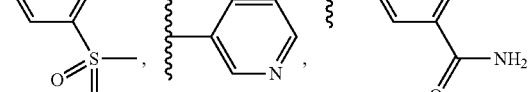

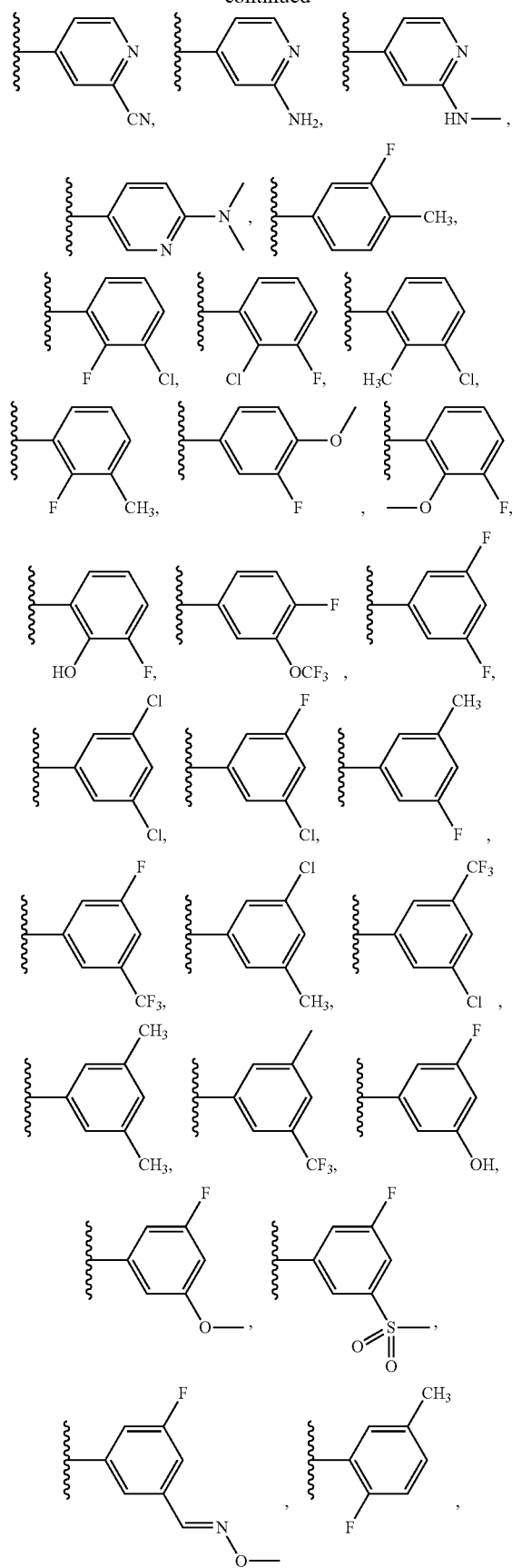
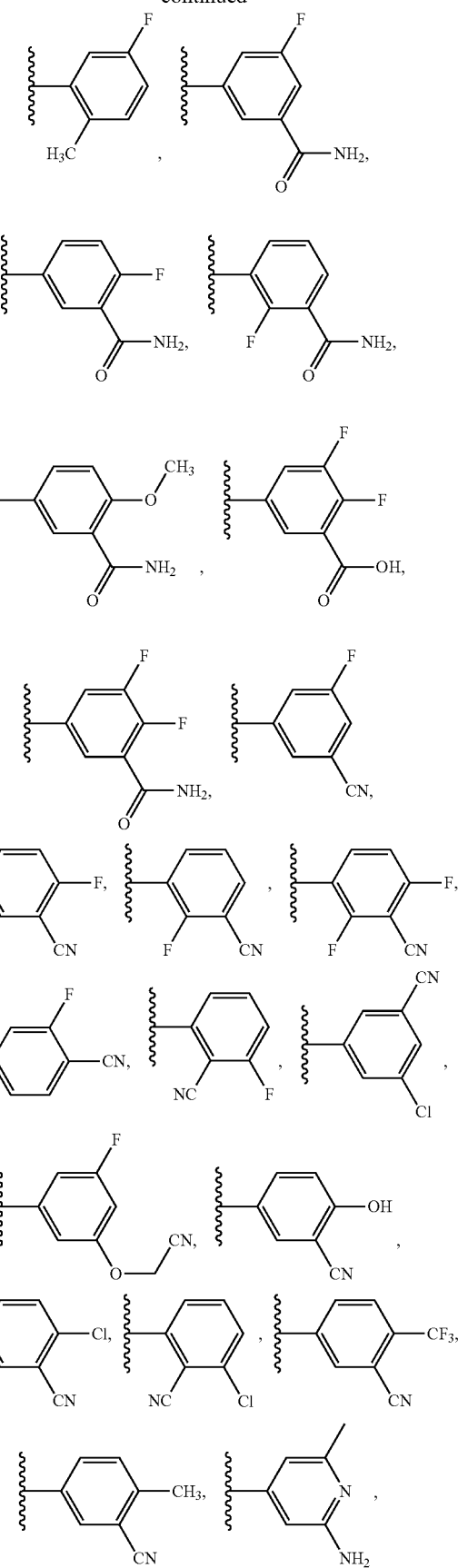

-continued
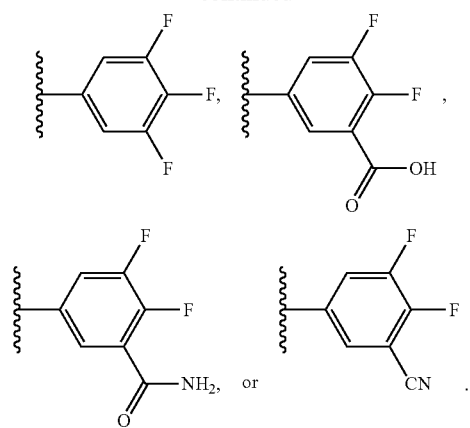
In some embodiments,
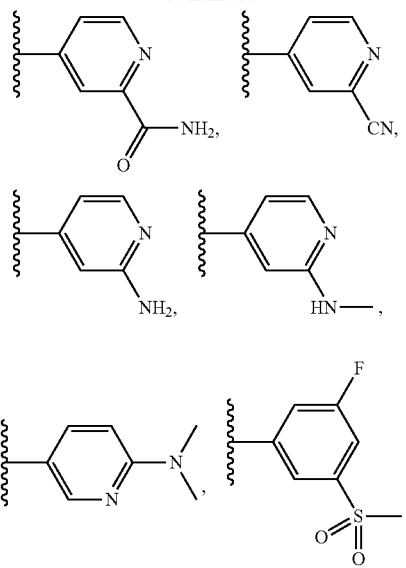
is
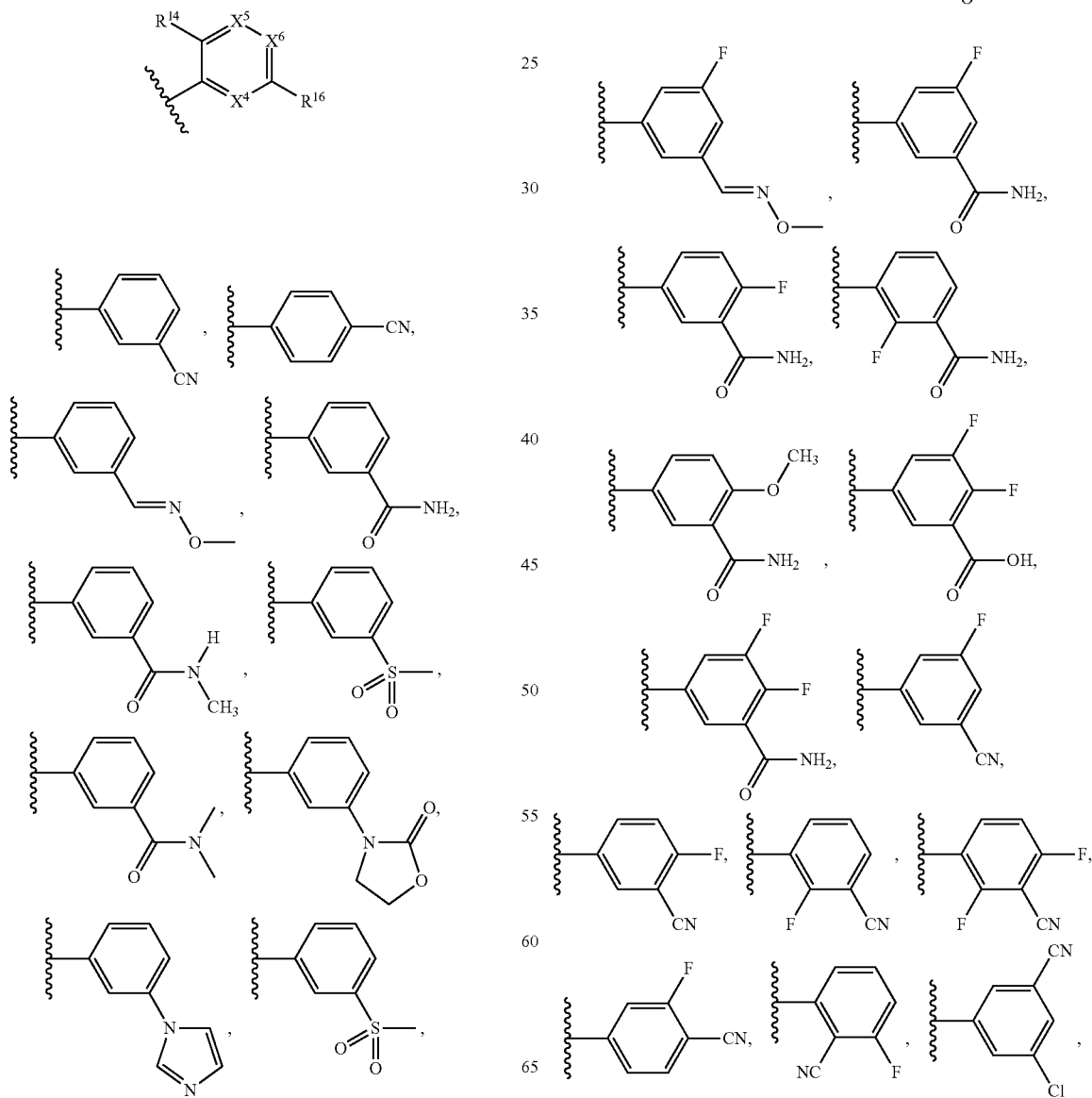

-continued

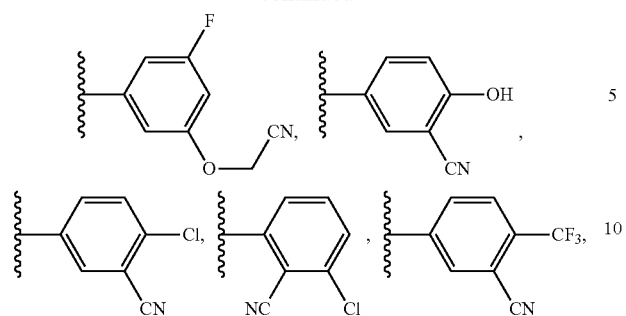

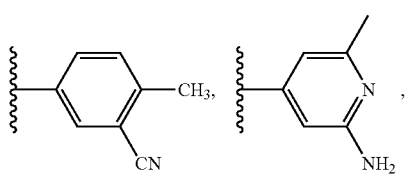

-continued

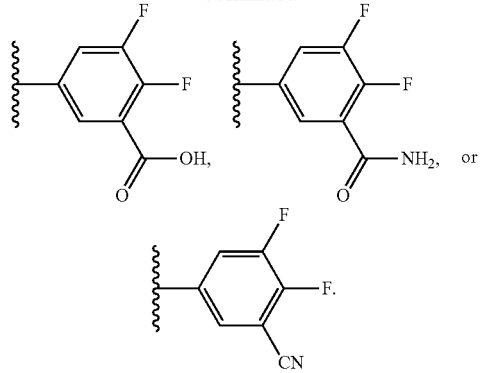

Any combination of the groups described above for the various variables is contemplated herein. Throughout the specification, groups and substituents thereof are chosen by one skilled in the field to provide stable moieties and compounds.

Exemplary compounds described herein include the compounds described in the following Tables:

TABLE 1

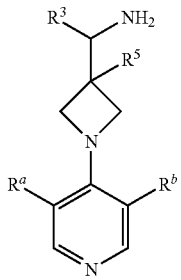

| Compound No. | $R^a$ | $R^3$ | $R^5$ | $R^b$ |
|---|---|---|---|---|
| 1-1 | 5-fluoro-1H-benzimidazol-2-yl | H | H | 3-methyl-5-fluorophenyl |
| 1-2 | 7-fluoro-1H-benzimidazol-2-yl | H | H | 3-methyl-5-fluorophenyl |
| 1-3 | 7-chloro-1H-benzimidazol-2-yl | H | H | 3-methyl-5-fluorophenyl |

TABLE 1-continued

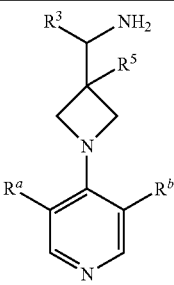

| Compound No. | R$^a$ | R$^3$ | R$^5$ | R$^b$ |
|---|---|---|---|---|
| 1-4 | 5-chloro-1H-benzimidazol-2-yl | H | H | 3-methyl-5-fluorophenyl |
| 1-5 | 4-cyano-1H-benzimidazol-2-yl | H | H | 3-methyl-5-fluorophenyl |
| 1-6 | 4,5-difluoro-1H-benzimidazol-2-yl | H | H | 3-methyl-5-fluorophenyl |
| 1-7 | 4,6-difluoro-1H-benzimidazol-2-yl (with methyl) | H | H | 3-methyl-5-fluorophenyl |
| 1-8 | 5-cyano-1H-benzimidazol-2-yl | H | H | 3-methyl-5-fluorophenyl |
| 1-9 | 4-methyl-1H-benzimidazol-2-yl | H | H | 3-methyl-5-fluorophenyl |
| 1-10 | 5-methyl-1H-benzimidazol-2-yl | H | H | 3-methyl-5-fluorophenyl |

TABLE 1-continued

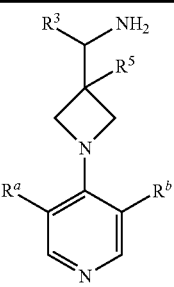

| Compound No. | $R^a$ | $R^3$ | $R^5$ | $R^b$ |
|---|---|---|---|---|
| 1-11 | 4-methoxy-1H-benzimidazol-2-yl | H | H | 3-fluoro-5-methylphenyl |
| 1-12 | 5-methoxy-1H-benzimidazol-2-yl | H | H | 3-fluoro-5-methylphenyl |
| 1-13 | 5,6-difluoro-1H-benzimidazol-2-yl | H | H | 3-fluoro-5-methylphenyl |
| 1-14 | 5-chloro-6-fluoro-1H-benzimidazol-2-yl | H | H | 3-fluoro-5-methylphenyl |
| 1-15 | 6-fluoro-4-methoxy-1H-benzimidazol-2-yl | H | H | 3-fluoro-5-methylphenyl |
| 1-16 | 4-fluoro-6-cyano-1H-benzimidazol-2-yl | H | H | 3-fluoro-5-methylphenyl |
| 1-17 | 5-fluoro-6-cyano-1H-benzimidazol-2-yl | H | H | 3-fluoro-5-methylphenyl |

TABLE 1-continued
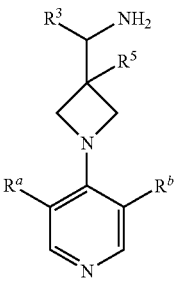
| Compound No. | R$^a$ | R$^3$ | R$^5$ | R$^b$ |
|---|---|---|---|---|
| 1-18 | 4-F, 6-Cl-benzimidazol-2-yl | H | H | 3-CH$_3$, 5-F-phenyl |
| 1-19 | 4,6-diF-benzimidazol-2-yl | H | H | 3,5-diCH$_3$-phenyl |
| 1-20 | 4,6-diF-benzimidazol-2-yl | H | H | 3-Cl, 5-CH$_3$-phenyl |
| 1-21 | 4,6-diF-benzimidazol-2-yl | H | H | 3,5-diF-phenyl |
| 1-22 | imidazo[4,5-c]pyridin-2-yl | H | H | 3-F, 5-CH$_3$-phenyl |
| 1-23 | imidazo[4,5-b]pyridin-2-yl | H | H | 3-F, 5-CH$_3$-phenyl |
| 1-24 | 4-F, 1-methyl-benzimidazol-2-yl | H | H | 3-F, 5-CH$_3$-phenyl |

TABLE 1-continued
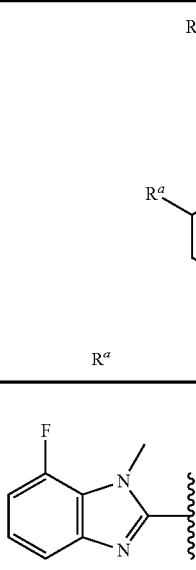
| Compound No. | $R^a$ | $R^3$ | $R^5$ | $R^b$ |
|---|---|---|---|---|
| 1-25 | 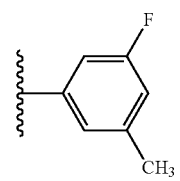 [SMILES: *c1cc(C)cc(F)c1] | H | H |  |
| 1-26 | 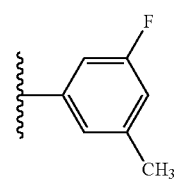 [SMILES: *c1cc(C)cc(F)c1] | H | OH | 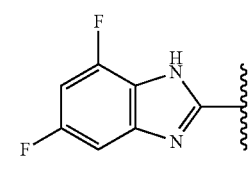 [SMILES: *c1nc2cc(F)cc(F)c2[nH]1] |
| 1-27 | 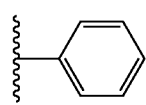 | H | H |  |
| 1-28 | 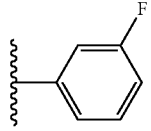 | H | H | 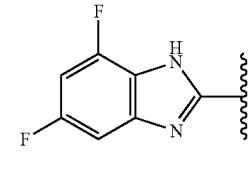 [SMILES: *c1nc2cc(F)cc(F)c2[nH]1] |
| 1-29 | 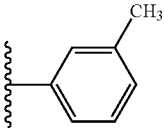 [SMILES: *c1cccc(C)c1] | H | H | 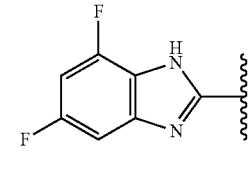 [SMILES: *c1nc2cc(F)cc(F)c2[nH]1] |
| 1-30 | 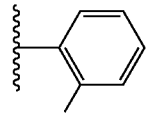 | H | H | 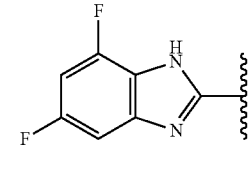 [SMILES: *c1nc2cc(F)cc(F)c2[nH]1] |
| 1-31 | 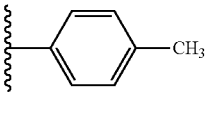 | H | H |  |

TABLE 1-continued

| Compound No. | R$^a$ | R$^3$ | R$^5$ | R$^b$ |
|---|---|---|---|---|
| 1-32 | 4,6-difluoro-1H-benzimidazol-2-yl | H | H | 5-methylpyridin-3-yl |
| 1-33 | 4,6-difluoro-1H-benzimidazol-2-yl | H | H | 3-methyl-5-(trifluoromethyl)phenyl |
| 1-34 | 4,6-difluoro-1H-benzimidazol-2-yl | H | H | 3-cyano-5-fluorophenyl |
| 1-35 | 4,6-difluoro-1H-benzimidazol-2-yl | H | H | 1H-indol-6-yl |
| 1-36 | 4,6-difluoro-1H-benzimidazol-2-yl | H | H | 1H-indol-7-yl |
| 1-37 | 4,7-difluoro-1H-benzimidazol-2-yl | H | H | 3-fluoro-5-methylphenyl |
| 1-38 | 4,6-difluoro-1H-benzimidazol-2-yl | H | H | 1-methyl-1H-pyrazol-5-yl |

TABLE 1-continued

| Compound No. | R$^a$ | R$^3$ | R$^5$ | R$^b$ |
|---|---|---|---|---|
| 1-39 | 4,6-difluoro-1H-benzimidazol-2-yl | H | H | 3-chloro-5-fluorophenyl |
| 1-40 | 4,6-difluoro-1H-benzimidazol-2-yl | H | H | 3-chloro-5-(trifluoromethyl)phenyl |
| 1-41 | 4,6-difluoro-1H-benzimidazol-2-yl | H | H | naphthalen-2-yl |
| 1-42 | 4,6-difluoro-1H-benzimidazol-2-yl | CH$_3$ | H | 3-fluoro-5-methylphenyl |
| 1-43 | 4,6-difluoro-1H-benzimidazol-2-yl | H | H | 4-fluorophenyl |
| 1-44 | 4,6-difluoro-1H-benzimidazol-2-yl | H | H | 2-fluorophenyl |
| 1-45 | 4,6-difluoro-1H-benzimidazol-2-yl | H | H | 4-fluoro-3-methylphenyl |

TABLE 1-continued

[Structure: azetidine with CH(R³)(NH₂)(R⁵) substituent at 3-position and pyridine (with Rᵃ and Rᵇ at 3,5-positions) at N1]

| Compound No. | Rᵃ | R³ | R⁵ | Rᵇ |
|---|---|---|---|---|
| 1-46 | 4,6-difluoro-1H-benzimidazol-2-yl | H | H | 5-fluoro-2-methylphenyl (with F and CH₃) |
| 1-47 | 4,6-difluoro-1H-benzimidazol-2-yl | H | H | 4-fluoro-3-methylphenyl |
| 1-48 | 4,6-difluoro-1H-benzimidazol-2-yl | H | H | 3,4,5-trifluorophenyl |
| 1-49 | 4,6-difluoro-1H-benzimidazol-2-yl | CH₂OH | H | 3-fluoro-5-methylphenyl |
| 1-50 | 4,6-difluoro-1H-benzimidazol-2-yl | H | CH₃ | 3-fluoro-5-methylphenyl |
| 1-51 | 4,6-difluoro-1H-benzimidazol-2-yl | CH₂CH₃ | H | 3-fluoro-5-methylphenyl |
| 1-52 | 4,6-difluoro-1H-benzimidazol-2-yl | H | H | naphthalen-1-yl |

TABLE 1-continued

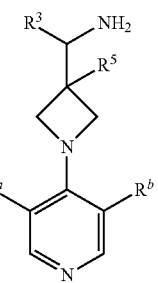

| Compound No. | $R^a$ | $R^3$ | $R^5$ | $R^b$ |
| --- | --- | --- | --- | --- |
| 1-53 | 4,6-difluoro-1H-benzimidazol-2-yl | H | H | 3-chlorophenyl |
| 1-54 | 4,6-difluoro-1H-benzimidazol-2-yl | H | H | 3-cyanophenyl |
| 1-55 | 4,6-difluoro-1H-benzimidazol-2-yl | H | H | 3-fluoro-4-methylphenyl |
| 1-56 | 1H-imidazol-2-yl | H | H | 3-fluoro-5-methylphenyl |
| 1-57 | 4,6-difluoro-1H-benzimidazol-2-yl | H | H | 2-fluoro-3-chlorophenyl |
| 1-58 | 4,6-difluoro-1H-benzimidazol-2-yl | H | H | 3-fluoro-5-methoxyphenyl |
| 1-59 | 4,6-difluoro-1H-benzimidazol-2-yl | H | H | 3-fluoro-5-chlorophenyl |

TABLE 1-continued

| Compound No. | $R^a$ | $R^3$ | $R^5$ | $R^b$ |
|---|---|---|---|---|
| 1-60 | 4,6-difluoro-1H-benzimidazol-2-yl | H | H | 3,5-dichlorophenyl |
| 1-61 | 4,6-difluoro-1H-benzimidazol-2-yl | CH₃ | H | 3-chloro-5-fluorophenyl |
| 1-62 | 4,6-difluoro-1H-benzimidazol-2-yl | H | F | 3-chloro-5-fluorophenyl |
| 1-63 | 4,6-difluoro-1H-benzimidazol-2-yl | CH₃ | H | 3-fluoro-5-(trifluoromethyl)phenyl |
| 1-64 | 4,6-difluoro-1H-benzimidazol-2-yl | CH₃ | H | 3-cyano-5-fluorophenyl |
| 1-65 | 4,6-difluoro-1H-benzimidazol-2-yl | CH₃ | H | 3-cyano-4-fluorophenyl |
| 1-66 | 4,6-difluoro-1H-benzimidazol-2-yl | H | H | 3-chloro-2-methylphenyl |

TABLE 1-continued
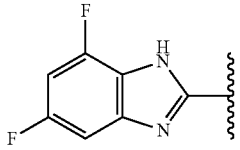 [SMILES: *c1nc2cc(F)cc(F)c2[nH]1]
| Compound No. | $R^a$ | $R^3$ | $R^5$ | $R^b$ |
|---|---|---|---|---|
| 1-67 | 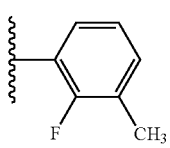 | H | H | 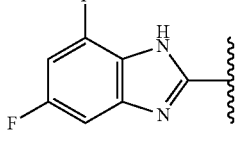 |
| 1-68 | 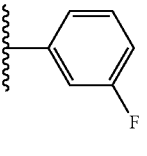 | CH$_3$ | CH$_3$ | 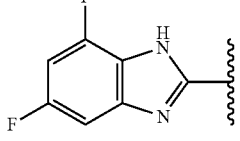 |
| 1-69 | 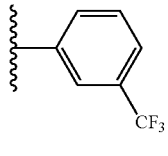 [SMILES: *c1cccc(C(F)(F)F)c1] | CH$_3$ | CH$_3$ | 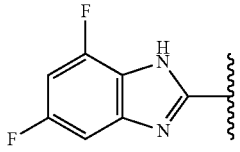 [SMILES: *c1nc2cc(F)cc(F)c2[nH]1] |
| 1-70 | 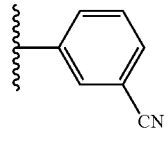 | CH$_3$ | CH$_3$ | 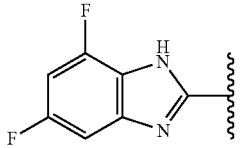 [SMILES: *c1nc2cc(F)cc(F)c2[nH]1] |
| 1-71 | 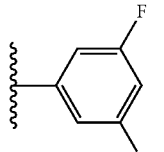 | CH$_3$ | H |  |
| 1-72 | 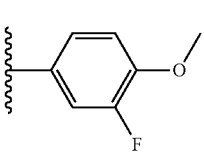 [SMILES: *c1ccc(OC)c(F)c1] | CH$_3$ | H | 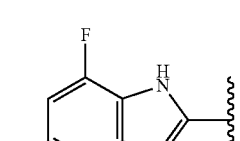 |
| 1-73 | 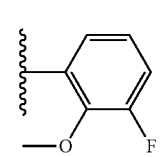 | CH$_3$ | H | |

TABLE 1-continued

| Compound No. | R$^a$ | R$^3$ | R$^5$ | R$^b$ |
|---|---|---|---|---|
| 1-74 | 4,6-difluoro-1H-benzimidazol-2-yl | CH$_3$ | H | 2-chloro-3-fluorophenyl |
| 1-75 | 4,6-difluoro-1H-benzimidazol-2-yl | CH$_3$ | H | 2-hydroxy-3-fluorophenyl |
| 1-76 | 4,6-difluoro-1H-benzimidazol-2-yl | CH$_3$ | H | 2-fluoro-3-methylphenyl |

Compounds in Table 1 are named:

1-1: 1-{1-[3-(5-fluoro-1H-1,3-benzodiazol-2-yl)-5-(3-fluoro-5-methylphenyl)pyridin-4-yl]azetidin-3-yl}methanamine;

1-2: 1-{1-[3-(4-fluoro-1H-1,3-benzodiazol-2-yl)-5-(3-fluoro-5-methylphenyl)pyridin-4-yl]azetidin-3-yl}methanamine;

1-3: 1-{1-[3-(4-chloro-1H-1,3-benzodiazol-2-yl)-5-(3-fluoro-5-methylphenyl)pyridin-4-yl]azetidin-3-yl}methanamine;

1-4: 1-{1-[3-(5-chloro-1H-1,3-benzodiazol-2-yl)-5-(3-fluoro-5-methylphenyl)pyridin-4-yl]azetidin-3-yl}methanamine;

1-5: 2-{4-[3-(aminomethyl)azetidin-1-yl]-5-(3-fluoro-5-methylphenyl)pyridin-3-yl}-1H-1,3-benzodiazole-4-carbonitrile;

1-6: 1-{1-[3-(4,5-difluoro-1H-1,3-benzodiazol-2-yl)-5-(3-fluoro-5-methylphenyl)pyridin-4-yl]azetidin-3-yl}methanamine;

1-7: 1-{1-[3-(4,6-difluoro-1H-1,3-benzodiazol-2-yl)-5-(3-fluoro-5-methylphenyl)pyridin-4-yl]azetidin-3-yl}methanamine;

1-8: 2-{4-[3-(aminomethyl)azetidin-1-yl]-5-(3-fluoro-5-methylphenyl)pyridin-3-yl}-1H-1,3-benzodiazole-5-carbonitrile;

1-9: 1-{1-[3-(3-fluoro-5-methylphenyl)-5-(4-methyl-1H-1,3-benzodiazol-2-yl)pyridin-4-yl]azetidin-3-yl}methanamine;

1-10: 1-{1-[3-(3-fluoro-5-methylphenyl)-5-(5-methyl-1H-1,3-benzodiazol-2-yl)pyridin-4-yl]azetidin-3-yl}methanamine;

1-11: 1-{1-[3-(3-fluoro-5-methylphenyl)-5-(4-methoxy-1H-1,3-benzodiazol-2-yl)pyridin-4-yl]azetidin-3-yl}methanamine;

1-12: 1-{1-[3-(3-fluoro-5-methylphenyl)-5-(5-methoxy-1H-1,3-benzodiazol-2-yl)pyridin-4-yl]azetidin-3-yl}methanamine;

1-13: 1-{1-[3-(5,6-difluoro-1H-1,3-benzodiazol-2-yl)-5-(3-fluoro-5-methylphenyl)pyridin-4-yl]azetidin-3-yl}methanamine;

1-14: 1-{1-[3-(5-chloro-6-fluoro-1H-1,3-benzodiazol-2-yl)-5-(3-fluoro-5-methylphenyl)pyridin-4-yl]azetidin-3-yl}methanamine;

1-15: 1-{1-[3-(6-fluoro-4-methoxy-1H-1,3-benzodiazol-2-yl)-5-(3-fluoro-5-methylphenyl)pyridin-4-yl]azetidin-3-yl}methanamine;

1-16: 2-{4-[3-(aminomethyl)azetidin-1-yl]-5-(3-fluoro-5-methylphenyl)pyridin-3-yl}-4-fluoro-1H-1,3-benzodiazole-6-carbonitrile;

1-17: 2-{4-[3-(aminomethyl)azetidin-1-yl]-5-(3-fluoro-5-methylphenyl)pyridin-3-yl}-6-fluoro-1H-1,3-benzodiazole-5-carbonitrile;

1-18: 1-{1-[3-(6-chloro-4-fluoro-1H-1,3-benzodiazol-2-yl)-5-(3-fluoro-5-methylphenyl)pyridin-4-yl]azetidin-3-yl}methanamine;

1-19: 1-{1-[3-(4,6-difluoro-1H-1,3-benzodiazol-2-yl)-5-(3,5-dimethylphenyl)pyridin-4-yl]azetidin-3-yl}methanamine;

1-20: 1-{1-[3-(3-chloro-5-methylphenyl)-5-(4,6-difluoro-1H-1,3-benzodiazol-2-yl)pyridin-4-yl]azetidin-3-yl}methanamine;

1-21: 1-{1-[3-(4,6-difluoro-1H-1,3-benzodiazol-2-yl)-5-(3,5-difluorophenyl)pyridin-4-yl]azetidin-3-yl}methanamine;

1-22: 1-{1-[3-(3-fluoro-5-methylphenyl)-5-{3H-imidazo[4,5-c]pyridin-2-yl}pyridin-4-yl]azetidin-3-yl}methanamine;

1-23: 1-{1-[3-(3-fluoro-5-methylphenyl)-5-{1H-imidazo[4,5-b]pyridin-2-yl}pyridin-4-yl]azetidin-3-yl}methanamine;

1-24: 1-{1-[3-(4-fluoro-1-methyl-1H-1,3-benzodiazol-2-yl)-5-(3-fluoro-5-methylphenyl)pyridin-4-yl]azetidin-3-yl}methanamine;

1-25: 1-{1-[3-(7-fluoro-1-methyl-1H-1,3-benzodiazol-2-yl)-5-(3-fluoro-5-methylphenyl)pyridin-4-yl]azetidin-3-yl}methanamine;

1-26: 3-(aminomethyl)-1-[3-(4,6-difluoro-1H-1,3-benzodiazol-2-yl)-5-(3-fluoro-5-methylphenyl)pyridin-4-yl]azetidin-3-ol;

1-27: 1-{1-[3-(4,6-difluoro-1H-1,3-benzodiazol-2-yl)-5-phenylpyridin-4-yl]azetidin-3-yl}methanamine;

1-28: 1-{1-[3-(4,6-difluoro-1H-1,3-benzodiazol-2-yl)-5-(3-fluorophenyl)pyridin-4-yl]azetidin-3-yl}methanamine;

1-29: 1-{1-[3-(4,6-difluoro-1H-1,3-benzodiazol-2-yl)-5-(3-methylphenyl)pyridin-4-yl]azetidin-3-yl}methanamine;

1-30: 1-{1-[3-(4,6-difluoro-1H-1,3-benzodiazol-2-yl)-5-(2-methylphenyl)pyridin-4-yl]azetidin-3-yl}methanamine;

1-31: 1-{1-[3-(4,6-difluoro-1H-1,3-benzodiazol-2-yl)-5-(4-methylphenyl)pyridin-4-yl]azetidin-3-yl}methanamine;

1-32: 1-{1-[5-(4,6-difluoro-1H-1,3-benzodiazol-2-yl)-5'-methyl-[3,3'-bipyridin]-4-yl]azetidin-3-yl}methanamine;

1-33: 1-{1-[3-(4,6-difluoro-1H-1,3-benzodiazol-2-yl)-5-[3-methyl-5-(trifluoromethyl)phenyl]pyridin-4-yl]azetidin-3-yl}methanamine;

1-34: 3-{4-[3-(aminomethyl)azetidin-1-yl]-5-(4,6-difluoro-1H-1,3-benzodiazol-2-yl)pyridin-3-yl}-5-fluorobenzonitrile;

1-35: 1-{1-[3-(4,6-difluoro-1H-1,3-benzodiazol-2-yl)-5-(1H-indol-6-yl)pyridin-4-yl]azetidin-3-yl}methanamine;

1-36: 1-{1-[3-(4,6-difluoro-1H-1,3-benzodiazol-2-yl)-5-(1H-indol-7-yl)pyridin-4-yl]azetidin-3-yl}methanamine;

1-37: 1-{1-[3-(4,7-difluoro-1H-1,3-benzodiazol-2-yl)-5-(3-fluoro-5-methylphenyl)pyridin-4-yl]azetidin-3-yl}methanamine;

1-38: 1-{1-[3-(4,6-difluoro-1H-1,3-benzodiazol-2-yl)-5-(1-methyl-1H-pyrazol-4-yl)pyridin-4-yl]azetidin-3-yl}methanamine;

1-39: 1-{1-[3-(3-chloro-5-fluorophenyl)-5-(4,6-difluoro-1H-1,3-benzodiazol-2-yl)pyridin-4-yl]azetidin-3-yl}methanamine;

1-40: 1-(1-{3-[3-chloro-5-(trifluoromethyl)phenyl]-5-(4,6-difluoro-1H-1,3-benzodiazol-2-yl)pyridin-4-yl}azetidin-3-yl)methanamine;

1-41: 1-{1-[3-(4,6-difluoro-1H-1,3-benzodiazol-2-yl)-5-(naphthalen-2-yl)pyridin-4-yl]azetidin-3-yl}methanamine;

1-42: 1-{1-[3-(4,6-difluoro-1H-1,3-benzodiazol-2-yl)-5-(3-fluoro-5-methylphenyl)pyridin-4-yl]azetidin-3-yl}ethan-1-amine;

1-43: 1-{1-[3-(4,6-difluoro-1H-1,3-benzodiazol-2-yl)-5-(4-fluorophenyl)pyridin-4-yl]azetidin-3-yl}methanamine;

1-44: 1-{1-[3-(4,6-difluoro-1H-1,3-benzodiazol-2-yl)-5-(2-fluorophenyl)pyridin-4-yl]azetidin-3-yl}methanamine;

1-45: 1-{1-[3-(4,6-difluoro-1H-1,3-benzodiazol-2-yl)-5-(2-fluoro-5-methylphenyl)pyridin-4-yl]azetidin-3-yl}methanamine;

1-46: 1-{1-[3-(4,6-difluoro-1H-1,3-benzodiazol-2-yl)-5-(5-fluoro-2-methylphenyl)pyridin-4-yl]azetidin-3-yl}methanamine;

1-47: 1-{1-[3-(4,6-difluoro-1H-1,3-benzodiazol-2-yl)-5-(4-fluoro-3-methylphenyl)pyridin-4-yl]azetidin-3-yl}methanamine;

1-48: 1-{1-[3-(4,6-difluoro-1H-1,3-benzodiazol-2-yl)-5-(3,4,5-trifluorophenyl)pyridin-4-yl]azetidin-3-yl}methanamine;

1-49: 2-amino-2-{1-[3-(4,6-difluoro-1H-1,3-benzodiazol-2-yl)-5-(3-fluoro-5-methylphenyl)pyridin-4-yl]azetidin-3-yl}ethan-1-ol;

1-50: 1-{1-[3-(4,6-difluoro-1H-1,3-benzodiazol-2-yl)-5-(3-fluoro-5-methylphenyl)pyridin-4-yl]-3-methylazetidin-3-yl}methanamine;

1-51: 1-{1-[3-(4,6-difluoro-1H-1,3-benzodiazol-2-yl)-5-(3-fluoro-5-methylphenyl)pyridin-4-yl]azetidin-3-yl}propan-1-amine;

1-52: 1-{1-[3-(4,6-difluoro-1H-1,3-benzodiazol-2-yl)-5-(naphthalen-1-yl)pyridin-4-yl]azetidin-3-yl}methanamine;

1-53: 1-{1-[3-(3-chlorophenyl)-5-(4,6-difluoro-1H-1,3-benzodiazol-2-yl)pyridin-4-yl]azetidin-3-yl}methanamine;

1-54: 3-{4-[3-(aminomethyl)azetidin-1-yl]-5-(4,6-difluoro-1H-1,3-benzodiazol-2-yl)pyridin-3-yl}benzonitrile;

1-55: 1-{1-[3-(4,6-difluoro-1H-1,3-benzodiazol-2-yl)-5-(3-fluoro-4-methylphenyl)pyridin-4-yl]azetidin-3-yl}methanamine;

1-56: 1-{1-[3-(3-fluoro-5-methylphenyl)-5-(1H-imidazol-2-yl)pyridin-4-yl]azetidin-3-yl}methanamine;

1-57: 1-{1-[3-(3-chloro-2-fluorophenyl)-5-(4,6-difluoro-1H-1,3-benzodiazol-2-yl)pyridin-4-yl]azetidin-3-yl}methanamine 1-58: 1-{1-[3-(4,6-difluoro-1H-1,3-benzodiazol-2-yl)-5-(3-fluoro-5-methoxyphenyl)pyridin-4-yl]azetidin-3-yl}methanamine;

1-59: 1-{1-[3-(3-chloro-5-methoxyphenyl)-5-(4,6-difluoro-1H-1,3-benzodiazol-2-yl)pyridin-4-yl]azetidin-3-yl}methanamine;

1-60: 1-{1-[3-(3,5-dichlorophenyl)-5-(4,6-difluoro-1H-1,3-benzodiazol-2-yl)pyridin-4-yl]azetidin-3-yl}methanamine;

1-61: 1-{1-[3-(3-chloro-5-fluorophenyl)-5-(4,6-difluoro-1H-1,3-benzodiazol-2-yl)pyridin-4-yl]azetidin-3-yl}ethan-1-amine;

1-62: 1-{1-[3-(3-chloro-5-fluorophenyl)-5-(4,6-difluoro-1H-1,3-benzodiazol-2-yl)pyridin-4-yl]-3-fluoroazetidin-3-yl}methanamine;

1-63: 1-{1-[3-(4,6-difluoro-1H-1,3-benzodiazol-2-yl)-5-[3-fluoro-5-(trifluoromethyl)phenyl]pyridin-4-yl]azetidin-3-yl}ethan-1-amine;

1-64: 3-{4-[3-(1-aminoethyl)azetidin-1-yl]-5-(4,6-difluoro-1H-1,3-benzodiazol-2-yl)pyridin-3-yl}-5-fluorobenzonitrile;

1-65: 5-{4-[3-(1-aminoethyl)azetidin-1-yl]-5-(4,6-difluoro-1H-1,3-benzodiazol-2-yl)pyridin-3-yl}-2-fluorobenzonitrile;

1-66: 1-{1-[3-(3-chloro-2-methylphenyl)-5-(4,6-difluoro-1H-1,3-benzodiazol-2-yl)pyridin-4-yl]azetidin-3-yl}methanamine;

1-67: 1-{1-[3-(4,6-difluoro-1H-1,3-benzodiazol-2-yl)-5-(2-fluoro-3-methylphenyl)pyridin-4-yl]azetidin-3-yl}methanamine;

1-68: 1-{1-[3-(4,6-difluoro-1H-1,3-benzodiazol-2-yl)-5-(3-fluorophenyl)pyridin-4-yl]-3-methylazetidin-3-yl}ethan-1-amine;

1-69: 1-{1-[3-(4,6-difluoro-1H-1,3-benzodiazol-2-yl)-5-[3-(trifluoromethyl)phenyl]pyridin-4-yl]-3-methylazetidin-3-yl}ethan-1-amine;

1-70: 3-{4-[3-(1-aminoethyl)-3-methylazetidin-1-yl]-5-(4,6-difluoro-1H-1,3-benzodiazol-2-yl)pyridin-3-yl}benzonitrile;

1-71: 1-{1-[3-(4,6-difluoro-1H-1,3-benzodiazol-2-yl)-5-[3-fluoro-5-(trifluoromethyl)phenyl]pyridin-4-yl]azetidin-3-yl}ethan-1-amine;

1-72: 1-{1-[3-(4,6-difluoro-1H-1,3-benzodiazol-2-yl)-5-(4-ethoxy-3-fluorophenyl)pyridin-4-yl]azetidin-3-yl}ethan-1-amine;

1-73: 1-{1-[3-(4,6-difluoro-1H-1,3-benzodiazol-2-yl)-5-(3-fluoro-2-methoxyphenyl)pyridin-4-yl]azetidin-3-yl}ethan-1-amine;

1-74: 1-{1-[3-(2-chloro-3-fluorophenyl)-5-(4,6-difluoro-1H-1,3-benzodiazol-2-yl)pyridin-4-yl]azetidin-3-yl}ethan-1-amine;

1-75: 2-{4-[3-(1-aminoethyl)azetidin-1-yl]-5-(4,6-difluoro-1H-1,3-benzodiazol-2-yl)pyridin-3-yl}-6-fluorophenol;

1-76: 1-{1-[3-(4,6-difluoro-1H-1,3-benzodiazol-2-yl)-5-(2-fluoro-3-methylphenyl)pyridin-4-yl]azetidin-3-yl}ethan-1-amine.

In some embodiments, provided herein is a pharmaceutically acceptable salt of a compound that is described in Table 1.

TABLE 2

| Compound No. | $R^a$ | $R^c$ | $R^b$ |
|---|---|---|---|
| 2-1 | 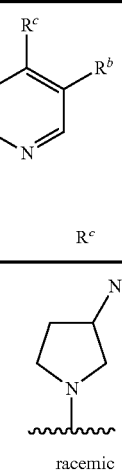 | 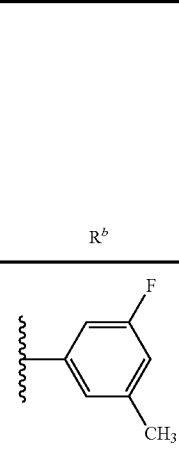 racemic | 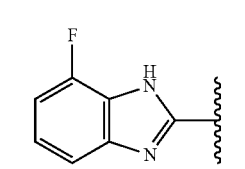 [SMILES: *c1nc2cccc(F)c2[nH]1] |
| 2-2 | 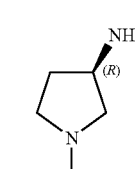 | 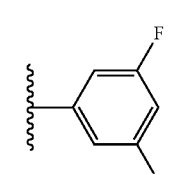 | 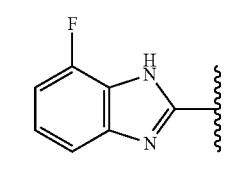 [SMILES: *c1nc2cccc(F)c2[nH]1] |
| 2-3 | 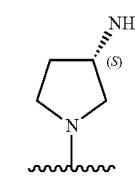 | 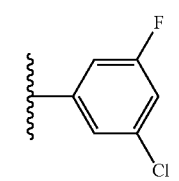 [SMILES: *c1cc(F)cc(Cl)c1] | 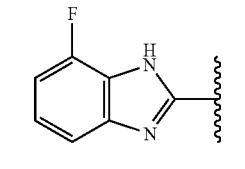 [SMILES: *c1nc2cccc(F)c2[nH]1] |
| 2-4 | 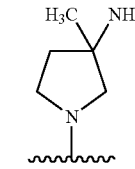 |  racemic | 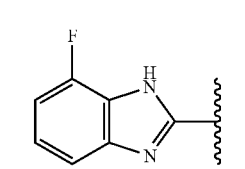 [SMILES: *c1nc2cccc(F)c2[nH]1] |
| 2-5 | 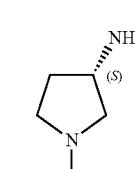 | 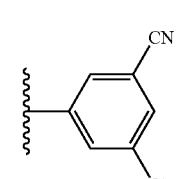 |  |

TABLE 2-continued

| Compound No. | R$^a$ | R$^c$ | R$^b$ |
|---|---|---|---|
| 2-6 | 4-fluoro-1H-benzimidazol-2-yl | 3-amino-3-methylpyrrolidin-1-yl (racemic) | 3-cyano-5-fluorophenyl |
| 2-7 | 4-fluoro-1H-benzimidazol-2-yl | (S)-3-aminopyrrolidin-1-yl | 3-cyanophenyl |
| 2-8 | 4-fluoro-1H-benzimidazol-2-yl | (S)-3-aminopyrrolidin-1-yl | 3-cyano-5-fluorophenyl |
| 2-9 | 4-fluoro-1H-benzimidazol-2-yl | (S)-3-aminopyrrolidin-1-yl | 3-fluoro-5-((methoxyimino)methyl)phenyl |
| 2-10 | 4-fluoro-1H-benzimidazol-2-yl | 3-amino-3-methylpyrrolidin-1-yl (racemic) | 3-(trifluoromethoxy)phenyl |
| 2-11 | 4-fluoro-1H-benzimidazol-2-yl | 3-amino-3-methylpyrrolidin-1-yl (racemic) | 3-methoxyphenyl |
| 2-12 | 4-fluoro-1H-benzimidazol-2-yl | (S)-3-aminopyrrolidin-1-yl | 3-((methoxyimino)methyl)phenyl |

TABLE 2-continued
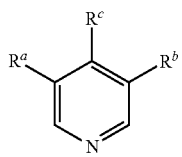
| Compound No. | $R^a$ | $R^c$ | $R^b$ |
|---|---|---|---|
| 2-13 | 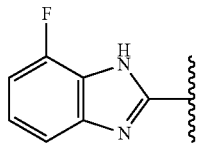 [SMILES: *c1nc2cccc(F)c2[nH]1] | 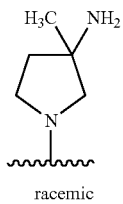 racemic | 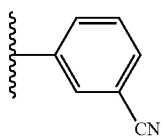 |
| 2-14 | 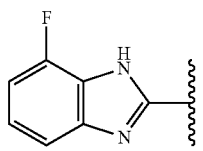 [SMILES: *c1nc2cccc(F)c2[nH]1] | 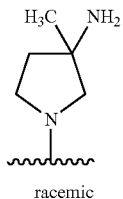 racemic | 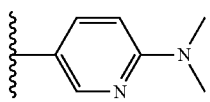 |
| 2-15 | 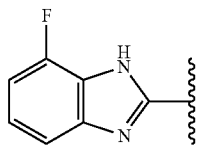 [SMILES: *c1nc2cccc(F)c2[nH]1] | 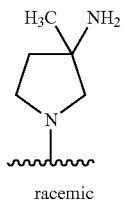 racemic | 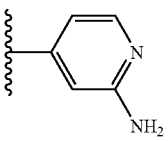 |
| 2-16 | 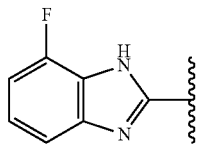 [SMILES: *c1nc2cccc(F)c2[nH]1] | 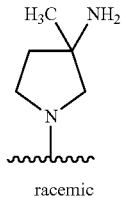 racemic | 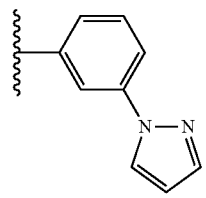 [SMILES: *c1cccc(-n2cccn2)c1] |
| 2-17 | 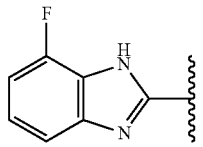 | 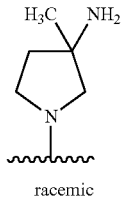 racemic | 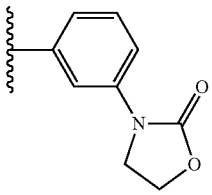 [SMILES: *c1cccc(N2CCOC2=O)c1] |
| 2-18 | 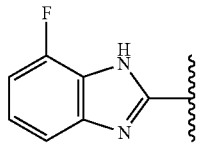 [SMILES: *c1nc2cccc(F)c2[nH]1] | 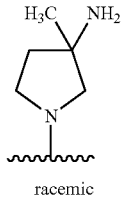 racemic | 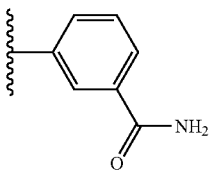 [SMILES: *c1cccc(C(N)=O)c1] |

TABLE 2-continued

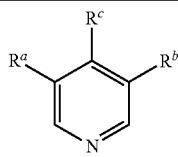

| Compound No. | $R^a$ | $R^c$ | $R^b$ |
|---|---|---|---|
| 2-19 | 7-fluoro-1H-benzimidazol-2-yl | 3-amino-3-methylpyrrolidin-1-yl (racemic) | 3-(N-methylcarbamoyl)phenyl |
| 2-20 | 7-fluoro-1H-benzimidazol-2-yl | 3-amino-3-methylpyrrolidin-1-yl (racemic) | 3-carbamoyl-5-fluorophenyl |
| 2-21 | 7-fluoro-1H-benzimidazol-2-yl | 3-amino-3-methylpyrrolidin-1-yl (racemic) | 3-(methylsulfonyl)phenyl |
| 2-22 | 7-fluoro-1H-benzimidazol-2-yl | 3-amino-3-methylpyrrolidin-1-yl (racemic) | 2,3-dihydrobenzofuran-6-yl |
| 2-23 | 7-fluoro-1H-benzimidazol-2-yl | (S)-3-aminopyrrolidin-1-yl | 3-cyano-4-fluorophenyl |
| 2-24 | 7-fluoro-1H-benzimidazol-2-yl | (S)-3-aminopyrrolidin-1-yl | 3-cyano-2-fluorophenyl |
| 2-25 | 7-fluoro-1H-benzimidazol-2-yl | (S)-3-aminopyrrolidin-1-yl | 3-fluoro-5-hydroxyphenyl |

TABLE 2-continued
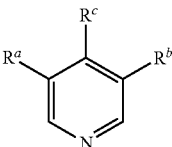
| Compound No. | $R^a$ | $R^c$ | $R^b$ |
|---|---|---|---|
| 2-26 | 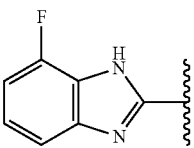 [SMILES: *c1nc2cccc(F)c2[nH]1] | 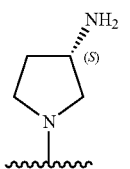<br>(S) | 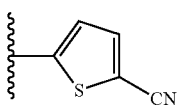 [SMILES: *c1ccc(C#N)s1] |
| 2-27 | 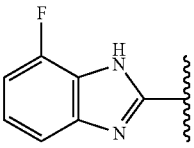 | 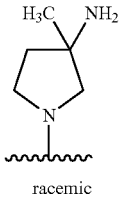<br>racemic | 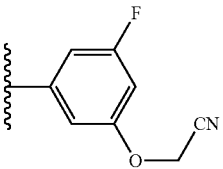 [SMILES: *c1cc(F)cc(OCC#N)c1] |
| 2-28 | 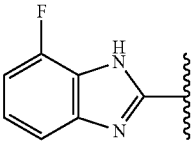 [SMILES: *c1nc2cccc(F)c2[nH]1] | 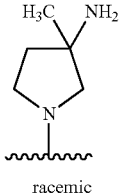<br>racemic | 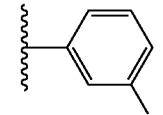 |
| 2-29 | 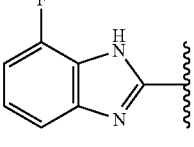 | 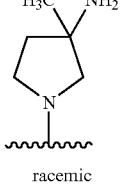<br>racemic | 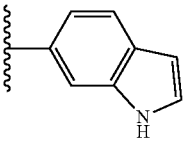 [SMILES: *c1ccc2cc[nH]c2c1] |
| 2-30 | 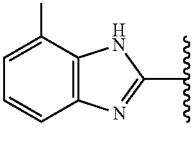 | 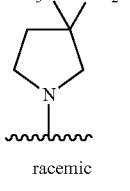<br>racemic | 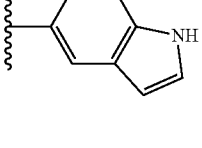 |
| 2-31 | 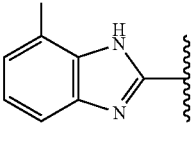 | 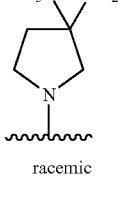<br>racemic | 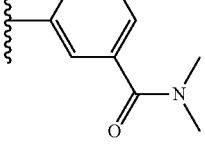 |
| 2-32 | 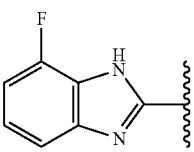 | 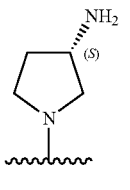<br>(S) | 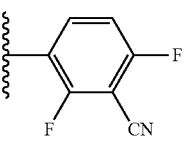 [SMILES: *c1ccc(F)c(C#N)c1F] |

TABLE 2-continued
| Compound No. | $R^a$ | $R^c$ | $R^b$ |
|---|---|---|---|
| 2-33 | 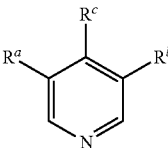 | 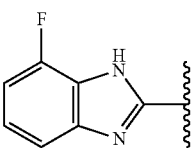 [SMILES: *c1nc2cccc(F)c2[nH]1]<br>mixture of cis and trans isomers | 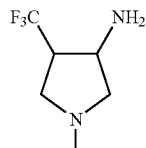 |
| 2-34 | 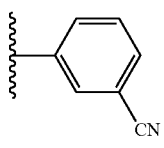 [SMILES: *c1cccc(C#N)c1] | 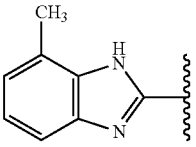 | 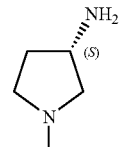 |
| 2-35 | 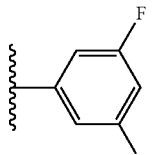 | 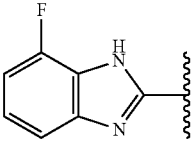 [SMILES: *c1nc2cccc(F)c2[nH]1] | 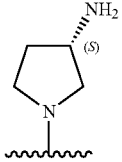 |
| 2-36 | 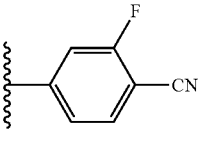 [SMILES: *c1ccc(C#N)c(F)c1] | 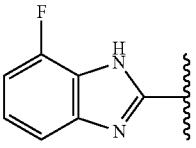 [SMILES: *c1nc2cccc(F)c2[nH]1] | 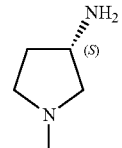 |
| 2-37 | 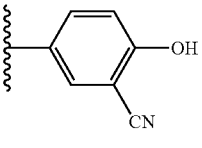 [SMILES: *c1ccc(O)c(C#N)c1] | 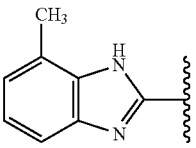 | 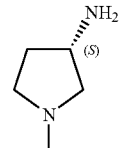 |
| 2-38 | 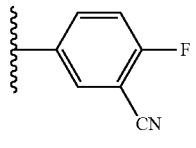 [SMILES: *c1ccc(F)c(C#N)c1] | 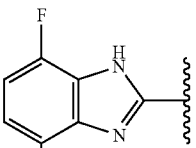 | 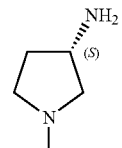 |
| 2-39 | 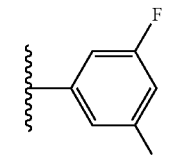 | 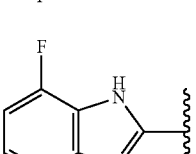 | 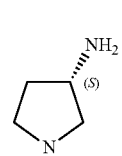 |

TABLE 2-continued

| Compound No. | $R^a$ | $R^c$ | $R^b$ |
|---|---|---|---|
| 2-40 | 4,7-difluoro-1H-benzimidazol-2-yl | (S)-3-aminopyrrolidin-1-yl | 2-cyano-3-fluorophenyl |
| 2-41 | 4,5,6,7-tetrafluoro-1H-benzimidazol-2-yl | (S)-3-aminopyrrolidin-1-yl | 3-cyanophenyl |
| 2-42 | 4-fluoro-1H-benzimidazol-2-yl | (S)-3-aminopyrrolidin-1-yl | 4-cyanophenyl |
| 2-43 | 4,7-difluoro-1H-benzimidazol-2-yl | (S)-3-aminopyrrolidin-1-yl | 3-carbamoylphenyl |
| 2-44 | 4,7-difluoro-1H-benzimidazol-2-yl | (S)-3-aminopyrrolidin-1-yl | 3-cyano-4-fluorophenyl |
| 2-45 | 4-fluoro-1H-benzimidazol-2-yl | trans, racemic 3-amino-4-methoxypyrrolidin-1-yl | 3-cyanophenyl |
| 2-46 | 4-fluoro-1H-benzimidazol-2-yl | cis, racemic 3-amino-4-methoxypyrrolidin-1-yl | 3-cyanophenyl |

TABLE 2-continued
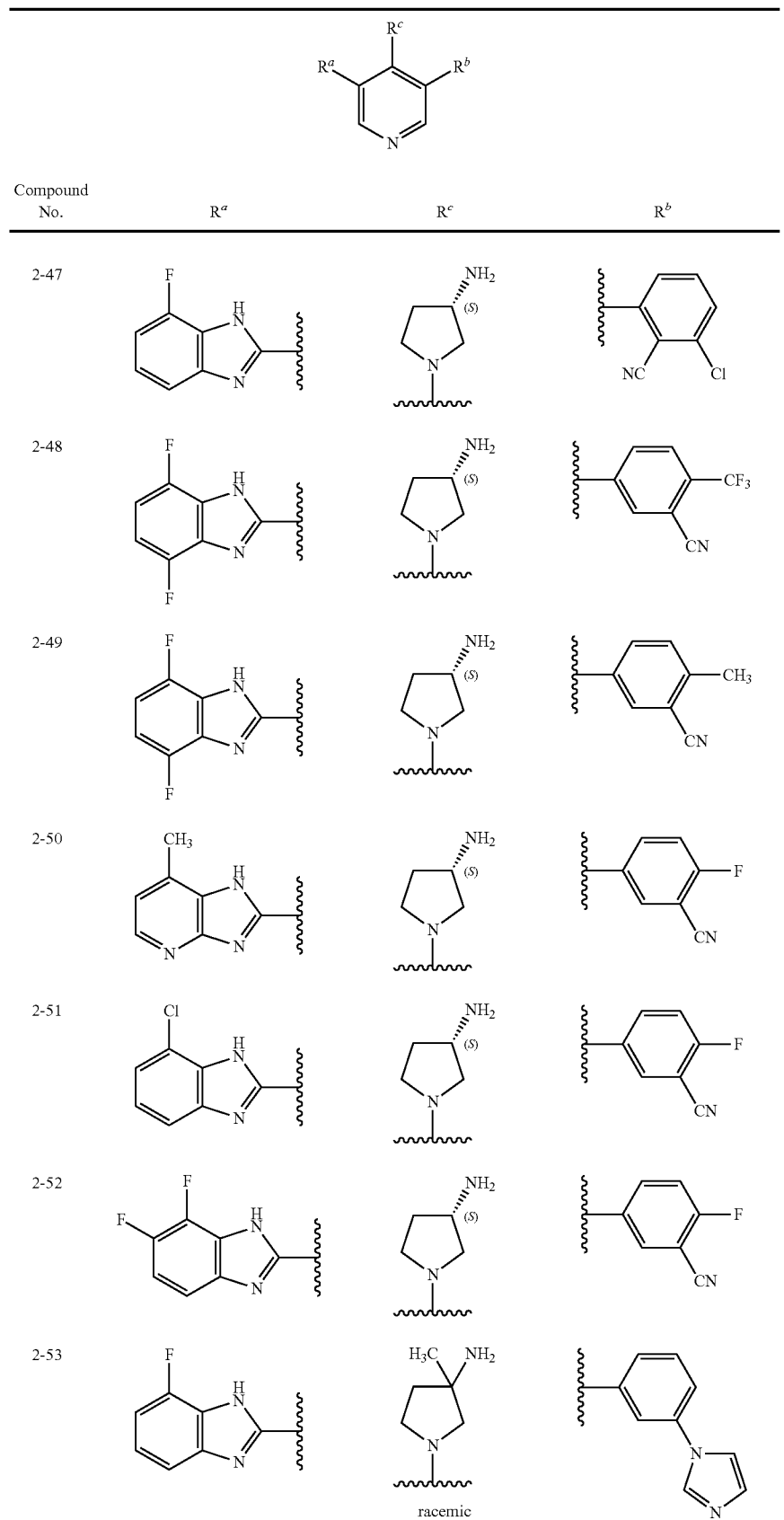

TABLE 2-continued
| Compound No. | R$^a$ | R$^c$ | R$^b$ |
|---|---|---|---|
| 2-54 | 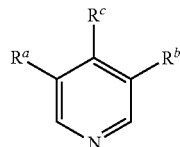 | 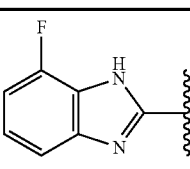 | 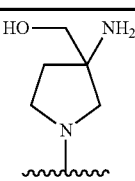 |
| 2-55 | 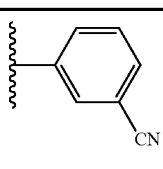 | 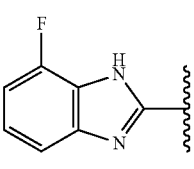 [SMILES: *c1nc2cccc(F)c2[nH]1] trans, racemic | 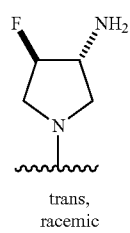 |
| 2-56 | 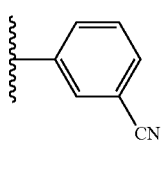 | 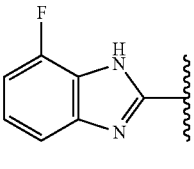 [SMILES: *c1nc2cccc(F)c2[nH]1] trans, racemic | 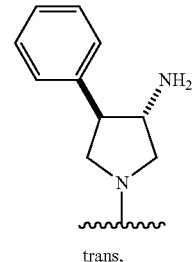 |
| 2-57 | 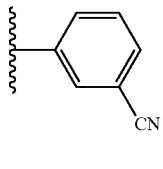 [SMILES: *c1cccc(C#N)c1] | 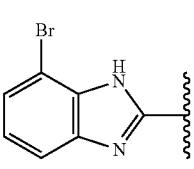 | 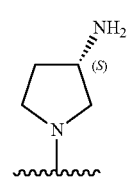 |
| 2-58 | 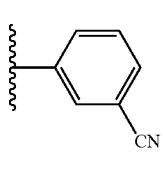 | 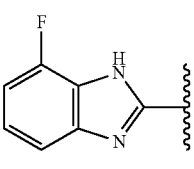 [SMILES: *c1nc2cccc(F)c2[nH]1] | 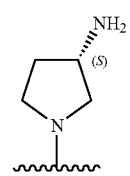 |
| 2-59 | 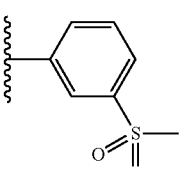 | 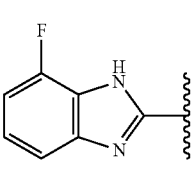 | 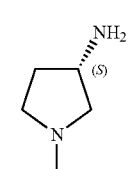 |
| 2-60 | 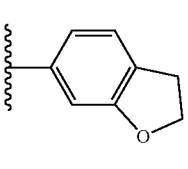 [SMILES: *c1ccc2c(c1)OCC2] | 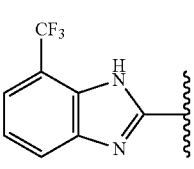 | 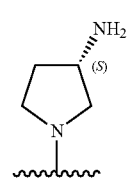 |

TABLE 2-continued

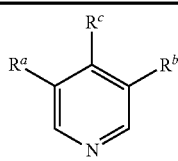

| Compound No. | $R^a$ | $R^c$ | $R^b$ |
|---|---|---|---|
| 2-61 | 4,7-difluoro-1H-benzimidazol-2-yl | (S)-3-aminopyrrolidin-1-yl | 3-carbamoyl-4-fluorophenyl |
| 2-62 | 4-chloro-1H-benzimidazol-2-yl | (S)-3-aminopyrrolidin-1-yl | 3-cyano-4-fluorophenyl |
| 2-63 | 4-fluoro-7-methyl-1H-benzimidazol-2-yl | (S)-3-aminopyrrolidin-1-yl | 3-cyano-5-fluorophenyl |
| 2-64 | 4-fluoro-1H-benzimidazol-2-yl | 3-amino-3-(trifluoromethyl)pyrrolidin-1-yl, racemic | 3-carbamoylphenyl |
| 2-65 | 4-methyl-1H-benzimidazol-2-yl | (S)-3-aminopyrrolidin-1-yl | 3-carbamoyl-5-fluorophenyl |
| 2-66 | 4-fluoro-1H-benzimidazol-2-yl | (2R,4S)-4-amino-2-(hydroxymethyl)pyrrolidin-1-yl | 3-cyano-5-fluorophenyl |
| 2-76 | 4-fluoro-1H-benzimidazol-2-yl | (S)-3-aminopyrrolidin-1-yl | 2-(methylamino)pyridin-4-yl |

TABLE 2-continued
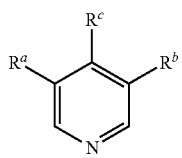
| Compound No. | $R^a$ | $R^c$ | $R^b$ |
|---|---|---|---|
| 2-68 | 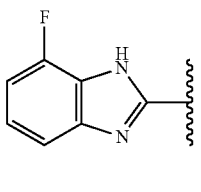 [SMILES: *c1nc2cccc(F)c2[nH]1] | 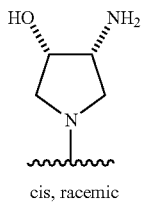 [SMILES: *N1C[C@@H](N)[C@@H](O)C1]<br>cis, racemic | 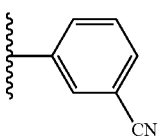 [SMILES: *c1cccc(C#N)c1] |
| 2-69 | 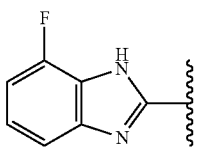 [SMILES: *c1nc2cccc(F)c2[nH]1] | 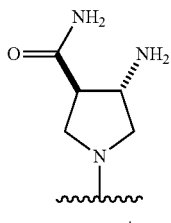<br>trans, racemic | 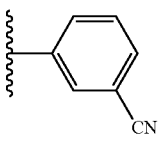 [SMILES: *c1cccc(C#N)c1] |
| 2-70 | 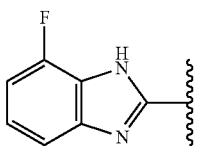 [SMILES: *c1nc2cccc(F)c2[nH]1] | 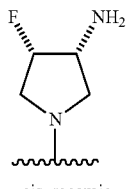<br>cis, racemic | 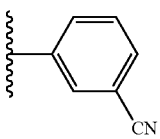 |
| 2-71 | 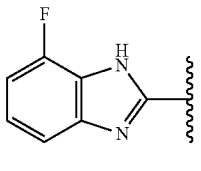 [SMILES: *c1nc2cccc(F)c2[nH]1] | 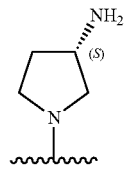 | 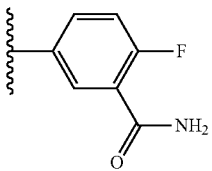 |
| 2-72 | 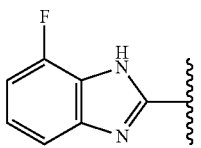 [SMILES: *c1nc2cccc(F)c2[nH]1] | 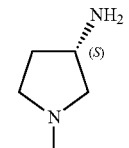 | 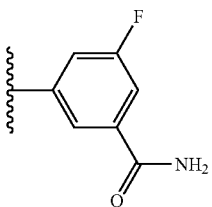 [SMILES: *c1cc(F)cc(C(N)=O)c1] |
| 2-73 | 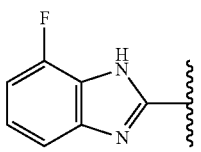 | 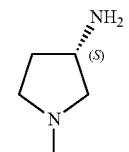 | 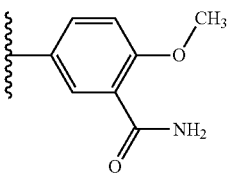 [SMILES: *c1ccc(OC)c(C(N)=O)c1] |

TABLE 2-continued
| Compound No. | Rᵃ | Rᶜ | Rᵇ |
|---|---|---|---|
| 2-74 | 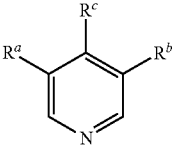 | 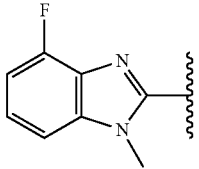 [SMILES: *c1nc2c(F)cccc2n1C] | 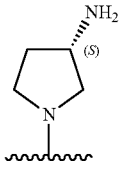 |
| 2-75 | 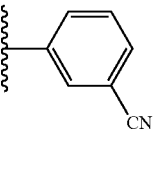 | 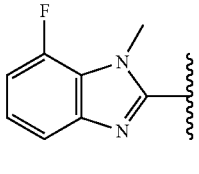 [SMILES: *c1nc2cccc(F)c2n1C] | 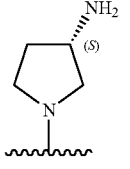 |
| 2-76 | 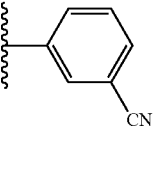 [SMILES: *c1cccc(C#N)c1] | 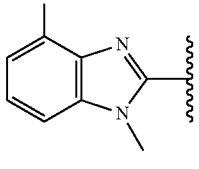 | 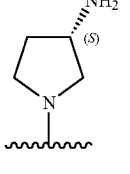 |
| 2-77 | 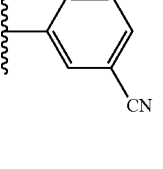 | 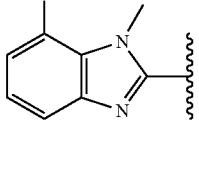 | 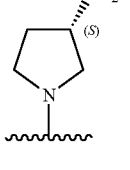 |
| 2-78 | 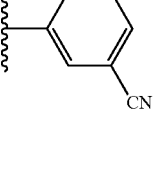 | 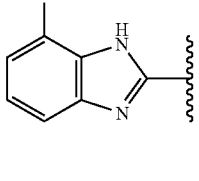 | 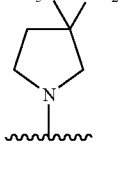 |
| 2-79 | 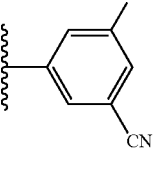 | 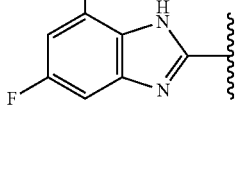 | 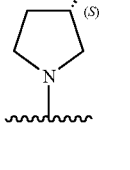 |
| 2-80 | 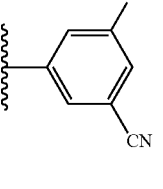 | 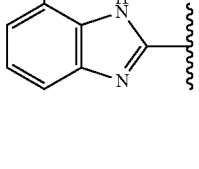 | 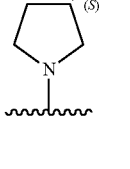 |

TABLE 2-continued
| Compound No. | $R^a$ | $R^c$ | $R^b$ |
|---|---|---|---|
| 2-81 | 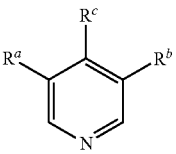 | 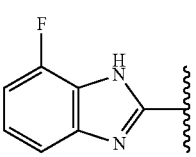<br>trans, racemic | 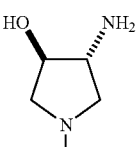 |
| 2-82 | 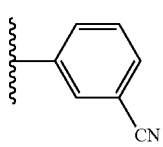 | 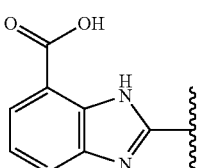 | 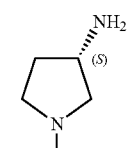 |
| 2-83 | 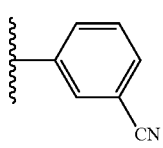 | 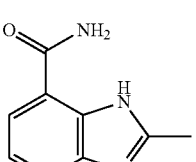 | 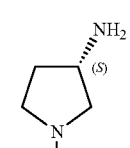 |
| 2-84 | 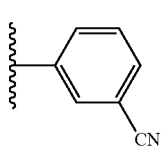 [SMILES: *c1cccc(C#N)c1] | 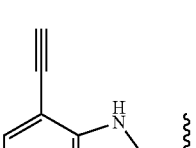 | 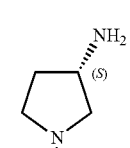 |
| 2-85 | 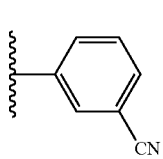 [SMILES: *c1cccc(C#N)c1] | 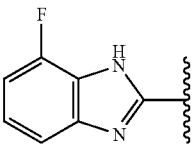 [SMILES: *c1nc2cccc(F)c2[nH]1] | 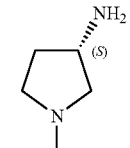 |
| 2-86 | 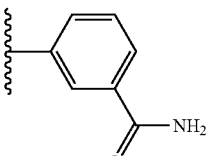 | 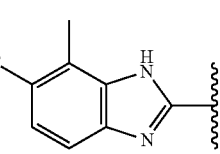 | 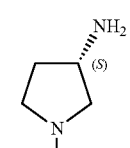 |
| 2-87 | 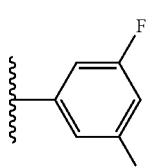 | 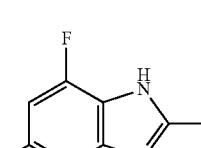 | 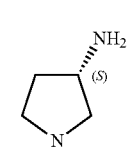 |

TABLE 2-continued
| Compound No. | R^a | R^c | R^b |
|---|---|---|---|
| 2-88 | 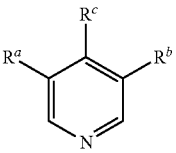 | 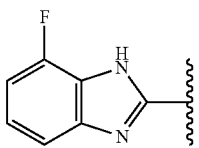 [SMILES: *c1nc2cccc(F)c2[nH]1] | 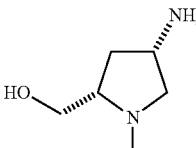 |
| 2-89 | 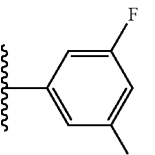 | 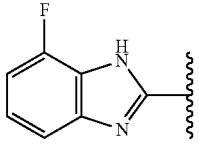 [SMILES: *c1nc2cccc(F)c2[nH]1]<br>trans, racemic | 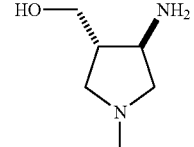 |
| 2-90 | 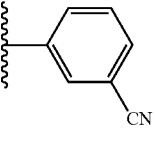 | 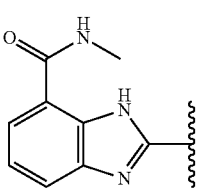 [SMILES: *c1nc2cccc(C(=O)NC)c2[nH]1] | 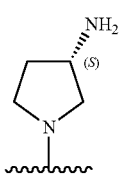 |
| 2-91 | 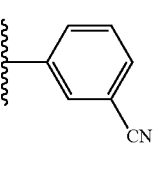 | 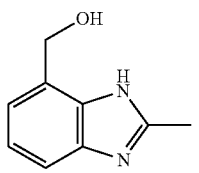 | 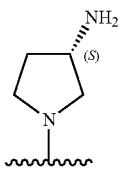 |
| 2-92 | 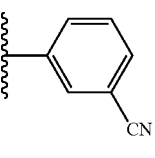 | 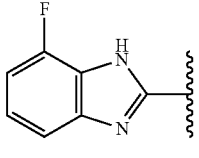 [SMILES: *c1nc2cccc(F)c2[nH]1] | 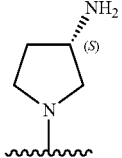 |
| 2-93 | 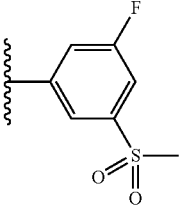 [SMILES: *c1cc(F)cc(S(C)(=O)=O)c1] | 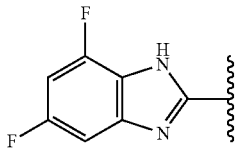 [SMILES: *c1nc2cc(F)cc(F)c2[nH]1] | 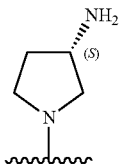 |
| 2-94 | 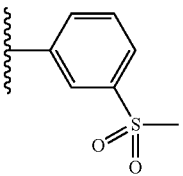 [SMILES: *c1cccc(S(C)(=O)=O)c1] | 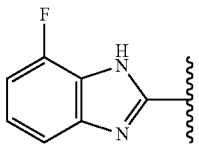 | 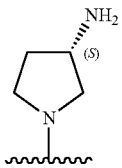 |

TABLE 2-continued
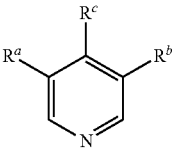
| Compound No. | R$^a$ | R$^c$ | R$^b$ |
|---|---|---|---|
| 2-95 | 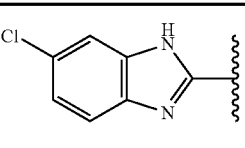 | 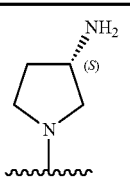 | 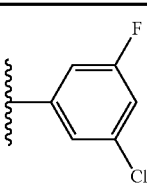 |
| 2-96 | 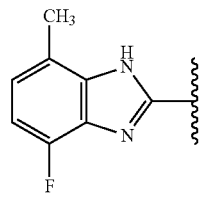 [SMILES: *c1nc2c(F)ccc(C)c2[nH]1] | 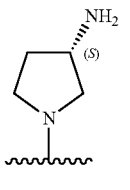 | 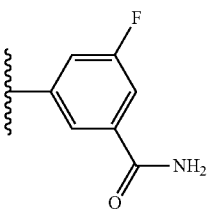 [SMILES: *c1cc(F)cc(C(N)=O)c1] |
| 2-97 | 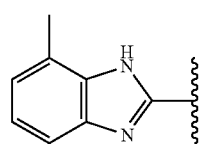 [SMILES: *c1nc2cccc(C)c2[nH]1] | 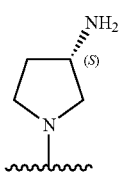 | 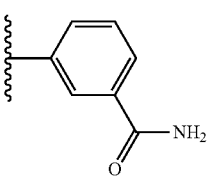 [SMILES: *c1cccc(C(N)=O)c1] |
| 2-98 | 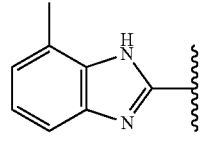 [SMILES: *c1nc2cccc(C)c2[nH]1] | 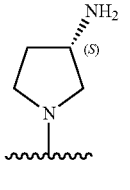 | 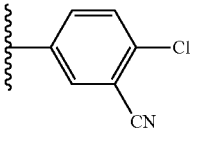 [SMILES: *c1ccc(Cl)c(C#N)c1] |
| 2-99 | 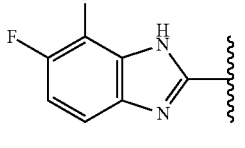 | 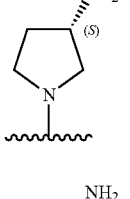 | 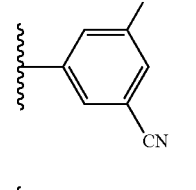 |
| 2-100 | 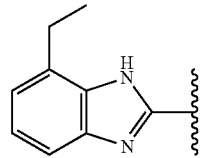 [SMILES: *c1nc2cccc(CC)c2[nH]1] | 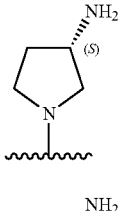 | 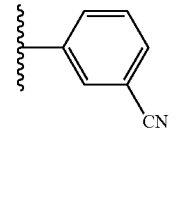 [SMILES: *c1cccc(C#N)c1] |
| 2-101 | 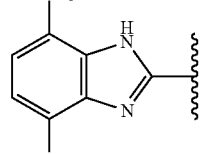 | 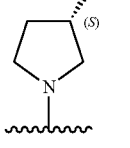 | 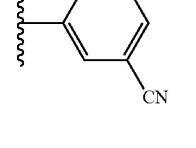 |

TABLE 2-continued
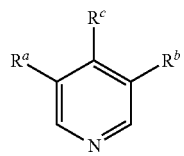
| Compound No. | R$^a$ | R$^c$ | R$^b$ |
|---|---|---|---|
| 2-102 | 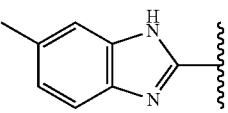 [SMILES: *c1nc2ccc(C)cc2[nH]1] | 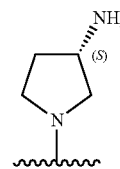 | 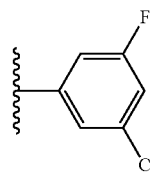 |
| 2-103 | 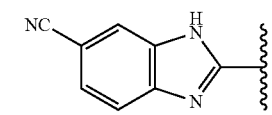 [SMILES: *c1nc2ccc(C#N)cc2[nH]1] | 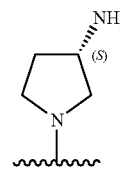 | 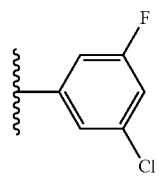 [SMILES: *c1cc(F)cc(Cl)c1] |
| 2-104 | 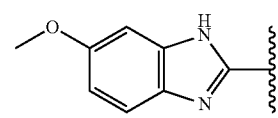 [SMILES: *c1nc2ccc(OC)cc2[nH]1] | 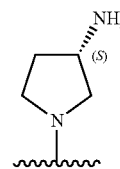 | 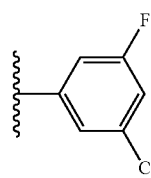 |
| 2-105 | 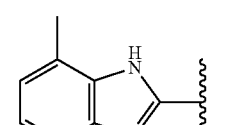 | 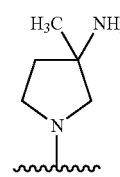<br>racemic | 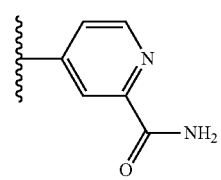 [SMILES: *c1ccnc(C(N)=O)c1] |
| 2-106 | 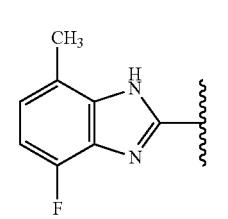 [SMILES: *c1nc2c(F)ccc(C)c2[nH]1] | 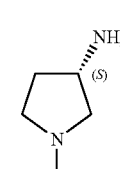 | 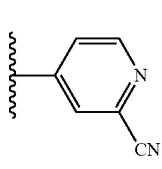 |
| 2-107 | 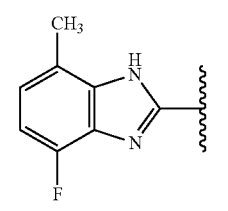 [SMILES: *c1nc2c(F)ccc(C)c2[nH]1] | 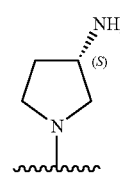 | 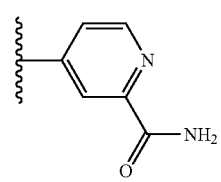 [SMILES: *c1ccnc(C(N)=O)c1] |
| 2-108 | 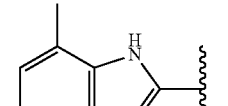 | 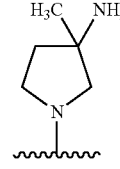<br>racemic | 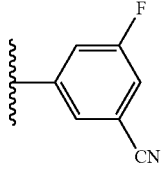 [SMILES: *c1cc(F)cc(C#N)c1] |

TABLE 2-continued
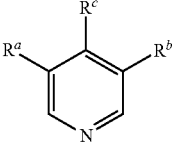
| Compound No. | $R^a$ | $R^c$ | $R^b$ |
|---|---|---|---|
| 2-109 | 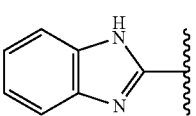 [SMILES: *c1nc2ccccc2[nH]1] | 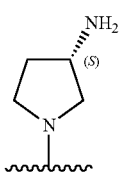 | 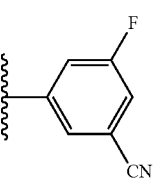 |
| 2-110 | 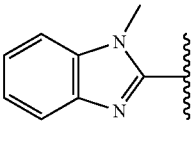 [SMILES: *c1nc2ccccc2n1C] | 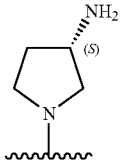 | 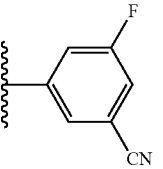 [SMILES: *c1cc(F)cc(C#N)c1] |
| 2-111 | 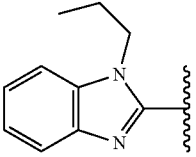 [SMILES: *c1nc2ccccc2n1CCC] | 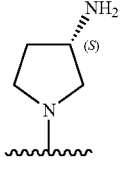 | 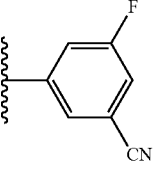 [SMILES: *c1cc(F)cc(C#N)c1] |
| 2-112 | 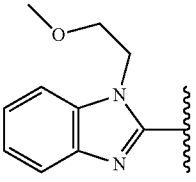 [SMILES: *c1nc2ccccc2n1CCOC] | 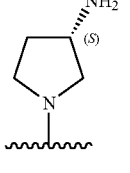 | 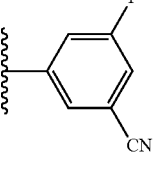 |
| 2-113 | 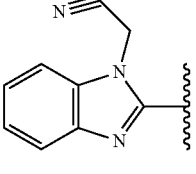 | 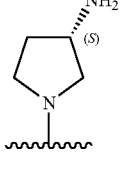 | 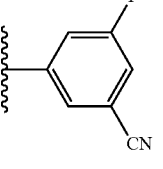 |
| 2-114 | 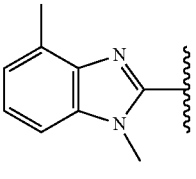 [SMILES: *c1nc2c(C)cccc2n1C] | 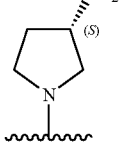 | 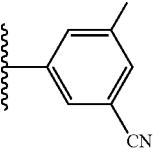 |
| 2-115 | 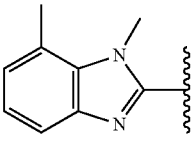 [SMILES: *c1nc2cccc(C)c2n1C] | 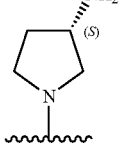 | 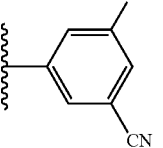 |

TABLE 2-continued

| Compound No. | $R^a$ | $R^c$ | $R^b$ |
|---|---|---|---|
| 2-116 | 4-Cl, 1-methyl-benzimidazol-2-yl | (S)-3-aminopyrrolidin-1-yl | 5-fluoro-3-cyanophenyl |
| 2-117 | 7-Cl, 1-methyl-benzimidazol-2-yl | (S)-3-aminopyrrolidin-1-yl | 3-fluoro-5-cyanophenyl |
| 2-118 | 7-methyl-1H-benzimidazol-2-yl | 3-amino-3-methylpyrrolidin-1-yl (racemic) | 3-fluoro-5-carbamoylphenyl |
| 2-119 | 7-methyl-3H-imidazo[4,5-b]pyridin-2-yl | 3-amino-3-methylpyrrolidin-1-yl (racemic) | 4-fluoro-3-cyanophenyl |
| 2-120 | 7-fluoro-1H-benzimidazol-2-yl | 3-amino-3-methylpyrrolidin-1-yl (racemic) | 3-fluoro-5-carbamoylphenyl |
| 2-121 | 7-fluoro-1H-benzimidazol-2-yl | 3-amino-3-methylpyrrolidin-1-yl (racemic) | 2-cyanopyridin-4-yl |

TABLE 2-continued
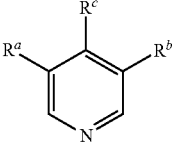
| Compound No. | $R^a$ | $R^c$ | $R^b$ |
|---|---|---|---|
| 2-122 | 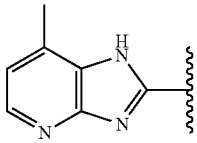 [SMILES: *c1nc2nccc(C)c2[nH]1] | 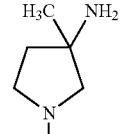 racemic | 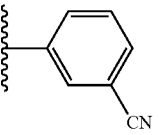 |
| 2-123 | 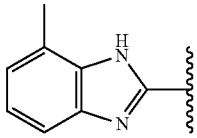 [SMILES: *c1nc2cccc(C)c2[nH]1] | 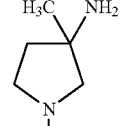 racemic | 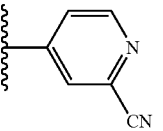 |
| 2-124 | 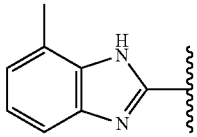 [SMILES: *c1nc2cccc(C)c2[nH]1] | 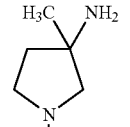 racemic | 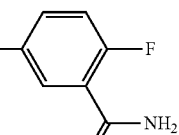 |
| 2-125 | 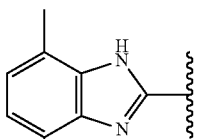 [SMILES: *c1nc2cccc(C)c2[nH]1] | 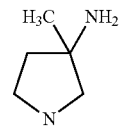 racemic | 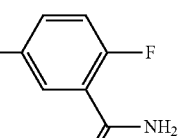 |
| 2-126 | 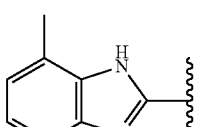 | 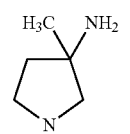 racemic | 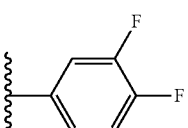 |
| 2-127 | 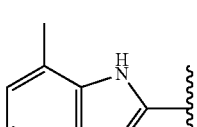 | 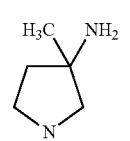 racemic | 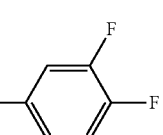 |

TABLE 2-continued

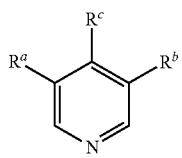

| Compound No. | $R^a$ | $R^c$ | $R^b$ |
|---|---|---|---|
| 2-128 | 7-methyl-1H-benzimidazol-2-yl | (S)-3-aminopyrrolidin-1-yl | 2-cyanopyridin-4-yl |
| 2-129 | 4-methyl-1H-indol-2-yl | (S)-3-aminopyrrolidin-1-yl | 3-cyano-5-fluorophenyl |
| 2-130 | 7-fluoro-1H-benzimidazol-2-yl | (S)-3-aminopyrrolidin-1-yl | 2-amino-6-methylpyridin-4-yl |
| 2-131 | 4-chloro-1-methyl-1H-benzimidazol-2-yl | (S)-3-aminopyrrolidin-1-yl | 3-cyano-4-fluorophenyl |
| 2-132 | 7-methyl-1-methyl-1H-benzimidazol-2-yl | (S)-3-aminopyrrolidin-1-yl | 3-cyano-4-fluorophenyl |
| 2-133 | 4-chloro-1-methyl-1H-benzimidazol-2-yl | (S)-3-aminopyrrolidin-1-yl | 3-cyano-4-fluorophenyl |
| 2-134 | 7-methyl-1-methyl-1H-benzimidazol-2-yl | (S)-3-aminopyrrolidin-1-yl | 3-cyano-4-fluorophenyl |

TABLE 2-continued

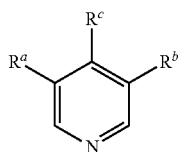

| Compound No. | $R^a$ | $R^c$ | $R^b$ |
|---|---|---|---|
| 2-135 | 4-methyl-1H-benzimidazol-2-yl | (S)-3-amino-3-(hydroxymethyl)pyrrolidin-1-yl | 3-fluoro-5-cyanophenyl |
| 2-136 | 4-methyl-1H-benzimidazol-2-yl | (R)-3-amino-3-(hydroxymethyl)pyrrolidin-1-yl | 3-fluoro-5-cyanophenyl |
| 2-137 | 7-methyl-1H-indol-2-yl | (S)-3-aminopyrrolidin-1-yl | 3-fluoro-5-cyanophenyl |
| 2-138 | 4-methyl-1H-benzimidazol-2-yl | 3-amino-3-methylpyrrolidin-1-yl, racemic | 3-carbamoyl-2-fluorophenyl |
| 2-139 | 4-methyl-1H-benzimidazol-2-yl | (S)-3-aminopyrrolidin-1-yl | 3,4-difluoro-5-cyanophenyl |
| 2-140 | 4-methyl-1H-imidazo[4,5-b]pyridin-2-yl | 3-amino-3-methylpyrrolidin-1-yl, racemic | 3,4-difluoro-5-cyanophenyl |
| 2-141 | 4-methyl-1H-benzimidazol-2-yl | (S)-3-aminopyrrolidin-1-yl | 4-fluoro-3-(trifluoromethoxy)phenyl |

TABLE 2-continued
| Compound No. | $R^a$ | $R^c$ | $R^b$ |
|---|---|---|---|
| 2-142 | 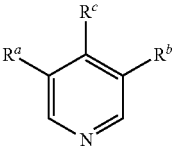 | 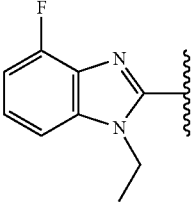 [SMILES: *c1nc2c(F)cccc2n1CC] | 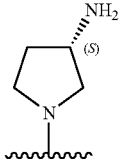 |
| 2-143 | 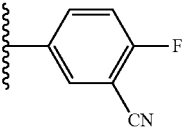 [SMILES: *c1ccc(F)c(C#N)c1] | 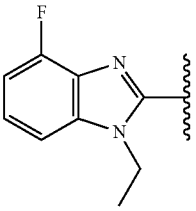 [SMILES: *c1nc2c(F)cccc2n1CC] | 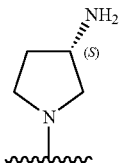 |
| 2-144 | 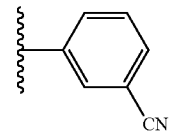 | 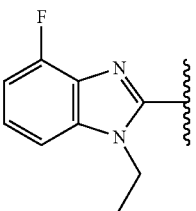 [SMILES: *c1nc2c(F)cccc2n1CC] | 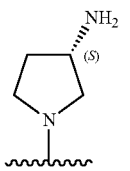 |
| 2-145 | 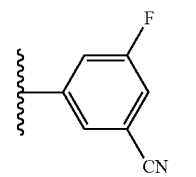 [SMILES: *c1cc(F)cc(C#N)c1] | 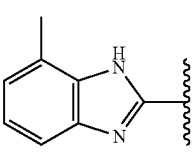 [SMILES: *c1nc2cccc(C)c2[nH]1] | 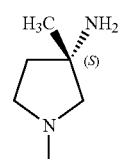 |
| 2-146 | 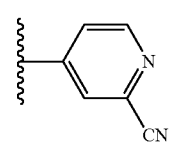 [SMILES: *c1ccnc(C#N)c1] | 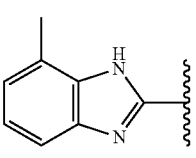 [SMILES: *c1nc2cccc(C)c2[nH]1] | 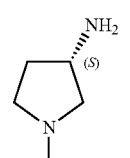 |
| 2-147 | 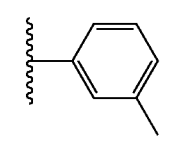 | 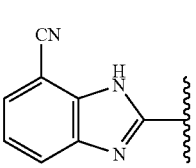 [SMILES: *c1nc2cccc(C#N)c2[nH]1]<br>racemic | 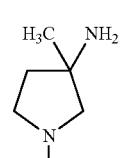 |

TABLE 2-continued
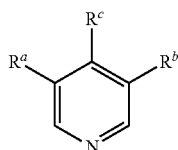
| Compound No. | $R^a$ | $R^c$ | $R^b$ |
|---|---|---|---|
| 2-148 | 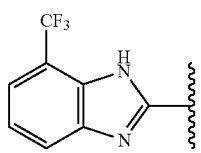 [SMILES: *c1nc2cccc(C(F)(F)F)c2[nH]1] | 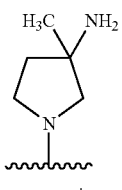 racemic | 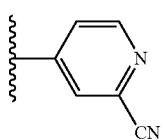 |
| 2-149 | 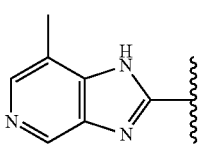 [SMILES: *c1nc2cncc(C)c2[nH]1] | 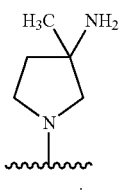 racemic | 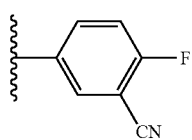 |
| 2-150 | 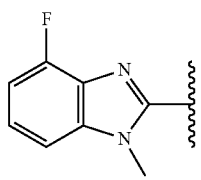 [SMILES: *c1nc2c(F)cccc2n1C] | 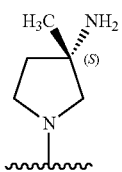 | 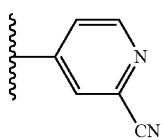 [SMILES: *c1ccnc(C#N)c1] |
| 2-151 | 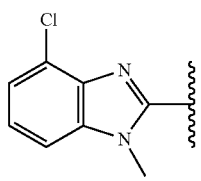 | 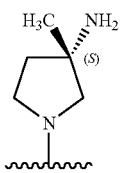 | 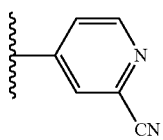 [SMILES: *c1ccnc(C#N)c1] |
| 2-152 | 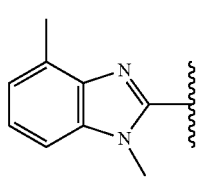 | 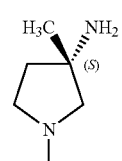 | 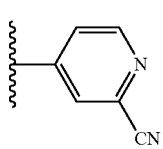 [SMILES: *c1ccnc(C#N)c1] |
| 2-153 | 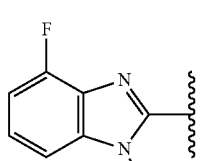 | 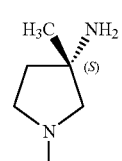 | 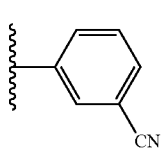 |
| 2-154 | 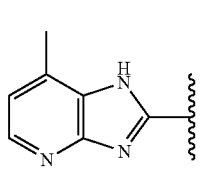 [SMILES: *c1nc2nccc(C)c2[nH]1] | 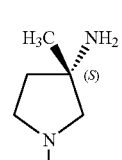 | 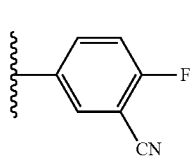 |

TABLE 2-continued
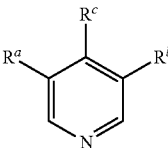
| Compound No. | $R^a$ | $R^c$ | $R^b$ |
|---|---|---|---|
| 2-155 | 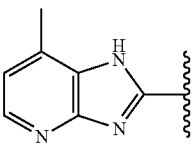 [SMILES: *c1nc2nccc(C)c2[nH]1] | 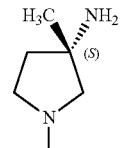 | 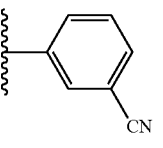 |
| 2-156 | 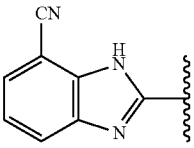 | 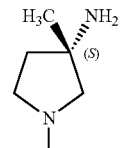 | 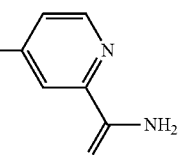 |
| 2-157 |  | 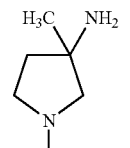<br>racemic | 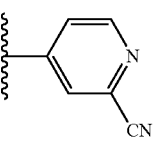 |
| 2-158 | 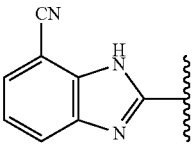 [SMILES: *c1nc2cccc(C#N)c2[nH]1] | 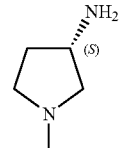 | 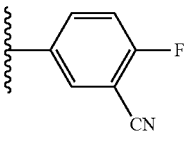 [SMILES: *c1ccc(F)c(C#N)c1] |
| 2-159 | 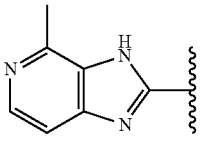 [SMILES: *c1nc2ccnc(C)c2[nH]1] | 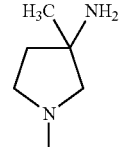<br>racemic | 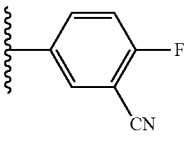 |
| 2-160 | 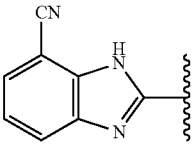 | 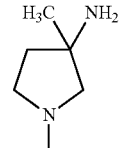<br>racemic | 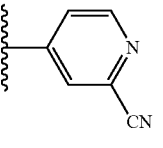 [SMILES: *c1ccnc(C#N)c1] |
| 2-161 | 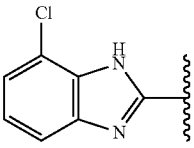 | 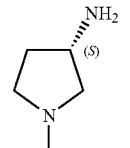 | 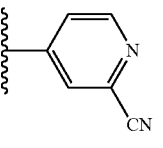 [SMILES: *c1ccnc(C#N)c1] |

TABLE 2-continued

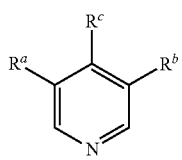

| Compound No. | R<sup>a</sup> | R<sup>c</sup> | R<sup>b</sup> |
| --- | --- | --- | --- |
| 2-162 | 4-fluoro-1H-benzimidazol-2-yl | (S)-3-amino-3-methylpyrrolidin-1-yl | 2-cyanopyridin-4-yl |
| 2-163 | 4-chloro-1H-benzimidazol-2-yl | (S)-3-amino-3-methylpyrrolidin-1-yl | 2-cyanopyridin-4-yl |
| 2-164 | 5-fluoro-4-methyl-1H-benzimidazol-2-yl | (S)-3-amino-3-methylpyrrolidin-1-yl | 2-cyanopyridin-4-yl |
| 2-165 | 7-methyl-3H-imidazo[4,5-b]pyridin-2-yl | (S)-3-amino-3-methylpyrrolidin-1-yl | 3,4-difluoro-5-cyanophenyl |
| 2-166 | 6-fluoro-4-methyl-1H-benzimidazol-2-yl | (S)-3-amino-3-methylpyrrolidin-1-yl | 2-cyanopyridin-4-yl |
| 2-167 | 3H-imidazo[4,5-b]pyridin-2-yl | (S)-3-amino-3-methylpyrrolidin-1-yl | 4-fluoro-3-cyanophenyl |
| 2-168 | 5-fluoro-3H-imidazo[4,5-b]pyridin-2-yl | (S)-3-amino-3-methylpyrrolidin-1-yl | 4-fluoro-3-cyanophenyl |

TABLE 2-continued
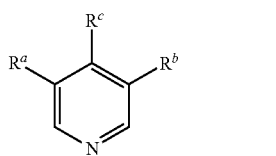
| Compound No. | R$^a$ | R$^c$ | R$^b$ |
|---|---|---|---|
| 2-169 | 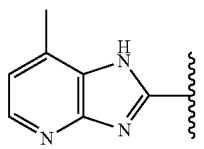 [SMILES: *c1nc2nccc(C)c2[nH]1] | 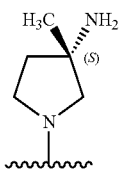 | 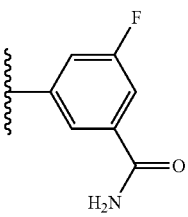 [SMILES: *c1cc(F)cc(C(N)=O)c1] |
| 2-170 | 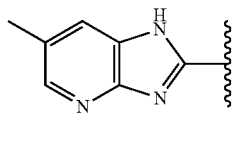 [SMILES: *c1nc2ncc(C)cc2[nH]1] | 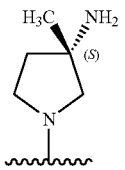 | 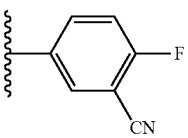 [SMILES: *c1ccc(F)c(C#N)c1] |
| 2-171 | 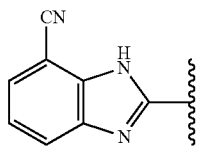 | 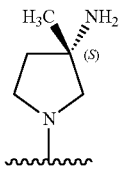 | 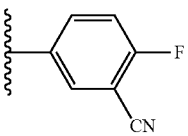 [SMILES: *c1ccc(F)c(C#N)c1] |
| 2-172 | 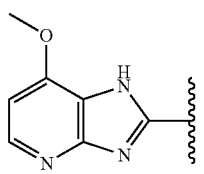 [SMILES: *c1nc2nccc(OC)c2[nH]1] | 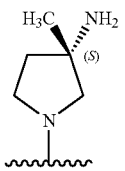 | 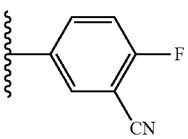 |
| 2-173 | 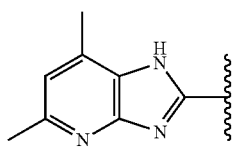 [SMILES: *c1nc2nc(C)cc(C)c2[nH]1] | 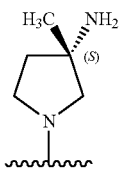 | 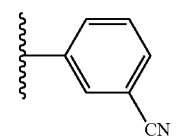 [SMILES: *c1cccc(C#N)c1] |
| 2-174 | 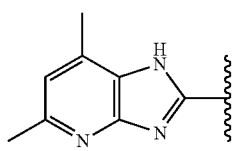 [SMILES: *c1nc2nc(C)cc(C)c2[nH]1] | 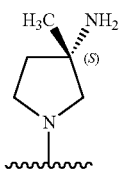 | 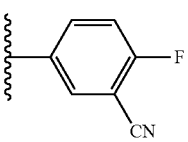 [SMILES: *c1ccc(F)c(C#N)c1] |
| 2-175 | 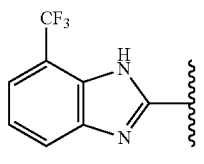 | 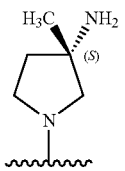 | 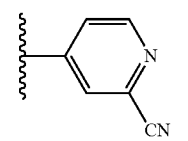 [SMILES: *c1ccnc(C#N)c1] |

TABLE 2-continued
| Compound No. | R$^a$ | R$^c$ | R$^b$ |
|---|---|---|---|
| 2-176 | 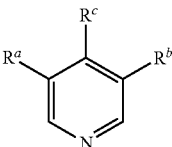 | 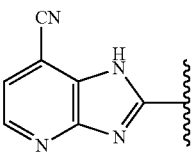 [SMILES: *c1nc2nccc(C#N)c2[nH]1] | 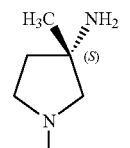 |
| 2-177 | 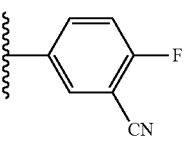 [SMILES: *c1ccc(F)c(C#N)c1] | 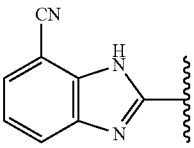 [SMILES: *c1nc2cccc(C#N)c2[nH]1] | 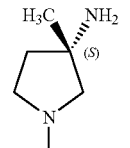 |
| 2-178 | 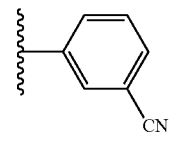 [SMILES: *c1cccc(C#N)c1] | 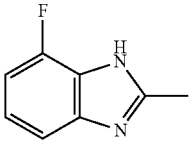 | 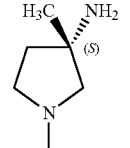 |
| 2-179 | 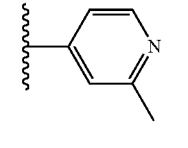 | 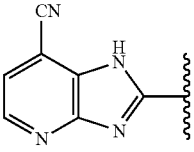 [SMILES: *c1nc2nccc(C#N)c2[nH]1] | 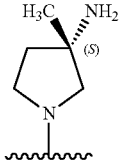 |
| 2-180 | 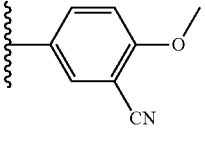 | 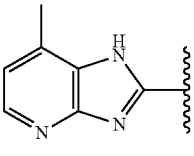 [SMILES: *c1nc2nccc(C)c2[nH]1] | 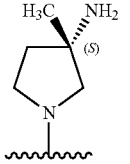 |
| 2-181 | 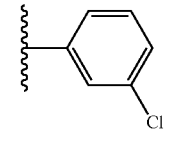 [SMILES: *c1cccc(Cl)c1] | 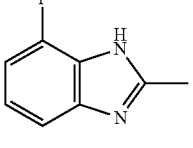 | 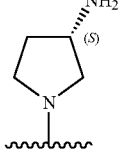 |
| 2-182 | 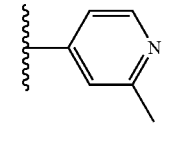 | 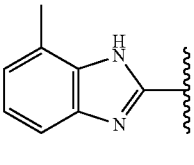 [SMILES: *c1nc2cccc(C)c2[nH]1] | 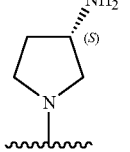 |
| 2-183 | 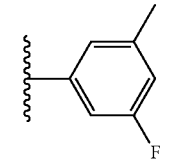 [SMILES: *c1cc(C)cc(F)c1] | 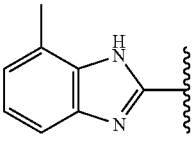 [SMILES: *c1nc2cccc(C)c2[nH]1] | 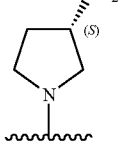 |

TABLE 2-continued
| Compound No. | R$^a$ | R$^c$ | R$^b$ |
|---|---|---|---|
| 2-184 | 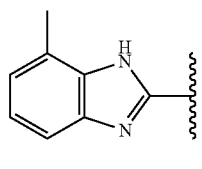 | 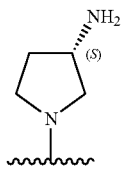 | 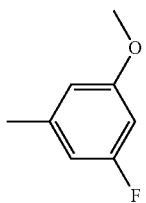 |
| 2-185 | 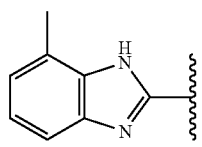 [SMILES: *c1nc2cccc(C)c2[nH]1] | 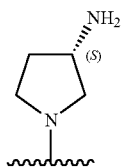 | 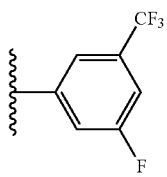 [SMILES: *c1cc(F)cc(C(F)(F)F)c1] |
| 2-186 | 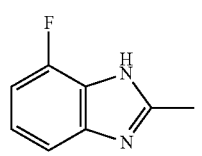 | 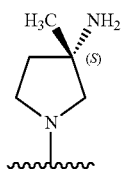 | 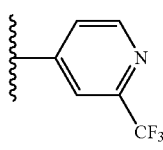 |
| 2-187 | 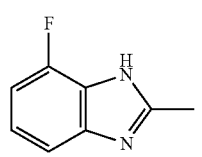 | 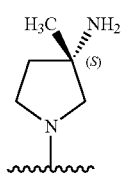 | 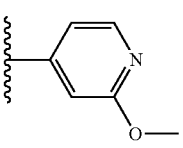 |
| 2-188 | 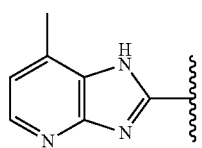 [SMILES: *c1nc2nccc(C)c2[nH]1] | 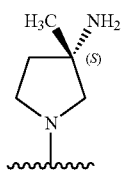 | 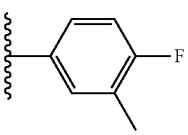 |
| 2-189 | 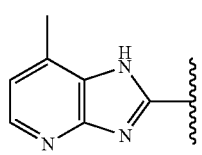 [SMILES: *c1nc2nccc(C)c2[nH]1] | 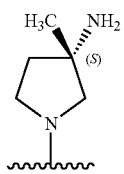 | 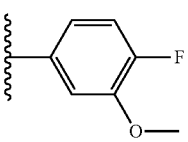 [SMILES: *c1ccc(F)c(OC)c1] |
| 2-190 | 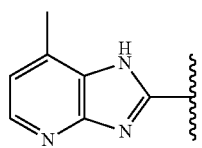 [SMILES: *c1nc2nccc(C)c2[nH]1] | 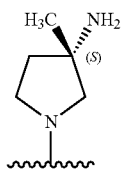 | 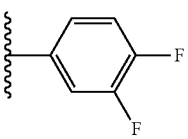 |

TABLE 2-continued
| Compound No. | R^a | R^c | R^b |
|---|---|---|---|
| 2-191 | 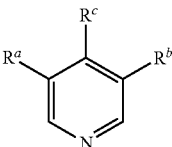 | 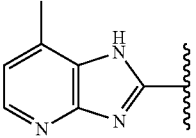 [SMILES: *c1nc2nccc(C)c2[nH]1] | 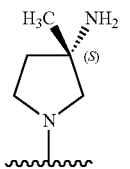 |
| 2-192 | 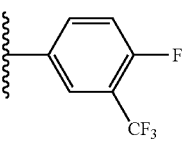 | 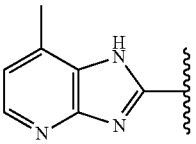 [SMILES: *c1nc2nccc(C)c2[nH]1] | 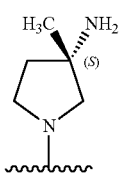 |
| 2-193 | 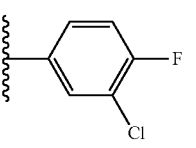 [SMILES: *c1ccc(F)c(Cl)c1] | 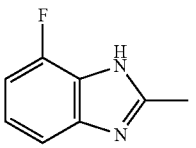 | 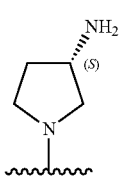 |
| 2-194 | 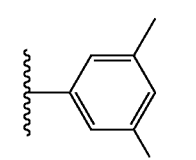 |  | 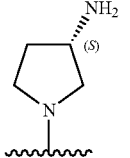 |
| 2-195 | 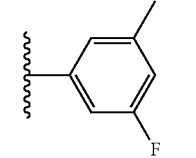 | 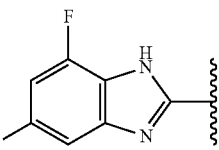 | 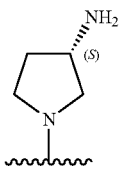 |
| 2-196 | 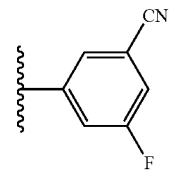 [SMILES: *c1cc(F)cc(C#N)c1] | 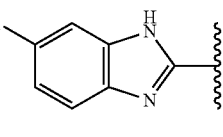 | 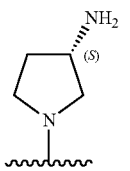 |
| 2-197 | 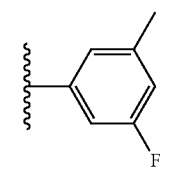 [SMILES: *c1cc(C)cc(F)c1] | 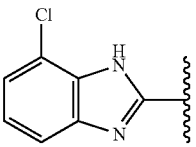 [SMILES: *c1nc2cccc(Cl)c2[nH]1] | 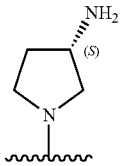 |
| 2-198 | 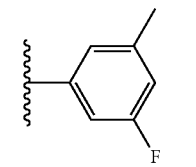 [SMILES: *c1cc(C)cc(F)c1] | 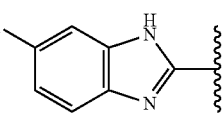 | 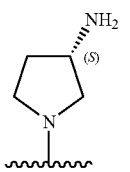 |

TABLE 2-continued

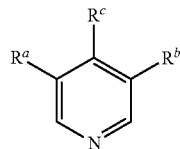

| Compound No. | R$^a$ | R$^c$ | R$^b$ |
|---|---|---|---|
| 2-199 | 7-methyl-1H-benzimidazol-2-yl | (R)-3-aminopyrrolidin-1-yl | 3-methylphenyl |
| 2-200 | 7-fluoro-1H-benzimidazol-2-yl | (S)-3-amino-3-methylpyrrolidin-1-yl | 3-cyanophenyl |
| 2-201 | 7-methyl-1H-benzimidazol-2-yl | (S)-3-aminopyrrolidin-1-yl | 3,5-difluorophenyl |
| 2-202 | 7-methyl-3H-imidazo[4,5-b]pyridin-2-yl | (S)-3-amino-3-methylpyrrolidin-1-yl | 3-cyano-5-fluorophenyl |

Compounds in Table 2 are named:

2-1: 1-[3-(4,6-difluoro-1H-1,3-benzodiazol-2-yl)-5-(3-fluoro-5-methylphenyl)pyridin-4-yl]pyrrolidin-3-amine;
2-2: (3R)-1-[3-(3-chloro-5-fluorophenyl)-5-(4-fluoro-1H-1,3-benzodiazol-2-yl)pyridin-4-yl]pyrrolidin-3-amine;
2-3: (3 S)-1-[3-(3-chloro-5-fluorophenyl)-5-(4-fluoro-1H-1,3-benzodiazol-2-yl)pyridin-4-yl]pyrrolidin-3-amine;
2-4: 1-[3-(3-chloro-5-fluorophenyl)-5-(4-fluoro-1H-1,3-benzodiazol-2-yl)pyridin-4-yl]-3-methylpyrrolidin-3-amine;
2-5: 3-{4-[(3S)-3-aminopyrrolidin-1-yl]-5-(4-fluoro-1H-1,3-benzodiazol-2-yl)pyridin-3-yl}-5-chlorobenzonitrile;
2-6: 3-[4-(3-amino-3-methylpyrrolidin-1-yl)-5-(4-fluoro-1H-1,3-benzodiazol-2-yl)pyridin-3-yl]-5-fluorobenzonitrile;
2-7: 3-{4-[(3S)-3-aminopyrrolidin-1-yl]-5-(4-fluoro-1H-1,3-benzodiazol-2-yl)pyridin-3-yl}benzonitrile;
2-8: 3-{4-[(3S)-3-aminopyrrolidin-1-yl]-5-(4-fluoro-1H-1,3-benzodiazol-2-yl)pyridin-3-yl}-5-fluorobenzonitrile;
2-9: (3S)-1-[3-(4-fluoro-1H-1,3-benzodiazol-2-yl)-5-{3-fluoro-5-[(methoxyimino)methyl]phenyl}pyridin-4-yl]pyrrolidin-3-amine;
2-10: 1-[3-(4-fluoro-1H-1,3-benzodiazol-2-yl)-5-[3-(trifluoromethoxy)phenyl]pyridin-4-yl]-3-methylpyrrolidin-3-amine;
2-11: 1-[3-(4-fluoro-1H-1,3-benzodiazol-2-yl)-5-(3-methoxyphenyl)pyridin-4-yl]-3-methylpyrrolidin-3-amine;
2-12: (3S)-1-[3-(4-fluoro-1H-1,3-benzodiazol-2-yl)-5-{3-[(methoxyimino)methyl]phenyl}pyridin-4-yl]pyrrolidin-3-amine;
2-13: 3-[4-(3-amino-3-methylpyrrolidin-1-yl)-5-(4-fluoro-1H-1,3-benzodiazol-2-yl)pyridin-3-yl]benzonitrile;
2-14: 4'-(3-amino-3-methylpyrrolidin-1-yl)-5'-(4-fluoro-1H-1,3-benzodiazol-2-yl)-N,N-dimethyl-[3,3'-bipyridin]-6-amine;
2-15: 4-(3-amino-3-methylpyrrolidin-1-yl)-5-(4-fluoro-1H-1,3-benzodiazol-2-yl)-[3,4'-bipyridin]-2'-amine;
2-16: 1-[3-(4-fluoro-1H-1,3-benzodiazol-2-yl)-5-[3-(1H-pyrazol-1-yl)phenyl]pyridin-4-yl]-3-methylpyrrolidin-3-amine;
2-17: 3-{3-[4-(3-amino-3-methylpyrrolidin-1-yl)-5-(4-fluoro-1H-1,3-benzodiazol-2-yl)pyridin-3-yl]phenyl}-1,3-oxazolidin-2-one;
2-18: 3-[4-(3-amino-3-methylpyrrolidin-1-yl)-5-(4-fluoro-1H-1,3-benzodiazol-2-yl)pyridin-3-yl]benzamide;
2-19: 3-[4-(3-amino-3-methylpyrrolidin-1-yl)-5-(4-fluoro-1H-1,3-benzodiazol-2-yl)pyridin-3-yl]-N-methylbenzamide;
2-20: 3-[4-(3-amino-3-methylpyrrolidin-1-yl)-5-(4-fluoro-1H-1,3-benzodiazol-2-yl)pyridin-3-yl]-5-fluorobenzamide;

2-21: 1-[3-(4-fluoro-1H-1,3-benzodiazol-2-yl)-5-(3-methanesulfonylphenyl)pyridin-4-yl]-3-methylpyrrolidin-3-amine;

2-22: 1-[3-(2,3-dihydro-1-benzofuran-6-yl)-5-(4-fluoro-1H-1,3-benzodiazol-2-yl)pyridin-4-yl]-3-methylpyrrolidin-3-amine;

2-23: 5-{4-[(3S)-3-aminopyrrolidin-1-yl]-5-(4-fluoro-1H-1,3-benzodiazol-2-yl)pyridin-3-yl}-2-fluorobenzonitrile;

2-24: 3-{4-[(3S)-3-aminopyrrolidin-1-yl]-5-(4-fluoro-1H-1,3-benzodiazol-2-yl)pyridin-3-yl}-2-fluorobenzonitrile;

2-25: 3-{4-[(3S)-3-aminopyrrolidin-1-yl]-5-(4-fluoro-1H-1,3-benzodiazol-2-yl)pyridin-3-yl}-5-fluorophenol;

2-26: 5-{4-[(3S)-3-aminopyrrolidin-1-yl]-5-(4-fluoro-1H-1,3-benzodiazol-2-yl)pyridin-3-yl}thiophene-2-carbonitrile;

2-27: 2-{3-[4-(3-amino-3-methylpyrrolidin-1-yl)-5-(4-fluoro-1H-1,3-benzodiazol-2-yl)pyridin-3-yl]-5-fluorophenoxy}acetonitrile;

2-28: 1-[3-(3-chlorophenyl)-5-(4-fluoro-1H-1,3-benzodiazol-2-yl)pyridin-4-yl]-3-methylpyrrolidin-3-amine;

2-29: 1-[3-(4-fluoro-1H-1,3-benzodiazol-2-yl)-5-(1H-indol-6-yl)pyridin-4-yl]-3-methylpyrrolidin-3-amine 2-30: 1-[3-(4-fluoro-1H-1,3-benzodiazol-2-yl)-5-(1H-indol-5-yl)pyridin-4-yl]-3-methylpyrrolidin-3-amine;

2-31: 3-[4-(3-amino-3-methylpyrrolidin-1-yl)-5-(4-fluoro-1H-1,3-benzodiazol-2-yl)pyridin-3-yl]-N,N-dimethylbenzamide;

2-32: 3-{4-[(3S)-3-aminopyrrolidin-1-yl]-5-(4-fluoro-1H-1,3-benzodiazol-2-yl)pyridin-3-yl}-2,6-difluorobenzonitrile;

2-33: 3-{4-[3-amino-4-(trifluoromethyl)pyrrolidin-1-yl]-5-(4-fluoro-1H-1,3-benzodiazol-2-yl)pyridin-3-yl}benzonitrile;

2-34: 3-{4-[(3S)-3-aminopyrrolidin-1-yl]-5-(4-methyl-1H-1,3-benzodiazol-2-yl)pyridin-3-yl}-5-fluorobenzonitrile;

2-35: 4-{4-[(3S)-3-aminopyrrolidin-1-yl]-5-(4-fluoro-1H-1,3-benzodiazol-2-yl)pyridin-3-yl}-2-fluorobenzonitrile;

2-36: 5-{4-[(3S)-3-aminopyrrolidin-1-yl]-5-(4-fluoro-1H-1,3-benzodiazol-2-yl)pyridin-3-yl}-2-hydroxybenzonitrile;

2-37: 5-{4-[(3S)-3-aminopyrrolidin-1-yl]-5-(4-methyl-1H-1,3-benzodiazol-2-yl)pyridin-3-yl}-2-fluorobenzonitrile;

2-38: 3-{4-[(3S)-3-aminopyrrolidin-1-yl]-5-(4,7-difluoro-1H-1,3-benzodiazol-2-yl)pyridin-3-yl}-5-fluorobenzonitrile;

2-39: 5-{4-[(3S)-3-aminopyrrolidin-1-yl]-5-(4-fluoro-1H-1,3-benzodiazol-2-yl)pyridin-3-yl}-2-chlorobenzonitrile;

2-40: 2-{4-[(3S)-3-aminopyrrolidin-1-yl]-5-(4,7-difluoro-1H-1,3-benzodiazol-2-yl)pyridin-3-yl}-6-fluorobenzonitrile;

2-41: 3-{4-[(3S)-3-aminopyrrolidin-1-yl]-5-(4,5,6,7-tetrafluoro-1H-1,3-benzodiazol-2-yl)pyridin-3-yl}benzonitrile;

2-42: 4-{4-[(3S)-3-aminopyrrolidin-1-yl]-5-(4-fluoro-1H-1,3-benzodiazol-2-yl)pyridin-3-yl}benzonitrile;

2-43: 3-{4-[(3S)-3-aminopyrrolidin-1-yl]-5-(4,7-difluoro-1H-1,3-benzodiazol-2-yl)pyridin-3-yl}benzamide;

2-44: 5-{4-[(3S)-3-aminopyrrolidin-1-yl]-5-(4,7-difluoro-1H-1,3-benzodiazol-2-yl)pyridin-3-yl}-2-fluorobenzonitrile;

2-45: 3-{4-[trans-3-amino-4-methoxypyrrolidin-1-yl]-5-(4-fluoro-1H-1,3-benzodiazol-2-yl)pyridin-3-yl}benzonitrile;

2-46: 3-{4-[cis-3-amino-4-methoxypyrrolidin-1-yl]-5-(4-fluoro-1H-1,3-benzodiazol-2-yl)pyridin-3-yl}benzonitrile;

2-47: 2-{4-[(3S)-3-aminopyrrolidin-1-yl]-5-(4-fluoro-1H-1,3-benzodiazol-2-yl)pyridin-3-yl}-6-chlorobenzonitrile;

2-48: 5-{4-[(3S)-3-aminopyrrolidin-1-yl]-5-(4,7-difluoro-1H-1,3-benzodiazol-2-yl)pyridin-3-yl}-2-(trifluoromethyl)benzonitrile;

2-49: 5-{4-[(3S)-3-aminopyrrolidin-1-yl]-5-(4,7-difluoro-1H-1,3-benzodiazol-2-yl)pyridin-3-yl}-2-methylbenzonitrile;

2-50: 5-{4-[(3S)-3-aminopyrrolidin-1-yl]-5-{7-methyl-1H-imidazo[4,5-b]pyridin-2-yl}pyridin-3-yl}-2-fluorobenzonitrile;

2-51: 5-{4-[(3S)-3-aminopyrrolidin-1-yl]-5-(4-chloro-1H-1,3-benzodiazol-2-yl)pyridin-3-yl}-2-fluorobenzonitrile;

2-52: 5-{4-[(3S)-3-aminopyrrolidin-1-yl]-5-(4,5-difluoro-1H-1,3-benzodiazol-2-yl)pyridin-3-yl}-2-fluorobenzonitrile;

2-53: 1-[3-(4-fluoro-1H-1,3-benzodiazol-2-yl)-5-[(1H-imidazol-1-yl)phenyl]pyridin-4-yl]-3-methylpyrrolidin-3-amine;

2-54: 3-{4-[3-amino-3-(hydroxymethyl)pyrrolidin-1-yl]-5-(4-fluoro-1H-1,3-benzodiazol-2-yl)pyridin-3-yl}benzonitrile;

2-55: 3-{4-[trans-3-amino-4-fluoropyrrolidin-1-yl]-5-(4-fluoro-1H-1,3-benzodiazol-2-yl)pyridin-3-yl}benzonitrile;

2-56: 3-{4-[trans-3-amino-4-phenylpyrrolidin-1-yl]-5-(4-fluoro-1H-1,3-benzodiazol-2-yl)pyridin-3-yl}benzonitrile;

2-57: 3-{4-[(3S)-3-aminopyrrolidin-1-yl]-5-(4-bromo-1H-1,3-benzodiazol-2-yl)pyridin-3-yl}benzonitrile;

2-58: (3S)-1-[3-(4-fluoro-1H-1,3-benzodiazol-2-yl)-5-(3-methanesulfonylphenyl)pyridin-4-yl]pyrrolidin-3-amine;

2-59: (3S)-1-[3-(2,3-dihydro-1-benzofuran-6-yl)-5-(4-fluoro-1H-1,3-benzodiazol-2-yl)pyridin-4-yl]pyrrolidin-3-amine;

2-60: 5-{4-[(3S)-3-aminopyrrolidin-1-yl]-5-[4-(trifluoromethyl)-1H-1,3-benzodiazol-2-yl]pyridin-3-yl}-2-fluorobenzonitrile;

2-61: 5-{4-[(3S)-3-aminopyrrolidin-1-yl]-5-(4,7-difluoro-1H-1,3-benzodiazol-2-yl)pyridin-3-yl}-2-fluorobenzamide;

2-62: 3-{4-[(3S)-3-aminopyrrolidin-1-yl]-5-(4-chloro-1H-1,3-benzodiazol-2-yl)pyridin-3-yl}-5-fluorobenzonitrile;

2-63: 3-{4-[(3S)-3-aminopyrrolidin-1-yl]-5-(7-fluoro-4-methyl-1H-1,3-benzodiazol-2-yl)pyridin-3-yl}-5-fluorobenzonitrile;

2-64: 3-{4-[3-amino-3-(trifluoromethyl)pyrrolidin-1-yl]-5-(4-fluoro-1H-1,3-benzodiazol-2-yl)pyridin-3-yl}benzamide;

2-65: 3-{4-[(3S)-3-aminopyrrolidin-1-yl]-5-(4-methyl-1H-1,3-benzodiazol-2-yl)pyridin-3-yl}-5-fluorobenzamide;

2-66: 3-{4-[(2R,4S)-4-amino-2-(hydroxymethyl)pyrrolidin-1-yl]-5-(4-fluoro-1H-1,3-benzodiazol-2-yl)pyridin-3-yl}-5-fluorobenzonitrile;

2-67: 4-[(3S)-3-aminopyrrolidin-1-yl]-5-(4-fluoro-1H-1,3-benzodiazol-2-yl)-N-methyl-[3,4'-bipyridin]-2'-amine;

2-68: 3-{4-[cis-3-amino-4-hydroxypyrrolidin-1-yl]-5-(4-fluoro-1H-1,3-benzodiazol-2-yl)pyridin-3-yl}benzonitrile;

2-69: trans-4-amino-1-[3-(3-cyanophenyl)-5-(4-fluoro-1H-1,3-benzodiazol-2-yl)pyridin-4-yl]pyrrolidine-3-carboxamide;

2-70: 3-{4-[cis-3-amino-4-fluoropyrrolidin-1-yl]-5-(4-fluoro-1H-1,3-benzodiazol-2-yl)pyridin-3-yl}benzonitrile;

2-71: 5-{4-[(3S)-3-aminopyrrolidin-1-yl]-5-(4-fluoro-1H-1,3-benzodiazol-2-yl)pyridin-3-yl}-2-fluorobenzamide;

2-72: 3-{4-[(3S)-3-aminopyrrolidin-1-yl]-5-(4-fluoro-1H,1,3-benzodiazol-2-yl)pyridin-3-yl}-5-fluorobenzamide;

2-73: 5-{4-[(3S)-3-aminopyrrolidin-1-yl]-5-(4-fluoro-1H-1,3-benzodiazol-2-yl)pyridin-3-yl}-2-methoxybenzamide;

2-74: 3-{4-[(3S)-3-aminopyrrolidin-1-yl]-5-(4-fluoro-1-methyl-1H-1,3-benzodiazol-2-yl)pyridin-3-yl}benzonitrile;

2-75: 3-{4-[(3S)-3-aminopyrrolidin-1-yl]-5-(7-fluoro-1-methyl-1H-1,3-benzodiazol-2-yl)pyridin-3-yl}benzonitrile;

2-76: 3-{4-[(3S)-3-aminopyrrolidin-1-yl]-5-(4-chloro-1-methyl-1H-1,3-benzodiazol-2-yl)pyridin-3-yl}benzonitrile;

2-77: 3-{4-[(3S)-3-aminopyrrolidin-1-yl]-5-(4-chloro-1-methyl-1H-1,3-benzodiazol-2-yl)pyridin-3-yl}benzonitrile;

2-78: 3-{4-[3-amino-3-(trifluoromethyl)pyrrolidin-1-yl]-5-(4-fluoro-1H-1,3-benzodiazol-2-yl)pyridin-3-yl}-5-fluorobenzonitrile;

2-79: 3-{4-[(3S)-3-aminopyrrolidin-1-yl]-5-(6-fluoro-4-methyl-1H-1,3-benzodiazol-2-yl)pyridin-3-yl}-5-fluorobenzonitrile;

2-80: 3-{4-[(3S)-3-aminopyrrolidin-1-yl]-5-(4-methyl-1H-1,3-benzodiazol-2-yl)pyridin-3-yl}benzonitrile;

2-81: 3-{4-[trans-3-amino-4-hydroxypyrrolidin-1-yl]-5-(4-fluoro-1H-1,3-benzodiazol-2-yl)pyridin-3-yl}benzonitrile;

2-82: 2-{4-[(3S)-3-aminopyrrolidin-1-yl]-5-(3-cyanophenyl)pyridin-3-yl}-1H-1,3-benzodiazole-4-carboxylic acid;

2-83: 2-{4-[(3S)-3-aminopyrrolidin-1-yl]-5-(3-cyanophenyl)pyridin-3-yl}-1H-1,3-benzodiazole-4-carboxamide;

2-84: 3-{4-[(3S)-3-aminopyrrolidin-1-yl]-5-(4-ethynyl-1H-1,3-benzodiazol-2-yl)pyridin-3-yl}benzonitrile;

2-85: 3-{4-[(3S)-3-aminopyrrolidin-1-yl]-5-(4-fluoro-1H-1,3-benzodiazol-2-yl)pyridin-3-yl}benzamide;

2-86: 3-{4-[(3S)-3-aminopyrrolidin-1-yl]-5-(5-fluoro-4-methyl-1H-1,3-benzodiazol-2-yl)pyridin-3-yl}-5-fluorobenzonitrile;

2-87: 3-{4-[(3S)-3-aminopyrrolidin-1-yl]-5-(4,6-difluoro-1H-1,3-benzodiazol-2-yl)pyridin-3-yl}-5-fluorobenzonitrile;

2-88: 3-{4-[(2S,4S)-4-amino-2-(hydroxymethyl)pyrrolidin-1-yl]-5-(4-fluoro-1H-1,3-benzodiazol-2-yl)pyridin-3-yl}-5-fluorobenzonitrile;

2-89: 3-{4-[trans-3-amino-4-(hydroxymethyl)pyrrolidin-1-yl]-5-(4-fluoro-1H-1,3-benzodiazol-2-yl)pyridin-3-yl}benzonitrile;

2-90: 2-{4-[(3S)-3-aminopyrrolidin-1-yl]-5-(3-cyanophenyl)pyridin-3-yl}-N-methyl-1H-1,3-benzodiazole-4-carboxamide;

2-91: 3-{4-[(3S)-3-aminopyrrolidin-1-yl]-5-[4-(hydroxymethyl)-1H-1,3-benzodiazol-2-yl]pyridin-3-yl}benzonitrile;

2-92: (3S)-1-[3-(4-fluoro-1H-1,3-benzodiazol-2-yl)-5-(3-fluoro-5-methanesulfonylphenyl)pyridin-4-yl]pyrrolidin-3-amine;

2-93: (3S)-1-[3-(4,6-difluoro-1H-1,3-benzodiazol-2-yl)-5-(3-methanesulfonylphenyl)pyridin-4-yl]pyrrolidin-3-amine;

2-94: (3S)-1-[3-(3-chloro-5-fluorophenyl)-5-(6-fluoro-1H-1,3-benzodiazol-2-yl)pyridin-4-yl]pyrrolidin-3-amine;

2-95: (3S)-1-[3-(5-chloro-1H-1,3-benzodiazol-2-yl)-5-(3-chloro-5-fluorophenyl)pyridin-4-yl]pyrrolidin-3-amine;

2-96: 3-{4-[(3S)-3-aminopyrrolidin-1-yl]-5-(7-fluoro-4-methyl-1H-1,3-benzodiazol-2-yl)pyridin-3-yl}-5-fluorobenzamide;

2-97: 3-{4-[(3S)-3-aminopyrrolidin-1-yl]-5-(4-methyl-1H-1,3-benzodiazol-2-yl)pyridin-3-yl}benzamide;

2-98: 5-{4-[(3S)-3-aminopyrrolidin-1-yl]-5-(4-methyl-1H-1,3-benzodiazol-2-yl)pyridin-3-yl}-2-chlorobenzonitrile;

2-99: 3-{4-[(3S)-3-aminopyrrolidin-1-yl]-5-(4,5-difluoro-1H-1,3-benzodiazol-2-yl)pyridin-3-yl}-5-fluorobenzonitrile;

2-100: 3-{4-[(3S)-3-aminopyrrolidin-1-yl]-5-(4-ethyl-1H-1,3-benzodiazol-2-yl)pyridin-3-yl}benzonitrile;

2-101: 3-{4-[(3S)-3-aminopyrrolidin-1-yl]-5-(7-fluoro-4-methyl-1H-1,3-benzodiazol-2-yl)pyridin-3-yl}benzonitrile;

2-102: (3S)-1-[3-(3-chloro-5-fluorophenyl)-5-(5-methyl-1H-1,3-benzodiazol-2-yl)pyridin-4-yl]pyrrolidin-3-amine;

2-103: 2-{4-[(3S)-3-aminopyrrolidin-1-yl]-5-(3-chloro-5-fluorophenyl)pyridin-3-yl}-1H-1,3-benzodiazole-5-carbonitrile;

2-104: (3S)-1-[3-(3-chloro-5-fluorophenyl)-5-(5-methoxy-1H-1,3-benzodiazol-2-yl)pyridin-4-yl]pyrrolidin-3-amine;

2-105: 4-(3-amino-3-methylpyrrolidin-1-yl)-5-(4-methyl-1H-1,3-benzodiazol-2-yl)-[3,4'-bipyridine]-2'-carboxamide;

2-106: 4-[(3S)-3-aminopyrrolidin-1-yl]-5-(7-fluoro-4-methyl-1H-1,3-benzodiazol-2-yl)-[3,4'-bipyridine]-2'-carbonitrile;

2-107: 4-[(3S)-3-aminopyrrolidin-1-yl]-5-(7-fluoro-4-methyl-1H-1,3-benzodiazol-2-yl)-[3,4'-bipyridine]-2'-carboxamide;

2-108: 3-[4-(3-amino-3-methylpyrrolidin-1-yl)-5-{7-methyl-1H-imidazo[4,5-b]pyridin-2-yl}pyridin-3-yl]-5-fluorobenzonitrile;

2-109: 3-{4-[(3S)-3-aminopyrrolidin-1-yl]-5-(1H-1,3-benzodiazol-2-yl)pyridin-3-yl}-5-fluorobenzonitrile;

2-110: 3-{4-[(3S)-3-aminopyrrolidin-1-yl]-5-(1-methyl-1H-1,3-benzodiazol-2-yl)pyridin-3-yl}-5-fluorobenzonitrile;

2-111: 3-{4-[(3S)-3-aminopyrrolidin-1-yl]-5-(1-propyl-1H-1,3-benzodiazol-2-yl)pyridin-3-yl}-5-fluorobenzonitrile;

2-112: 3-{4-[(3S)-3-aminopyrrolidin-1-yl]-5-[1-(2-methoxyethyl)-1H-1,3-benzodiazol-2-yl]pyridin-3-yl}-5-fluorobenzonitrile;

2-113: 3-{4-[(3S)-3-aminopyrrolidin-1-yl]-5-[1-(cyanomethyl)-1H-1,3-benzodiazol-2-yl]pyridin-3-yl}-5-fluorobenzonitrile;

2-114: 3-{4-[(3S)-3-aminopyrrolidin-1-yl]-5-(1,4-dimethyl-1H-1,3-benzodiazol-2-yl)pyridin-3-yl}-5-fluorobenzonitrile;

2-115: 3-{4-[(3S)-3-aminopyrrolidin-1-yl]-5-(1,7-dimethyl-1H-1,3-benzodiazol-2-yl)pyridin-3-yl}-5-fluorobenzonitrile;

2-116: 3-{4-[(3S)-3-aminopyrrolidin-1-yl]-5-(4-chloro-1-methyl-1H-1,3-benzodiazol-2-yl)pyridin-3-yl}-5-fluorobenzonitrile;

2-117: 3-{4-[(3S)-3-aminopyrrolidin-1-yl]-5-(7-chloro-1-methyl-1H-1,3-benzodiazol-2-yl)pyridin-3-yl}-5-fluorobenzonitrile;

2-118: 3-[4-(3-amino-3-methylpyrrolidin-1-yl)-5-(4-methyl-1H-1,3-benzodiazol-2-yl)pyridin-3-yl]-5-fluorobenzamide;

2-119: 5-[4-(3-amino-3-methylpyrrolidin-1-yl)-5-{7-methyl-1H-imidazo[4,5-b]pyridin-2-yl}pyridin-3-yl]-2-fluorobenzonitrile;

2-120: 5-[4-(3-amino-3-methylpyrrolidin-1-yl)-5-(4-fluoro-1H-1,3-benzodiazol-2-yl)pyridin-3-yl]-2-fluorobenzamide;

2-121: 4-(3-amino-3-methylpyrrolidin-1-yl)-5-(4-fluoro-1H-1,3-benzodiazol-2-yl)-[3,4'-bipyridine]-2'-carbonitrile;
2-122: 3-[4-(3-amino-3-methylpyrrolidin-1-yl)-5-{7-methyl-1H-imidazo[4,5-b]pyridin-2-yl}pyridin-3-yl]benzonitrile;
2-123: 4-(3-amino-3-methylpyrrolidin-1-yl)-5-(4-methyl-1H-1,3-benzodiazol-2-yl)-[3,4'-bipyridine]-2'-carbonitrile;
2-124: 5-[4-(3-amino-3-methylpyrrolidin-1-yl)-5-(4-methyl-1H-1,3-benzodiazol-2-yl)pyridin-3-yl]-2-fluorobenzamide;
2-125: 5-[4-(3-amino-3-methylpyrrolidin-1-yl)-5-(7-fluoro-4-methyl-1H-1,3-benzodiazol-2-yl)pyridin-3-yl]-2-fluorobenzamide;
2-126: 5-[4-(3-amino-3-methylpyrrolidin-1-yl)-5-(4-methyl-1H-1,3-benzodiazol-2-yl)pyridin-3-yl]-2,3-difluorobenzoic acid;
2-127: 5-[4-(3-amino-3-methylpyrrolidin-1-yl)-5-(4-methyl-1H-1,3-benzodiazol-2-yl)pyridin-3-yl]-2,3-difluorobenzamide;
2-128: 4-[(3S)-3-aminopyrrolidin-1-yl]-5-(4-methyl-1H-1,3-benzodiazol-2-yl)-[3,4'-bipyridine]-2'-carbonitrile;
2-129: 3-{4-[(3 S)-3-aminopyrrolidin-1-yl]-5-(4-methyl-1H-indol-2-yl)pyridin-3-yl}-5-fluorobenzonitrile;
2-130: 4-[(3S)-3-aminopyrrolidin-1-yl]-5-(4-fluoro-1H-1,3-benzodiazol-2-yl)-6'-methyl-[3,4'-bipyridin]-2'-amine;
2-131: 5-{4-[(3S)-3-aminopyrrolidin-1-yl]-5-(4-chloro-1-methyl-1H-1,3-benzodiazol-2-yl)pyridin-3-yl}-2-fluorobenzonitrile;
2-132: 5-{4-[(3S)-3-aminopyrrolidin-1-yl]-5-(1,4-dimethyl-1H-1,3-benzodiazol-2-yl)pyridin-3-yl}-2-fluorobenzonitrile;
2-133: 5-{4-[(3S)-3-aminopyrrolidin-1-yl]-5-(7-chloro-1-methyl-1H-1,3-benzodiazol-2-yl)pyridin-3-yl}-2-fluorobenzonitrile;
2-134: 5-{4-[(3S)-3-aminopyrrolidin-1-yl]-5-(1,7-dimethyl-1H-1,3-benzodiazol-2-yl)pyridin-3-yl}-2-fluorobenzonitrile;
2-135: 3-{4-[(3S)-3-amino-3-(hydroxymethyl)pyrrolidin-1-yl]-5-(4-methyl-1H-1,3-benzodiazol-2-yl)pyridin-3-yl}-5-fluorobenzonitrile;
2-136: 3-{4-[(3R)-3-amino-3-(hydroxymethyl)pyrrolidin-1-yl]-5-(4-methyl-1H-1,3-benzodiazol-2-yl)pyridin-3-yl}-5-fluorobenzonitrile;
2-137: 3-{4[(3S)-3-aminopyrrolidin-1-yl]-5-(7-methyl-1H-indol-2-yl)pyridin-3-yl}-5-fluorobenzonitrile;
2-138: 3-[4-(3-amino-3-methylpyrrolidin-1-yl)-5-(4-methyl-1H-1,3-benzodiazol-2-yl)pyridin-3-yl]-2-fluorobenzamide;
2-139: 5-{4-[(3S)-3-aminopyrrolidin-1-yl]-5-(4-methyl-1H-1,3-benzodiazol-2-yl)pyridin-3-yl}-2,3-difluorobenzonitrile;
2-140: 5-[4-(3-amino-3-methylpyrrolidin-1-yl)-5-{7-methyl-1H-imidazo[4,5-b]pyridin-2-yl}pyridin-3-yl]-2,3-difluorobenzonitrile;
2-141: (3S)- 1-{3-[4-fluoro-3-(trifluoromethoxy)phenyl]-5-(4-methyl-1H-1,3-benzodiazol-2-yl)pyridin-4-yl}pyrrolidin-3-amine;
2-142: 5-{4-[(3S)-3-aminopyrrolidin-1-yl]-5-(1-ethyl-4-fluoro-1H-1,3-benzodiazol-2-yl)pyridin-3-yl}-2-fluorobenzonitrile;
2-143: 3-{4-[(3S)-3-aminopyrrolidin-1-yl]-5-(1-ethyl-4-fluoro-1H-1,3-benzodiazol-2-yl)pyridin-3-yl}benzonitrile;
2-144: 3-{4-[(3S)-3-aminopyrrolidin-1-yl]-5-(1-ethyl-4-fluoro-1H-1,3-benzodiazol-2-yl)pyridin-3-yl}-5-fluorobenzonitrile;
2-145: 4-[(3S)-3-amino-3-methylpyrrolidin-1-yl]-5-(4-methyl-1H-1,3-benzodiazol-2-yl)-[3,4'-bipyridine]-2'-carbonitrile;
2-146: (3S)-1-[3-(4-methyl-1H-1,3-benzodiazol-2-yl)-5-(3-methylphenyl)pyridin-4-yl]pyrrolidin-3-amine;
2-147: 2-[4-(3-amino-3-methylpyrrolidin-1-yl)-5-(3-cyano-4-fluorophenyl)pyridin-3-yl]-1H-1,3-benzodiazole-4-carbonitrile;
2-148: 4-(3-amino-3-methylpyrrolidin-1-yl)-5-[4-(trifluoromethyl)-1H-1,3-benzodiazol-2-yl]-[3,4'-bipyridine]-2'-carbonitrile;
2-149: 5-[4-(3-amino-3-methylpyrrolidin-1-yl)-5-{7-methyl-3H-imidazo[4,5-c]pyridin-2-yl}pyridin-3-yl]-2-fluorobenzonitrile;
2-150: 4-[(3S)-3-amino-3-methylpyrrolidin-1-yl]-5-(4-fluoro-1-methyl-1H-1,3-benzodiazol-2-yl)-[3,4'-bipyridine]-2'-carbonitrile;
2-151: 4-[(3S)-3-amino-3-methylpyrrolidin-1-yl]-5-(4-chloro-1-methyl-1H-1,3-benzodiazol-2-yl)-[3,4'-bipyridine]-2'-carbonitrile;
2-152: 4-[(3S)-3-amino-3-methylpyrrolidin-1-yl]-5-(1,4-dimethyl-1H-1,3-benzodiazol-2-yl)-[3,4'-bipyridine]-2'-carbonitrile;
2-153: 3-{4-[(3S)-3-amino-3-methylpyrrolidin-1-yl]-5-(4-fluoro-1-methyl-1H-1,3-benzodiazol-2-yl)pyridin-3-yl}benzonitrile;
2-154: 5-{4-[(3S)-3-amino-3-methylpyrrolidin-1-yl]-5-{7-methyl-1H-imidazo[4,5-b]pyridin-2-yl}pyridin-3-yl]-2-fluorobenzonitrile;
2-155: 3-{4-[(3S)-3-amino-3-methylpyrrolidin-1-yl]-5-{7-methyl-1H-imidazo[4,5-b]pyridin-2-yl}pyridin-3-yl}benzonitrile;
2-156: 4-[(3S)-3-amino-3-methylpyrrolidin-1-yl]-5-(4-methyl-1H-1,3-benzodiazol-2-yl)-[3,4'-bipyridine]-2'-carboxamide;
2-157: 4-(3-amino-3-methylpyrrolidin-1-yl)-5-(4-chloro-1H-1,3-benzodiazol-2-yl)-[3,4'-bipyridine]-2'-carbonitrile;
2-158: 2-{4-[(3S)-3-aminopyrrolidin-1-yl]-5-(3-cyano-4-fluorophenyl)pyridin-3-yl}-1H-1,3-benzodiazole-4-carbonitrile;
2-159: 5-[4-(3-amino-3-methylpyrrolidin-1-yl)-5-{4-methyl-3H-imidazo[4,5-c]pyridin-2-yl}pyridin-3-yl]-2-fluorobenzonitrile;
2-160: 4-(3-amino-3-methylpyrrolidin-1-yl)-5-(4-cyano-1H-1,3-benzodiazol-2-yl)-[3,4'-bipyridine]-2'-carbonitrile;
2-161: 4-[(3S)-3-aminopyrrolidin-1-yl]-5-(4-chloro-1H-1,3-benzodiazol-2-yl)-[3,4'-bipyridine]-2'-carbonitrile;
2-162: 4-[(3S)-3-amino-3-methylpyrrolidin-1-yl]-5-(4-fluoro-1H-1,3-benzodiazol-2-yl)-[3,4'-bipyridine]-2'-carbonitrile;
2-163: 4-[(3S)-3-amino-3-methylpyrrolidin-1-yl]-5-(4-chloro-1H-1,3-benzodiazol-2-yl)-[3,4'-bipyridine]-2'-carbonitrile;
2-164: 4-[(3S)-3-amino-3-methylpyrrolidin-1-yl]-5-(5-fluoro-4-methyl-1H-1,3-benzodiazol-2-yl)-[3,4'-bipyridine]-2'-carbonitrile;
2-165: 5-{4-[(3S)-3-amino-3-methylpyrrolidin-1-yl]-5-{7-methyl-1H-imidazo[4,5-b]pyridin-2-yl}pyridin-3-yl}-2,3-difluorobenzonitrile;
2-166: 4-[(3S)-3-amino-3-methylpyrrolidin-1-yl]-5-(6-fluoro-4-methyl-1H-1,3-benzodiazol-2-yl)-[3,4'-bipyridine]-2'-carbonitrile;

2-167: 5-{4-[(3S)-3-amino-3-methylpyrrolidin-1-yl]-5-{1H-imidazo[4,5-b]pyridin-2-yl}pyridin-3-yl}-2-fluorobenzonitrile;

2-168: 5-{4-[(3S)-3-amino-3-methylpyrrolidin-1-yl]-5-{6-fluoro-1H-imidazo[4,5-b]pyridin-2-yl}pyridin-3-yl}-2-fluorobenzonitrile;

2-169: 3-{4-[(3S)-3-amino-3-methylpyrrolidin-1-yl]-5-{7-methyl-1H-imidazo[4,5-b]pyridin-2-yl}pyridin-3-yl}-5-fluorobenzamide;

2-170: 5-{4-[(3S)-3-amino-3-methylpyrrolidin-1-yl]-5-{6-methyl-1H-imidazo[4,5-b]pyridin-2-yl}pyridin-3-yl}-2-fluorobenzonitrile;

2-171: 2-{4-[(3S)-3-amino-3-methylpyrrolidin-1-yl]-5-(3-cyano-4-fluorophenyl)pyridin-3-yl}-1H-1,3-benzodiazole-7-carbonitrile;

2-172: 5-{4-[(3S)-3-amino-3-methylpyrrolidin-1-yl]-5-{7-methoxy-1H-imidazo[4,5-b]pyridin-2-yl}pyridin-3-yl}-2-fluorobenzonitrile;

2-173: 3-{4-[(3S)-3-amino-3-methylpyrrolidin-1-yl]-5-{5,7-dimethyl-1H-imidazo[4,5-b]pyridin-2-yl}pyridin-3-yl}benzonitrile;

2-174: 5-{4-[(3S)-3-amino-3-methylpyrrolidin-1-yl]-5-{5,7-dimethyl-1H-imidazo[4,5-b]pyridin-2-yl}pyridin-3-yl}-2-fluorobenzonitrile;

2-175: 4-[(3S)-3-amino-3-methylpyrrolidin-1-yl]-5-[7-(trifluoromethyl)-1H-1,3-benzodiazol-2-yl]-[3,4'-bipyridine]-2'-carbonitrile;

2-176: 2-{4-[(3S)-3-amino-3-methylpyrrolidin-1-yl]-5-(3-cyano-4-fluorophenyl)pyridin-3-yl}-1H-imidazo[4,5-b]pyridine-7-carbonitrile;

2-177: 2-{4-[(3 S)-3-amino-3-methylpyrrolidin-1-yl]-5-(3-cyanophenyl)pyridin-3-yl}-1H-1,3-benzodiazole-7-carbonitrile;

2-178: (3S)-1-[5-(4-fluoro-1H-1,3-benzodiazol-2-yl)-2'-methyl-[3,4'-bipyridin]-4-yl]-3-methylpyrrolidin-3-amine;

2-179: 2-{4-[(3S)-3-amino-3-methylpyrrolidin-1-yl]-5-(3-cyano-4-methoxyphenyl)pyridin-3-yl}-1H-imidazo[4,5-b]pyridine-7-carbonitrile;

2-180: (3S)-1-[3-(3-chlorophenyl)-5-{7-methyl-1H-imidazo[4,5-b]pyridin-2-yl}pyridin-4-yl]-3-methylpyrrolidin-3-amine;

2-181: (3S)-1-[5-(4-fluoro-1H-1,3-benzodiazol-2-yl)-2'-methyl-[3,4'-bipyridin]-4-yl]pyrrolidin-3-amine;

2-182: (3S)-1-[3-(3-fluoro-5-methylphenyl)-5-(4-methyl-1H-1,3-benzodiazol-2-yl)pyridin-4-yl]pyrrolidin-3-amine;

2-183: (3S)-1-[3-(3-chloro-5-fluorophenyl)-5-(4-methyl-1H-1,3-benzodiazol-2-yl)pyridin-4-yl]pyrrolidin-3-amine;

2-184: (3S)-1-[3-(3-fluoro-5-methoxyphenyl)-5-(4-methyl-1H-1,3-benzodiazol-2-yl)pyridin-4-yl]pyrrolidin-3-amine;

2-185: (3S)-1-{3-[3-fluoro-5-(trifluoromethyl)phenyl]-5-(4-methyl-1H-1,3-benzodiazol-2-yl)pyridin-4-yl}pyrrolidin-3-amine;

2-186: (3S)-1-[5-(4-fluoro-1H-1,3-benzodiazol-2-yl)-2'-(trifluoromethyl)-[3,4'-bipyridin]-4-yl]-3-methylpyrrolidin-3-amine;

2-187: (3S)-1-[5-(4-fluoro-1H-1,3-benzodiazol-2-yl)-2'-methoxy-[3,4'-bipyridin]-4-yl]-3-methylpyrrolidin-3-amine;

2-188: (3S)-1-[3-(4-fluoro-3-methylphenyl)-5-{7-methyl-1H-imidazo[4,5-b]pyridin-2-yl}pyridin-4-yl]-3-methylpyrrolidin-3-amine;

2-189: (3S)-1-[3-(4-fluoro-3-methoxyphenyl)-5-{7-methyl-1H-imidazo[4,5-b]pyridin-2-yl}pyridin-4-yl]-3-methylpyrrolidin-3-amine;

2-190: (3S)-1-[3-(3,4-difluorophenyl)-5-{7-methyl-1H-imidazo[4,5-b]pyridin-2-yl}pyridin-4-yl]-3-methylpyrrolidin-3-amine;

2-191: (3S)-1-{3-[4-fluoro-3-(trifluoromethyl)phenyl]-5-{7-methyl-1H-imidazo[4,5-b]pyridin-2-yl}pyridin-4-yl}-3-methylpyrrolidin-3-amine;

2-192: (3S)-1-[3-(3-chloro-4-fluorophenyl)-5-{7-methyl-1H-imidazo[4,5-b]pyridin-2-yl}pyridin-4-yl]-3-methylpyrrolidin-3-amine;

2-193: (3S)-1-[3-(4-fluoro-1H-1,3-benzodiazol-2-yl)-5-(3-fluoro-5-methylphenyl)pyridin-4-yl]pyrrolidin-3-amine;

2-194: 1-[3-(4,6-difluoro-1H-1,3-benzodiazol-2-yl)-5-(3-fluoro-5-methylphenyl)pyridin-4-yl]pyrrolidin-3-amine;

2-195: 3-{4-[(3S)-3-aminopyrrolidin-1-yl]-5-(4,6-difluoro-1H-1,3-benzodiazol-2-yl)pyridin-3-yl}-5-fluorobenzonitrile;

2-196: (3S)-1-[3-(6-chloro-1H-1,3-benzodiazol-2-yl)-5-(3-fluoro-5-methylphenyl)pyridin-4-yl]pyrrolidin-3-amine;

2-197: (3S)-1-[3-(7-chloro-1H-1,3-benzodiazol-2-yl)-5-(3-fluoro-5-methylphenyl)pyridin-4-yl]pyrrolidin-3-amine;

2-198: 3-{4-[(3S)-3-aminopyrrolidin-1-yl]-5-(6-chloro-1H-1,3-benzodiazol-2-yl)pyridin-3-yl}-5-fluorobenzonitrile;

2-199: (3R)-1-[3-(4-methyl-1H-1,3-benzodiazol-2-yl)-5-(3-methylphenyl)pyridin-4-yl]pyrrolidin-3-amine;

2-200: 3-{4-[(3S)-3-amino-3-methylpyrrolidin-1-yl]-5-(4-fluoro-1H-1,3-benzodiazol-2-yl)pyridin-3-yl}benzonitrile;

2-201: (3S)-1-[3-(3,5-difluorophenyl)-5-(4-methyl-1H-1,3-benzodiazol-2-yl)pyridin-4-yl]pyrrolidin-3-amine;

2-202: 3-{4-[(3S)-3-amino-3-methylpyrrolidin-1-yl]-5-{7-methyl-1H-imidazo[4,5-b]pyridin-2-yl}pyridin-3-yl}-5-fluorobenzonitrile.

In one aspect, compounds described herein are in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

"Pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Zürich:Wiley-VCH/NHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviors. Also, because the salt-forming molecule can be in equilibrium with a neutral form, passage through biological membranes can be adjusted.

In some embodiments, pharmaceutically acceptable salts are obtained by reacting a compound of Formula (I) with an acid. In some embodiments, the compound of Formula (I) (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethane-sulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (−L); malonic acid; mandelic acid (DL); methanesulfonic acid; naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid.

In some embodiments, a compound of Formula (I) is prepared as a chloride salt, sulfate salt, bromide salt, mesylate salt, maleate salt, citrate salt or phosphate salt.

In some embodiments, pharmaceutically acceptable salts are obtained by reacting a compound of Formula (I) with a base. In some embodiments, the compound of Formula (I) is acidic and is reacted with a base. In such situations, an acidic proton of the compound of Formula (I) is replaced by a metal ion, e.g., lithium, sodium, potassium, magnesium, calcium, or an aluminum ion. In some cases, compounds described herein coordinate with an organic base, such as, but not limited to, ethanolamine, diethanolamine, triethanolamine, tromethamine, meglumine, N-methylglucamine, dicyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, magnesium salt, meglumine salt, N-methylglucamine salt or ammonium salt.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

The methods and formulations described herein include the use of N-oxides (if appropriate), or pharmaceutically acceptable salts of compounds having the structure of Formula (I), as well as active metabolites of these compounds having the same type of activity.

In some embodiments, sites on the organic radicals (e.g. alkyl groups, aromatic rings) of compounds of Formula (I) are susceptible to various metabolic reactions. Incorporation of appropriate substituents on the organic radicals will reduce, minimize or eliminate this metabolic pathway. In specific embodiments, the appropriate substituent to decrease or eliminate the susceptibility of the aromatic ring to metabolic reactions is, by way of example only, a halogen, deuterium, an alkyl group, a haloalkyl group, or a deuteroalkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine chlorine, iodine, phosphorus, such as, for example, $^{2}H$, $^{3}H$, $^{13}C$, $^{14}C$, $^{15}N$, $^{18}O$, $^{17}O$, $^{35}S$, $^{18}F$, $^{36}Cl$, $^{123}I$, $^{124}I$, $^{125}I$, $^{131}I$, $^{32}P$ and $^{33}P$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In some embodiments, the compounds of Formula (I) possess one or more stereocenters and each stereocenter exists independently in either the R or S configuration. In some embodiments, the compound of Formula (I) exists in the R configuration. In some embodiments, the compound of Formula (I) exists in the S configuration. The compounds presented herein include all diastereomeric, individual enantiomers, atropisomers, and epimeric forms as well as the appropriate mixtures thereof. The compounds and methods provided herein include all cis, trans, syn, anti, entgegen (E), and zusammen (Z) isomers as well as the appropriate mixtures thereof.

Individual stereoisomers are obtained, if desired, by methods such as, stereoselective synthesis and/or the separation of stereoisomers by chiral chromatographic columns or the separation of diastereomers by either non-chiral or chiral chromatographic columns or crystallization and recrystallization in a proper solvent or a mixture of solvents. In certain embodiments, compounds of Formula (I) are prepared as their individual stereoisomers by reacting a racemic mixture of the compound with an optically active resolving agent to form a pair of diastereoisomeric compounds/salts, separating the diastereomers and recovering the optically pure individual enantiomers. In some embodiments, resolution of individual enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In some embodiments, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they are easier to administer than the parent drug. They are, for instance, bioavailable by oral administration whereas the parent is not. Further or alternatively, the prodrug also has improved solubility in pharmaceutical compositions over the parent drug. In some embodiments, the design of a prodrug increases the effective water solubility. An example, without limitation, of a prodrug is a compound described herein, which is administered as an ester (the "prodrug") but then is metabolically hydrolyzed to provide the active entity. A further example of a prodrug is a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of the compounds described herein include, but are not limited to, esters, ethers, carbonates, thiocarbonates, N-acyl derivatives, N-acyloxyalkyl derivatives, N-alkyloxyacyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like. In some embodiments, a hydroxyl group in the compounds disclosed herein is a prodrug wherein the hydroxyl is then metabolized in vivo to provide a carboxylic acid group. In some embodiments, a carboxyl group is used to provide an ester or amide (i.e. the prodrug), which is then metabolized in vivo to provide a carboxylic acid group. In some embodiments, compounds described herein are prepared as alkyl ester prodrugs.

Prodrug forms of the herein described compounds, wherein the prodrug is metabolized in vivo to produce a compound of Formula (I) as set forth herein are included within the scope of the claims. In some cases, some of the herein-described compounds is a prodrug for another derivative or active compound.

In some embodiments, any one of the hydroxyl group(s), amino group(s) and/or carboxylic acid group(s) are functionalized in a suitable manner to provide a prodrug moiety. In some embodiments, the prodrug moiety is as described above.

In additional or further embodiments, the compounds described herein are metabolized upon administration to an organism in need to produce a metabolite that is then used to produce a desired effect, including a desired therapeutic effect.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulfhydryl groups. Metabolites of the compounds disclosed herein are optionally identified either by administration of compounds to a host and analysis of tissue samples from the host, or by incubation of compounds with hepatic cells in vitro and analysis of the resulting compounds.

In some instances, heterocyclic rings may exist in tautomeric forms. In such situations, it is understood that the structures of said compounds are illustrated or named in one tautomeric form but could be illustrated or named in the alternative tautomeric form. The alternative tautomeric forms are expressly included in this disclosure, such as, for example, the structures illustrated below. For example, benzimidazoles or imidazoles could exist in the following tautomeric forms:

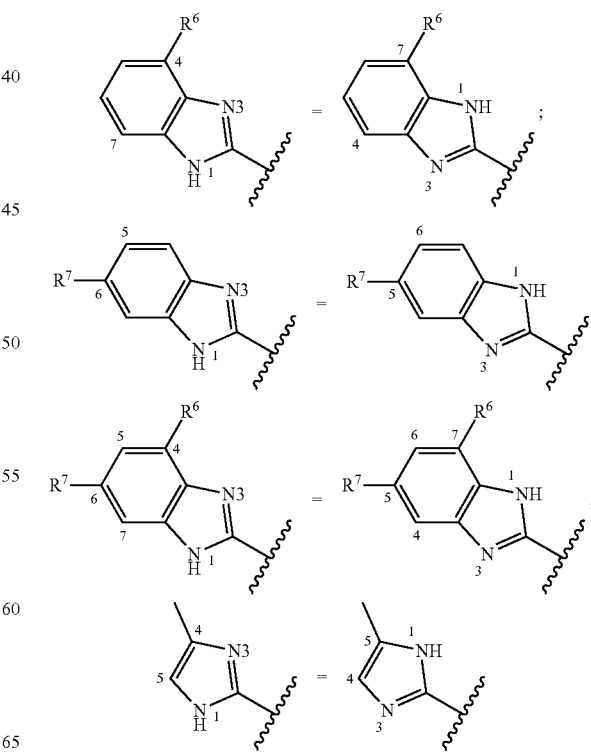

Synthesis of Compounds

Compounds of Formula (I) described herein are synthesized using standard synthetic techniques or using methods known in the art in combination with methods described herein.

Unless otherwise indicated, conventional methods of mass spectroscopy, NMR, HPLC are employed.

Compounds are prepared using standard organic chemistry techniques such as those described in, for example, March's Advanced Organic Chemistry, 6$^{th}$ Edition, John Wiley and Sons, Inc. Alternative reaction conditions for the synthetic transformations described herein may be employed such as variation of solvent, reaction temperature, reaction time, as well as different chemical reagents and other reaction conditions.

In some other embodiments, compounds described herein are prepared as described in Scheme A.

Scheme A

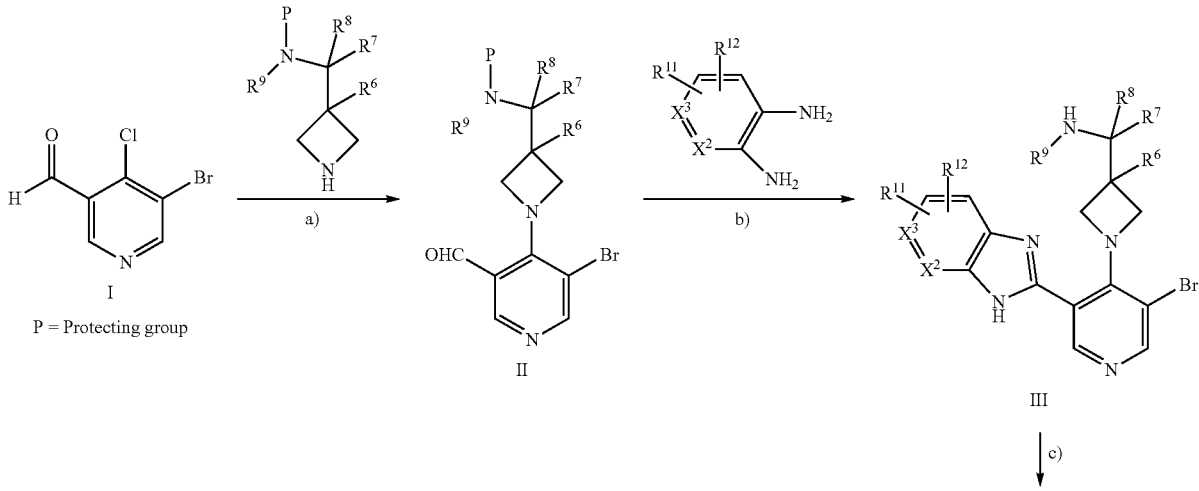

P = Protecting group

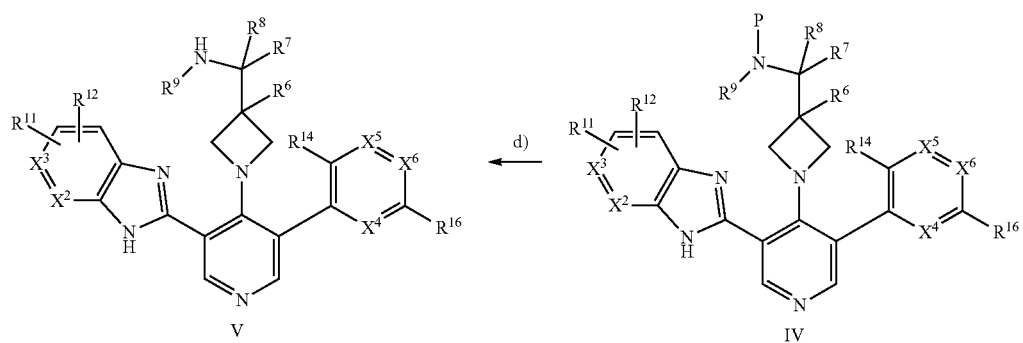

a) DIPEA, THF; b) DMF/H$_2$O, Air; c) boronic acid/ester, Pd; d) de-protection

Nucleophilic substitution of I by protected aminoazetidine afforded intermediate II. Compound II was treated with 1,2-diaminobenzenes by heating in wet DMF or NMP or DMSO or other solvents with or without Na₂S₂O₅ under atmospheric oxygen to yield intermediate III. Subsequently, compound III was converted to intermediate IV by an organometallic coupling reaction such as Suzuki-Miyaura reaction, which undergoes de-protection to afford compound V.

In some other embodiments, compounds described herein are prepared as described in Scheme B.

Scheme B

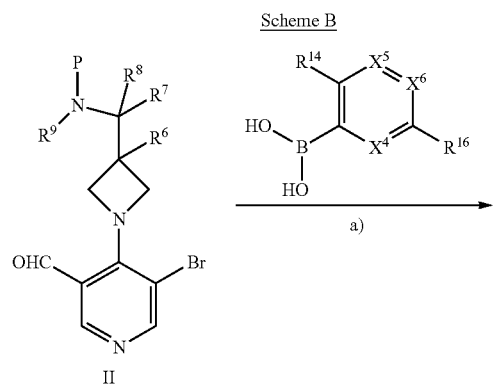

P = protecting group

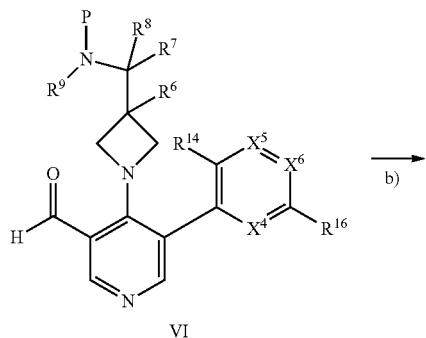

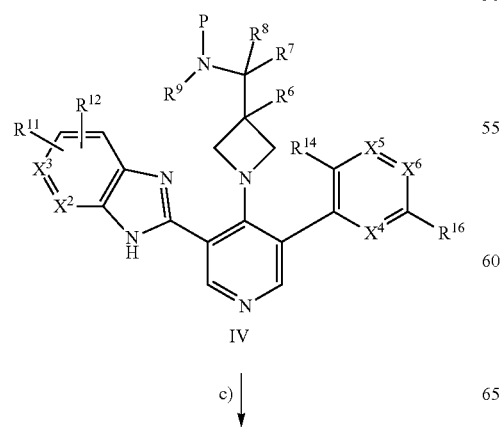

-continued

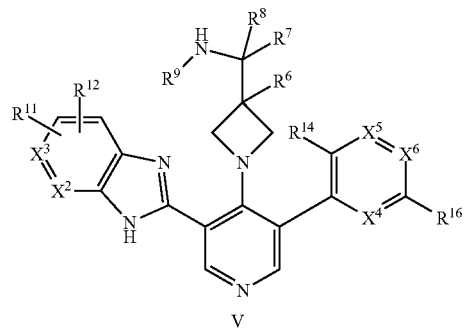

a) boronic acid/ester, Pd; b) DMF/H₂O, Air; c) de-protection

Intermediate II first undergoes organometallic coupling reaction such as Suzuki-Miyaura reaction to produce aldehyde VI, which then reacted with corresponding 1,2-diaminobenzenes to generate benzimidazole intermediate IV by heating in wet DMF or NMP or DMSO or other solvents with or without Na₂S₂O₅ under atmospheric oxygen. Subsequent removal of the protecting group using appropriate de-protection methods yielded compound V.

In some other embodiments, compounds described herein are prepared as described in Scheme C.

Scheme C

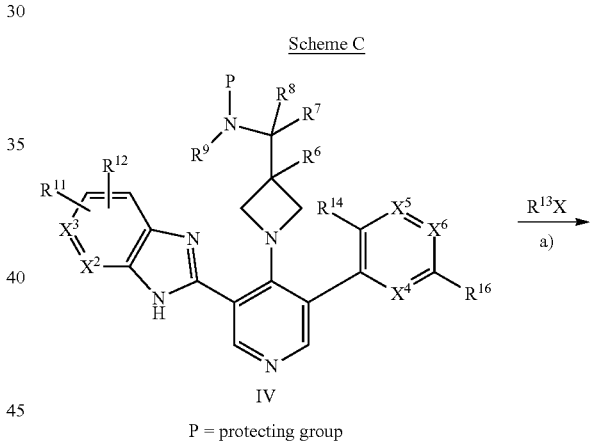

P = protecting group

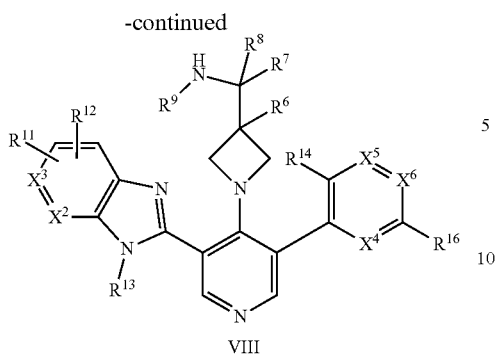

VIII a) NaOH, R¹³X; d) de-protection;

Intermediate IV can be treated with alkyl halides in the presence of base such as NaOH to give intermediate VII, which further undergoes de-protection to afford final compound VIII.

In some other embodiments, compounds described herein are prepared as described in Scheme D.

Scheme D

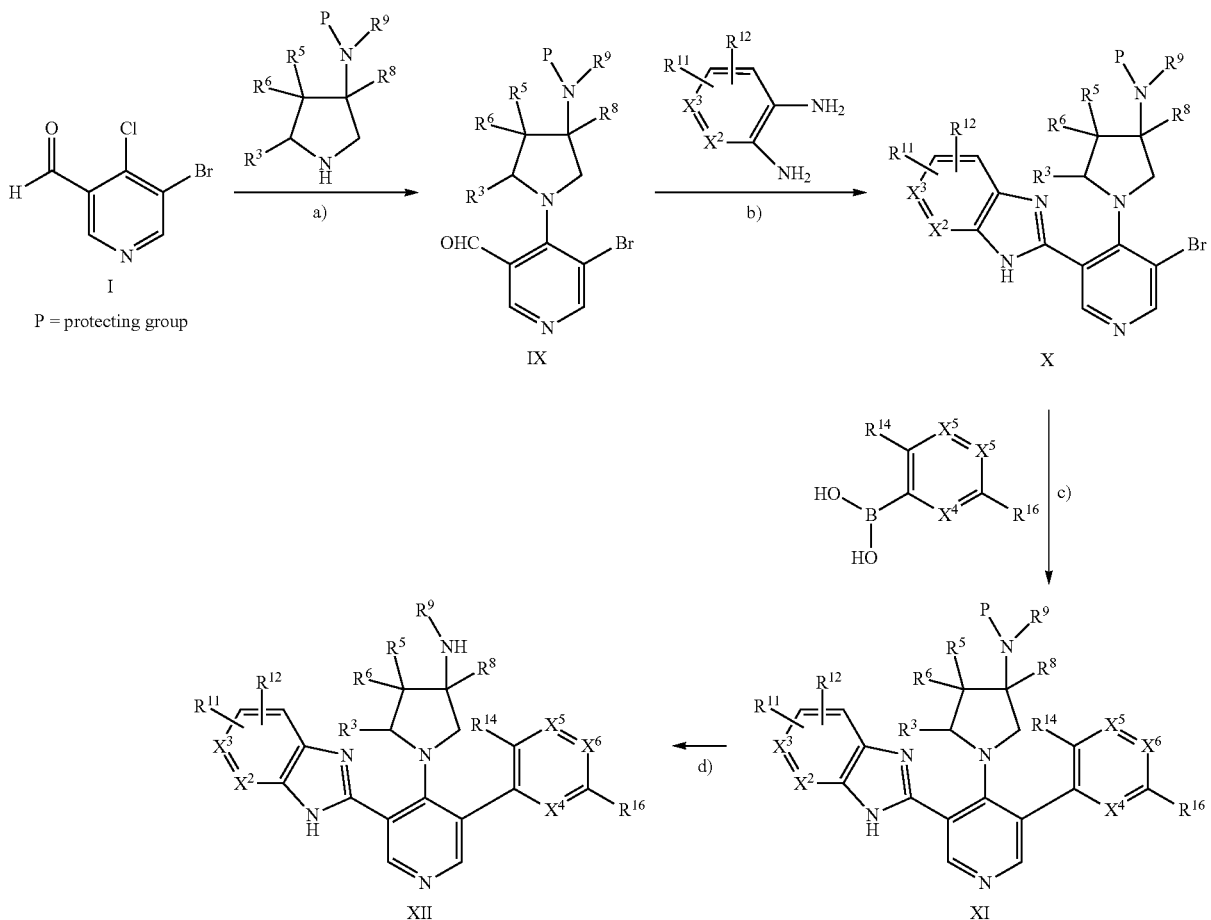

a) DIPEA, THF; b) DMF/H₂O, Air; c) boronic acid/ester, Pd; d) de-protection;

Nucleophilic substitution of I with protected aminopyrrolidine afforded intermediate IX. Compound IX was treated with 1,2-diaminobenzenes by heating in wet DMF or NMP or DMSO or other solvents with or without Na$_2$S$_2$O$_5$ under atmospheric oxygen to yield intermediate X. Subsequently, compound X was converted to intermediate XI by an organometallic coupling reaction such as Suzuki-Miyaura reaction. Removal of the protecting group using appropriate de-protection methods yielded final compound XII.

In some other embodiments, compounds described herein are prepared as described in Scheme E.

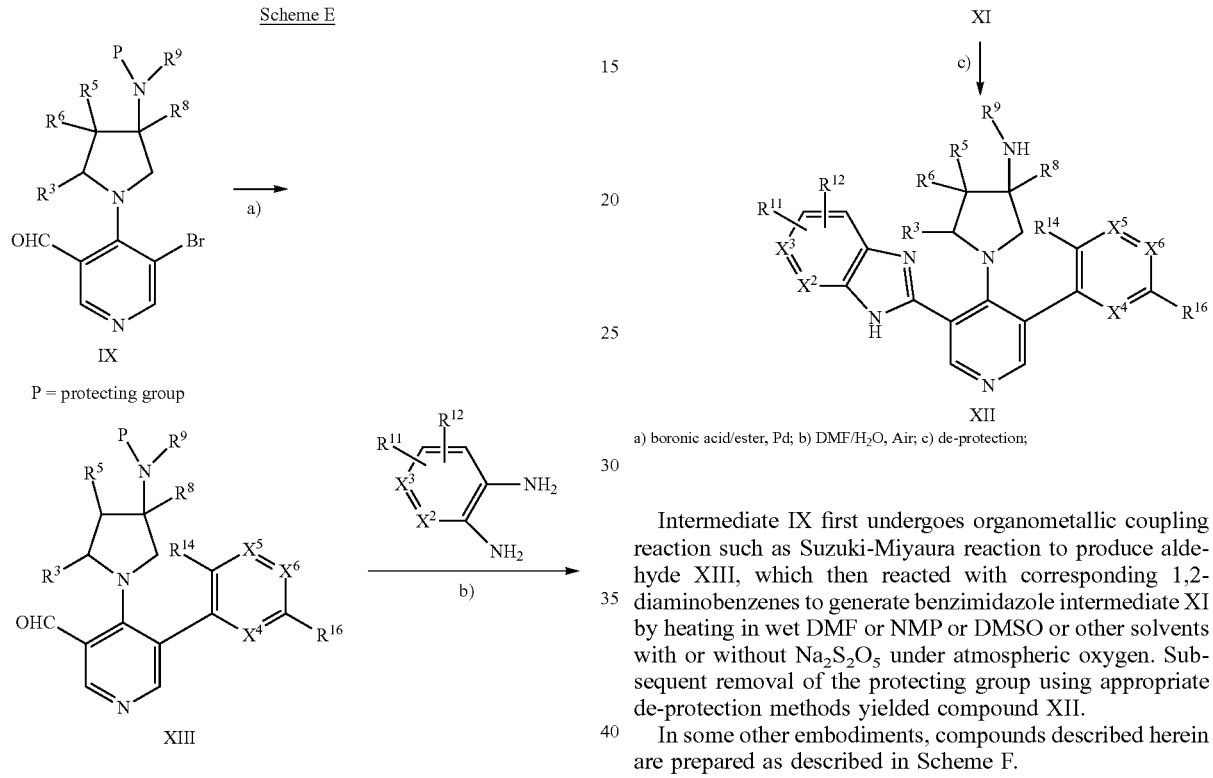

Intermediate IX first undergoes organometallic coupling reaction such as Suzuki-Miyaura reaction to produce aldehyde XIII, which then reacted with corresponding 1,2-diaminobenzenes to generate benzimidazole intermediate XI by heating in wet DMF or NMP or DMSO or other solvents with or without Na$_2$S$_2$O$_5$ under atmospheric oxygen. Subsequent removal of the protecting group using appropriate de-protection methods yielded compound XII.

In some other embodiments, compounds described herein are prepared as described in Scheme F.

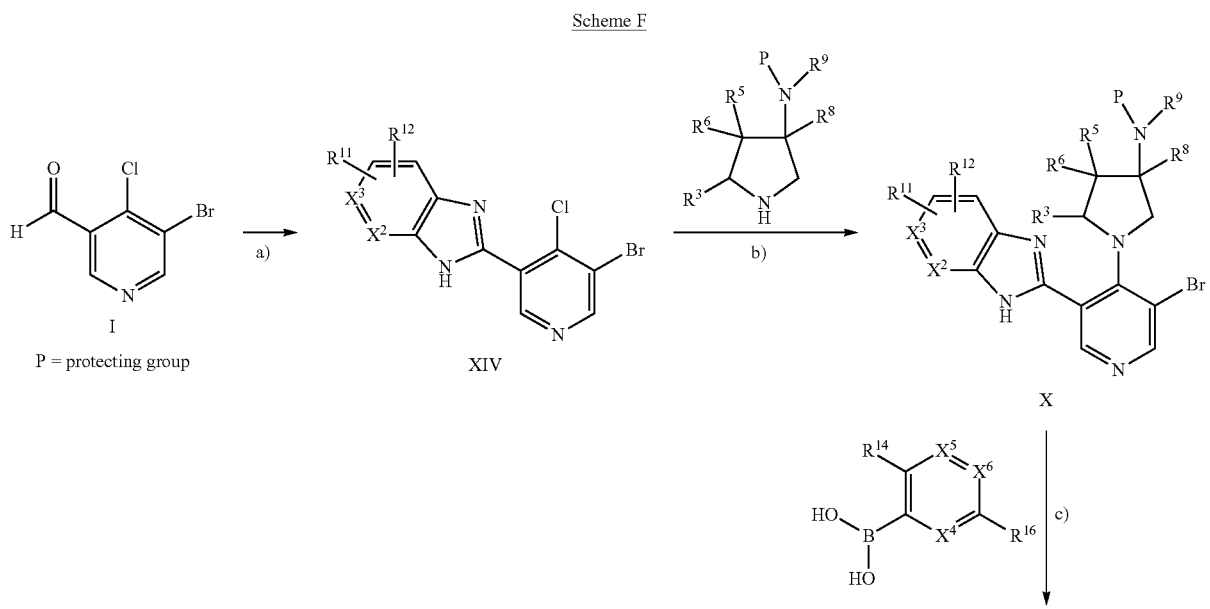

-continued

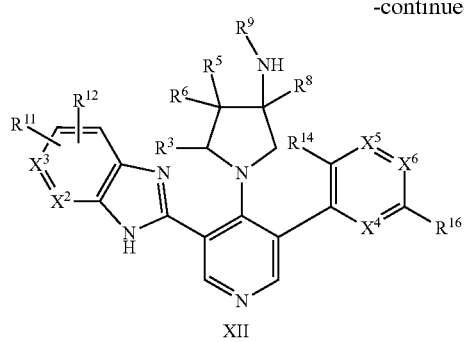
XII

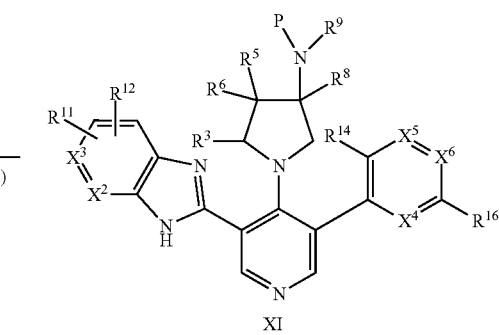
XI a) DMF/H₂O, Air; b) DIPEA, THF; c) boronic acid/ester, Pd; d) de-protection;

Compound I can react with 1,2-diaminobenzenes by heating in wet DMF or NMP or DMSO or other solvents with or without $Na_2S_2O_5$ under atmospheric oxygen to afford intermediate XIV, which undergoes nucleophilic substitution with protected 3-aminopyrrolidine to generate intermediate X. Subsequently, compound X was converted to intermediate XI by an organometallic coupling reaction such as Suzuki-Miyaura reaction. Removal of the protecting group using appropriate de-protection methods yielded compound XII.

-continued

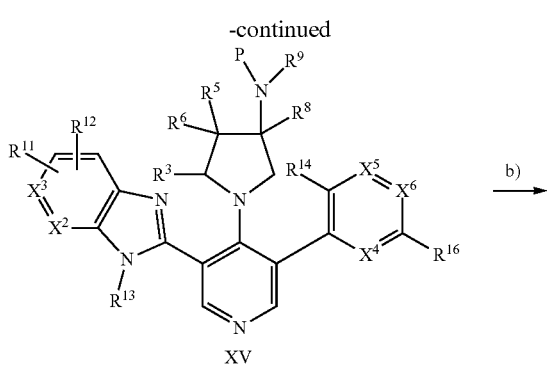
XV

In some other embodiments, compounds described herein are prepared as described in Scheme G.

Scheme G

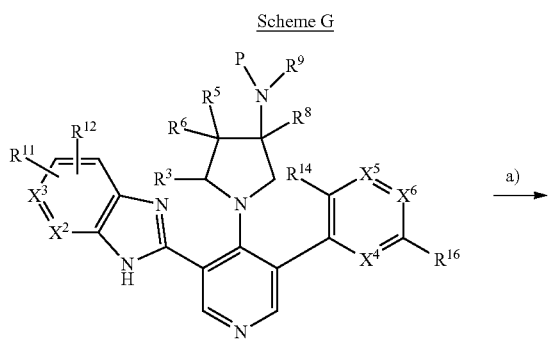
XI

P = protecting group

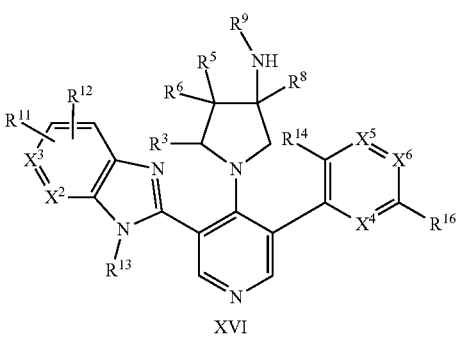
XVI a) NaOH, $R^{13}X$; b) de-protection;

Intermediate XI can be treated with alkyl halides in the presence of base such as NaOH to give intermediate XV, which further undergoes de-protection to afford final compound XVI.

In some other embodiments, compounds described herein are prepared as described in Scheme H.

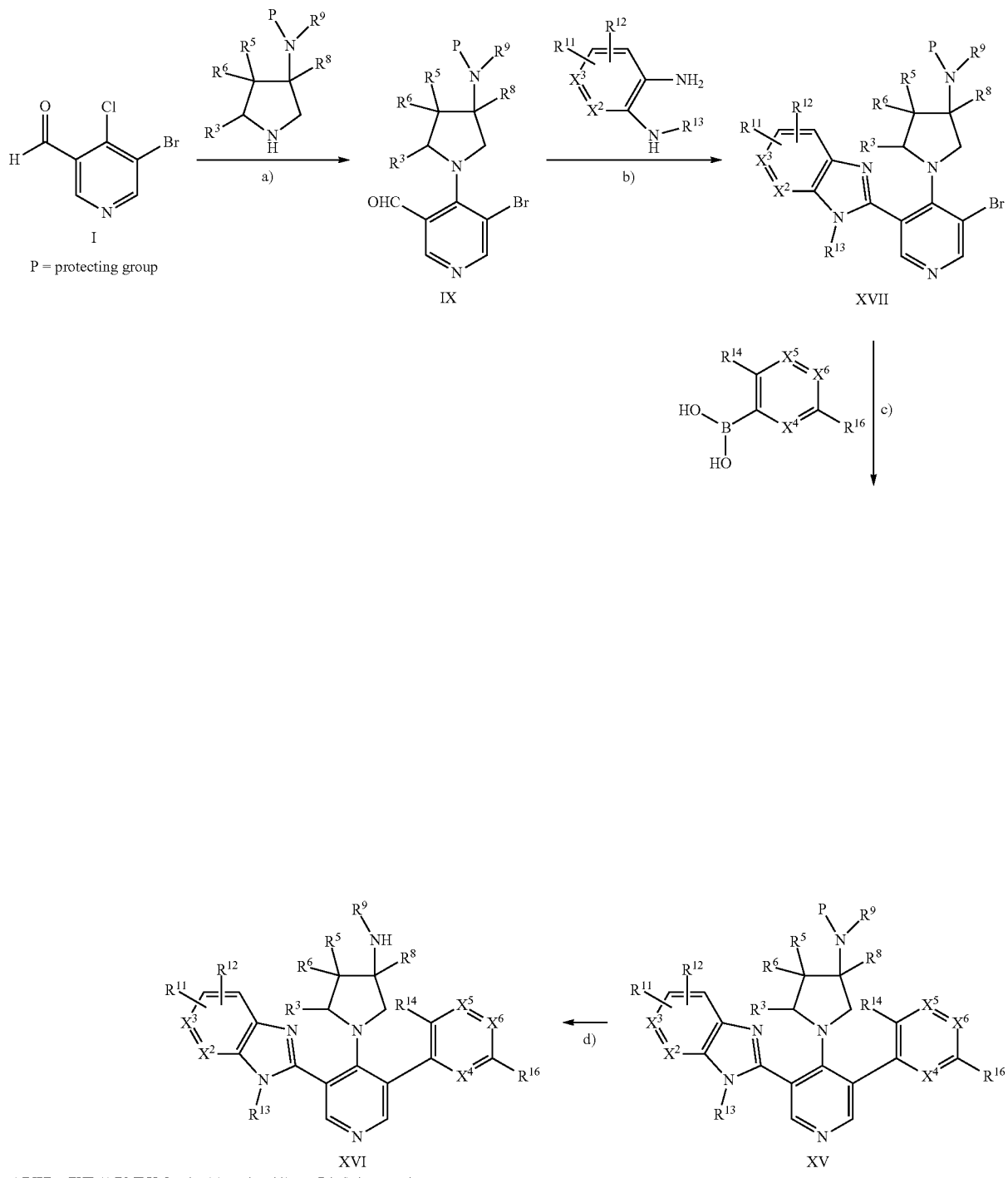

a) DIPEA, THF; b) DMF/H₂O, Air; c) boronic acid/ester, Pd; d) de-protection;

Nucleophilic substitution of I with protected aminopyrrolidine afforded intermediate IX. Compound IX was treated with substituted 1,2-diaminobenzenes by heating in wet DMF or NMP or DMSO or other solvents with or without $Na_2S_2O_5$ under atmospheric oxygen to yield intermediate XVII. Subsequently, compound XVII was converted to intermediate XV by an organometallic coupling reaction such as Suzuki-Miyaura reaction. Removal of the protecting group using appropriate de-protection methods yielded final compound XVI.

In some other embodiments, compounds described herein are prepared as described in Scheme I.

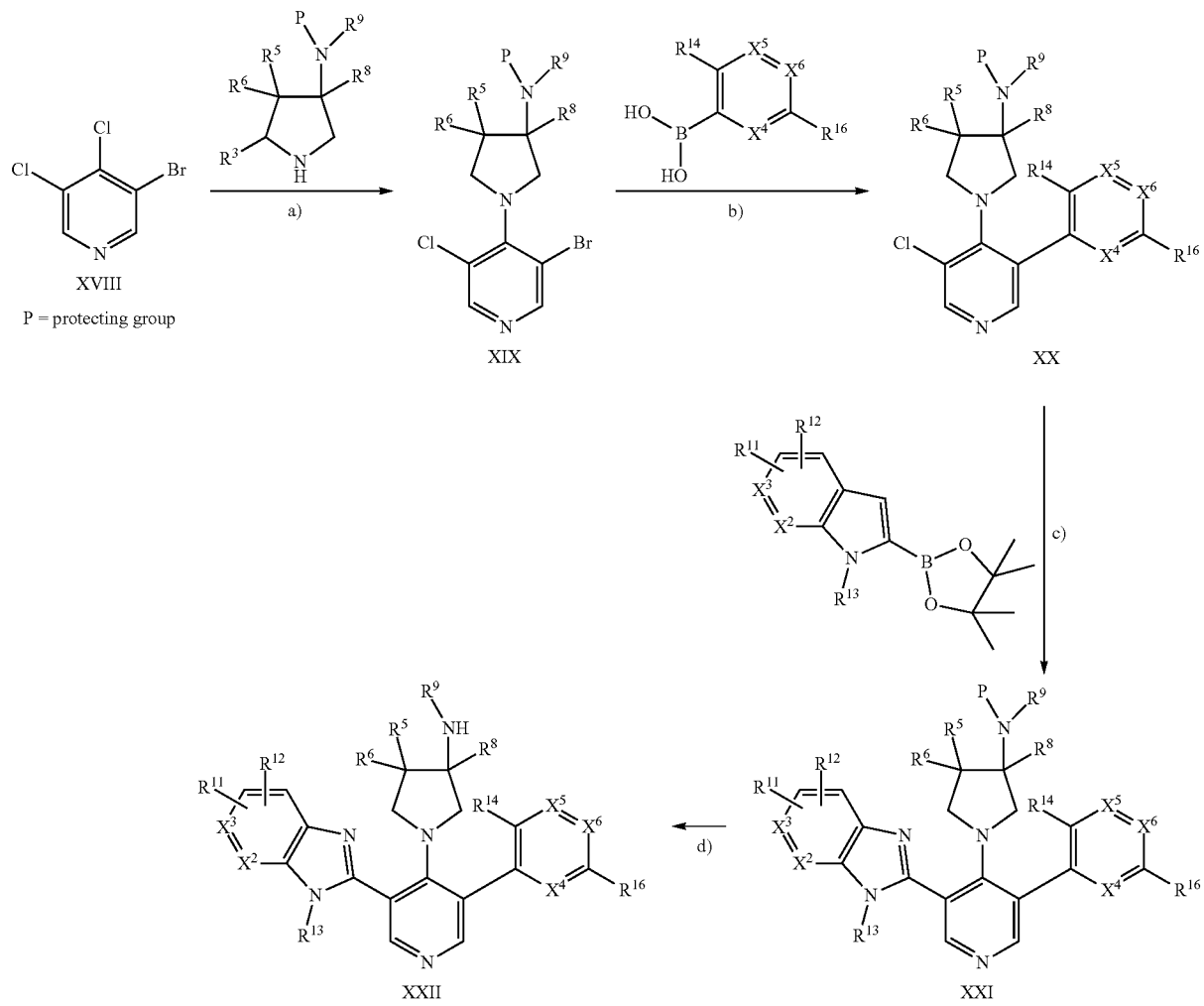

Scheme I a) DIPEA, DMSO; b) boronic acid/ester, Pd; c) boronic acid/ester, Pd; d) de-protection;

Nucleophilic substitution of XVIII with protected aminopyrrolidine afforded intermediate XIX which undergoes organometallic coupling reaction such as Suzuki-Miyaura reaction to produce XX. Compound XX can be converted to intermediate XXI by another organometallic coupling reaction such as Suzuki-Miyaura reaction. Removal of the protecting group using appropriate de-protection methods yielded final compound XXII.

In some embodiments, compounds are prepared as described in the Examples.

Certain Terminology

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

As used herein, $C_1$-$C_x$ includes $C_1$-$C_2$, $C_1$-$C_3$ . . . $C_1$-$C_x$. By way of example only, a group designated as "$C_1$-$C_6$" indicates that there are one to six carbon atoms in the moiety, i.e. groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

An "alkyl" group refers to an aliphatic hydrocarbon group. The alkyl group is branched or straight chain. In some embodiments, the "alkyl" group has 1 to 10 carbon atoms, i.e. a $C_1$-$C_{10}$alkyl. Whenever it appears herein, a numerical range such as "1 to 10" refers to each integer in the given range; e.g., "1 to 10 carbon atoms" means that the alkyl group consist of 1 carbon atom, 2 carbon atoms, 3 carbon atoms, etc., up to and including 10 carbon atoms, although the present definition also covers the occurrence of the term "alkyl" where no numerical range is designated. In some embodiments, an alkyl is a $C_1$-$C_6$alkyl. In one aspect the alkyl is methyl, ethyl, propyl, iso-propyl, n-butyl, iso-butyl, sec-butyl, or t-butyl. Typical alkyl groups include, but are in no way limited to, methyl, ethyl, propyl, isopropyl, butyl, isobutyl, sec-butyl, tertiary butyl, pentyl, neopentyl, or hexyl.

An "alkylene" group refers to a divalent alkyl radical. Any of the above mentioned monovalent alkyl groups may be an alkylene by abstraction of a second hydrogen atom from the alkyl. In some embodiments, an alkelene is a $C_1$-$C_6$alkylene. In other embodiments, an alkylene is a $C_1$-$C_4$alkylene. Typical alkylene groups include, but are not limited to, —$CH_2$—, —$CH_2CH_2$—, —$CH_2CH_2CH_2$—, —$CH_2CH_2CH_2CH_2$—, and the like. In some embodiments, an alkylene is —$CH_2$—.

An "alkoxy" group refers to a (alkyl)O— group, where alkyl is as defined herein.

The term "alkylamine" refers to the —N(alkyl)$_x$H$_y$ group, where x is 0 and y is 2, or where x is 1 and y is 1, or where x is 2 and y is 0.

An "hydroxyalkyl" refers to an alkyl in which one hydrogen atom is replaced by a hydroxyl. In some embodiments, a hydroxyalkyl is a $C_1$-$C_4$hydroxyalkyl. Typical hydroxyalkyl groups include, but are not limited to, —$CH_2OH$, —$CH_2CH_2OH$, —$CH_2CH_2CH_2OH$, —$CH_2CH_2CH_2CH_2OH$, and the like.

An "aminoalkyl" refers to an alkyl in which one hydrogen atom is replaced by an amino. In some embodiments, aminoalkyl is a $C_1$-$C_4$aminoalkyl. Typical aminoalkyl groups include, but are not limited to, —$CH_2NH_2$, —$CH_2CH_2NH_2$, —$CH_2CH_2CH_2NH_2$, —$CH_2CH_2CH_2CH_2NH_2$, and the like.

The term "alkenyl" refers to a type of alkyl group in which at least one carbon-carbon double bond is present. In one embodiment, an alkenyl group has the formula —C(R)=CR$_2$, wherein R refers to the remaining portions of the alkenyl group, which may be the same or different. In some embodiments, R is H or an alkyl. In some embodiments, an alkenyl is selected from ethenyl (i.e., vinyl), propenyl (i.e., allyl), butenyl, pentenyl, pentadienyl, and the like. Non-limiting examples of an alkenyl group include —CH═CH$_2$, —C(CH$_3$)═CH$_2$, —CH═CHCH$_3$, —C(CH$_3$)═CHCH$_3$, and —CH$_2$CH═CH$_2$.

The term "alkynyl" refers to a type of alkyl group in which at least one carbon-carbon triple bond is present. In one embodiment, an alkenyl group has the formula —C≡C—R, wherein R refers to the remaining portions of the alkynyl group. In some embodiments, R is H or an alkyl. In some embodiments, an alkynyl is selected from ethynyl, propynyl, butynyl, pentynyl, hexynyl, and the like. Non-limiting examples of an alkynyl group include —C≡CH, —C≡CCH$_3$—C≡CCH$_2$CH$_3$, —CH$_2$C≡CH.

The term "heteroalkyl" refers to an alkyl group in which one or more skeletal atoms of the alkyl are selected from an atom other than carbon, e.g., oxygen, nitrogen (e.g. —NH——N(alkyl)-, sulfur, or combinations thereof. A heteroalkyl is attached to the rest of the molecule at a carbon atom of the heteroalkyl. In one aspect, a heteroalkyl is a $C_1$-$C_6$heteroalkyl.

The term "aromatic" refers to a planar ring having a delocalized π-electron system containing 4n+2 π electrons, where n is an integer. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" or "carbocycle" refers to a ring or ring system where the atoms forming the backbone of the ring are all carbon atoms. The term thus distinguishes carbocyclic from "heterocyclic" rings or "heterocycles" in which the ring backbone contains at least one atom which is different from carbon. In some embodiments, at least one of the two rings of a bicyclic carbocycle is aromatic. In some embodiments, both rings of a bicyclic carbocycle are aromatic. Carbocycles include aryls and cycloalkyls.

As used herein, the term "aryl" refers to an aromatic ring wherein each of the atoms forming the ring is a carbon atom. In one aspect, aryl is phenyl or a naphthyl. In some embodiments, an aryl is a phenyl. In some embodiments, an aryl is a phenyl, naphthyl, indanyl, indenyl, or tetrahyodronaphthyl. In some embodiments, an aryl is a $C_6$-$C_{10}$aryl. Depending on the structure, an aryl group is a monoradical or a diradical (i.e., an arylene group).

The term "cycloalkyl" refers to a monocyclic or polycyclic aliphatic, non-aromatic radical, wherein each of the atoms forming the ring (i.e. skeletal atoms) is a carbon atom. In some embodiments, cycloalkyls are spirocyclic or bridged compounds. In some embodiments, cycloalkyls are optionally fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, norbornyl and bicycle[1.1.1]pentyl. In some embodiments, a cycloalkyl is a $C_3$-$C_6$cycloalkyl.

The term "halo" or, alternatively, "halogen" or "halide" means fluoro, chloro, bromo or iodo. In some embodiments, halo is fluoro, chloro, or bromo.

The term "fluoroalkyl" refers to an alkyl in which one or more hydrogen atoms are replaced by a fluorine atom. In one aspect, a fluoralkyl is a $C_1$-$C_6$fluoroalkyl.

The term "heterocycle" or "heterocyclic" refers to heteroaromatic rings (also known as heteroaryls) and heterocycloalkyl rings containing one to four heteroatoms in the ring(s), where each heteroatom in the ring(s) is selected from O, S and N, wherein each heterocyclic group has from 3 to 10 atoms in its ring system, and with the proviso that any ring does not contain two adjacent O or S atoms. Non-aromatic heterocyclic groups (also known as heterocycloalkyls) include rings having 3 to 10 atoms in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (═O) moieties, such as pyrrolidin-2-one. In some embodiments, at least one of the two rings of a bicyclic heterocycle is aromatic. In some embodiments, both rings of a bicyclic heterocycle are aromatic.

The terms "heteroaryl" or, alternatively, "heteroaromatic" refers to an aryl group that includes one or more ring heteroatoms selected from nitrogen, oxygen and sulfur. Illustrative examples of heteroaryl groups include monocyclic heteroaryls and bicyclic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Monocyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl.

A "heterocycloalkyl" group refers to a cycloalkyl group that includes at least one heteroatom selected from nitrogen, oxygen and sulfur. In some embodiments, a heterocycloalkyl is fused with an aryl or heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. The term heterocycloalkyl also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "optionally substituted" or "substituted" means that the referenced group is optionally substituted with one or more additional group(s) individually and independently selected from halogen, —CN, —NH$_2$, —NH(alkyl), —N(alkyl)$_2$, —OH, —CO$_2$H, —CO$_2$alkyl, —C(═O)NH$_2$, —C(═O)NH(alkyl), —C(═O)N(alkyl)$_2$, —S(═O)$_2$NH$_2$, —S(═O)$_2$NH(alkyl), —S(═O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from halogen, —CN, —NH$_2$, —NH(CH$_3$), —N(CH$_3$)$_2$, 13 OH, —CO$_2$H, —CO$_2$(C$_1$-C$_4$alkyl), —C(═O)NH$_2$, —C(═O)NH(C$_1$-C$_4$alkyl), —C(═O)N(C$_1$-C$_4$alkyl)$_2$, —S(═O)$_2$NH$_2$, —S(═O)$_2$NH(C$_1$-C$_4$alkyl), —S(═O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, –SC$_1$-C$_4$alkyl, —S(═O)C$_1$-C$_4$alkyl, and —S(═O)$_2$C$_1$-C$_4$alkyl. In some embodiments, optional substituents are independently selected from halogen, —CN, —NH$_2$, —OH, —NH(CH$_3$), —N(CH$_3$)$_2$, —CH$_3$, —CH$_2$CH$_3$, —CF$_3$, —OCH$_3$, and —OCF$_3$. In some embodiments, substituted groups are substituted with one or two of the preceding groups. In some embodiments, an optional substituent on an aliphatic carbon atom (acyclic or cyclic) includes oxo (═O).

In some embodiments, each substituted alkyl, substituted fluoroalkyl, substituted heteroalkyl, substituted carbocycle, and substituted heterocycle is substituted with one or more RS groups independently selected from the group consisting of halogen, C$_1$-C$_6$alkyl, monocyclic carbocycle, monocyclic heterocycle, —CN, —OR$^{16}$, —CO$_2$R$^{16}$, —C(═O)N(R$^{16}$)$_2$, —N(R$^{16}$)$_2$, —NR$^{16}$C(═O)R$^{17}$, —SR$^{16}$, —S(═O)R$^{17}$, —SO$_2$R$^{17}$, or —SO$_2$N(R$^{16}$)$_2$; each R$^{16}$ is independently selected from hydrogen, C$_1$-C$_6$alkyl, C$_1$-C$_6$heteroalkyl, C$_3$-C$_6$cycloalkyl, C$_2$-C$_6$heterocycloalkyl, phenyl, benzyl, 5-membered heteroaryl and 6-membered heteroaryl; or two R$^{16}$ groups are taken together with the N atom to which they are attached to form a N-containing heterocycle; each R$^{17}$ is independently selected from C$_1$-C$_6$alkyl, C$_1$-C$_6$heteroalkyl, C$_3$-C$_6$cycloalkyl, C$_2$-C$_6$heterocycloalkyl, phenyl, benzyl, 5-membered heteroaryl and 6-membered heteroaryl.

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an agonist.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formula (I), or a pharmaceutically acceptable salt thereof, and a co-agent, are both administered to a patient simultaneously in the form of a single entity or dosage. The term "non-fixed combination" means that the active ingredients, e.g. a compound of Formula (I), or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "article of manufacture" and "kit" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the compounds described herein are administered either alone or in combination with pharmaceutically acceptable carriers, excipients or diluents, in a pharmaceutical composition. Administration of the compounds and compositions described herein can be effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, compounds described herein can be administered locally to the area in need of treatment, by for example, local infusion during surgery, topical application such as creams or ointments, injection, catheter, or implant. The administration can also be by direct injection at the site of a diseased tissue or organ.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi- dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non- aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical compositions may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Pharmaceutical compositions suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation.

Pharmaceutical compositions for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

It should be understood that in addition to the ingredients particularly mentioned above, the compounds and compositions described herein may include other agents conventional in the art having regard to the type of formulation in question, for example those suitable for oral administration may include flavoring agents.

Methods of Dosing and Treatment Regimens

In one embodiment, the compounds of Formula (I), or a pharmaceutically acceptable salt thereof, are used in the preparation of medicaments for the treatment of diseases or conditions in a mammal that would benefit from modulation of somatostatin activity. Methods for treating any of the diseases or conditions described herein in a mammal in need of such treatment, involves administration of pharmaceutical compositions that include at least one compound of Formula (I) or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound of Formula (I), or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-2000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound of Formula (I), or a pharmaceutically acceptable salt thereof, described herein are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound of Formula (I), or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non- systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

Combination Treatments

In certain instances, it is appropriate to administer at least one compound of Formula (I), or a pharmaceutically acceptable salt thereof, in combination with one or more other therapeutic agents.

In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another agent (which also includes a therapeutic regimen) that also has therapeutic benefit.

In one specific embodiment, a compound of Formula (I), or a pharmaceutically acceptable salt thereof, is co-administered with a second therapeutic agent, wherein the compound of Formula (I), or a pharmaceutically acceptable salt thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient is simply be additive of the two therapeutic agents or the patient experiences a synergistic benefit.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds of Formula (I), or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject.

EXAMPLES

As used above, and throughout the description of the invention, the following abbreviations, unless otherwise indicated, shall be understood to have the following meanings:

Abbreviations:
Pd(PPh$_3$)4: tetrakis(triphenylphosphine)palladium(0);
Pd(dppf)Cl$_2$: [1,1'-bis(diphenylphosphino)ferrocene]palladium(II) dichloride;
Pd(PPh3)$_2$Cl$_2$: bis(triphenylphosphine)palladium(II) dichloride;
PdAMphos or Pd (amphos)Cl$_2$: bis(di-tert-butyl(4-dimethylaminophenyl)phosphine)dichloropalladium(II);
Pd(DtBPF)Cl$_2$: [1,1'-Bis(di-tert-butylphosphino)ferrocene]dichloropalladium(II);
P(t-Bu)3: tri-tert-buytlphosphine;
HBF$_4$: tetrafluoroboric acid;
DBU: 1,8-diazabicyclo[5.4.0]undec-7-ene;
DIEA: N,N-diisopropylethylamine;
Prep-HPLC: preparative high performance liquid chromatography;
LCMS: Liquid chromatography-mass spectrometry
MS: mass spectrometry
AcOH : acetic acid
TFA: trifluoroacetic acid;
HCl: hydrochloric acid or hydrochloride;
MeCN or CH$_3$CN or ACN: acetonitrile;
H$_2$O: water;
DMSO: dimethyl sulfoxide;
DMF: dimethylformamide
DCM: dichloromethane
NBS: N-bromosuccinimide;
Br$_2$: bromine;
NCS: N-Chlorosuccinimide
rt: room temperature;
SST: somatostatin;
SSTR: somatostatin receptor;
TBAF: tetrabutylammonium fluoride;
hrs: hours;
h or hr: hour;
min: minute
N$_2$: nitrogen gas;
mg: milligrams;
mL: milliliter;
eq. or equiv: equivalents;
mmol: millimole
ppts: precipitates;
K$_2$CO$_3$: potassium carbonate
NaHCO$_3$: sodium bicarbonate
OsO$_4$: osmium tetraoxide
t-BuOH: tert-butyl alcohol
EtOAc: ethyl acetate
Na$_2$SO$_4$: sodium sulfate The following examples are provided for illustrative purposes only and not to limit the scope of the claims provided herein.

Synthesis of Compounds

Example 1. 1-{1-[3-(4-fluoro-1H-1,3-benzodiazol-2-yl)-5-(3-fluoro-5-methylphenyl)pyridin-4-yl]azetidin-3-yl}methanamine (Compound 1-2)

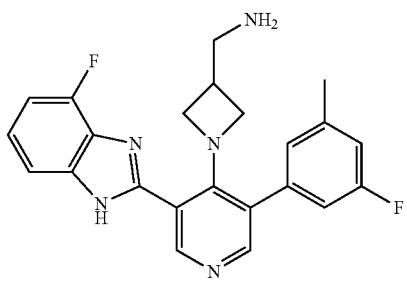 [SMILES: Cc1cc(F)cc(-c2cncc(-c3nc4c(F)cccc4[nH]3)c2N2CC(CN)C2)c1]

Step 1-1, preparation of tert-butyl N-{[1-(3-bromo-5-formylpyridin-4-yl)azetidin-3-yl]methyl}carbamate: to a 100-mL round-bottom flask was placed 5-bromo-4-chloropyridine-3-carbaldehyde (1.0 equiv, 9.1 mmol, 2.0 g,), THF (25 mL), TEA (2.0 equiv, 18.14 mmol, 1.8 g) and tert-butyl N-(azetidin-3-ylmethyl)carbamate (1.2 equiv, 10.7 mmol, 2.0 g). The resulting solution was purged with nitrogen and stirred at 70° C. for overnight. The reaction mixture was concentrated and purified by silica gel column chromatography eluting with ethyl acetate/petroleum ether to afford 2.1 g (63%) of tert-butyl N-[[1-(3-bromo-5-formylpyridin-4-yl)azetidin-3-yl]methyl]carbamate as a yellow solid. LCMS (M+H)$^+$=370.1, 372.1.

Step 1-2, preparation of tert-butyl N-([1-[3-(3-fluoro-5-methylphenyl)-5-formylpyridin-4-yl]azetidin-3-yl]methyl) carbamate: to a 250-mL round-bottom flask was placed tert-butyl N-[[1-(3-bromo-5-formylpyridin-4-yl)azetidin-3-yl]methyl]carbamate (1.0 equiv, 5.4 mmol, 2 g), 3-fluoro- 5-methylphenyl)boronic acid (1.2 equiv, 6.5 mmol, 1.0 g), K$_3$PO$_4$ (3.0 equiv,), 22.1 mmol, 4.7 g), Pd$_2$(dba)$_3$CHCl$_3$ (0.05 equiv, 0.27 mmol, 280 mg), P(t-Bu)$_3$HBF$_4$ (0.10 equiv, 0.54 mmol, 157 mg), 1,4-dioxane (20 mL) and water (2.0 mL). The resulting solution was purged with nitrogen and stirred at 70° C. for 1 h. The reaction mixture was filtered and the filtrate was concentrated under vacuum. The residue was applied onto a silica gel column eluting with ethyl acetate/petroleum ether to afford 2.1 g (97%) of tert-butyl N-([1-[3-(3-fluoro-5-methylphenyl)-5-formylpyridin-4-yl]azetidin-3-yl]methyl)carbamate as a yellow solid. LCMS (M+H)$^+$=400.2.

Step 1-3, preparation of tert-butyl N-([1-[3-(4-fluoro-1H-1,3-benzodiazol-2-yl)-5-(3-fluoro-5-methylphenyl)pyridin-4-yl]azetidin-3-yl]methyl)carbamate: to a 8-mL vial was placed 3-fluorobenzene-1,2-diamine (3.0 equiv, 0.24 mmol, 30 mg), tert-butyl N-([1-[3-(3-fluoro-5-methylphenyl)-5-formylpyridin-4-yl]azetidin-3-yl]methyl)carbamate (1.0 equiv, 0.08 mmol, 30 mg), Na$_2$S$_2$O$_5$ (2.0 equiv, 0.16 mmol, 29 mg), and N,N-dimethylformamide (1.0 mL). The resulting solution was stirred for 3 hrs at 100° C. and cooled down to rt. The reaction mixture was filtered and the filtrate was purified by Prep-HPLC on XBridge Prep C$_{18}$ column (19× 150 mm) eluting with two mobile phases of water (0.05% TFA) and acetonitrile (from 26% acetonitrile up to 44% acetonitrile in 6 min) at the flow rate of 20 ml/min resulting in 35 mg (75%) of tert-butyl N-([1-[3-(4-fluoro-1H-1,3-benzodiazol-2-yl)-5-(3-fluoro-5-methylphenyl)pyridin-4-yl]azetidin-3-yl]methyl)carbamate as an off-white solid. LCMS (M+H)$^+$=506.4.

Step 1-4, preparation of [1-[3-(4-fluoro-1H-1,3-benzodiazol-2-yl)-5-(3-fluoro-5-methylphenyl)pyridin-4-yl]azetidin-3-yl]methanamine: to a 50-mL round-bottom flask was placed tert-butyl N-([1-[3-(4-fluoro-1H-1,3-benzodiazol-2-yl)-5-(3-fluoro-5-methylphenyl)pyridin-4-yl]azetidin-3-yl]methyl)carbamate (1.0 equiv, 0.06 mmol, 35 mg), dichloromethane (2.0 mL), and trifluoroacetic acid (1.0 mL). The resulting solution was stirred at rt for 2 hrs. The resulting mixture was concentrated under vacuum and freeze-dried which resulted in 20 mg (68%) of [1-[3-(4-fluoro-1H-1,3-benzodiazol-2-yl)-5-(3-fluoro-5-methylphenyl)pyridin-4-yl]azetidin-3-yl]methanamine trifluoroacetic acid salt as a light brown solid. LCMS (M+H)$^+$=406.1.

The following compounds were prepared similarly to Example 1 with appropriate substituting reagents and substrates at different steps and they may require additional functional group modifications on benzimidazoyl side chain via well-known chemistry with appropriate reagents. Different salt such as HCl or formic acid maybe obtained.

| Compound no. | MS (M + H)$^+$ |
| --- | --- |
| 1-1 | 406.3 |
| 1-2 | 406.1 |
| 1-3 | 422.1 |
| 1-4 | 422.1 |
| 1-5 | 413.1 |
| 1-6 | 424.1 |
| 1-7 | 424.1 |
| 1-8 | 413.1 |
| 1-9 | 402.2 |
| 1-10 | 402.2 |
| 1-11 | 418.1 |
| 1-12 | 418.2 |
| 1-13 | 424.1 |
| 1-14 | 440.2 |
| 1-15 | 436.2 |
| 1-16 | 431.1 |
| 1-17 | 431.2 |
| 1-18 | 440.1 |
| 1-19 | 420.2 |
| 1-20 | 440.1 |
| 1-21 | 428.1 |
| 1-22 | 389.2 |
| 1-23 | 389.2 |

Example 2. 1-{1-[3-(4,6-difluoro-1H-1,3-benzodiazol-2-yl)-5-phenylpyridin-4-yl]azetidin-3-yl}methanamine (Compound 1-27)

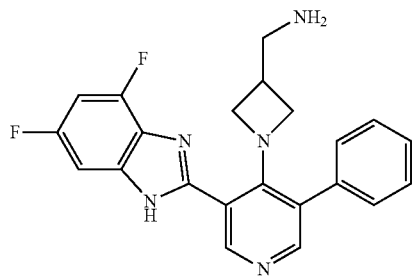 [SMILES: NCC1CN(c2c(-c3ccccc3)cncc2-c2nc3c(F)cc(F)cc3[nH]2)C1]

Step 2-1, preparation of tert-butyl N-([1-[3-bromo-5-(5,7-difluoro-1H-1,3-benzodiazol-2-yl)pyridin-4-yl]azetidin-3-yl]methyl)carbamate: to a 40-mL round-bottom flask was placed tert-butyl N-[[1-(3-bromo-5-formylpyridin-4-yl)azetidin-3-yl]methyl]carbamate (1.0 equiv, 1.1 mmol, 400 mg, Step 1-1, Example 1), 3,5-difluorobenzene-1,2-diamine (3.0 equiv, 3.33 mmol, 480 mg), Na$_2$S$_2$O$_5$ (2.0 equiv, 2.16 mmol, 400 mg) and NMP (5.0 mL). The resulting solution was stirred at 100° C. for 16 hrs. The reaction mixture was quenched with 50 mL of water and extracted with 3×20 mL of ethyl acetate. Organic layers were combined, washed with water (4×30 mL), dried over anhydrous sodium sulfate, filtered and concentrated under vacuum. The residue obtained was applied onto a silica gel column eluting with ethyl acetate/petroleum ether to afford 400 mg (75%) of tert-butyl N-([1-[3-bromo-5-(4,6-difluoro-1H-1,3-benzodiazol-2-yl)pyridin-4-yl]azetidin-3-yl]methyl)carbamate as a light brown solid. LCMS (M+H)$^+$=494.1, 496.0.

Step 2-2, preparation of tert-butyl N-([1-[3-(4,6-difluoro-1H-1,3-benzodiazol-2-yl)-5-phenylpyridin-4-yl]azetidin-3-yl]methyl)carbamate: to a 8-mL sealed tube was placed tert-butyl N-([1-[3-bromo-5-(4,6-difluoro-1H-1,3-benzodiazol-2-yl)pyridin-4-yl]azetidin-3-yl]methyl)carbamate (1.0 equiv, 0.08 mmol, 40 mg), phenylboronic acid (2.0 equiv, 0.16 mmol, 20 mg), dioxane (2.0 ml), water (0.2 mL), K$_2$CO$_3$ (3.0 equiv, 34 mg), and Pd(dppf)Cl$_2$ (0.1 equiv, 0.01 mmol, 6 mg). The resulting solution was stirred for 6 hrs at 100° C. in an oil bath. The resulting mixture was concentrated under vacuum. The crude residue was purified by Prep-HPLC on SunFire Prep C$_{18}$ OBD Column (19×150 mm, 5 μm) eluting with two mobile phases of water (0.05% TFA) and ACN at flow rate of 20 ml/min resulting in 35 mg (88%) of tert-butyl N-([1-[3-(4,6-difluoro-1H-1,3-benzodiazol-2-yl)-5-phenylpyridin-4-yl]azetidin-3-yl]methyl)carbamate as a light yellow solid. LCMS (M+H)$^+$=492.2.

Step 2-3, preparation of 1-{1-[3-(4,6-difluoro-1H-1,3-benzodiazol-2-yl)-5-phenylpyridin-4-yl]azetidin-3- yl}methanamine: to a 50-mL round-bottom flask was placed tert-butyl N-([1-[3-(4,6-difluoro-1H-1,3-benzodiazol-2-yl)-5-phenylpyridin-4-yl]azetidin-3-yl]methyl)carbamate (1.0 equiv, 0.07 mmol, 35 mg), dichloromethane (5.0 mL), and trifluoroacetic acid (1.0 mL). The resulting solution was stirred for 1 h at rt and concentrated under vacuum. The residue was dried under reduced pressure to afford 29.2 mg (81%) of TFA salt of the title product as a light brown solid. LCMS $(M+H)^+=392.2$.

The following compounds were prepared similarly to Example 2 with appropriate substituting reagents and substrates at different steps and they may require additional functional group modifications on benzimidazoyl side chain via well-known chemistry with appropriate reagents. Different salt such as HCl or formic acid maybe obtained.

| Compound no. | MS $(M + H)^+$ |
| --- | --- |
| 1-28 | 410.1 |
| 1-29 | 406.2 |
| 1-30 | 406.2 |
| 1-31 | 406.2 |
| 1-32 | 407.2 |
| 1-33 | 474.2 |
| 1-34 | 435.2 |
| 1-35 | 431.4 |
| 1-36 | 431.1 |
| 1-37 | 424.1 |
| 1-38 | 396.2 |
| 1-39 | 444.1 |
| 1-40 | 494.1 |
| 1-41 | 442.2 |
| 1-43 | 410.2 |
| 1-44 | 410.1 |
| 1-45 | 424.2 |
| 1-46 | 424.2 |
| 1-47 | 424.2 |
| 1-48 | 446.1 |
| 1-50 | 438.3 |
| 1-52 | 442.2 |
| 1-53 | 426.2 |
| 1-54 | 417.2 |
| 1-55 | 424.1 |
| 1-56 | 338.4 |
| 1-57 | 444.1 |
| 1-58 | 440.2 |
| 1-59 | 456.1 |
| 1-60 | 460.1 |
| 1-62 | 462.2 |
| 1-66 | 440.1 |
| 1-67 | 424.2 |

Example 3. 1-{1-[3-(4-fluoro-1-methyl-1H-1,3-benzodiazol-2-yl)-5-(3-fluoro-5-methylphenyl)pyridin-4-yl]azetidin-3-yl}methanamine (Compound 1-24)

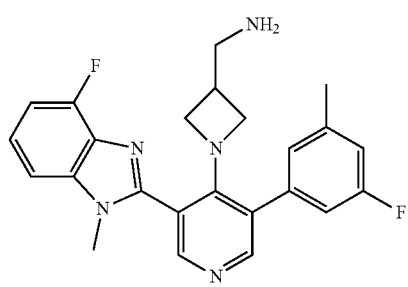 [SMILES: Cc1cc(F)cc(-c2cncc(-c3nc4c(F)cccc4n3C)c2N2CC(CN)C2)c1]

Step 3-1, preparation of tert-butyl N-([1-[3-(7-fluoro-1-methyl-1H-1,3-benzodiazol-2-yl)-5-(3-fluoro-5-methylphenyl)pyridin-4-yl]azetidin-3-yl]methyl)carbamate: to a 8-mL sealed tube was placed tert-butyl N-([1-[3-(4-fluoro-1H-1,3-benzodiazol-2-yl)-5-(3-fluoro-5-methylphenyl)pyridin-4-yl]azetidin-3-yl]methyl)carbamate (1.00 equiv, 0.25 mmol, 126 mg, "Example 1, Step 1-3"), N,N-dimethylformamide (2.0 mL), sodium hydroxide (3.00 equiv, 0.72 mmol, 29 mg), and iodomethane (1.10 equiv, 0.27 mmol, 38 mg). The resulting solution was stirred at 50° C. for 30 min in an oil bath. The reaction mixture was cooled to rt and purified by Prep-HPLC using the following conditions (Prep-HPLC-006): Column, XBridge Prep $C_{18}$ OBD Column, 19×150 mm 5 μm; mobile phase A: Water (10 mmol/L $NH_4HCO_3$+ 0.1% $NH_3$. $H_2O$); mobile phase B: ACN; gradient: B 55.0% to 65.0% in 6 min; Detector, UV 220 nm. This resulted in two compounds, 30 mg (23%) of tert-butyl N-([1-[3-(4-fluoro-1-methyl-1H-1,3-benzodiazol-2-yl)-5-(3-fluoro-5-methylphenyl)pyridin-4-yl]azetidin-3-yl]methyl)carbamate as a colorless solid, and 32 mg (25%) of tert-butyl N-([1-[3-(7-fluoro-1-methyl-1H-1,3-benzodiazol-2-yl)-5-(3-fluoro-5-methylphenyl)pyridin-4-yl]azetidin-3-yl]methyl) carbamate as a colorless solid. The former material was used for next step synthesis and the latter material was saved for the synthesis of Example 4. LCMS $(M+H)^+=520.2$ for both isomers.

Step 3-2, preparation of 1-{1-[3-(4-fluoro-1-methyl-1H-1,3-benzodiazol-2-yl)-5-(3-fluoro-5-methylphenyl)pyridin-4-yl]azetidin-3-yl}methanamine: to a 50-mL round-bottom flask was placed tert-butyl N-([1-[3-(4-fluoro-1-methyl-1H-1,3-benzodiazol-2-yl)-5-(3-fluoro-5-methylphenyl)pyridin-4-yl]azetidin-3-yl]methyl)carbamate (1.0 equiv, 0.06 mmol, 30 mg), dichloromethane (2.0 mL) and trifluoroacetic acid (1.0 mL). The resulting solution was stirred at rt for 1 h, then concentrated and dried in oven under reduced pressure to afford 19.0 mg (62%) of TFA salt of [1-[3-(4-fluoro-1-methyl-1H-1,3-benzodiazol-2-yl)-5-(3-fluoro-5-methylphenyl)pyridin-4-yl]azetidin-3-yl]methanamine as an off-white solid. LCMS $(M+H)^+=420.2$. The structure of this compound was confirmed by NOESY NMR spectroscopy.

Example 4. 1-{1-[3-(7-Fluoro-1-methyl-1H-1,3-benzodiazol-2-yl)-5-(3-fluoro-5-methylphenyl)pyridin-4-yl]azetidin-3-yl}methanamine (Compound 1-25)

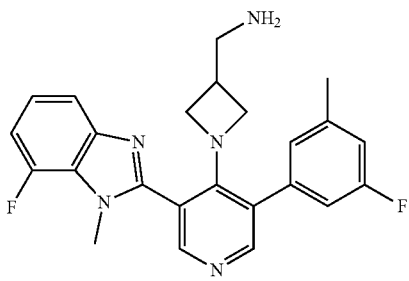 [SMILES: Cc1cc(F)cc(-c2cncc(-c3nc4cccc(F)c4n3C)c2N2CC(CN)C2)c1]

Step 4-1, preparation of 1-{1-[3-(7-fluoro-1-methyl-1H-1,3-benzodiazol-2-yl)-5-(3-fluoro-5-methylphenyl)pyridin-4-yl]azetidin-3-yl}methanamine: to a 50-mL round-bottom flask was placed tert-butyl N-([1-[3-(7-fluoro-1-methyl-1H-1,3-benzodiazol-2-yl)-5-(3-fluoro-5-methylphenyl)pyridin-4-yl]azetidin-3-yl]methyl)carbamate (1.0 equiv, 0.06 mmol, 32 mg, "Example 3, step 3-1"), dichloromethane (2.0 mL), and trifluoroacetic acid (1.0 mL). The resulting solution was stirred for 1 h at rt, concentrated and dried under reduced pressure to afford 19.6 mg (60%) of TFA salt of [1-[3-(7-fluoro-1-methyl-1H-1,3-benzodiazol-2-yl)-5-(3-fluoro-5-methylphenyl)pyridin-4-yl]azetidin-3-yl]methanamine as an off-white solid. LCMS (M+H)$^+$=420.2. The structure of this compound was confirmed by NOESY NMR spectroscopy.

Example 5. 3-(aminomethyl)-1-[3-(4,6-difluoro-1H-1,3-benzodiazol-2-yl)-5-(3-fluoro-5-methylphenyl)pyridin-4-yl]azetidin-3-ol (Compound 1-28)

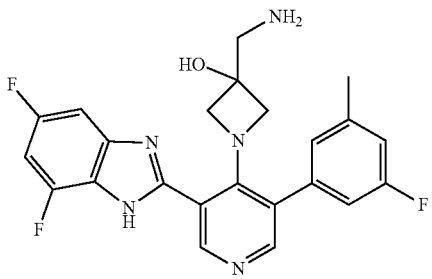 [SMILES: Cc1cc(F)cc(-c2cncc(-c3nc4cc(F)cc(F)c4[nH]3)c2N2CC(O)(CN)C2)c1]

Step 5-1, preparation of tert-butyl 3-({[(benzyloxy)carbonyl]amino}methyl)-3-hydroxyazetidine-1-carboxylate: to a dichloromethane (6.0 mL) solution of tert-butyl 3-(aminomethyl)-3-hydroxyazetidine-1-carboxylate (1.0 equiv, 1.18 mmol, 252 mg) was added N-(benzyloxycarbonyloxy)succinimide (1.5 equiv, 1.77 mmol, 452 mg) at 0° C. The resulting mixture was warmed up to rt and stirred at the same temperature for 20 hrs. The reaction solution was concentrated, diluted with ethyl acetate, and washed with water, saturated NH$_4$Cl, saturated NaHCO$_3$ and brine. The organic layer was dried with anhydrous Na$_2$SO$_4$, filtered and concentrated. The residue obtained was applied onto a silica gel column eluting with ethyl acetate/hexane to afford 364 mg (49%) of tert-butyl 3-({[(benzyloxy)carbonyl]amino}methyl)-3-hydroxyazetidine-1-carboxylate as a colorless oil. LCMS (M+H)$^+$=337.3.

Step 5-2, preparation of benzyl N-{[1-(3-bromo-5-formylpyridin-4-yl)-3-hydroxyazetidin-3-yl]methyl}carbamate: to a dioxane (1.0 mL) solution of tert-butyl 3-({[(benzyloxy)carbonyl]amino}methyl)-3-hydroxyazetidine-1-carboxylate (1.0 equiv, 1.08 mmol, 364 mg) was added 4.0 M HCl in dioxane (10 equiv, 10.8 mmol, 2.7 mL). The mixture was stirred at rt for 2 hrs, concentrated under reduced pressure. The residue was dried under high vacuum and used for next step without further purification. This crude material (1.0 equiv, 1.08 mmol) was combined with 5-bromo-4-chloropyridine-3-carbaldehyde (1.0 equiv, 1.08 mmol, 238 mg), anhydrous THF (3.0 mL), and DIPEA (3.0 equiv, 3.24 mmol, 0.534 mL) and stirred at 70° C. for 4 hrs. The reaction solution was then concentrated, diluted with ethyl acetate, washed with water and brine, dried with Na$_2$SO$_4$, filtered and concentrated. The residue obtained was applied onto a silica gel column eluting with methanol/dichloromethane to afford 172 mg of the title compound. LCMS (M+H)$^+$=420.2, 422.1.

Step 5-3, preparation of benzyl N-({1-[3-(3-fluoro-5-methylphenyl)-5-formylpyridin-4-tl]-3-hydroxyazetidin-3-yl}methyl)carbamate: to a THF (4.0 mL) solution of benzyl N-{[1-(3-bromo-5-formylpyridin-4-yl)-3-hydroxyazetidin-3-yl]methyl}carbamate (1.0 equiv, 0.41 mmol, 172 mg) and 3-fluoro-5-methylphenyl boronic acid (3.0 equiv, 1.23 mmol, 189 mg) was added tris(dibenzylideneacetone)dipalladium/tri-tert-butyl phosphonium tetrafluoroborate mixture (mole ratio: 1/1.2) complex (0.05 equiv, 0.021 mmol, 27 mg) and K$_3$PO$_4$.H$_2$O (3.0 equiv, 1.23 mmol, 282 mg). N$_2$ was bubbled through the reaction solution for 5 min and 0.4 mL of water was added. The resulting mixture was stirred at rt for 1.5 hrs and LCMS analysis showed incomplete conversion. 3-fluoro-5-methylphenyl boronic acid (3.0 equiv, 1.23 mmol, 189 mg), tris(dibenzylideneacetone)dipalladium/tri-tert-butyl phosphonium tetrafluoroborate mixture (mole ratio: 1/1.2) complex (0.05 equiv, 0.021 mmol, 27 mg) and K$_3$PO$_4$.H$_2$O (3.0 eq., 1.23 mmol, 282 mg) were added under N$_2$. The resulting mixture was stirred at rt for 1 h and LCMS analysis showed complete consumption of starting material. The reaction solution was diluted with ethyl acetate (50 mL) and washed with water and brine. The organic layer was dried with Na$_2$SO$_4$, filtered and concentrated. The residue obtained was purified by silica gel chromatography eluting with ethyl acetate/dichloromethane (0-50%) to give 83 mg of the title compound. MS (M+H)$^+$=450.1.

Step 5-4, preparation of benzyl N-({1-[3-(4,6-difluoro-1H-1,3-benzodiazol-2-yl)-5-(3-fluoro-5-methylphenyl)pyridin-4-yl]-3-hydroxyazetidin-3-yl}methyl)carbamate: to a DMF (1.0 mL) solution of benzyl N-({1-[3-(3-fluoro-5-methylphenyl)-5-formylpyridin-4-yl]-3-hydroxyazetidin-3-yl}methyl)carbamate (1.0 equiv, 0.034 mmol, 16 mg) was added 3,5-difluorobenzene-1,2-diamine (10 equiv, 0.34 mmol, 48 mg) and water (0.1 mL). The resulting mixture was stirred at 100° C. under air for 48 hrs. The reaction solution was diluted with ethyl acetate (20 mL) and washed with water and brine. The organic layer was dried with Na$_2$SO$_4$, filtered and concentrated. The residue obtained was purified by silica gel chromatography eluting with MeOH/DCM (0-5%) to give 14 mg of the title compound. MS (M+H)$^+$=574.1.

Step 5-5, preparation of 3-(aminomethyl)-1-[3-(4,6-difluoro-1H-1,3-benzodiazol-2-yl)-5-(3-fluoro-5-methylphenyl)pyridin-4-yl]azetidin-3-ol: benzyl N-({1-[3-(4,6-difluoro-1H-1,3-benzodiazol-2-yl)-5-(3-fluoro-5-methylphenyl)pyridin-4-yl]-3-hydroxyazetidin-3-yl}methyl)carbamate (1.0 equiv, 0.024 mmol, 14 mg) was combined with trifluoroacetic acid (0.8 mL) and thioanisole (0.1 mL). The resulting mixture was heated at 60° C. for 40 min. The reaction solution was concentrated and the residue obtained was purified by a RP C$_{18}$ column chromatography eluting with MeCN/water (0-30%). Pure fractions were combined, neutralized with saturated NaHCO$_3$ and NaCl, extracted with dichloromethane and dried with MgSO$_4$. The organic layer was concentrated and dried under high vacuum to give 2.0 mg of the desired product. MS (M+H)$^+$=440.5.

Example 6. 2-Amino-2-{1-[3-(4,6-difluoro-1H-1,3-benzodiazol-2-yl)-5-(3-fluoro-5-methylphenyl)pyridin-4-yl]azetidin-3-yl}ethan-1-ol (Compound 1-49)

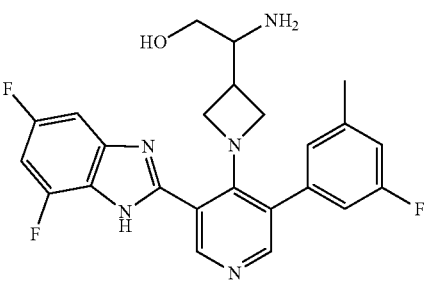 [SMILES: Cc1cc(F)cc(-c2cncc(-c3nc4cc(F)cc(F)c4[nH]3)c2N2CC(C(N)CO)C2)c1]

Step 6-1, preparation of tert-butyl 3-(1-{[(benzyloxy)carbonyl]amino}-2-methoxy-2-oxoethyl)azetidine-1-carboxylate: from tert-butyl 3-(1-amino-2-methoxy-2-oxoethyl)azetidine-1-carboxylate (1.0 equiv, 4.09 mmol, 1.0 g) and N-(benzyloxycarbonyloxy)succinimide (1.5 equiv, 6.14 mmol, 1.53 g), the title compound (674 mg) was prepared as a clear oil using a similar method to the one described in "Example 5, Step 5-1". MS (M+H)$^+$=379.1.

Step 6-2, preparation of 2-{[(benzyloxy)carbonyl]amino}-2-{1-[(tert-butoxy)carbonyl]azetidin-3-yl}acetic acid: to a THF/water solution (3.5 mL/3.5 mL) of tert-butyl 3-(1-{[(benzyloxy)carbonyl]amino}-2-methoxy-2-oxoethyl)azetidine-1-carboxylate (1.0 equiv, 1.4 mmol, 530 mg) was added LiOH.H$_2$O (1.5 equiv, 2.1 mmol, 90 mg) at 0° C. The resulting mixture was stirred at the same temperature for 2 hrs and LCMS analysis showed complete consumption of starting material. The pH of reaction solution was adjusted to 4-5 with aqueous HCl (1.0 M) and the resulting mixture was extracted with ethyl acetate and washed with brine. The organic layer was dried with Na$_2$SO$_4$, filtered and concentrated to give 497 mg of the desired product as a white foam. This material was used for next step without further purification. MS (M+H)$^+$=365.3.

Step 6-3, preparation of tert-butyl 3-(1-{[(benzyloxy)carbonyl]amino}-2-hydroxyethyl)azetidine-1-carboxylate: 2-{[(benzyloxy)carbonyl]amino}-2-{1-[(tert-butoxy)carbonyl]azetidin-3-yl}acetic acid (1.0 equiv, 1.37 mmol, 497 mg) was combined with 1.0 M BH$_3$.THF complex in THF (4 equiv, 5.46 mmol, 5.5 mL) and the resulting mixture was stirred at ambient temperature for overnight. At 0° C., 10 mL water was added into the reaction solution drop-wise to quench the excess BH$_3$.THF complex, and the resulting mixture was diluted with ethyl acetate. The organic layer was separated, washed with brine, dried over Na$_2$SO$_4$, filtered and concentrated to afford 256 mg of the desired product as a clean oil. The residue obtained was used for next step without further purification. MS (M+H)$^+$=351.4.

Step 6-4, preparation of benzyl N-{1-[1-(3-bromo-5-formylpyridin-4-yl)azetidin-3-yl]-2-hydroxyethyl}carbamate: to a dioxane (1.0 mL) solution of tert-butyl 3-(1-{[(benzyloxy)carbonyl]amino}-2-hydroxyethyl)azetidine-1-carboxylate (256 mg) was added 4.0 M HCl in dioxane (1.8 mL) and the resulting mixture was stirred at ambient temperature for 2 h. The reaction mixture was concentrated and dried under vacuum to afford 216 mg of the HCl salt of benzyl N-[1-(azetidin-3-yl)-2-hydroxyethyl]carbamate. This material was combined with 5-bromo-4-chloropyridine-3-carbaldehyde (1.0 equiv, 0.76 mmol, 167 mg), DIPEA (3.0 equiv, 2.27 mmol, 0.40 mL), and THF (5.0 mL). The resulting mixture was heated at 70° C. overnight. The reaction solution was concentrated and the residue obtained was purified by reverse phase C$_{18}$ chromatography eluting with MeCN/water (0-50%). Pure fractions were combined, neutralized with saturated NaHCO$_3$ and NaCl, extracted with dichloromethane and dried with MgSO$_4$. The organic layer was concentrated and dried under high vacuum to give 47 mg of the desired product. MS (M+H)$^+$=434.2, 436.3.

Step 6-5, preparation of benzyl N-(1-{1-[3-(3-fluoro-5-methylphenyl)-5-formylpyridin-4-yl]azetidin-3-yl}-2-hydroxyethyl)carbamate: to a dioxane solution (1.5 mL) of benzyl N-{1-[1-(3-bromo-5-formylpyridin-4-yl)azetidin-3-yl]-2-hydroxyethyl}carbamate (1.0 equiv, 0.10 mmol, 47 mg) was added Pd(Amphos)Cl$_2$ (0.15 equiv, 0.015 mmol, 11 mg), 3-fluoro-5-methylphenyl boronic acid (3.0 equiv, 0.30 mmol, 50 mg) and K$_2$CO$_3$ (3.0 equiv, 0.30 mmol, 42 mg). N$_2$ was bubbled through the reaction solution for 5 min and 0.15 mL water was added. The resulting mixture was heated at 100° C. for 1.5 hrs and LCMS analysis showed that starting material was completely consumed. The reaction solution was concentrated with silica gel and the residue obtained was applied onto a silica gel chromatography eluting with ethyl acetate/hexane (0~100%) to give 23 mg of the desired product. MS (M+H)$^+$=464.3.

Step 6-6, preparation of benzyl N-(1-{1-[3-(4,6-difluoro-1H-1,3-benzodiazol-2-yl)-5-(3-fluoro-5-methylphenyl)pyridin-4-yl]azetidin-3-yl}-2-hydroxyethyl)carbamate: from benzyl N-(1-{1-[3-(3-fluoro-5-methylphenyl)-5-formylpyridin-4-yl]azetidin-3-yl}-2-hydroxyethyl)carbamate (1.0 equiv, 0.049 mmol, 23 mg) and 3,5-difluorobenzene-1,2-diamine (10 equiv, 0.49 mmol, 70 mg), the title compound (9 mg) was prepared as a brown foam using a similar method to the one described in "Example 5, Step 5-4". MS (M+H)$^+$=588.2.

Step 6-7, preparation of 2-amino-2-{1-[3-(4,6-difluoro-1H-1,3-benzodiazol-2-yl)-5-(3-fluoro-5-methylphenyl)pyridin-4-yl]azetidin-3-yl}ethan-1-ol: from benzyl N-(1-{1-[3-(4,6-difluoro-1H-1,3-benzodiazol-2-yl)-5-(3-fluoro-5-methylphenyl)pyridin-4-yl]azetidin-3-yl}-2-hydroxyethyl)carbamate (9.0 mg), the title compound (2.0 mg) was prepared using a similar method to the one described in "Example 5, Step 5-5". MS (M+H)$^+$=454.4.

Example 7. 1-{1-[3-(4,6-difluoro-1H-1,3-benzodiazol-2-yl)-5-(3-fluoro-5-methylphenyl)pyridin-4-yl]azetidin-3-y}propan-1-amine (Compound 1-51)

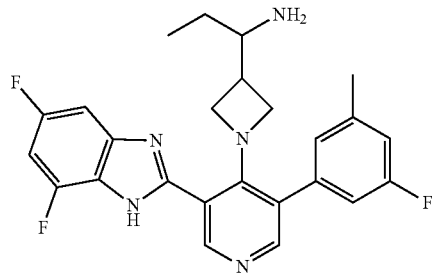 [SMILES: CCC(N)C1CN(c2c(-c3cc(C)cc(F)c3)cncc2-c2nc3cc(F)cc(F)c3[nH]2)C1]

Step 7-1, preparation of tert-butyl 3-[(1E)-[(2-methylpropane-2-sulfonyl)imino]methyl]azetidine-1-carboxylatebenzyl N-[1-(azetidin-3-yl)-2-hydroxyethyl]carbamate: to a dichloromethane (10 mL) solution of tert-butyl 3-formylazetidine-1-carboxylate (1.0 equiv, 3.24 mmol, 600 mg) was added 2-methyl-2-propanesulfinamide (1.0 equiv, 3.24 mmol, 393 mg) and CuSO$_4$ (2.2 equiv, 7.13 mmol, 1.14 g). The reaction mixture was stirred at rt overnight. The resulting suspension was filtered through a Celite pad and the filtrate was collected, concentrated and dried under vacuum to afford 919 mg of the title compound as a colorless oil. This crude material was used for next step without further purification. MS (M+H)$^+$=289.4.

Step 7-2, preparation of tert-butyl 3-[1-(2-methylpropane-2-sulfonamido)propyl]azetidine-1-carboxylate: to a dichloromethane (20 mL) solution of crude tert-butyl 3-[(1E)-[(2-methylpropane-2-sulfonyl)imino]methyl]azetidine-1-carboxylatebenzyl N-[1-(azetidin-3-yl)-2-hydroxyethyl]carbamate (1.0 equiv, 3.24 mmol, 919 mg) was added 0.9 M ethyl magnesium bromide solution (1.2 equiv, 4.25 mmol, 3.83 mL) at 0° C. under atmospheric N$_2$. The resulting mixture was stirred at the same temperature for 0.5 h and LCMS analysis showed complete consumption of starting material. The reaction solution was quenched with saturated NH$_4$Cl (3.0 mL), diluted with water (20 mL), and extracted with dichloromethane. The organic layers were combined, dried with MgSO$_4$, filtered and concentrated to give 0.975 g of tert-butyl 3-[1-(2-methylpropane-2-sulfonamido)propyl] azetidine-1-carboxylate as a colorless oil. This crude material was used for next step without further purification. MS (M+H)$^+$=319.2.

Step 7-3, preparation of tert-butyl 3-(1-aminopropyl)azetidine-1-carboxylate: to a methanol (20 mL) solution of tert-butyl 3-[1-(2-methylpropane-2-sulfonamido)propyl] azetidine-1-carboxylate (1.0 equiv, 3.24 mmol, 0.975 g) was added 4.0 M HCl in dioxane (1.3 equiv, 4.16 mmol, 1.04 mL) dropwise at 0° C. The resulting mixture was stirred at the same temperature for 5 hrs. Saturated NaHCO$_3$ solution was added to neutralize excess acid, and the resulting mixture was extracted with dichloromethane (3×50 mL). The organic layers were combined, dried with MgSO$_4$, filtered and concentrated to give 860 mg of the desired product as a colorless oil. This crude material was used for next step without further purification. MS (M+H)$^+$=319.2.

Step 7-4, preparation of tert-butyl 3-(1-{[(benzyloxy) carbonyl]amino}propyl)azetidine-1-carboxylate: from tert-butyl 3-(1-aminopropyl)azetidine-1-carboxylate (1.0 equiv, 860 mg, 3.2 mmol) and N-(benzyloxycarbonyloxy)succinimide (1.5 equiv, 4.8 mmol, 1.20 g), the title compound (458 mg) was prepared as a clear oil using a similar method to the one described in "Example 5, Step 5-1". MS (M+H)$^+$=349.5.

Step 7-5, preparation of benzyl N-[1-(azetidin-3-yl)propyl]carbamate: from tert-butyl 3-(1-{[(benzyloxy)carbonyl] amino}propyl)azetidine-1-carboxylate (1.0 equiv, 1.32 mmol, 458 mg), the title compound (320 mg) was prepared as a HCl salt using a similar method to the one described in "Example 5, Step 5-2". MS (M+H)$^+$=249.2.

Step 7-6, preparation of benzyl N-{1-[1-(3-bromo-5-formylpyridin-4-yl)azetidin-3-yl]propyl}carbamate: to a dioxane solution (8.0 mL) of 5-bromo-4-chloropyridine-3-carbaldehyde (1.0 equiv, 1.0 mmol, 221 mg) was added the HCl salt of benzyl N-[1-(azetidin-3-yl)propyl]carbamate (1.2 equiv, 320 mg, 1.20 mmol) and DIPEA (1.5 mL). The resulting mixture was heated at 90° C. for 1 h and LCMS analysis showed complete consumption of starting material. The reaction solution was concentrated and diluted with ethyl acetate, washed with water and brine, dried with Na$_2$SO$_4$, filtered and concentrated. The residue obtained was purified by silica gel chromatography eluting with ethyl acetate/dichloromethane (0~80%) to give 81 mg of the title compound. MS (M+H)$^+$=432.3, 434.3.

Step 7-7, preparation of benzyl N-(1-{1-[3-(3-fluoro-5-methylphenyl)-5-formylpyridin-4-yl]azetidin-3-yl}propyl) carbamate: to a dioxane solution (2.0 mL) of benzyl N-{1-[1-(3-bromo-5-formylpyridin-4-yl)azetidin-3-yl] propyl}carbamate (1.0 equiv, 0.19 mmol, 81 mg) was added Pd(dppf)Cl$_2$ (0.20 equiv, 0.038 mmol, 28 mg), 3-fluoro-5-methylphenyl boronic acid (3.0 equiv, 0.57 mmol, 96 mg) and K$_2$CO$_3$ (5.0 equiv, 0.95 mmol, 130 mg). N$_2$ was bubbled through the reaction solution for 5 min and 0.20 mL water was added. The resulting mixture was heated at 100° C. for 1 h and LCMS analysis showed that starting material was completely consumed. The reaction solution was concentrated and the residue obtained was purified by silica gel chromatography eluting with ethyl acetate/dichloromethane (0~100%) to give 20 mg of the title compound. MS (M+H)$^+$=462.4.

Step 7-8, preparation of benzyl N-(1-{1-[3-(4,6-difluoro-1H-1,3-benzodiazol-2-yl)-5-(3-fluoro-5-methylphenyl)pyridin-4-yl]azetidin-3-yl}propyl)carbamate: from benzyl N-(1-{1-[3-(3-fluoro-5-methylphenyl)-5-formylpyridin-4-yl] azetidin-3-yl}propyl)carbamate (1.0 equiv, 0.043 mmol, 20 mg) and 3,5-difluorobenzene-1,2-diamine (3.0 equiv, 0.13 mmol, 20 mg), the title compound (30 mg) was prepared using a similar method to the one described in "Example 5, Step 5-4". MS (M+H)$^+$=586.4.

Step 7-9, preparation of 1-{1-[3-(4,6-difluoro-1H-1,3-benzodiazol-2-yl)-5-(3-fluoro-5-methylphenyl)pyridin-4-yl]azetidin-3-yl}propan-1-amine: benzyl N-(1-{1-[3-(4,6-difluoro-1H-1,3-benzodiazol-2-yl)-5-(3-fluoro-5-methylphenyl)pyridin-4-yl]azetidin-3-yl}propyl)carbamate (1.0 equiv, 0.052 mmol, 30 mg) was combined with trifluoroacetic acid (0.8 mL) and thioanisole (0.1 mL). The resulting mixture was heated at 60° C. for 0.5 h and LCMS analysis showed complete consumption of starting material. The reaction solution was concentrated and the residue obtained was purified by reverse phase C$_{18}$ chromatography eluting with MeCN/water (0~30%). Pure fractions were combined, neutralized with saturated NaHCO$_3$ and NaCl, extracted with ethyl acetate and dried with MgSO$_4$. The organic was combined with 2.0 M HCl in EtOEt (0.3 mL), concentrated, and dried under high vacuum to give 8.0 mg of the title compound as HCl salt. MS (M+H)$^+$=452.3.

Example 8. 3-{4-[3-(1-aminoethyl)azetidin-1-yl]-5-(4,6-difluoro-1H-1,3-benzodiazol-2-yl)pyridin-3-yl}-5-fluorobenzonitrile (Compound 1-64)

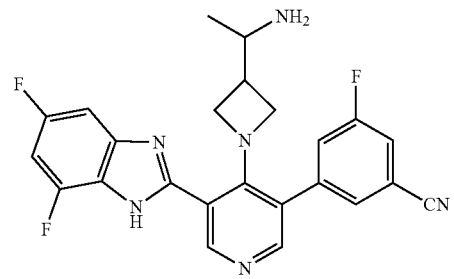 [SMILES: CC(N)C1CN(c2c(-c3cc(F)cc(C#N)c3)cncc2-c2nc3cc(F)cc(F)c3[nH]2)C1]

Step 8-1, preparation of tert-butyl 3-[(1E)-[(2-methylpropane-2-sulfonyl)imino]methyl]azetidine-1-carboxylate: from tert-butyl 3-formylazetidine-1-carboxylate (1.0 equiv, 27 mmol, 5.0 g), the title compound (8.0 g) was prepared as described in "Example 7, Step 7-1".

Step 8-2, preparation of tert-butyl 3-[1-(2-methylpropane-2-sulfonamido)ethyl]azetidine-1-carboxylate: to a dichloromethane (120 mL) solution of tert-butyl 3-[(1E)-[(2-methylpropane-2-sulfonyl)imino]methyl]azetidine-1-carboxylate (1.0 equiv, 27 mmol, 8.0 g) was added 1.0 M methyl magnesium bromide solution (1.5 equiv, 42 mmol, 42 mL) at 0° C. via an addition funnel over 20 min. The resulting mixture was stirred at the same temperature for 0.5 h and LCMS analysis showed complete consumption of starting material. The reaction solution was quenched with saturated NH$_4$Cl (10 mL), diluted with water (100 mL), and then extracted with dichloromethane (3×100 mL). The organic layers were combined, dried over MgSO$_4$, filtered and concentrated to give 10.0 g of tert-butyl 3-(1-{[(benzyloxy) carbonyl]amino}ethyl)azetidine-1-carboxylate as colorless oil. This crude material was used for next step without further purification. MS (M+H)$^+$=305.4.

Step 8-3, preparation of tert-butyl 3-(1-aminoethyl)azetidine-1-carboxylate: from tert-butyl 3-[1-(2-methylpropane-2-sulfonamido)ethyl]azetidine-1-carboxylate (1.0 equiv, 27 mmol, 10.0 g), the title compound (8.0 g) was prepared using a similar method to the one described in "Example 7, Step 7-3". This crude material was used for next step without further purification. MS (M+H)⁺=201.4.

Step 8-4, preparation of tert-butyl 3-(1-{[(benzyloxy) carbonyl]amino}ethyl)azetidine-1-carboxylate: from tert-butyl 3-(1-aminoethyl)azetidine-1-carboxylate (1.0 equiv, 27 mmol, 8.0 g) and N-(benzyloxycarbonyloxy)succinimide (1.3 equiv, 35 mmol, 8.75 g), the title compound (3.21 g) was prepared as a clear oil using a similar method to the one described in "Example 5, Step 5-1". MS (M+H)⁺=335.4.

Step 8-5, preparation of benzyl N-[1-(azetidin-3-yl)ethyl]carbamate: to the dichloromethane (5.0 mL) solution of tert-butyl 3-(1-{[(benzyloxy)carbonyl]amino}ethyl)azetidine-1-carboxylate (1.0 equiv, 1.97 mmol, 661 mg) was added trifluoroacetic acid (10 equiv, 19.7 mmol, 1.50 mL). The resulting mixture was stirred at rt for 2 hrs and LCMS analysis showed complete consumption of starting material. The reaction solution was diluted with dichloromethane and neutralized with saturated NaHCO₃. The organic layer was washed with brine, dried with anhydrous Na₂SO₄, filtered and concentrated to give 443 mg of the title compound as a brown oil. MS (M+H)⁺=235.1.

Step 8-6, preparation of benzyl N-{1-[1-(3-bromo-5-formylpyridin-4-yl)azetidin-3-tl]ethyl}carbamate: to a THF solution (8.0 mL) of benzyl N-[1-(azetidin-3-yl)ethyl]carbamate (1.0 equiv, 1.89 mmol, 443 mg) was added 5-bromo-4-chloropyridine-3-carbaldehyde (0.9 equiv, 1.70 mmol, 376 mg) and DIPEA (3.0 equiv, 5.67 mmol, 0.94 mL). The resulting mixture was heated at 70° C. for overnight. The reaction solution was concentrated, diluted with dichloromethane, washed with water and brine, dried with anhydrous Na₂SO₄, filtered and concentrated. The residue obtained was purified by silica gel chromatography eluting with ethyl acetate/dichloromethane (0-40%) to give 190 mg of the desired product as light brown oil. MS (M+H)⁺= 418.2. 419.7.

Step 8-7, preparation of benzyl N-(1-{1-[3-bromo-5-(4,6-difluoro-1H-1,3-benzodiazol-2-yl)pyridin-4-yl]azetidin-3-yl}ethyl)carbamate: from benzyl N-{1-[1-(3-bromo-5-formylpyridin-4-yl)azetidin-3-yl]ethyl}carbamate (1.0 equiv, 0.45 mmol, 190 mg) and 3,5-difluorobenzene-1,2-diamine (5.0 equiv, 2.25 mmol, 328 mg), the title compound (177 mg) was prepared using a similar method to the one described in "Example 5, Step 5-4". MS (M+H)⁺=542.2, 544.3.

Step 8-8, preparation of benzyl N-(1-{1-[3-(3-cyano-5-fluorophenyl)-5-(4,6-difluoro-1H-1,3-benzodiazol-2-yl) pyridin-4-yl]azetidin-3-yl}ethyl)carbamate: to a dioxane solution (1.0 mL) of benzyl N-(1-{1-[3-bromo-5-(4,6-difluoro-1H-1,3-benzodiazol-2-yl)pyridin-4-yl]azetidin-3-yl}ethyl)carbamate (1.0 equiv, 0.039 mmol, 21 mg) was added Pd(Amphos)Cl₂ (0.15 equiv, 0.006 mmol, 4.3 mg), 3-cyano-5-fluorophenyl boronic acid (3.0 equiv, 0.12 mmol, 30 mg) and K₂CO₃ (4.0 equiv, 0.16 mmol, 21 mg). N₂ was bubbled through the reaction mixture for 5 min and 0.1 mL of water was added. N₂ was bubbled through the reaction mixture for another 5 min and the resulting mixture was heated at 100° C. for 1.5 hrs. The reaction solution was diluted with dichloromethane, washed with water and brine, dried with anhydrous Na₂SO₄, filtered and concentrated. The residue obtained was purified by silica gel chromatography eluting with ethyl acetate/dichloromethane (0-50%) to give 15.3 mg of the title compound. MS (M+H)⁺=583.3.

Step 8-9, preparation of 3-{4-[3-(1-aminoethyl)azetidin-1-yl]-5-(4,6-difluoro-1H-1,3-benzodiazol-2-yl)pyridin-3-yl}-5-fluorobenzonitrile: from benzyl N-(1-{1-[3-(3-cyano-5-fluorophenyl)-5-(4,6-difluoro-1H-1,3-benzodiazol-2-yl) pyridin-4-yl]azetidin-3-yl}ethyl)carbamate (15.3 mg), the title compound (3.6 mg) was prepared using a similar method to the one described in "Example 5, Step 5-5". MS (M+H)⁺=449.3.

The following compounds were prepared similarly to Example 8 with appropriate substituting reagents and substrates at different steps and they may require additional functional group modifications on benzimidazoyl side chain via well-known chemistry with appropriate reagents. Different salt such as HCl or formic acid maybe obtained.

| Compound no. | MS (M + H)⁺ |
| --- | --- |
| 1-62 | 458.4 |
| 1-63 | 492.4 |
| 1-64 | 449.3 |
| 1-65 | 449.4 |
| 1-68 | 438.2 |
| 1-69 | 488.4 |
| 1-70 | 445.2 |
| 1-71 | 492.4 |
| 1-72 | 468.4 |
| 1-73 | 454.3 |
| 1-74 | 458.3 |
| 1-75 | 440.4 |
| 1-76 | 438.4 |

Example 9. 3-{4-[(3S)-3-aminopyrrolidin-1-yl]-5-(4-methyl-1H-1,3-benzodiazol-2-yl)pyridin-3-yl}-5-fluorobenzonitrile (Compound 2-34)

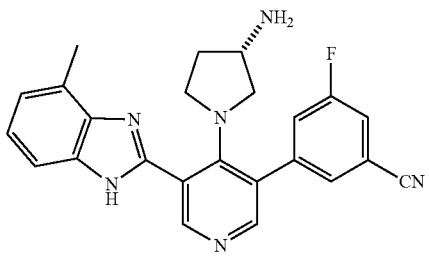 [SMILES: Cc1cccc2[nH]c(-c3cncc(-c4cc(F)cc(C#N)c4)c3N3CC[C@H](N)C3)nc12]

Step 9-1, preparation of tert-butyl N-[(3S)-1-(3-bromo-5-formylpyridin-4-yl)pyrrolidin-3-yl]carbamate: to a dioxane (20 mL) solution of 5-bromo-4-chloropyridine-3-carbaldehyde (1.0 equiv, 5.0 mmol, 1.10 g) was added (S)-3-boc-aminopyrrolidine (1.4 equiv, 7.0 mmol, 1.30 g) and DIPEA (5.0 mL). The resulting mixture was heated at 95° C. for 1 h and LCMS analysis showed complete consumption of starting material. The reaction solution was concentrated and diluted with ethyl acetate, washed with water and brine, dried with Na₂SO₄, filtered and concentrated. The residue obtained was purified by silica gel chromatography eluting with ethyl acetate/hexane (0-50%) to give 1.1 g of the title compound. MS (M+H)⁺=370.2, 372.0.

Step 9-2, preparation of tert-butyl N-[(3S)-1-[3-bromo-5-(4-methyl-1H-1,3-benzodiazol-2-yl)pyridin-4-yl]pyrrolidin-3-yl]carbamate: to a DMF (5.0 mL) solution of tert-butyl N-[(3S)-1-(3-bromo-5-formylpyridin-4-yl)pyrrolidin-3-yl]carbamate (1.0 equiv, 0.7 mmol, 260 mg) was added 2,3-diaminotoluene (2.0 equiv, 1.40 mmol, 170 mg) and water (0.5 mL). The resulting mixture was heated at 100° C. with air for 24 hrs, then cooled down to rt and water (20 mL) was added. The resulting suspension was filtered and the solid collected was washed with water (3×5 mL) to give 224 mg of tert-butyl N-[(3S)-1-[3-bromo-5-(4-methyl-1H-1,3-benzodiazol-2-yl)pyridin-4-yl]pyrrolidin-3-yl]carbamate as a brown solid. This material was used for next step without further purification. MS (M+H)$^+$=472.2, 474.3.

Step 9-3, preparation of tert-butyl N-[(3S)-1-[3-(3-cyano-5-fluorophenyl)-5-(4-methyl-1H-1,3-benzodiazol-2-yl)pyridin-4-yl]pyrrolidin-3-yl]carbamate: to a dioxane solution (3.0 mL) of tert-butyl N-[(3S)-1-[3-bromo-5-(4-methyl-1H-1,3-benzodiazol-2-yl)pyridin-4-yl]pyrrolidin-3-yl]carbamate (1.0 equiv, 0.24 mmol, 112 mg) was added Pd(Amphos)$Cl_2$ (0.1 equiv, 0.024 mmol, 16 mg), 3-cyano-5-fluorophenyl boronic acid (3.0 equiv, 0.72 mmol, 120 mg) and $K_2CO_3$ (3.0 equiv, 0.72 mmol, 100 mg). $N_2$ was bubbled through the reaction solution for 5 min and 0.3 mL water was added. The resulting mixture was heated at 100° C. for 0.5 h and LCMS analysis showed complete consumption of starting material. The reaction solution was concentrated and the residue obtained was purified by silica gel chromatography eluting with ethyl acetate/dichloromethane (0~100%) to give 92 mg of the title compound. MS (M+H)$^+$=513.4.

Step 9-4, preparation of 3-{4-[(3S)-3-aminopyrrolidin-1-yl]-5-(4-methyl-1H-1,3-benzodiazol-2-yl)pyridin-3-yl}-5-fluorobenzonitrile: to a dichloromethane (1.0 mL) solution of tert-butyl N-[(3S)-1-[3-(3-cyano-5-fluorophenyl)-5-(4-methyl-1H-1,3-benzodiazol-2-yl)pyridin-4-yl]pyrrolidin-3-yl]carbamate (1.0 equiv, 92 mg, 0.18 mmol) was added trifluoroacetic acid (0.6 mL). The resulting mixture was stirred at ambient temperature for 0.5 h and LCMS analysis showed complete consumption of starting material. The reaction solution was concentrated and the residue obtained was purified by reverse phase $C_{18}$ chromatography eluting with MeCN/water (0-30%) with 0.05% of TFA. Pure fractions were combined, neutralized with saturated $NaHCO_3$ and NaCl, extracted with ethyl acetate and dried with $MgSO_4$. The organic solutions were combined and treated with 2.0 M HCl in ethyl ether (0.3 mL), concentrated, and dried under high vacuum to give 55 mg of the desired product as an HCl salt. MS (M+H)$^+$=413.4.

The following compounds were prepared similarly to Example 9 with appropriate substituting reagents and substrates at different steps and they may require additional functional group modifications via well-known chemistry with appropriate reagents. The cyclization reaction of aldehydes with 1,2-diaminobenzenes can be carried out by heating in wet DMF, NMP, DMSO or other solvents with or without $Na_2S_2O_5$ under atmospheric oxygen. Different salt such as HCl or formic acid or TFA salt maybe obtained.

| Compound no. | MS (M + H)$^+$ |
| --- | --- |
| 2-2 | 426.2 |
| 2-3 | 426.3 |
| 2-4 | 440.2 |
| 2-5 | 433.1 |
| 2-6 | 431.3 |
| 2-7 | 399.1 |
| 2-8 | 417.2 |
| 2-10 | 472.5 |
| 2-11 | 418.2 |
| 2-13 | 413.2 |
| 2-14 | 432.2 |
| 2-15 | 404.2 |
| 2-16 | 454.2 |
| 2-17 | 473.2 |
| 2-20 | 449.1 |
| 2-21 | 466.2 |
| 2-22 | 430.2 |
| 2-23 | 417.4 |
| 2-24 | 417.3 |
| 2-25 | 408.3 |
| 2-26 | 405.3 |
| 2-27 | 443.2 |
| 2-28 | 422.2 |
| 2-29 | 427.2 |
| 2-30 | 427.2 |
| 2-32 | 435.2 |
| 2-33 | 467.4 |
| 2-35 | 417.4 |
| 2-36 | 415.4 |
| 2-37 | 413.3 |
| 2-38 | 435.4 |
| 2-39 | 433.3 |
| 2-40 | 435.4 |
| 2-42 | 399.2 |
| 2-43 | 435.1 |
| 2-44 | 435.2 |
| 2-45 | 429.3 |
| 2-46 | 429.4 |
| 2-47 | 433.3 |
| 2-48 | 485.4 |
| 2-49 | 431.4 |
| 2-50 | 414.4 |
| 2-53 | 454.2 |
| 2-56 | 475.3 |
| 2-58 | 452.2 |
| 2-59 | 416.2 |
| 2-61 | 453.2 |
| 2-64 | 416.2 |
| 2-65 | 431.4 |
| 2-78 | 485.4 |
| 2-80 | 385.4 |
| 2-81 | 415.2 |
| 2-85 | 417.2 |
| 2-92 | 470.1 |
| 2-96 | 449.2 |
| 2-97 | 413.3 |
| 2-98 | 429.3 |
| 2-108 | 428.5 |
| 2-119 | 428.4 |
| 2-120 | 449.4 |
| 2-121 | 414.3 |
| 2-122 | 410.4 |
| 2-123 | 410.4 |
| 2-126 | 464.2 |
| 2-128 | 396.3 |
| 2-130 | 404.2 |
| 2-135 | 443.1 |
| 2-136 | 443.2 |
| 2-140 | 446.1 |
| 2-148 | 464.2 |
| 2-157 | 430.1 |
| 2-178 | 403.5 |
| 2-186 | 457.4 |
| 2-187 | 419.2 |
| 2-188 | 417.4 |
| 2-189 | 433.1 |
| 2-190 | 420.9 |
| 2-191 | 471.3 |
| 2-192 | 437.2 |
| 2-200 | 413.3 |

Example 10. 3-{4-[(3S)-3-aminopyrrolidin-1-yl]-5-(7-fluoro-4-methyl-1H-1,3-benzodiazol-2-yl)pyridin-3-yl}-5-fluorobenzonitrile (Compound 2-63)

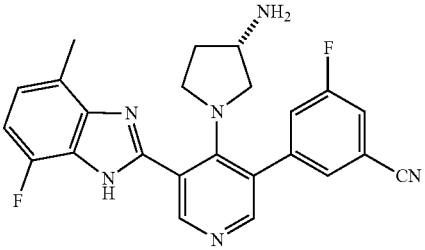 [SMILES: Cc1ccc(F)c2[nH]c(-c3cncc(-c4cc(F)cc(C#N)c4)c3N3CC[C@H](N)C3)nc12]

Step 10-1, preparation of tert-butyl N-[(3S)-1-[3-(3-cyano-5-fluorophenyl)-5-formylpyridin-4-yl]pyrrolidin-3-yl]carbamate: from tert-butyl N-[(3S)-1-(3-bromo-5-formylpyridin-4-yl)pyrrolidin-3-yl]carbamate (1.0 equiv, 1.88 mmol, 0.70 g, prepared as described in "Example 9, Step 9-1") and 3-cyano-5-fluorophenyl boronic (2.1 equiv, 4.0 mmol, 660 mg), the title compound (633 mg) was prepared using a similar method to the one described in "Example 9, Step 9-3". MS (M+H)⁺=411.4.

Step 10-2, preparation of tert-butyl N-[(3S)-1-[3-(3-cyano-5-fluorophenyl)-5-(7-fluoro-4-methyl-1H-1,3-benzodiazol-2-yl)pyridin-4-yl]pyrrolidin-3-yl]carbamate: to an EtOH solution (1.0 mL) of tert-butyl N-[(3S)-1-[3-(3-cyano-5-fluorophenyl)-5-formylpyridin-4-yl]pyrrolidin-3-yl]carbamate (1.0 equiv, 0.10 mmol, 41 mg) and 3-fluoro-6-methyl-2-nitroaniline (3.0 equiv, 0.30 mmol, 53 mg) was added freshly prepared 1.0 M $Na_2S_2O_4$ solution (10.0 equiv, 1.0 mmol, 1.0 mL). The resulting mixture was heated at 60° C. for overnight, then cooled to rt and diluted with dichloromethane. The solution was washed with water and brine, dried over anhydrous $Na_2SO_4$, filtered and concentrated. The remaining residue was purified by silica gel chromatography eluting with ethyl acetate/dichloromethane (0-60%) to give 17 mg of the desired product. MS (M+H)⁺=531.3.

Step 10-3, preparation of 3-{4-[(3S)-3-aminopyrrolidin-1-yl]-5-(7-fluoro-4-methyl-1H-1,3-benzodiazol-2-yl)pyridin-3-yl}-5-fluorobenzonitrile: from tert-butyl N-[(3S)-1-[3-(3-cyano-5-fluorophenyl)-5-(7-fluoro-4-methyl-1H-1,3-benzodiazol-2-yl)pyridin-4-yl]pyrrolidin-3-yl]carbamate (17 mg), the title compound (9.0 mg) was prepared as HCl salt using a similar method to the one described in "Example 9, Step 9-4". MS (M+H)⁺=431.5.

The following compounds were prepared similarly to Example 10 with appropriate substituting reagents and substrates at different steps and they may require additional functional group modifications on benzimidazoyl side chain via well-known chemistry with appropriate reagents. Different salt such as HCl or formic acid maybe obtained.

| Compound no. | MS (M + H)⁺ |
|---|---|
| 2-79 | 431.5 |
| 2-86 | 431.5 |

Example 11. 4-[(3S)-3-aminopyrrolidin-1-yl]-5-(7-fluoro-4-methyl-1H-1,3-benzodiazol-2-yl)-[3,4'-bipyridine]-2'-carbonitrile (Compound 2-106)

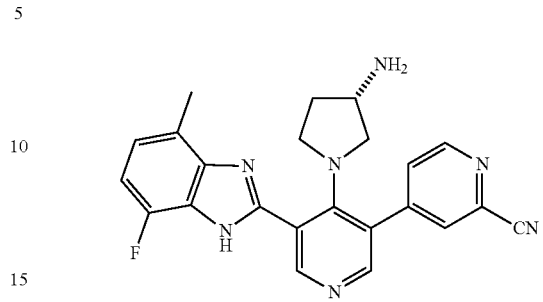

Step 11-1, preparation of tert-butyl N-[(3S)-1-[3-bromo-5-(7-fluoro-4-methyl-1H-1,3-benzodiazol-2-yl)pyridin-4-yl]pyrrolidin-3-yl]carbamate: from tert-butyl N-[(3S)-1-(3-bromo-5-formylpyridin-4-yl)pyrrolidin-3-yl]carbamate (1.0 equiv, 1.34 mmol, 0.50 g, prepared as described in "Example 9, Step 9-1") and 3-fluoro-6-methyl-2-nitroaniline (3.0 equiv, 4.0 mmol, 680 mg), the title compound (319 mg) was prepared using a similar method to the one described in "Example 10, Step 10-2". MS (M+H)⁺=490.2, 492.3.

Step 11-2, preparation of tert-butyl N-[(3S)-1-[2'-cyano-5-(7-fluoro-4-methyl-1H-1,3-benzodiazol-2-yl)-[3,4'-bipyridin]-4-yl]pyrrolidin-3-yl]carbamate: from tert-butyl N-[(3S)-1-[3-bromo-5-(7-fluoro-4-methyl-1H-1,3-benzodiazol-2-yl)pyridin-4-yl]pyrrolidin-3-yl]carbamate (1.0 equiv, 0.15 mmol, 75 mg) and 4-(4,4,5,5-tetramethyl-1,3,2-dioxaborolan-2-yl)pyridine-2-carbonitrile (3.0 equiv, 0.45 mmol, 110 mg), the title compound (27 mg) was prepared using a similar method to the one described in "Example 9, Step 9-3". MS (M+H)⁺=514.5.

Step 11-3, preparation of 4-[(3S)-3-aminopyrrolidin-1-yl]-5-(7-fluoro-4-methyl-1H-1,3-benzodiazol-2-yl)-[3,4'-bipyridine]-2'-carbonitrile: from tert-butyl N-[(3S)-1-[2'-cyano-5-(7-fluoro-4-methyl-1H-1,3-benzodiazol-2-yl)-[3,4'-bipyridin]-4-yl]pyrrolidin-3-yl]carbamate (8.3 mg), the title compound (3.6 mg) was prepared as free amine using a similar method to the one described in "Example 9, Step 9-4". MS (M+H)⁺=414.2.

The following compounds were prepared similarly to Example 11 with appropriate substituting reagents and substrates at different steps and they may require additional functional group modifications on benzimidazoyl side chain via well-known chemistry with appropriate reagents. Different salt such as HCl or formic acid maybe obtained.

| Compound no. | MS (M + H)⁺ |
|---|---|
| 2-101 | 413.3 |

Example 12. (3S)-1-[3-(4-fluoro-1H-1,3-benzodiazol-2-yl)-5-{3-fluoro-5-[(methoxyimino)methyl]phenyl}pyridin-4-yl]pyrrolidin-3-amine (Compound 2-9)

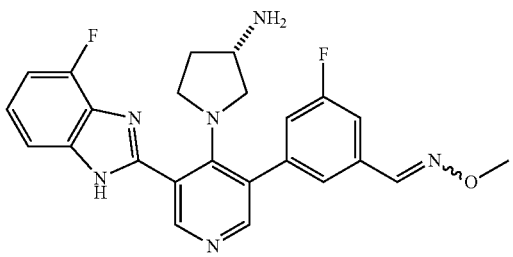 [SMILES: CON=Cc1cc(F)cc(-c2cncc(-c3nc4c(F)cccc4[nH]3)c2N2CC[C@H](N)C2)c1]

Step 12-1, preparation of tert-butyl N-[(3S)-1-[3-bromo-5-(7-fluoro-1H-1,3-benzodiazol-2-yl)pyridin-4-yl]pyrrolidin-3-yl]carbamate: from tert-butyl N-[(3S)-1-(3-bromo-5-formylpyridin-4-yl)pyrrolidin-3-yl]carbamate (1.0 equiv, 1.65 mmol, 610 mg) and 2,3-diaminofluorobenzene (2.0 equiv, 3.3 mmol, 424 mg), the title compound (649 mg) was prepared using a similar method to the one described in "Example 9, Step 9-2". MS (M+H)$^+$=476.2, 478.2.

Step 12-2, preparation of tert-butyl N-[(3S)-1-[3-(4-fluoro-1H-1,3-benzodiazol-2-yl)-5-(3-fluoro-5-formylphenyl)pyridin-4-yl]pyrrolidin-3-yl]carbamate: from tert-butyl N-[(3S)-1-[3-bromo-5-(7-fluoro-1H-1,3-benzodiazol-2-yl)pyridin-4-yl]pyrrolidin-3-yl]carbamate (1.0 equiv, 0.20 mmol, 96 mg) and 3-fluoro-5-formylphenyl boronic acid (2.0 equiv, 0.4 mmol, 86 mg), the title compound (41 mg) was prepared using a similar method to the one described in "Example 9, Step 9-3". MS (M+H)$^+$=520.5.

Step 12-3, preparation of (3S)-1-[3-(4-fluoro-1H-1,3-benzodiazol-2-yl)-5-{3-fluoro-5-[(methoxyimino)methyl]phenyl}pyridin-4-yl]pyrrolidin-3-amine: to a dichloromethane solution (1.0 mL) of tert-butyl N-[(3S)-1-[3-(4-fluoro-1H-1,3-benzodiazol-2-yl)-5-(3-fluoro-5-formylphenyl)pyridin-4-yl]pyrrolidin-3-yl]carbamate (1.0 equiv, 41 mg, 0.079 mmol) was added pyridine (8.0 equiv, 0.63 mmol, 0.051 mL) and the HCl salt of O-methylhydroxylamine (4.0 equiv, 0.32 mmol, 26 mg). The resulting mixture was stirred at ambient temperature for 0.5 h and LCMS analysis showed complete consumption of starting material. Trifluoroacetic acid (0.5 mL) was added into the reaction solution at 0° C. drop-wise, and the resulting mixture was stirred at ambient temperature for 1 h. The aqueous solution was extracted with dichloromethane, dried with Na$_2$SO$_4$, filtered and concentrated. The remaining residue was purified by reverse phase C$_{18}$ chromatography eluting with MeCN/water containing 0.05% TFA (0 to 40%). Pure fractions were combined, neutralized with saturated NaHCO$_3$, solid NaCl was added, extracted dichloromethane, dried with MgSO$_4$, concentrated and dried under high vacuum to afford 24 mg of (3S)-1-[3-(4-fluoro-1H-1,3-benzodiazol-2-yl)-5-{3-fluoro-5-[(methoxyimino)methyl]phenyl}pyridin-4-yl]pyrrolidin-3-amine. MS (M+1)$^+$=449.2.

The following compounds were prepared similarly to Example 12 with appropriate substituting reagents and substrates at different steps and they may require additional functional group modifications on benzimidazoyl side chain via known synthetic methods with appropriate reagents. Different salt such as HCl or formic acid maybe obtained.

| Compound no. | MS (M + H)$^+$ |
|---|---|
| 2-12 | 431.4 |

Example 13. 3-{4-[3-amino-3-(hydroxymethyl)pyrrolidin-1-yl]-5-(4-fluoro-1H-1,3-benzodiazol-2-yl)pyridin-3-yl}benzonitrile (Compound 2-54)

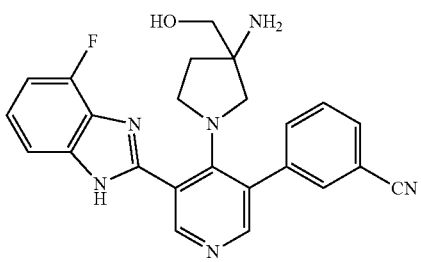 [SMILES: N#Cc1cccc(-c2cncc(-c3nc4c(F)cccc4[nH]3)c2N2CCC(N)(CO)C2)c1]

Step 13-1, preparation of 2-(5-bromo-4-chloropyridin-3-yl)-4-fluoro-1H-1,3-benzodiazole: to a DMF (5.0 mL) of 5-bromo-4-chloropyridine-3-carbaldehyde (1.0 equiv, 1.0 mmol, 220 mg) was added 2,3-diaminofluorobenzene (1.5 equiv, 1.5 mmol, 187 mg) and water (0.5 mL). The resulting mixture was heated at 100° C. with air for 1 day, was cooled down to rt and water (20 mL) was added. The resulting mixture was extracted with ethyl acetate, washed with brine, dried and concentrated. The residue obtained was purified by silica gel chromatography eluting with EtOAc/hexane (0-50%) to afford 270 mg of the title compound. MS (M+H)$^+$=328.2.

Step 13-2, preparation of tert-butyl N-{1-[3-bromo-5-(4-fluoro-1H-1,3-benzodiazol-2-yl)pyridin-4-yl]-3-(hydroxymethyl)pyrrolidin-3-yl}carbamate: to a DMF solution of 2-(5-bromo-4-chloropyridin-3-yl)-4-fluoro-1H-1,3-benzodiazole (1.0 equiv, 0.06 mmol, 20 mg) was added tert-butyl N-[3-(hydroxymethyl)pyrrolidin-3-yl]carbamate (1.2 equiv, 0.07 mmol, 16 mg) and triethylamine (3.0 equiv, 0.17 mmol, 17 mg). The resulting mixture was heated at 80° C. for 2 hrs. The reaction solution was diluted with ethyl acetate, washed with water and brine, dried and concentrated. The residue obtained was purified by silica gel chromatography eluting with EtOAc/hexane (50%) to afford 30 mg of the title compound. MS (M+H)$^+$=506.1, 508.2.

Step 13-3, preparation of tert-butyl N-{1-[3-(3-cyanophenyl)-5-(4-fluoro-1H-1,3-benzodiazol-2-yl)pyridin-4-yl]-3-(hydroxymethyl)pyrrolidin-3-yl}carbamate: to a dioxane (1.0 mL) solution of tert-butyl N-{1-[3-bromo-5-(4-fluoro-1H-1,3-benzodiazol-2-yl)pyridin-4-yl]-3-(hydroxymethyl)pyrrolidin-3-yl}carbamate (1.0 equiv, 0.06 mmol, 30 mg) was added 3-cyanophenyl boronic acid (3.0 equiv, 0.18 mmol, 26 mg), Pd(Amphos)Cl$_2$ (0.10 equiv, 0.01 mmol, 4.2 mg), K$_2$CO$_3$ and water (0.1 mL). The resulting mixture was heated at 80° C. for 1 h. The reaction mixture was concentrated and purified by Prep-HPLC using the following conditions (Prep-HPLC-013): Column, SunFire Prep C$_{18}$ OBD Column, 19×150 mm, 5 µm, 10 nm; mobile phase A: Water (0.05% TFA) and mobile phase B: ACN; gradient: B from 16.0% to 36.0% in 6 min with flow rate at 20 ml/min. Detector, UV 220 nm. Combined fractions containing the product were concentrated to afford 15 mg (48%) of the desired product as a white solid. MS (M+H)$^+$=514.2.

Step 13-4, preparation of 3-{4-[3-amino-3-(hydroxymethyl)pyrrolidin-1-yl]-5-(4-fluoro-1H-1,3-benzodiazol-2-yl)pyridin-3-yl}benzonitrile: to a dichloromethane (2.0 mL) solution of tert-butyl N-{1-[3-(3-cyanophenyl)-5-(4-fluoro-1H-1,3-benzodiazol-2-yl)pyridin-4-yl]-3-(hydroxymethyl)pyrrolidin-3-yl}carbamate (1.0 equiv, 0.03 mmol, 15 mg) was added trifluoroacetic acid (1.0 mL). The resulting mixture was stirred at rt for 30 min. The reaction solution was concentrated and purified by Prep-HPLC using the following conditions (Prep-HPLC-013): Column, SunFire Prep $C_{18}$ OBD Column, 19×150 mm, 5 μm, 10 nm; mobile phase A: Water (0.05% TFA) and mobile phase B: ACN (0.1% TFA), gradient: B from 4.0% to 32.0% in 6 min; flow rate: 20 ml/min; Detector, UV 220 nm, which resulted in 9.4 mg (61%) of the TFA salt of the title compound as a white solid. MS $(M+H)^+=429.2$.

The following compounds were prepared similarly to Example 13 with appropriate substituting reagents and substrates at different steps and they may require additional functional group modifications on benzimidazoyl side chain via well-known chemistry with appropriate reagents. Different salt such as HCl or formic acid maybe obtained.

| Compound no. | MS (M + H)+ |
|---|---|
| 2-55 | 417.2 |
| 2-66 | 447.2 |
| 2-68 | 415.2 |
| 2-70 | 417.2 |
| 2-88 | 447.3 |
| 2-93 | 470.3 |
| 2-145 | 410.1 |

Example 14. 3-{4-[(3S)-3-aminopyrrolidin-1-yl]-5-(4-chloro-1-methyl-1H-1,3-benzodiazol-2-yl)pyridin-3-yl}benzonitrile (Compound 2-75)

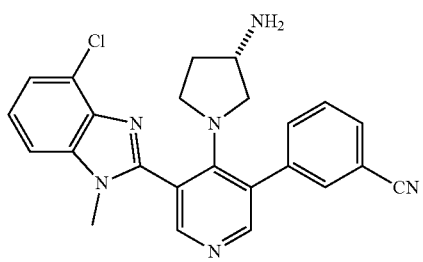 [SMILES: Cn1c(-c2cncc(-c3cccc(C#N)c3)c2N2CC[C@H](N)C2)nc2c(Cl)cccc21]

Step 14-1, preparation of tert-butyl N-[(3S)-1-[3-(3-cyanophenyl)-5-formylpyridin-4-yl]pyrrolidin-3-yl]carbamate: to a 40 mL round-bottom flask was added tert-butyl N-[(3S)-1-(3-bromo-5-formylpyridin-4-yl)pyrrolidin-3-yl]carbamate (1.00 equiv, 3.78 mmol, 1.4 g, "Example 9, step 9-1"), 3-cyanophenyl boronic acid (2.00 equiv, 7.49 mmol, 1.1 g,), $Pd_2(dba)_3\cdot CHCl_3$ (0.10 equiv, 0.38 mmol, 393 mg), P(t-Bu)$_3$·HBF$_4$ (0.20 equiv, 0.76 mmol, 226 mg), K$_3$PO$_4$ (3.00 equiv, 11.31 mmol, 2.4 g), toluene (20 mL), and water (2 mL) under N$_2$. The resulting solution was stirred for 2 h at 80° C. The reaction mixture was cooled to room temperature and concentrated under vacuum. The residue obtained was applied onto a silica gel column eluting with chloroform/methanol resulting in 870 mg (59%) of tert-butyl N-[(3S)-1-[3-(3-cyanophenyl)-5-formylpyridin-4-yl]pyrrolidin-3-yl]carbamate as a yellow solid. MS $(M+H)^+=393.2$.

Step 14-2, preparation of tert-butyl N-[(3S)-1-[3-(4-chloro-1H-1,3-benzodiazol-2-yl)-5-(3-cyanophenyl)pyridin-4-yl]pyrrolidin-3-yl]carbamate: to an 8 mL round-bottom flask was placed tert-butyl N-[(3S)-1-[3-(3-cyanophenyl)-5-formylpyridin-4-yl]pyrrolidin-3-yl]carbamate (1.00 equiv, 0.38 mmol, 150 mg), 3-chlorobenzene-1,2-diamine (1.50 equiv, 0.56 mmol, 80 mg), DMSO (3.0 mL), and Na$_2$S$_2$O$_5$ (2.00 equiv, 0.76 mmol, 145 mg). The resulting solution was stirred at 100° C. for 16 hrs, then cooled to rt and quenched with 10 mL of water, followed by extraction with ethyl acetate (3×15 mL), and the organic layers were combined, washed with 15 mL of water, dried over anhydrous sodium sulfate, filtered and concentrated under vacuum. The residue obtained was applied onto a silica gel column eluting with ethyl acetate/petroleum ether to afford 150 mg (76%) of tert-butyl N-[(3S)-1-[3-(4-chloro-1H-1,3-benzodiazol-2-yl)-5-(3-cyanophenyl)pyridin-4-yl]pyrrolidin-3-yl]carbamate as a light yellow solid. MS $(M+H)^+=516.0$.

Step 14-3, preparation of tert-butyl N-[(3S)-1-[3-(4-chloro-1-methyl-1H-1,3-benzodiazol-2-yl)-5-(3-cyanophenyl)pyridin-4-yl]pyrrolidin-3-yl]carbamate: to a 8 mL round-bottom flask was placed tert-butyl N-[(3S)-1-[3-(7-chloro-1H-1,3-benzodiazol-2-yl)-5-(3-cyanophenyl)pyridin-4-yl]pyrrolidin-3-yl]carbamate (1.0 equiv, 0.27 mmol, 140 mg), Cs$_2$CO$_3$ (3.0 equiv, 0.82 mmol, 266 mg), N,N-dimethylformamide (5.0 mL). This was followed by the addition of MeI (0.9 equiv, 0.24 mmol, 35 mg) drop-wise with stirring at 0° C. The resulting solution was stirred at 0° C. for 30 min, then quenched by the addition of 10 mL of water. The resulting solution was extracted with ethyl acetate (3×15 mL) and the organic layers were combined, washed with water (3×15 mL), dried over anhydrous sodium sulfate, filtered and concentrated under vacuum. The crude product was further purified by Prep-HPLC with the following conditions (Waters I): Column, Xbridge Prep C$_{18}$ OBD column, 5 μm, 19×150 mm; mobile phase A: Water (0.05% TFA) and mobile phase B: CH$_3$CN; gradient: B from 30% CH$_3$CN to 38% in 6 min; flow rate:20 ml/min; Detector, UV 220 & 254 nm. This separation resulted in two pure products: 50 mg (35%) of tert-butyl N-[(3S)-1-[3-(4-chloro-1-methyl-1H-1,3-benzodiazol-2-yl)-5-(3-cyanophenyl)pyridin-4-yl]pyrrolidin-3-yl]carbamate and 50 mg (35%) of tert-butyl N-[(3S)-1-[3-(7-chloro-1-methyl-1H-1,3-benzodiazol-2-yl)-5-(3-cyanophenyl)pyridin-4-yl]pyrrolidin-3-yl]carbamate. The former material was used for next step and the latter material was saved for the synthesis of Example 15. MS $(M+H)^+=529.1$ for both products.

Step 14-4, preparation of 3-[4-[(3S)-3-aminopyrrolidin-1-yl]-5-(4-chloro-1-methyl-1H-1,3-benzodiazol-2-yl)pyridin-3-yl]benzonitrile: a mixture of tert-butyl N-[(3S)-1-[3-(4-chloro-1-methyl-1H-1,3-benzodiazol-2-yl)-5-(3-cyanophenyl)pyridin-4-yl]pyrrolidin-3-yl]carbamate (1.0 equiv, 0.09 mmol, 50 mg), dichloromethane (5.0 mL) and trifluoroacetic acid (1.0 mL) was stirred at rt for 1 h, then concentrated under vacuum. The remaining residue was diluted with water/ACN and freeze-dried to afford 35.1 mg (68%) of TFA salt of 3-[4-[(3S)-3-aminopyrrolidin-1-yl]-5-(4-chloro-1-methyl-1H-1,3-benzodiazol-2-yl)pyridin-3-yl]benzonitrile as an off-white solid. MS $(M+H)^+=429.1$. The structure of this compound has been confirmed by $^1$H NMR and NOESY-NMR analyses.

The following compounds were prepared similarly to Example 14 with appropriate substituting reagents and substrates at different steps and they may require additional functional group modifications on benzimidazoyl side chain via well-known chemistry with appropriate reagents. Different salt such as HCl or formic acid maybe obtained.

| Compound no. | MS (M + H)+ |
|---|---|
| 2-74 | 413.2 |
| 2-114 | 427.2 |
| 2-116 | 447.2 |
| 2-110 | 413.2 |
| 2-111 | 441.2 |
| 2-112 | 457.2 |
| 2-113 | 438.1 |
| 2-114 | 427.2 |
| 2-115 | 447.2 |
| 2-131 | 447.1 |
| 2-132 | 427.2 |

Example 15. 3-{4-[(3S)-3-aminopyrrolidin-1-yl]-5-(7-chloro-1-methyl-1H-1,3-benzodiazol-2-yl)pyridin-3-yl}benzonitrile (Compound 2-76)

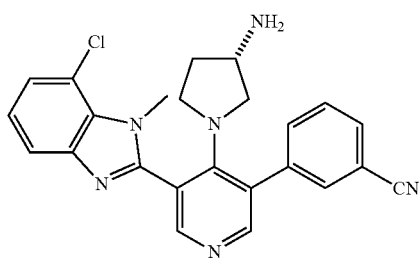 [SMILES: Cn1c(-c2cncc(-c3cccc(C#N)c3)c2N2CC[C@H](N)C2)nc2cccc(Cl)c21]

Step 15-1, preparation of N-[(3S)-1-[3-(7-chloro-1-methyl-1H-1,3-benzodiazol-2-yl)-5-(3-cyanophenyl)pyridin-4-yl]pyrrolidin-3-yl]carbamate: Using the similar procedure outlined in Step 14-4, example 14, t-butyl N-[(3S)-1-[3-(7-chloro-1-methyl-1H-1,3-benzodiazol-2-yl)-5-(3-cyanophenyl)pyridin-4-yl]pyrrolidin-3-yl]carbamate (50 mg, "Example 14, Step 14-3") was converted to 31.0 mg (60%) of TFA salt of 3-[4-[(3S)-3-aminopyrrolidin-1-yl]-5-(7-chloro-1-methyl-1H-indol-2-yl)pyridin-3-yl]benzonitrile as an off-white solid. MS (M+H)+=429.1. The structure of this compound has been confirmed by ¹H NMR and NOESY-NMR analyses.

The following compounds were prepared similarly to Example 15 with appropriate substituting reagents and substrates at different steps and they may require additional functional group modifications on benzimidazoyl side chain via well-known chemistry with appropriate reagents. Different salt such as HCl or formic acid maybe obtained.

| Compound no. | MS (M + H)+ |
|---|---|
| 2-75 | 413.2 |
| 2-115 | 427.2 |
| 2-117 | 447.1 |
| 2-133 | 447.1 |
| 2-134 | 427.2 |

Example 16. 3-{4-[(3S)-3-Aminopyrrolidin-1-yl]-5-(4-ethynyl-1H-1,3-benzodiazol-2-yl)pyridin-3-yl}benzonitrile (Compound 2-84)

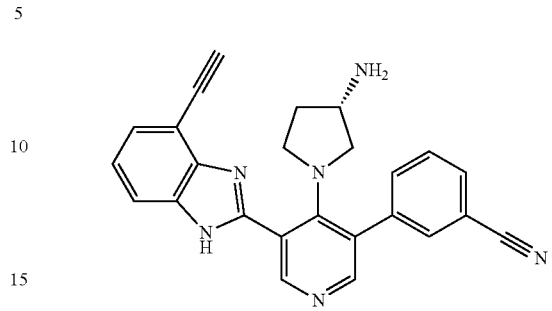

Step 16-1, preparation of N-[(3S)-1-[3-(4-bromo-1H-1,3-benzodiazol-2-yl)-5-(3-cyanophenyl)pyridin-4-yl]pyrrolidin-3-yl]carbamate: Similarly to Step 14-2, Example 14, the title compound (100 mg, 70%) was obtained from tert-butyl N-[(3S)-1-[3-(3-cyanophenyl)-5-formylpyridin-4-yl]pyrrolidin-3-yl]carbamate (1.0 equiv, 0.25 mmol, 100 mg, "Example 14, step 14-1"), 3-bromobenzene-1,2-diamine (1.5 equiv, 0.38 mmol, 71 mg), Na₂S₂O₅ (2.0 equiv, 0.50 mmol, 209 mg), and DMSO (3.0 mL) as a light yellow solid. MS (M+1)+=560.5, 562.5.

Step 16-2, preparation of tert-butyl N-[(3S)-1-[3-(3-cyanophenyl)-5-[4-[2-(trimethylsilyl)ethynyl]-1H-L3-benzodiazol-2-yl]pyridin-4-yl]pyrrolidin-3-yl]carbamate: to an 8 mL round-bottom was placed tert-butyl N-[(3S)-1-[3-(4-bromo-1H-1,3-benzodiazol-2-yl)-5-(3-cyanophenyl)pyridin-4-yl]pyrrolidin-3-yl]carbamate (1.0 equiv, 0.11 mmol, 61 mg), trimethyl[2-(tripropylstannyl)ethynyl]silane (3.0 equiv, 0.33 mmol, 114 mg), Pd(Amphos)Cl₂ (0.1 equiv, 0.011 mmol, 7.8 mg,), and toluene (3.0 mL) under N₂. The resulting solution was stirred at 90° C. for 3 h. The reaction mixture was cooled to room temperature and concentrated under vacuum. The crude material was purified by reverse phase Prep-HPLC to afford 40 mg (64%) of title compound as a light yellow solid. MS (M+1)+=577.3.

Step 16-3, preparation of 3-{4-[(3S)-3-aminopyrrolidin-1-yl]-5-(7-ethynyl-1H-1,3-benzodiazol-2-yl)pyridin-3-yl}benzonitrile: a mixture of tert-butyl N-[(3S)-1-[3-(3-cyanophenyl)-5-[4-[2-(trimethylsilyl)ethynyl]-1H-1,3-benzodiazol-2-yl]pyridin-4-yl]pyrrolidin-3-yl]carbamate (1.00 equiv, 0.07 mmol, 40 mg) in dichloromethane (5.0 mL)/trifluoroacetic acid (1.0 mL was stirred at rt for 30 min and then concentrated under vacuum. The residue was stirred in tetrahydrofuran (5.0 mL) in the presence of TBAF (3.0 equiv, 0.21 mmol, 54 mg) at rt for 30 min, then quenched with 10 mL of water and extracted with ethyl acetate (3×10 mL). Organic layers were combined, washed with brine, dried over anhydrous sodium sulfate, filtered and concentrated. The crude product was purified by reverse phase Prep-HPLC to produce 4.8 mg (13%) of TFA salt of 3-[4-[(3S)-3-aminopyrrolidin-1-yl]-5-(4-ethynyl-1H-1,3-benzodiazol-2-yl)pyridin-3-yl]benzonitrile as an off-white solid. MS (M+1)+=405.2.

Example 17. 3-{4-[(3S)-3-aminopyrrolidin-1-yl]-5-(4-ethyl-1H-1,3-benzodiazol-2-yl)pyridin-3-yl}benzonitrile (Compound 2-100)

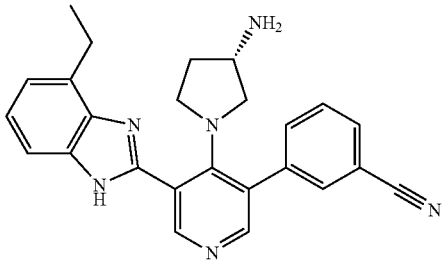 [SMILES: CCc1cccc2[nH]c(-c3cncc(-c4cccc(C#N)c4)c3N3CC[C@H](N)C3)nc12]

Step 17-1, preparation of N-(2-ethylphenyl)acetamide: to a 100 mL 3-necked round-bottom flask was placed 2-ethylaniline (1.0 equiv, 42.1 mmol, 5.1 g), acetyl acetate (1.8 equiv, 75.8 mmol, 7.0 mL), and AcOH (20 mL). The resulting solution was stirred at room temperature for 22 hrs. The reaction was quenched with 50 mL of water and extracted with 3×50 mL of ethyl acetate. Organic layers were combined, washed with 3×50 mL of water, dried over anhydrous sodium sulfate, filtered and concentrated under vacuum. The residue was applied onto a silica gel column eluting with ethyl acetate/petroleum ether to afford 7.0 g of N-(2-ethylphenyl)acetamide as an off-white solid. MS $(M+1)^+$=164.1.

Step 17-2, preparation of N-(2-ethyl-6-nitrophenyl)acetamide: to a 50 mL 3-necked round-bottom flask was placed N-(2-ethylphenyl)acetamide (1.00 equiv, 18.38 mmol, 3.0 g) and AcOH (3.0 mL). $HNO_3$ (4 mL) was added drop-wise with stirring. After completion of the addition of $HNO_3$, the resulting solution was stirred at rt for 16 hrs, then quenched with 50 mL of water and the pH of solution was adjusted to 8.0 with aqueous sodium bicarbonate. The resulting solution was extracted with 3×50 mL of ethyl acetate, and the organic layers were combined, washed with brine, dried over anhydrous sodium sulfate, filtered and concentrated under vacuum. The residue was applied onto a silica gel column eluting with ethyl acetate/petroleum ether to afford 500 mg (13%) of N-(2-ethyl-6-nitrophenyl)acetamide as yellow oil. MS $(M+H)^+$=209.1.

Step 17-3, preparation of 2-ethyl-6-nitroaniline: to a 50 mL round-bottom flask was placed N-(2-ethyl-6-nitrophenyl)acetamide (1.0 equiv, 2.40 mmol, 500 mg), ethanol (6.0 mL), and concentrated hydrogen chloride (8.0 mL). The resulting solution was stirred at 80° C. overnight, then quenched with 50 mL of water and the pH of resulting solution was adjusted to 8.0 with sodium bicarbonate. The resulting solution was extracted with 3×50 mL of ethyl acetate. The organic layers were combined, washed with brine, dried over anhydrous sodium sulfate, filtered and concentrated under vacuum to afford 500 mg of the title compound as a yellow solid. MS $(M+H)^+$=167.1.

Step 17-4, preparation of 3-ethylbenzene-1,2-diamine: to a 40 mL round-bottom flask was placed 2-ethyl-6-nitroaniline (1.0 equiv, 3.0 mmol, 500 mg), Fe (5.0 equiv, 14.8 mmol, 838 mg), $NH_4Cl$ (5.00 equiv, 14.8 mmol, 793 mg), water (3.0 mL), and propan-2-ol (15 mL). The resulting solution was stirred at 80° C. for 30 min. then cooled to rt and concentrated under vacuum. The residue obtained was applied onto a silica gel column eluting with ethyl acetate/ petroleum ether to afford 350 mg (85%) of the title compound as brown oil. MS $(M+H)^+$=137.1.

Step 17-5, preparation of tert-butyl N-[(1S)-3-[3-(3-cyanophenyl)-5-(4-ethyl-1H-1,3-benzodiazol-2-yl)pyridin-4-yl]cyclopentyl]carbamate: from 3-ethylbenzene-1,2-diamine (2.0 equiv, 0.15 mmol, 21 mg) and tert-butyl N-[(1S)-3-[3-(3-cyanophenyl)-5-formylpyridin-4-yl]cyclopentyl]carbamate (1.0 equiv, 0.08 mmol, 30 mg), the title compound (32 mg) was prepared using a similar method to the one described in "Example 14, Step 14-2". MS $(M+H)^+$=509.3.

Step 17-6, preparation of 3-{4-[(3S)-3-aminopyrrolidin-1-yl]-5-(4-ethyl-1H-1,3-benzodiazol-2-yl)pyridin-3-yl}benzonitrile: the title compound was prepared using a similar method to Step 13-4, Example 13, from tert-butyl N-[(3S)-1-[3-(3-cyanophenyl)-5-(4-ethyl-1H-1,3-benzodiazol-2-yl)pyridin-4-yl]pyrrolidin-3-yl]carbamate of the above step to afford 29.2 mg (89%) of TFA salt of 3-[4-[(3S)-3-aminopyrrolidin-1-yl]-5-(4-ethyl-1H-1,3-benzodiazol-2-yl)pyridin-3-yl]benzonitrile as an off-white solid. MS $(M+H)^+$=409.2.

Example 18. 3-{4-[(3S)-3-aminopyrrolidin-1-yl]-5-[7-(hydroxymethyl)-1H-1,3-benzodiazol-2-yl]pyridin-3-yl}benzonitrile (Compound 2-91)

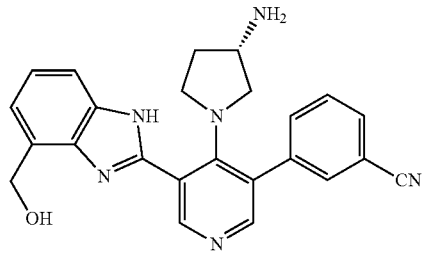 [SMILES: N#Cc1cccc(-c2cncc(-c3nc4c(CO)cccc4[nH]3)c2N2CC[C@H](N)C2)c1]

Step 18-1, preparation of methyl 2-[4-[(3S)-3-[[(tert-butoxy)carbonyl]amino]pyrrolidin-1-yl]-5-(3-cyanophenyl)pyridin-3-yl]-1H-1,3-benzodiazole-4-carboxylate: from tert-butyl N-[(3S)-1-[3-(3-cyanophenyl)-5-formylpyridin-4-yl]pyrrolidin-3-yl]carbamate (Step 14-1, Example 14, 1.0 equiv, 0.25 mmol, 100 mg) and methyl 2,3-diaminobenzoate (1.5 equiv, 0.39 mmol, 64 mg), the title compound (100 mg) was prepared using a similar method to the one described in "Example 14, Step 14-2". MS $(M+H)^+$=538.6.

Step 18-2, preparation of tert-butyl N-[(3S)-1-[3-(3-cyanophenyl)-5-[4-(hydroxymethyl)-1H-1,3-benzodiazol-2-yl]pyridin-4-yl]pyrrolidin-3-yl]carbamate: to a 8 mL sealed tube was placed methyl 2-[4-[(3S)-3-[[(tert-butoxy)carbonyl]amino]pyrrolidin-1-yl]-5-(3-cyanophenyl)pyridin-3-yl]-1H-1,3-benzodiazole-4-carboxylate (1.0 equiv, 0.06 mmol, 30 mg), $NaBH_4$ (3.0 equiv, 0.19 mmol, 7 mg), and ethanol (2.0 mL). The resulting solution was stirred at 80° C. for 16 hrs, then cooled to rt. The solid was filtered out and the solution was concentrated. The crude was purified by Prep-HPLC with SunFire Prep $C_{18}$ OBD Column, 19×150 mm 5 μ10 nm and two mobile phases of Water (A, 0.05% TFA) and $CH_3CN$ (B). The title compound was eluted within the following gradient step of 20% of B to 40% of B in 6 min with flow rate at 20 mL/min. The combined fractions containing the pure title compound were freeze-dried to afford 5 mg (18%) of brown solid. MS $(M+H)^+$=511.3.

Step 18-3, preparation of 3-{4-[(3S)-3-aminopyrrolidin-1-yl]-5-[7-(hydroxymethyl)-1H-1,3-benzodiazol-2-yl]pyridin-3-yl}benzonitrile: using a similar method to Step 13-4, Example 13, tert-butyl N-[(3S)-1-[3-(3-cyanophenyl)-5-[4-(hydroxymethyl)-1H-1,3-benzodiazol-2-yl]pyridin-4-yl]pyrrolidin-3-yl]carbamate (5 mg), was converted into 1.7 mg (33%) of TFA salt of 3-[4-[(3S)-3-aminopyrrolidin-1-yl]-5-[4-(hydroxymethyl)-1H-1,3-benzodiazol-2-yl]pyridin-3-yl]benzonitrile as colorless oil. MS (M+H)$^+$=411.3.

Example 19. 2-{4-[(3S)-3-aminopyrrolidin-1-yl]-5-(3-cyanophenyl)pyridin-3-yl}-1H-1,3-benzodiazole-4-carboxamide (Compound 2-83)

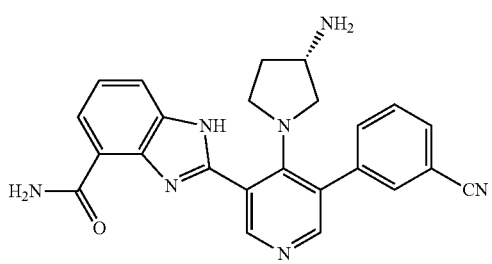 [SMILES: N#Cc1cccc(-c2cncc(-c3nc4c(C(N)=O)cccc4[nH]3)c2N2CC[C@H](N)C2)c1]

Step 19-1, preparation of tert-butyl N-[(3S)-1-[3-(4-carbamoyl-1H-1,3-benzodiazol-2-yl)-5-(3-cyanophenyl)pyridin-4-yl]pyrrolidin-3-yl]carbamate: to a 8 mL sealed tube was placed methyl 2-[4-[(3S)-3-[[(tert-butoxy)carbonyl]amino]pyrrolidin-1-yl]-5-(3-cyanophenyl)pyridin-3-yl]-1H-1,3-benzodiazole-4-carboxylate (1.0 equiv, 0.02 mmol, 10 mg, "Example 18, step 18-1"), and NH$_3$/MeOH (3.0 mL). The resulting solution was stirred at 80° C. for 16 hrs. The reaction mixture was cooled to room temperature and solids were filtered out. The crude product was purified by reverse phase Prep-HPLC using SunFire Prep C$_{18}$ OBD Column (19×150 mm, 5 µm, 10 nm) with two mobile phases of Water (0.05% TFA, A) and CH$_3$CN (B). The fractions containing the title compound was eluted within the gradient of 20% B to 40% B in 7 min to afford 6 mg (51%) of tert-butyl N-[(3S)-1-[3-(4-carbamoyl-1H-1,3-benzodiazol-2-yl)-5-(3-cyanophenyl)pyridin-4-yl]pyrrolidin-3-yl]carbamate as an off-white solid. MS (M+H)$^+$=524.3.

Step 19-2, preparation of 2-{4-[(3S)-3-aminopyrrolidin-1-yl]-5-(3-cyanophenyl)pyridin-3-yl}-1H-1,3-benzodiazole-4-carboxamide: using similar method of Step 13-4, Example 13, tert-butyl N-[(3S)-1-[3-(4-carbamoyl-1H-1,3-benzodiazol-2-yl)-5-(3-cyanophenyl)pyridin-4-yl]pyrrolidin-3-yl]carbamate (6 mg) was converted to 5.2 mg (84%) of TFA salt of 2-[4-[(3S)-3-aminopyrrolidin-1-yl]-5-(3-cyanophenyl)pyridin-3-yl]-1H-1,3-benzodiazole-4-carboxamide as an off-white solid. MS (M+H)$^+$=424.4.

The following compounds were prepared similarly to Example 19 with appropriate substituting reagents and substrates at different steps and they may require additional functional group modifications on benzimidazoyl side chain via well-known chemistry with appropriate reagents. Different salt such as HCl or formic acid maybe obtained.

| Compound no. | MS (M + H)$^+$ |
|---|---|
| 2-90 | 438.2 |

Example 20. 4-[(3S)-3-aminopyrrolidin-1-yl]-5-(7-fluoro-4-methyl-1H-1,3-benzodiazol-2-yl)-[3,4'-bipyridine]-2'-carboxamide (Compound 2-107)

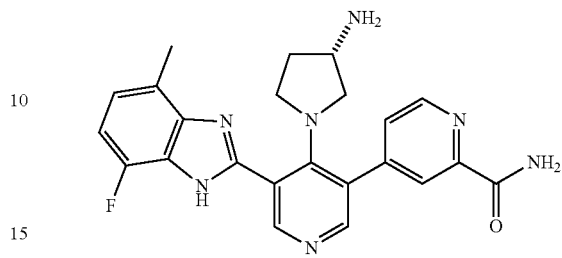

Step 20-1, preparation of tert-butyl N-[(3S)-1-[2'-carbamoyl-5-(7-fluoro-4-methyl-1H-1,3-benzodiazol-2-yl)-[3,4'-bipyridin]-4-yl]pyrrolidin-3-yl]carbamate: to a DMSO solution (0.5 mL) of tert-butyl N-[(3S)-1-[2'-cyano-5-(7-fluoro-4-methyl-1H-1,3-benzodiazol-2-yl)-[3,4'-bipyridin]-4-yl]pyrrolidin-3-yl]carbamate (1.0 equiv, 0.035 mmol, 18 mg, Step 11-2, Example 11) was added 30% H$_2$O (13 equiv, 0.46 mmol, 0.065 mL) and K$_2$CO$_3$ (0.15 equiv, 0.005 mmol, 1.0 mg). The resulting mixture was stirred at rt for 2 hrs, diluted with water, extracted with dichloromethane, dried with MgSO$_4$, filtered and concentrated to give 20 mg of crude product. This material was used for next step without further purification. MS (M+H)$^+$=532.3.

Step 20-2, preparation of 4-[(3S)-3-aminopyrrolidin-1-yl]-5-(7-fluoro-4-methyl-1H-1,3-benzodiazol-2-yl)-[3,4'-bipyridine]-2'-carboxamide: from crude tert-butyl N-[(3S)-1-[2'-carbamoyl-5-(7-fluoro-4-methyl-1H-1,3-benzodiazol-2-yl)-[3,4'-bipyridin]-4-yl]pyrrolidin-3-yl]carbamate (1.0 equiv, 20 mg, 0.035 mmol), the title compound (2.0 mg) was prepared as a HCl salt using a similar method to the one described in "Example 9, Step 9-4". MS (M+H)$^+$=432.3.

The following compounds were prepared similarly to Example 20 with appropriate substituting reagents and substrates at different steps and they may require additional functional group modifications on benzimidazoyl side chain via well-known chemistry with appropriate reagents. Different salt such as HCl or formic acid maybe obtained. Particularly, the conversion of cyano group to carboxylic amide was carried out using HCl in ethyl acetate for the synthesis of compound 2-156.

| Compound no. | MS (M + H)$^+$ |
|---|---|
| 2-138 | 445.3 |
| 2-156 | 428.2 |

Example 21. 2-{4-[(3S)-3-aminopyrrolidin-1-yl]-5-(3-cyanophenyl)pyridin-3-yl}-1H-1,3-benzodiazole-4-carboxylic acid (Compound 2-82)

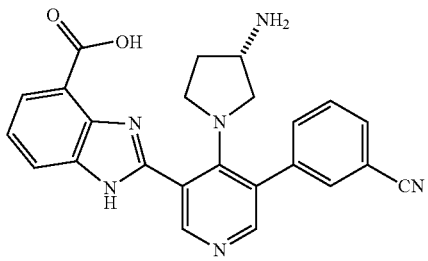 [SMILES: N#Cc1cccc(-c2cncc(-c3nc4c(C(=O)O)cccc4[nH]3)c2N2CC[C@H](N)C2)c1]

Step 21-1, preparation of 2-[4-[(3S)-3-[[(tert-butoxy)carbonyl]amino]pyrrolidin-1-yl]-5-(3-cyanophenyl)pyridin-3-yl]-1H-1,3-benzodiazole-4-carboxylic acid: to a 100 mL round-bottom flask was placed methyl 2-[4-[(3S)-3-[[(tert-butoxy)carbonyl]amino]pyrrolidin-1-yl]-5-(3-cyanophenyl)pyridin-3-yl]-1H-1,3-benzodiazole-4-carboxylate (1.0 equiv, 0.07 mmol, 40 mg, "Example 18, step 18-1"), sodium hydroxide (5.0 equiv, 0.35 mmol, 14 mg), methanol (5.0 mL) and water (0.5 mL). The resulting solution was stirred at 50° C. for 16 hrs. The solids were filtered out. The crude product was concentrated and purified by reverse phase Prep-HPLC resulting in 20 mg (51%) of 2-[4-[(3S)-3-[[(tert-butoxy)carbonyl]amino]pyrrolidin-1-yl]-5-(3-cyanophenyl)pyridin-3-yl]-1H-1,3-benzodiazole-4-carboxylic acid as an off-white solid. MS (M+H)$^+$=525.1.

Step 21-2, preparation of 2-{4-[(3S)-3-aminopyrrolidin-1-yl]-5-(3-cyanophenyl)pyridin-3-yl}-1H-1,3-benzodiazole-4-carboxylic acid: to an 8 mL vial was placed 2-[4-[(3S)-3-[[(tert-butoxy)carbonyl]amino]pyrrolidin-1-yl]-5-(3-cyanophenyl)pyridin-3-yl]-1H-1,3-benzodiazole-4-carboxylic acid (1.0 equiv, 0.02 mmol, 10 mg), dichloromethane (1.0 mL), and trifluoroacetic acid (0.2 mL). The resulting solution was stirred for 2 hrs at rt. The resulting mixture was concentrated under vacuum and lyophilized to afford 5.2 mg (51%) of TFA salt of the title compound as a light brown solid. MS (M+H)$^+$=425.2.

Example 22. 3-[4-(3-amino-3-methylpyrrolidin-1-yl)-5-(4-fluoro-1H-1,3-benzodiazol-2-yl)pyridin-3-yl]benzamide (Compound 2-18)

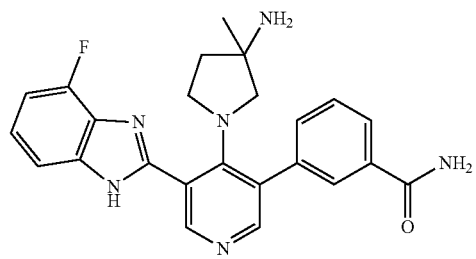 [SMILES: CC1(N)CCN(c2c(-c3cccc(C(N)=O)c3)cncc2-c2nc3c(F)cccc3[nH]2)C1]

Step 22-1, preparation of tert-butyl N-[1-(3-bromo-5-formylpyridin-4-yl)-3-methylpyrrolidin-3-yl]carbamate: from 5-bromo-4-chloropyridine-3-carbaldehyde (1.2 equiv, 1.21 mmol, 267 mg) and 3-(boc-amino)-3-methylpyrrolidine (1.0 equiv, 1.21 mmol, 250 mg), the title compound (308 mg) was prepared using a similar method to the one described in "Example 9, Step 9-1". MS (M+H)$^+$=384.2, 386.1.

Step 22-2, preparation of tert-butyl N-{1-[3-bromo-5-(4-fluoro-1H-1,3-benzodiazol-2-yl)pyridin-4-yl]-3-methylpyrrolidin-3-yl}carbamate: from tert-butyl N-[1-(3-bromo-5-formylpyridin-4-yl)-3-methylpyrrolidin-3-yl]carbamate (1.0 equiv, 0.47 mmol, 182 mg) and 2,3-diaminofluorobenzene (2.0 equiv, 0.94 mmol, 120 mg), the title compound (183 mg) was prepared using a similar method to the one described in "Example 9, Step 9-2". MS (M+H)$^+$=490.2, 492.0.

Step 22-3, preparation of methyl 3-[4-(3-{[(tert-butoxy)carbonyl]amino}-3-methylpyrrolidin-1-yl)-5-(4-fluoro-1H-1,3-benzodiazol-2-yl)pyridin-3-yl]benzoate: from tert-butyl N-{1- [3-bromo-5-(4-fluoro-1H-1,3-benzodiazol-2-yl)pyridin-4-yl]-3-methylpyrrolidin-3-yl}carbamate (1.0 equiv, 0.20 mmol, 100 mg) and [3-(methoxycarbonyl)phenyl]boronic acid (3.0 equiv, 0.61 mmol, 109 mg), the title compound (60 mg) was prepared using a similar method to the one described in "Example 9, Step 9-3". MS (M+H)$^+$=546.3.

Step 22-4, preparation of tert-butyl N-{1-[3-(3-carbamoylphenyl)-5-(4-fluoro-1H-1,3-benzodiazol-2-yl)pyridin-4-yl]-3-methylpyrrolidin-3-yl}carbamate: methyl 3-[4-(3-{[(tert-butoxy)carbonyl]amino}-3-methylpyrrolidin-1-yl)-5-(4-fluoro-1H-1,3-benzodiazol-2-yl)pyridin-3-yl]benzoate (1.0 equiv, 40 mg, 0.07 mmol) was combined with NH$_3$/H$_2$O (2.5 mL) and the resulting mixture was stirred at rt for 2 hrs, then concentrated. The residue obtained was purified by reverse phase Prep-HPLC resulting in 10 mg of the title compound as a yellow solid. MS (M+H)$^+$=531.2.

Step 22-5, preparation of 3-[4-(3-amino-3-methylpyrrolidin-1-yl)-5-(4-fluoro-1H-1,3-benzodiazol-2-yl)pyridin-3-yl]benzamide: from tert-butyl N-{1-[3-(3-carbamoylphenyl)-5-(4-fluoro-1H-1,3-benzodiazol-2-yl)pyridin-4-yl]-3-methylpyrrolidin-3-yl}carbamate (10 mg), the title compound (5.6 mg) was prepared using a similar method to the one described in "Example 14, Step 14-4". MS (M+H)$^+$= 431.2.

The following compounds were prepared similarly to Example 22 with appropriate substituting reagents and substrates at different steps and they may require additional functional group modifications on benzimidazoyl side chain via well-known chemistry with appropriate reagents. Different salt such as HCl or formic acid maybe obtained.

| Compound no. | MS (M + H)$^+$ |
|---|---|
| 2-19 | 445.2 |
| 2-31 | 459.2 |
| 2-76 | 404.1 |
| 2-71 | 435.2 |
| 2-72 | 435.2 |
| 2-73 | 447.3 |
| 2-85 | 417.2 |
| 2-105 | 428.2 |
| 2-118 | 455.2 |

Example 23. trans-4-amino-1-[3-(3-cyanophenyl)-5-(4-fluoro-1H-1,3-benzodiazol-2-yl)pyridin-4-yl]pyrrolidine-3-carboxamide (Compound 2-69)

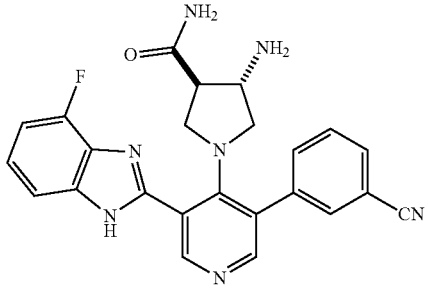 [SMILES: N#Cc1cccc(-c2cncc(-c3nc4c(F)cccc4[nH]3)c2N2C[C@@H](N)[C@H](C(N)=O)C2)c1]

Step 23-1, preparation of methyl trans-1-[3-bromo-5-(4-fluoro-1H-1,3-benzodiazol-2-yl)pyridin-4-yl]-4-{[(tert-butoxy)carbonyl]amino}pyrrolidine-3-carboxylate: from 2-(5-bromo-4-chloropyridin-3-yl)-7-fluoro-1H-1,3-benzodiazole (1.0 equiv, 0.15 mmol, 50 mg, "Example 13, step 13-1") and methyl trans-4-{[(tert-butoxy)carbonyl]amino}pyrrolidine-3-carboxylate (1.2 equiv, 0.18 mmol, 45 mg), the title compound (60 mg) was prepared using a similar method to the one described in "Example 9, Step 9-1". MS (M+H)$^+$=534.1, 536.1.

Step 23-2, preparation of methyl trans-4-{[(tert-butoxy)carbonyl]amino}-1-[3-(3-cyanophenyl)-5-(4-fluoro-1H-1,3-benzodiazol-2-yl)pyridin-4-yl]pyrrolidine-3-carboxylate: from methyl trans-1-[3-bromo-5-(4-fluoro-1H-1,3-benzodiazol-2-yl)pyridin-4-yl]-4-{[(tert-butoxy)carbonyl]amino}pyrrolidine-3-carboxylate (1.0 equiv, 0.11 mmol, 60 mg) and (3-cyanophenyl)boronic acid (2.0 equiv, 0.22 mmol, 33 mg), the title compound (60 mg) was prepared using a similar method to the one described in "Example 9, Step 9-3". MS (M+H)$^+$=546.3.

Step 23-3, preparation of tert-butyl N-[trans-4-carbamoyl-1-[3-(3-cyanophenyl)-5-(4-fluoro-1H-1,3-benzodiazol-2-yl)pyridin-4-yl]pyrrolidin-3-yl]carbamate: to an 8 mL vial was added methyl trans-4-{[(tert-butoxy)carbonyl]amino}-1-[3-(3-cyanophenyl)-5-(4-fluoro-1H-1,3-benzodiazol-2-yl)pyridin-4-yl]pyrrolidine-3-carboxylate (1.0 equiv, 0.04 mmol, 20 mg) and NH$_3$/H$_2$O (1.0 mL). The resulting mixture was stirred at 40° C. for overnight. The reaction solution was concentrated and the residue obtained was purified by reverse phase Prep-HPLC resulting in 6.0 mg of the title compound as a light yellow solid. MS (M+H)$^+$=542.2.

Step 23-4, preparation of trans-4-amino-1-[3-(3-cyanophenyl)-5-(4-fluoro-1H-1,3-benzodiazol-2-yl)pyridin-4-yl]pyrrolidine-3-carboxamide: from tert-butyl N-[trans-4-carbamoyl-1-[3-(3-cyanophenyl)-5-(4-fluoro-1H-1,3-benzodiazol-2-yl)pyridin-4-yl]pyrrolidin-3-yl]carbamate (6.0 mg), the title compound (3.9 mg) was prepared using a similar method to the one described in "Example 14, Step 14-4". MS (M+H)$^+$=442.1.

Example 24. 5-[4-(3-Amino-3-methylpyrrolidin-1-yl)-5-(4-methyl-1H-1,3-benzodiazol-2-yl)pyridin-3-yl]-2,3-difluorobenzamide (Compound 2-127)

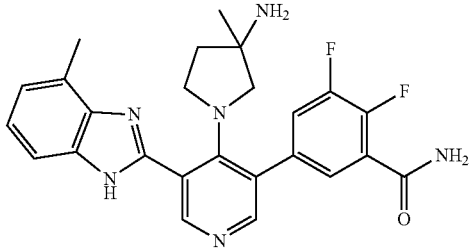 [SMILES: Cc1cccc2[nH]c(-c3cncc(-c4cc(F)c(F)c(C(N)=O)c4)c3N3CCC(C)(N)C3)nc12]

Step 24-1, preparation of tert-butyl N-{1-[3-bromo-5-(4-methyl-1H-1,3-benzodiazol-2-yl)pyridin-4-yl]-3-methylpyrrolidin-3-yl}carbamate: from tert-butyl N-[1-(3-bromo-5-formylpyridin-4-yl)-3-methylpyrrolidin-3-yl]carbamate (1.0 equiv, 0.64 mmol, 264 mg, "Example 22, Step 22-1") and 2,3-diaminotoluene (2.5 equiv, 1.6 mmol, 200 mg), the title compound (223 mg) was prepared using a similar method to the one described in "Example 9, Step 9-2". MS (M+H)$^+$=486.3, 488.4.

Step 24-1, preparation of 5-[4-(3-{[(tert-butoxy)carbonyl]amino}-3-methylpyrrolidin-1-yl)-5-(4-methyl-1H-1,3-benzodiazol-2-yl)pyridin-3-yl]-2,3-difluorobenzoic acid: from tert-butyl N-{1-[3-bromo-5-(4-methyl-1H-1,3-benzodiazol-2-yl)pyridin-4-yl]-3-methylpyrrolidin-3-yl}carbamate (1.0 equiv, 0.46 mmol, 223 mg) and 3-carboxy-4,5-difluorophenylboronic acid (3.0 equiv, 1.38 mmol, 280 mg), the title compound (63 mg) was prepared using a similar method to the one described in "Example 9, Step 9-3". MS (M+H)$^+$=564.5.

Step 24-3, preparation of tert-butyl N-{1-[3-(3-carbamoyl-4,5-difluorophenyl)-5-(4-methyl-1H-1,3-benzodiazol-2-yl)pyridin-4-yl]-3-methylpyrrolidin-3-yl}carbamate: to a DMF (2.0 mL) solution of 5-[4-(3-{[(tert-butoxy)carbonyl]amino}-3-methylpyrrolidin-1-yl)-5-(4-methyl-1H-1,3-benzodiazol-2-yl)pyridin-3-yl]-2,3-difluorobenzoic acid (1.0 equiv, 0.11 mmol, 63 mg) was added DIPEA (5.0 equiv, 0.55 mmol, 0.10 mL), HATU (1.4 equiv, 0.16 mmol, 60 mg) and NH$_4$Cl (3.0 equiv, 0.33 mmol, 18 mg). The resulting mixture was heated at 70° C. for 0.5 h and LCMS analysis showed complete consumption of starting material. The reaction mixture was diluted with ethyl acetate, washed with water and brine, dried with Na$_2$SO$_4$ and concentrated. The residue obtained was purified by silica gel chromatography eluting with MeOH/DCM (0-10%) to afford 36 mg of the desire product as a clean oil. MS (M+H)$^+$=563.3.

Step 24-4, preparation of 5-[4-(3-amino-3-methylpyrrolidin-1-yl)-5-(4-methyl-1H-1,3-benzodiazol-2-yl)pyridin-3-yl]-2,3-difluorobenzamide: from tert-butyl N-{1-[3-(3-carbamoyl-4,5-difluorophenyl)-5-(4-methyl-1H-1,3-benzodiazol-2-yl)pyridin-4-yl]-3-methylpyrrolidin-3-yl}carbamate (1.0 equiv, 0.064 mmol, 36 mg), the title compound (14 mg) was prepared as HCl salt using a similar method to the one described in "Example 9, Step 9-4". MS (M+H)$^+$=463.2.

Example 25. 3-{4-[(3S)-3-aminopyrrolidin-1-yl]-5-(4-methyl-1H-indol-2-yl)pyridin-3-yl}-5-fluorobenzonitrile (Compound 2-129)

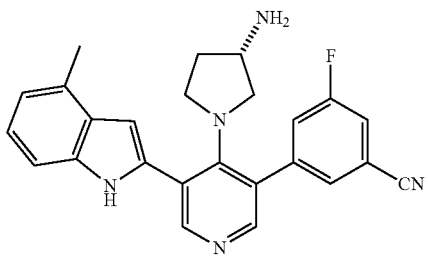 [SMILES: Cc1cccc2[nH]c(-c3cncc(-c4cc(F)cc(C#N)c4)c3N3CC[C@H](N)C3)cc12]

Step 25-1, preparation of tert-butyl N-[(3S)-1-(3-bromo-5-chloropyridin-4-yl)pyrrolidin-3-yl]carbamate: to a DMSO (4.0 mL) solution of 3-bromo-4,5-dichloropyridine (1.0 equiv, 1.0 mmol, 227 mg) was added tert-butyl N-[(3S)-pyrrolidin-3-yl]carbamate (1.5 equiv, 1.50 mmol, 280 mg) and DIPEA (1.50 mL). The resulting mixture was heated at 130° C. for 1 h, then cooled to rt and diluted with ethyl acetate. The ethyl acetate was then washed with water and brine, dried with $Na_2SO_4$ and concentrated. The residue obtained was purified by reverse phase $C_{18}$ chromatography eluting with MeCN/water (0-60%). Pure fractions were combined, neutralized with saturated $NaHCO_3$ and NaCl, extracted with ethyl acetate and dried with $MgSO_4$. The organic was concentrated and dried under high vacuum to give 216 mg of the desired product. MS $(M+H)^+$=376.2, 378.2.

Step 25-2, preparation of tert-butyl N-[(3S)-1-[3-chloro-5-(3-cyano-5-fluorophenyl)pyridin-4-yl]pyrrolidin-3-yl]carbamate: to a dioxane (4.0 mL) solution of tert-butyl N-[(3S)-1-(3-bromo-5-chloropyridin-4-yl)pyrrolidin-3-yl]carbamate (1.0 equiv, 0.57 mmol, 216 mg) was added Pd(dppf)Cl$_2$ (0.1 equiv, 0.057 mmol, 42 mg), (3-cyano-5-fluorophenyl)boronic acid (2.0 equiv, 1.14 mmol, 189 mg), $K_2CO_3$ (2.5 equiv, 1.43 mmol, 196 mg) and water (0.4 mL) under atmospheric $N_2$. The resulting mixture was heated at 95° C. for 0.5 h, concentrated and purified by silica gel chromatography eluting with ethyl acetate/hexane (0-100%) to afford 126 mg of the desired product. MS $(M+H)^+$=417.3.

Step 25-3, preparation of tert-butyl N-[(3S)-1-[3-(3-cyano-5-fluorophenyl)-5-(4-methyl-1H-indol-2-yl)pyridin-4-yl]pyrrolidin-3-yl]carbamate: to a dioxane (1.0 mL) solution of tert-butyl N-[(3S)-1-[3-chloro-5-(3-cyano-5-fluorophenyl)pyridin-4-yl]pyrrolidin-3-yl]carbamate (1.0 equiv, 0.10 mmol, 42 mg) was added Pd(Amphos)Cl$_2$ (0.1 equiv, 0.01 mmol, 7.1 mg), 4-methylindole-2-boronic acid pinacol ester (2.0 equiv, 0.20 mmol, 53 mg), $K_2CO_3$ (3.0 equiv, 0.30 mmol, 42 mg) and water (0.1 mL) under atmospheric $N_2$. The resulting mixture was heated at 95° C. for 1 h, cooled to rt, then diluted with ethyl acetate. The ethyl acetate was washed with water and brine, dried with MgSO$_4$, filtered and concentrated. The crude product obtained was used for next step without further purification. MS $(M+H)^+$=512.4.

Step 25-4, preparation of 3-{4-[(3S)-3-aminopyrrolidin-1-yl]-5-(4-methyl-1H-indol-2-yl)pyridin-3-yl}-5-fluorobenzonitrile: to a dichloromethane (1.0 mL) solution of crude tert-butyl N-[(3S)-1-[3-(3-cyano-5-fluorophenyl)-5-(4-methyl-1H-indol-2-yl)pyridin-4-yl]pyrrolidin-3-yl]carbamate was added TFA (0.3 mL). The resulting mixture was stirred at rt for 0.5 h, concentrated and then purified by reverse phase $C_{18}$ chromatography eluting with MeCN/water (0-40%). Pure fractions were combined, neutralized with saturated $NaHCO_3$ and NaCl, extracted with ethyl acetate, dried with $MgSO_4$ and filtered. The organic was concentrated after addition of HCl in EtOEt (2.0 M, 0.2 mL) and dried under high vacuum to give 11 mg of the title compound as HCl salt. MS $(M+H)^+$=412.3.

The following compounds were prepared similarly to Example 25 with appropriate substituting reagents and substrates at different steps.

| Compound no. | MS (M + H)$^+$ |
| --- | --- |
| 2-137 | 412.3 |

Example 26. 5-{4-[(3S)-3-aminopyrrolidin-1-yl]-5-(1-ethyl-4-fluoro-1H-1,3-benzodiazol-2-yl)pyridin-3-yl}-2-fluorobenzonitrile (Compound 2-142)

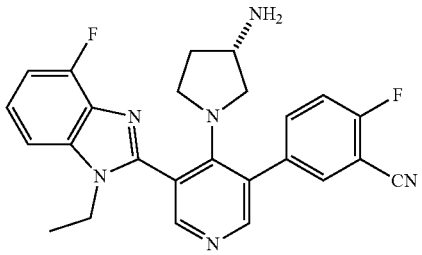 [SMILES: CCn1c(-c2cncc(-c3ccc(F)c(C#N)c3)c2N2CC[C@H](N)C2)nc2c(F)cccc21]

Step 26-1, preparation of N-ethyl-3-fluoro-2-nitroaniline: 1,3-difluoro-2-nitrobenzene (1.0 equiv, 6.29 mmol, 1.0 g) was combined with ethyl amine solution (2.0 M in THF, 12 mL) and the resulting mixture was stirred at rt for 3 hrs, then concentrated and dried under vacuum to afford 1.0 g (86%) of the desired product as an orange solid. MS $(M+H)^+$=185.2.

Step 26-2, preparation of N1-ethyl-3-fluorobenzene-1,2-diamine: to a 40 mL vial was placed N-ethyl-3-fluoro-2-nitroaniline (1.0 equiv, 2.71 mmol, 500 mg), propan-2-ol (10 mL), Fe (5.0 equiv, 13.57 mmol, 758.1 mg), NH$_4$Cl (5.0 equiv, 13.57 mmol, 726.1 mg) and water (1.0 mL). The resulting solution was stirred at 80° C. for 30 min. The reaction mixture was cooled to room temperature and filtered. The filtrate was concentrated and applied onto a silica gel column eluting with ethyl acetate/petroleum ether (1:3) to afford 240 mg (57%) of the title compound as a grey oil. MS $(M+H)^+$=155.2.

Step 26-3, preparation of tert-butyl (S)-(1-(3-bromo-5-(1-ethyl-4-fluoro-1H-benzo[d]imidazol-2-yl)pyridin-4-yl)pyrrolidin-3-yl)carbamate: to a DMSO (10 mL) solution of tert-butyl (S)-(1-(3-bromo-5-formylpyridin-4-yl)pyrrolidin-3-yl)carbamate (1.0 equiv, 0.542 mmol, 200 mg) was added N1-ethyl-3-fluorobenzene-1,2-diamine (2.0 equiv, 1.08 mmol, 167 mg) and Na$_2$S$_2$O$_5$ (2.00 equiv, 1.08 mmol, 205 mg). The resulting mixture was stirred at 100° C. for 1 h, quenched with water (10 mL) and extracted with ethyl acetate (3×10 ml). The organic layers were combined, washed with brine (3×10 mL), dried over anhydrous sodium sulfate, filtered and concentrated. The residue obtained was applied onto a silica gel column eluting with ethyl acetate/petroleum ether to afford 160 mg (55%) of the title compound as a yellow solid. MS $(M+H)^+$=504.1, 506.1.

Step 26-4, preparation of tert-butyl N-[(3S)-1-[3-(3-cyano-4-fluorophenyl)-5-(1-ethyl-4-fluoro-1H-1,3-benzodiazol-2-yl)pyridin-4-yl]pyrrolidin-3-yl]carbamate: to an 8 mL vial was placed tert-butyl N-[(3S)-1-[3-bromo-5-(1-ethyl-4-fluoro-1H-1,3-benzodiazol-2-yl)pyridin-4-yl]pyrrolidin-3-yl]carbamate (1.0 equiv, 0.08 mmol, 40 mg), (3-cyano-4-fluorophenyl)boronic acid (1.5 equiv, 0.12 mmol, 19.6 mg), $Pd_2(dba)_3 \cdot CHCl_3$ (0.1 equiv, 0.01 mmol, 8.2 mg), $P(t-Bu)_3 \cdot HBF_4$ (0.2 equiv, 0.02 mmol, 4.6 mg), $K_3PO_4$ (3.0 equiv, 0.24 mmol, 51 mg), toluene (3.0 mL) and $H_2O$ (0.3 mL) under atmospheric $N_2$. The resulting solution was stirred at 80° C. for 2 hrs, concentrated and purified by reverse phase Prep-HPLC to afford 20 mg (50%) of the title compound. MS $(M+H)^+$=545.6.

Step 26-5, preparation of 5-{4-[(3S)-3-aminopyrrolidin-1-yl]-5-(1-ethyl-4-fluoro-1H-1,3-benzodiazol-2-yl)pyridin-3-yl}-2-fluorobenzonitrile: to a dichloromethane (1.0 mL) solution of tert-butyl N-[(3S)-1-[3-(3-cyano-4-fluorophenyl)-5-(1-ethyl-4-fluoro-1H-1,3-benzodiazol-2-yl)pyridin-4-yl]pyrrolidin-3-yl]carbamate (1.0 equiv, 0.04 mmol, 20 mg) was added TFA (1.0 mL). The resulting mixture was stirred at rt for 1 h, concentrated and dried by lyophilization to produce 8.1 mg (39%) of TFA salt of 5-[4-[(3S)-3-aminopyrrolidin-1-yl]-5-(1-ethyl-4-fluoro-1H-1,3-benzodiazol-2-yl)pyridin-3-yl]-2-fluorobenzonitrile as a white solid. MS $(M+H)^+$=445.2.

The following compounds were prepared similarly to Example 26 with appropriate substituting reagents and substrates at different steps.

| Compound no. | MS (M + H)+ |
| --- | --- |
| 2-143 | 427.2 |
| 2-144 | 445.2 |

Example 27. 5-{4-[(3S)-3-aminopyrrolidin-1-yl]-5-(4-chloro-1H-1,3-benzodiazol-2-yl)pyridin-3-yl}-2-fluorobenzonitrile (Compound 2-51)

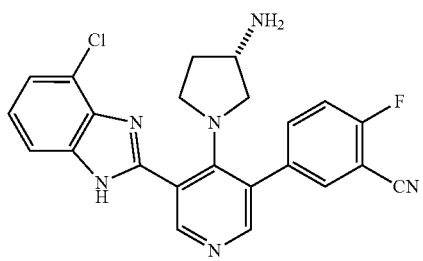 [SMILES: N#Cc1cc(-c2cncc(-c3nc4c(Cl)cccc4[nH]3)c2N2CC[C@H](N)C2)ccc1F]

Step 27-1, preparation of tert-butyl N-[(3S)-1-[3-(3-cyano-4-fluorophenyl)-5-formylpyridin-4-yl]pyrrolidin-3-yl]carbamate: to a dioxane solution (10 mL) of tert-butyl N-[(3S)-1-(3-bromo-5-formylpyridin-4-yl)pyrrolidin-3-yl]carbamate (1.0 equiv, 1.49 mmol, 550 mg, "Example 9, step 9-1") was added $Pd(Amphos)Cl_2$ (0.15 equiv, 0.22 mmol, 159 mg), 3-cyano-4-fluorophenyl boronic acid (2.5 equiv, 3.73 mmol, 625 mg) and $K_2CO_3$ (3.0 equiv, 4.47 mmol, 621 mg). $N_2$ was bubbled through the reaction solution for 5 min and 1.0 mL water was added. The resulting mixture was heated at 100° C. for 1.5 hrs, diluted with ethyl acetate (50 mL), then washed with water (10 mL) and brine (5 mL), dried and concentrated. The residue obtained was purified by silica gel chromatography eluting with MeOH/DCM (0-5%) to give 500 mg of the desired product as white solid. MS $(M+H)^+$=411.4.

Step 27-2, preparation of tert-butyl N-[(3S)-1-[3-(4-chloro-1H-1,3-benzodiazol-2-yl)-5-(3-cyano-4-fluorophenyl)pyridin-4-yl]pyrrolidin-3-yl]carbamate: to a DMF (2.0 mL) solution of tert-butyl N-[(3S)-1-[3-(3-cyano-4-fluorophenyl)-5-formylpyridin-4-yl]pyrrolidin-3-yl]carbamate (1.0 equiv, 0.30 mmol, 125 mg) was added 3-chlorobenzene-1,2-diamine (3.0 equiv, 1.20 mmol, 131 mg) and water (0.5 mL). The resulting mixture was heated at 100° C. under air for 12 hrs. cooled down to rt and water (10 mL) was added. The resulting suspension was filtered and the solid collected was washed with water (3×2.0 mL) to give 126 mg of the title compound as a brown solid. This material was used for next step without further purification. MS $(M+H)^+$=533.2.

Step 27-3, preparation of 5-{4-[(3S)-3-aminopyrrolidin-1-yl]-5-(4-chloro-1H-1,3-benzodiazol-2-yl)pyridin-3-yl}-2-fluorobenzonitrile: to a dichloromethane (1.25 mL) solution of crude tert-butyl N-[(3S)-1-[3-(4-chloro-1H-1,3-benzodiazol-2-yl)-5-(3-cyano-4-fluorophenyl)pyridin-4-yl]pyrrolidin-3-yl]carbamate (1.0 equiv, 126 mg, 0.24 mmol) was added trifluoroacetic acid (0.35 mL). The resulting mixture was stirred at rt for 1 h, concentrated and the residue obtained was purified by reverse phase $C_{18}$ chromatography eluting with MeCN/water (0-30%) with 0.05% of TFA. Pure fractions were combined, neutralized with saturated $NaHCO_3$ and NaCl, extracted with ethyl acetate and dried with $MgSO_4$. The organic was treated with 2.0 M HCl in EtOEt (0.10 mL), concentrated, and dried under high vacuum to give 24 mg of the title compound as an HCl salt. MS $(M+H)^+$=433.3.

The following compounds were prepared similarly to Example 27 with appropriate substituting reagents and substrates at different steps and they may require additional functional group modifications via well-known chemistry with appropriate reagents. The cyclization reaction of aldehydes with 1,2-diaminobenzenes can be carried out by heating in wet DMF, NMP, DMSO or other solvents with or without $Na_2S_2O_5$ under atmospheric oxygen. Different salt such as HCl or formic acid or TFA salt maybe obtained.

| Compound no. | MS (M + H)+ |
| --- | --- |
| 2-1 | 424.4 |
| 2-41 | 453.2 |
| 2-52 | 435.4 |
| 2-57 | 460.9 |
| 2-60 | 467.4 |
| 2-62 | 433.3 |
| 2-87 | 435.4 |
| 2-94 | 417.2 |
| 2-95 | 442.1 |
| 2-99 | 435.2 |
| 2-102 | 422.2 |
| 2-103 | 433.1 |
| 2-104 | 438.2 |
| 2-109 | 399.1 |
| 2-124 | 445.3 |
| 2-125 | 463.3 |
| 2-139 | 431.2 |
| 2-141 | 472.2 |
| 2-146 | 384.3 |
| 2-147 | 438.4 |
| 2-149 | 428.2 |
| 2-158 | 424.3 |
| 2-159 | 428.0 |
| 2-160 | 421.6 |
| 2-161 | 416.4 |
| 2-163 | 430.1 |

-continued

| Compound no. | MS (M + H)+ |
| --- | --- |
| 2-164 | 428.2 |
| 2-167 | 414.4 |
| 2-168 | 432.3 |
| 2-170 | 428.3 |
| 2-171 | 438.3 |
| 2-172 | 444.2 |
| 2-175 | 464.3 |
| 2-177 | 420.2 |
| 2-180 | 419.2 |
| 2-181 | 389.2 |
| 2-182 | 402.2 |
| 2-183 | 422.2 |
| 2-184 | 418.2 |
| 2-185 | 456.2 |
| 2-193 | 406.3 |
| 2-194 | 424.3 |
| 2-195 | 435.1 |
| 2-196 | 422.1 |
| 2-197 | 422.1 |
| 2-198 | 433.2 |
| 2-199 | 384.2 |
| 2-201 | 406.2 |
| 2-202 | 428.2 |

Example 28. 5-{4-[(3S)-3-amino-3-methylpyrrolidin-1-yl]-5-{7-methyl-1H-imidazo[4,5-b]pyridin-2-yl}pyridin-3-yl}-2,3-difluorobenzonitrile (Compound 2-165)

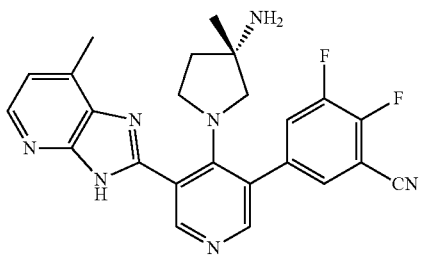 [SMILES: Cc1ccnc2[nH]c(-c3cncc(-c4cc(F)c(F)c(C#N)c4)c3N3CC[C@](C)(N)C3)nc12]

Step 28-1, preparation of tert-butyl N-[(3S)-1-(3-bromo-5-formylpyridin-4-yl)-3-methylpyrrolidin-3-yl]carbamate: to a 100 mL round-bottom flask was placed 5-bromo-4-chloropyridine-3-carbaldehyde (1.0 equiv, 13.6 mmol, 3.0 g), tert-butyl N-[(3S)-3-methylpyrrolidin-3-yl]carbamate (1.0 equiv, 13.6 mmol, 2.7 g), TEA (2.5 equiv, 34.0 mmol, 3.4 g) and MeCN (30 mL). The resulting solution was stirred at 80° C. for 2 hrs, cooled to rt and concentrated. The residue obtained was applied onto a silica gel column eluting with ethyl acetate/petroleum ether to afford 3.3 g (63.1%) of the title compound as a yellow solid. MS (M+H)+=384.2, 386.2.

Step 28-2, preparation of tert-butyl N-[(3S)-1-[3-(3-cyano-4,5-difluorophenyl)-5-formylpyridin-4-yl]-3-methylpyrrolidin-3-yl]carbamate: to a dioxane (4.0 mL) solution of tert-butyl N-[(3S)-1-(3-bromo-5-formylpyridin-4-yl)-3-methylpyrrolidin-3-yl]carbamate (1.0 equiv, 0.61 mmol, 235 mg) was added Pd(DtBPF)Cl₂ (0.06 equiv, 0.037 mmol, 24 mg), 2,3-difluoro-5-(4,4,5,5-tetramethyl-1,3,2-dioxaborolan-2-yl)benzonitrile (1.5 equiv, 0.92 mmol, 243 mg), K₂CO₃ (3.0 equiv, 2.76 mmol, 253 mg) and H₂O (0.4 mL). The resulting mixture was stirred at 80° C. for 1 h , then cooled to rt. The solid was filtered out and the filtrate was concentrated under vacuum. The residue obtained was applied onto a silica gel column eluting with ethyl acetate/petroleum ether to afford 170 mg (62.83%) of tert-butyl N-[(3S)-1-[3-(3-cyano-4,5-difluorophenyl)-5-formylpyridin-4-yl]-3-methylpyrrolidin-3-yl]carbamate as a yellow solid. MS (M+H)+=443.2.

Step 28-3, preparation of tert-butyl N-[(3S)-1-[3-(3-cyano-4,5-difluorophenyl)-5-[7-methyl-1H-imidazo[4,5-b]pyridin-2-yl]pyridin-4-yl]-3-methylpyrrolidin-3-yl]carbamate: to a NMP (3.0 mL) solution of tert-butyl N-[(3S)-1-[3-(3-cyano-4,5-difluorophenyl)-5-formylpyridin-4-yl]-3-methylpyrrolidin-3-yl]carbamate (1.0 equiv, 0.36 mmol, 160 mg) was added 4-methylpyridine-2,3-diamine (4.0 equiv, 1.45 mmol, 178 mg) and Na₂S₂O₅ (2.0 equiv, 0.72 mmol, 138 mg). The resulting solution was stirred at 100° C. for 8 hrs. The reaction mixture was cooled to rt and purified by reverse phase Prep-HPLC resulting in 90 mg (45.6%) of tert-butyl N-[(3S)-1-[3-(3-cyano-4,5-difluorophenyl)-5-[7-methyl-1H-imidazo[4,5-b]pyridin-2-yl]pyridin-4-yl]-3-methylpyrrolidin-3-yl]carbamate as a red solid. MS (M+H)+=546.2.

Step 28-4, preparation of 5-[4-[(3S)-3-amino-3-methylpyrrolidin-1-yl]-5-[7-methyl-1H-imidazo[4,5-b]pyridin-2-yl]pyridin-3-yl]-2,3-difluorobenzonitrile: to a DCM (3.0 mL) solution of N-[(3S)-1-[3-(3-cyano-4,5-difluorophenyl)-5-[7-methyl-1H-imidazo[4,5-b]pyridin-2-yl]pyridin-4-yl]-3-methylpyrrolidin-3-yl]carbamate (1.0 equiv, 0.09 mmol, 50 mg) was added TFA (1.0 mL). The resulting solution was stirred at rt for 1 h, concentrated and purified by Prep-HPLC using XBridge Prep C₁₈ OBD Column (5 μm, 19×150 mm) eluting with water (0.05% TFA) and ACN from 5.0% ACN up to 35.0% in 6 min at the flow rate of 20 ml/min to afford 16 mg (31.2%) of the TFA salt of the title compound upon freeze-drying as a red solid. MS (M+H)+=446.2.

Example 29. 4-[(3S)-3-amino-3-methylpyrrolidin-1-yl]-5-(4-chloro-1-methyl-1H-1,3-benzodiazol-2-yl)-[3,4'-bipyridine]-2'-carbonitrile (Compound 2-151)

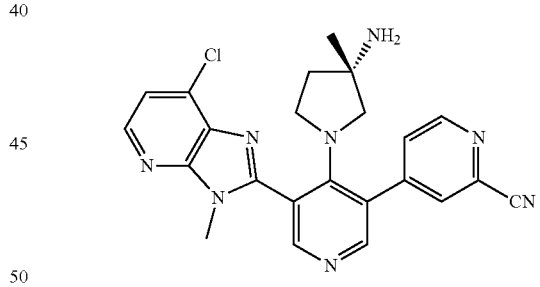

Step 29-1, preparation of 3-chloro-N-methyl-2-nitroaniline: 1-chloro-3-fluoro-2-nitrobenzene (1.0 equiv, 28.5 mmol, 5.0 g) was combined with N-methylamine in THF (2.0 M, 1.4 equiv, 40 mmol, 20 mL). The resulting mixture was stirred at rt for 6 hrs. The reaction solution was concentrated under vacuum to afford 5.0 g of crude 3-chloro-N-methyl-2-nitroaniline as an orange solid. MS (M+H)+=176.5.

Step 29-2, preparation of 3-chloro-N1-methylbenzene-1,2-diamine: to a 250 mL round-bottom flask was placed crude 3-chloro-N-methyl-2-nitroaniline (1.0 equiv, 26.8 mmol, 5.0 g), water (20 mL), propan-2-ol (100 mL), Fe (5.0 equiv, 134.0 mmol, 7.5 g), and NH₄Cl (5.0 equiv, 134.0 mmol, 7.2 g). The resulting solution was stirred at 80° C. for 3 hrs, filtered and filtrate was concentrated under vacuum. The residue obtained was applied onto a silica gel column eluting with ethyl acetate/petroleum ether to afford 1.2 g (28.6%) of 3-chloro-N1-methylbenzene-1,2-diamine as an orange solid. MS (M+H)+=157.0.

Step 29-3, preparation of tert-butyl N-[(3S)-1-[2-cyano-5-formyl-[3,4-bipyridin]-4-yl]-3-methylpyrrolidin-3-yl]carbamate: to a 40 mL flask was placed 4-bromopyridine-2-carbonitrile (1.0 equiv, 1.56 mmol, 286 mg), 4,4,5,5-tetramethyl-2-(4,4,5,5-tetramethyl-1,3,2-dioxaborolan-2-yl)-1,3,2-dioxaborolane (2.0 equiv, 3.12 mmol, 793 mg), Pd(dppf)Cl₂ (0.1 equiv, 0.16 mmol, 114 mg), KOAc (3.0 equiv, 4.68 mmol, 460 mg) and dioxane (10 mL) under nitrogen. The reaction solution was stirred at 90° C. for 1 h and cooled to rt. To this crude solution was added tert-butyl N-[(3S)-1-(3-bromo-5-formylpyridin-4-yl)-3-methylpyrrolidin-3-yl]carbamate (1.0 equiv, 1.56 mmol, 600 mg, "Step 28-1, Example 28"), Pd(DtBPF)Cl₂ (0.10 equiv, 0.16 mmol, 102 mg), K₂CO₃ (3.0 equiv, 4.68 mmol, 647 mg) and H₂O (1.0 mL) under nitrogen. The resulting solution was stirred at 80° C. for 1 h and cooled to rt, quenched with water (20 mL) and extracted with ethyl acetate (3×30 mL). Organic layers were combined, dried over anhydrous sodium sulfate, filtered and concentrated under vacuum. The residue obtained was applied onto a silica gel column eluting with ethyl acetate/petroleum ether resulting in 600 mg (94.3%) of title compound as a yellow solid. MS (M+H)+=408.2.

Step 29-4, preparation of tert-butyl N-[(3S)-1-[5-(4-chloro-1-methyl-1H-1,3-benzodiazol-2-yl)-2-cyano-[3,4-bipyridin]-4-yl]-3-methylpyrrolidin-3-yl]carbamate: to a 8 mL vial was placed tert-butyl N-[(3S)-1-[2-cyano-5-formyl-[3,4-bipyridin]-4-yl]-3-methylpyrrolidin-3-yl]carbamate (1.0 equiv, 0.15 mmol, 60 mg), 3-chloro-N1-methylbenzene-1,2-diamine (2.0 equiv, 0.29 mmol, 46.1 mg), Na₂S₂O₅ (2.0 equiv, 0.29 mmol, 56.0 mg) and DMSO (4.0 mL). The resulting solution was stirred at 100° C. for 3 hrs, cooled to rt. The crude was extracted with ethyl acetate, then concentrated and purified by Prep-HPLC using Xbridge Prep C₁₈ OBD Column (5 μm, 19×150 mm) eluting with water (0.05% TFA) and acetonitrile with gradient of B from 2% to 25% in 6 min and flow rate of 20 ml/min to afford 52 mg (64.9%) of the title compound as a light yellow solid. MS (M+H)+=545.1, 547.1.

Step 29-4, preparation of 4-[(3S)-3-amino-3-methylpyrrolidin-1-yl]-5-(4-chloro-1-methyl-1H-1,3-benzodiazol-2-yl)-[3,4'-bipyridine]-2'-carbonitrile: to a DCM (5.0 mL) of tert-butyl N-[(3S)-1-[5-(4-chloro-1-methyl-1H-1,3-benzodiazol-2-yl)-2-cyano-[3,4-bipyridin]-4-yl]-3-methylpyrrolidin-3-yl]carbamate (1.0 equiv, 0.10 mmol, 52 mg) was added TFA (1.0 mL). The resulting solution was stirred at rt for 1 h. The resulting mixture was concentrated under vacuum and lyophilized to produce 41.9 mg (78.6%) of the TFA salt of the title compound as a white solid. MS (M+H)+=444.1, 446.1.

The following compounds were prepared similarly to Example 29 with appropriate substituting reagents and substrates at different steps and they may require additional functional group modifications via well-known chemistry with appropriate reagents. The cyclization reaction of aldehydes with 1,2-diaminobenzenes can be carried out by heating in wet DMF, NMP, DMSO or other solvents with or without Na₂S₂O₅ under atmospheric oxygen. Different salt such as HCl or formic acid or TFA salt maybe obtained.

| Compound no. | MS (M + H)+ |
|---|---|
| 2-150 | 428.2 |
| 2-152 | 424.2 |
| 2-153 | 427.2 |

Example 30. 4-[(3S)-3-amino-3-methylpyrrolidin-1-yl]-5-(6-fluoro-4-methyl-1H-1,3-benzodiazol-2-yl)-[3,4'-bipyridine]-2'-carbonitrile (Compound 2-166)

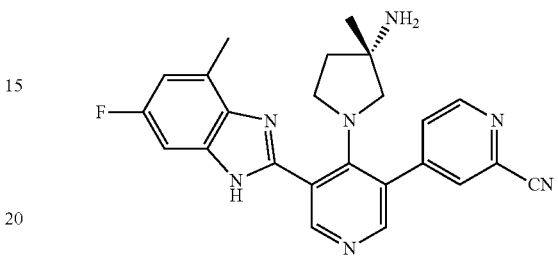

Step 30-1, preparation of N-[(3S)-1-[5-(4-bromo-6-fluoro-1H-1,3-benzodiazol-2-yl)-2-cyano-[3,4-bipyridin]-4-yl]-3-methylpyrrolidin-3-yl]carbamate: to a DMSO (1.0 mL) solution of tert-butyl N-[(3S)-1-[2-cyano-5-formyl-[3,4-bipyridin]-4-yl]-3-methylpyrrolidin-3-yl]carbamate (1.0 equiv, 0.10 mmol, 40 mg, "Example 29, step 29-3") was added 3-bromo-5-fluorobenzene-1,2-diamine (1.0 equiv, 0.10 mmol, 20.1 mg) and Na₂S₂O₅ (2.0 equiv, 0.20 mmol, 37.3 mg). The resulting solution was stirred at 70° C. for 2 h. The reaction solution was then quenched with water (5 mL) and extracted with ethyl acetate (3×10 mL). Organic layers were combined, dried over anhydrous sodium sulfate, filtered and concentrated under vacuum. The residue obtained was applied onto a silica gel column eluting with ethyl acetate/petroleum ether (1:1) to afford 32 mg (55.0%) of tert-butyl N-[(3S)-1-[5-(4-bromo-6-fluoro-1H-1,3-benzodiazol-2-yl)-2-cyano-[3,4-bipyridin]-4-yl]-3-methylpyrrolidin-3-yl]carbamate as a yellow solid. MS (M+H)+=592.1, 594.1.

Step 30-2, preparation of tert-butyl N-[(3S)-1-[2-cyano-5-(5-fluoro-7-methyl-1H-1,3-benzodiazol-2-yl)-[3,4-bipyridin]-4-yl]-3-methylpyrrolidin-3-yl]carbamate: to a dioxane (1.0 mL) solution of tert-butyl N-[(3S)-1-[5-(4-bromo-6-fluoro-1H-1,3-benzodiazol-2-yl)-2-cyano-[3,4-bipyridin]-4-yl]-3-methylpyrrolidin-3-yl]carbamate (1.0 equiv, 0.05 mmol, 32 mg) was added trimethyl-1,3,5,2,4,6-trioxatriborinane (1.0 equiv, 0.05 mmol, 6.8 mg), Pd(dppf)Cl₂ (0.10 equiv, 0.01 mmol, 4.0 mg), K₂CO₃ (3.0 equiv, 0.16 mmol, 22.4 mg) and H₂O (0.1 mL) under atmospheric nitrogen. The resulting solution was stirred at 80° C. for 1 h. The reaction solution was then quenched with water (5 mL) and extracted with ethyl acetate (3×10 mL). Organic layers were combined, dried over anhydrous sodium sulfate, filtered and concentrated under vacuum. The residue obtained was applied onto a silica gel column eluting with ethyl acetate/petroleum ether (1:1) to afford 20 mg (70.2%) of tert-butyl N-[(3S)-1-[2-cyano-5-(5-fluoro-7-methyl-1H-1,3-benzodiazol-2-yl)-[3,4-bipyridin]-4-yl]-3-methylpyrrolidin-3-yl]carbamate as a yellow solid. MS (M+H)+=528.2.

Step 30-3, preparation of 4-[(3S)-3-amino-3-methylpyrrolidin-1-yl]-5-(6-fluoro-4-methyl-1H-1,3-benzodiazol-2-yl)-[3,4'-bipyridine]-2'-carbonitrile: to a DCM (1.0 mL) solution of tert-butyl N-[(3S)-1-[2-cyano-5-(5-fluoro-7-methyl-1H-1,3-benzodiazol-2-yl)-[3,4-bipyridin]-4-yl]-3- methylpyrrolidin-3-yl]carbamate (1.0 equiv, 0.04 mmol, 20 mg) was added TFA (0.1 mL). The resulting solution was stirred at ambient temperature for 1 h. The resulting mixture was concentrated under vacuum. The crude product obtained was purified by Prep-HPLC using SunFire Prep $C_{18}$ OBD Column (19×150 mm 5 μm) eluting with water (0.05% TFA) and ACN resulting in 7.0 mg (34.1%) of the TFA salt of 4-[(3S)-3-amino-3-methylpyrrolidin-1-yl]-5-(6-fluoro-4-methyl-1H-1,3-benzodiazol-2-yl)-[3,4-bipyridine]-2-carbonitrile as a white solid. MS (M+H)$^+$=428.0.

Example 31. 5-{4-[(3S)-3-amino-3-methylpyrrolidin-1-yl]-5-{7-methyl-1H-imidazo[4,5-b]pyridin-2-yl}pyridin-3-yl}-2-fluorobenzonitrile (Compound 2-154)

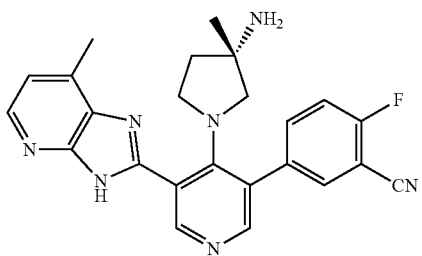 [SMILES: Cc1ccnc2[nH]c(-c3cncc(-c4ccc(F)c(C#N)c4)c3N3CC[C@](C)(N)C3)nc12]

Step 31-1, preparation of tert-butyl N-[(3S)-1-[3-(3-cyano-4-fluorophenyl)-5-formylpyridin-4-yl]-3-methylpyrrolidin-3-yl]carbamate: to a 50 mL round-bottom flask was placed tert-butyl N-[(3S)-1-(3-bromo-5-formylpyridin-4-yl)-3-methylpyrrolidin-3-yl]carbamate (1.0 equiv, 3.12 mmol, 1.2 g, "Step 28-1, Example 28"), 2-fluoro-5-(4,4,5,5-tetramethyl-1,3,2-dioxaborolan-2-yl)benzonitrile (1.0 equiv, 3.12 mmol, 772 mg), $Pd_2(dba)_3.CHCl_3$ (0.10 equiv, 0.31 mmol, 323 mg), $P(t-Bu)_3.HBF_4$ (0.20 equiv, 0.62 mmol, 180 mg), $K_3PO_4$ (3.0 equiv, 9.37 mmol, 2.0 g), dioxane (10 mL) and water (1.0 mL) under nitrogen. The resulting solution was stirred at 70° C. for 1 h and cooled to rt, quenched with water (20 mL) and then extracted with ethyl acetate (3×20 mL). Organic layers were combined, dried over anhydrous sodium sulfate, filtered and concentrated under vacuum. The residue obtained was applied onto a silica gel column eluting with ethyl acetate/petroleum ether to afford 900 mg (67.9%) of the title compound as a yellow solid. MS (M+H)$^+$=425.3.

Step 31-2, preparation of tert-butyl N-[(3S)-1-[3-(3-cyano-4-fluorophenyl)-5-{7-methyl-1H-imidazo[4,5-b]pyridin-2-yl}pyridin-4-yl]-3-methylpyrrolidin-3-yl]carbamate: to a 50 mL round-bottom flask was placed tert-butyl N-[(3S)-1-[3-(3-cyano-4-fluorophenyl)-5-formylpyridin-4-yl]-3-methylpyrrolidin-3-yl]carbamate (1.0 equiv, 1.88 mmol, 800 mg), 4-methylpyridine-2,3-diamine (2.5 equiv, 4.71 mmol, 580 mg), $Na_2S_2O_5$ (3.0 equiv, 5.65 mmol, 1075 mg) and DMSO (10 mL). The resulting solution was stirred at 100° C. for 6 hrs and cooled to rt, then diluted with water and extracted with ethyl acetate. The ethyl acetate solution was concentrated. The remaining residue was purified by Flash-Prep-HPLC with a $C_{18}$ reverse phase column eluting with water (0.05% $NH_4HCO_3$) and ACN to afford 700 mg (70.4%) of the title compound as a brown solid. MS (M+H)$^+$=528.2.

Step 31-3, preparation of 5-{4-[(3S)-3-amino-3-methylpyrrolidin-1-yl]-5-{7-methyl-1H-imidazo[4,5-b]pyridin-2-yl}pyridin-3-yl}-2-fluorobenzonitrile: to a DCM (1.0 mL) solution of tert-butyl N-[(3S)-1-[3-(3-cyano-4-fluorophenyl)-5-{7-methyl-1H-imidazo[4,5-b]pyridin-2-yl}pyridin-4-yl]-3-methylpyrrolidin-3-yl]carbamate (1.0 equiv, 0.09 mmol, 50 mg) and TFA (0.1 mL). The resulting solution was stirred at rt for 1 h. The reaction mixture was concentrated under vacuum. The remaining residue was chromatographed by Pre-HPLC using SunFire Prep $C_{18}$ OBD column (19×150 mm, 5 μm) with mobile phase A of water (0.05% TFA) and mobile phase B of ACN at the flow rate of 20 mL/min. The product was eluted out within the gradient of 13.0% B to 40.0% B in 6 min. The title compound (11.6 mg, 22.6%, TFA salt) was obtained after lyophilization as a brown solid. MS (M+H)$^+$=428.2.

Example 32. 4-[(3S)-3-amino-3-methylpyrrolidin-1-yl]-5-(4-fluoro-1H-1,3-benzodiazol-2-yl)-[3,4'-bipyridine]-2'-carbonitrile (Compound 2-162)

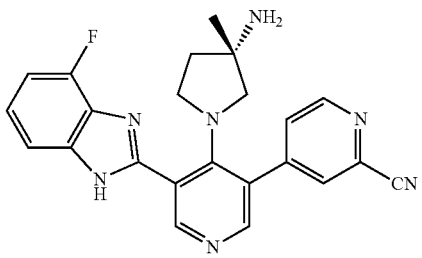 [SMILES: C[C@]1(N)CCN(c2c(-c3ccnc(C#N)c3)cncc2-c2nc3c(F)cccc3[nH]2)C1]

Step 32-1, preparation of tert-butyl N--[(3S)-1-[2'-cyano-5-(4-fluoro-1H-1,3-benzodiazol-2-yl)-[3,4'-bipyridin]-4-yl]-3-methylpyrrolidin-3-yl]carbamate: to a DMSO (1.0 mL) solution of tert-butyl N-[(3S)-1-[2-cyano-5-formyl-[3,4-bipyridin]-4-yl]-3-methylpyrrolidin-3-yl]carbamate (60 mg, 0.15 mmol, 1.0 equiv, "Step 29-3, Example 29") was added 3-fluorobenzene-1,2-diamine (19 mg, 0.15 mmol, 1.0 equiv) and $Na_2S_2O_5$ (56 mg, 0.30 mmol, 2.0 equiv). The resulting solution was stirred at 70° C. for 2 hrs and then quenched with water (5 mL) and extracted with ethyl acetate (3×10 mL). Organic layers were combined, dried over anhydrous sodium sulfate, filtered and concentrated under vacuum. The residue was applied onto a silica gel column eluting with ethyl acetate/petroleum ether to afford 45 mg (60.0%) of the title compound as a yellow solid. MS (M+H)$^+$=514.0.

Step 32-2, preparation of 4-[(3S)-3-amino-3-methylpyrrolidin-1-yl]-5-(4-fluoro-1H-1,3-benzodiazol-2-yl)-[3,4'-bipyridine]-2'-carbonitrile: to a DCM (1.0 mL) solution of tert-butyl N-[(3S)-1-[2'-cyano-5-(4-fluoro-1H-1,3-benzodiazol-2-yl)-[3,4'-bipyridin]-4-yl]-3-methylpyrrolidin-3-yl]carbamate was added TFA (0.10 mL). The reaction mixture was stirred at rt for 1 h and concentrated under vacuum. The residue obtained was purified by Prep-HPLC using SunFire Prep $C_{18}$ OBD Column (19×150 mm, 5 um) eluting with water (0.05% TFA) and ACN at flow rate of 20 ml/min. The fractions containing product was eluted out within the gradient of 15.0% ACN to 40.0% ACN in 6 min and combined, freeze-dried to afford the title compound (20.9 mg, TFA salt, 45.2%) as a white solid. MS (M+H)$^+$=414.1.

Example 33. 3-{4-[(3S)-3-amino-3-methylpyrroli-din-1-yl]-5-{7-methyl-1H-imidazo[4,5-b]pyridin-2-yl}pyridin-3-yl}benzonitrile (Compound 2-155)

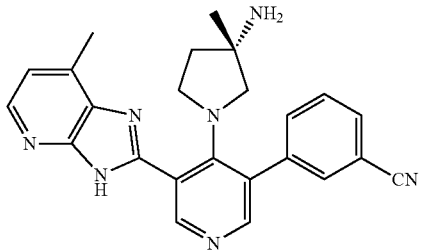 [SMILES: Cc1ccnc2[nH]c(-c3cncc(-c4cccc(C#N)c4)c3N3CC[C@](C)(N)C3)nc12]

Step 33-1, preparation of tert-butyl N-[(3S)-1-[3-(3-cyanophenyl)-5-formylpyridin-4-yl]-3-methylpyrrolidin-3-yl]carbamate: to a 100 mL round-bottom flask was placed tert-butyl N-[(3S)-1-(3-bromo-5-formylpyridin-4-yl)-3-methylpyrrolidin-3-yl]carbamate (1.0 equiv, 2.86 mmol, 1.1 g, "Step 28-1, Example 28"), 3-cyanophenyl boronic acid (2.0 equiv, 5.72 mmol, 841 mg), Pd(DtBPF)Cl$_2$ (0.05 equiv, 0.14 mmol, 93 mg), K$_2$CO$_3$ (3.0 equiv, 8.68 mmol, 1.2 g), dioxane (15 mL) and water (1.5 mL) under nitrogen. The resulting solution was stirred at 80° C. for 1 h and cooled to rt. The reaction mixture was filtered and the filtrate was concentrated. The residue obtained was applied onto a silica gel column eluting with ethyl acetate/petroleum ether to afford 1.0 g (85.9%) of the title compound as a yellow solid. MS (M+H)$^+$=407.2.

Step 33-2, preparation of tert-butyl N-[(3S)-1-[3-(3-cyanophenyl)-5-{7-methyl-1H-imidazo[4,5-b]pyridin-2-yl}pyridin-4-yl]-3-methylpyrrolidin-3-yl]carbamate: to a 100 mL round-bottom flask was placed tert-butyl N-[(3S)-1-[3-(3-cyanophenyl)-5-formylpyridin-4-yl]-3-methylpyrrolidin-3-yl]carbamate (1.0 equiv, 2.46 mmol, 1.0 g), 4-methylpyridine-2,3-diamine (4.0 equiv, 9.74 mmol, 1.2 g), Na$_2$S$_2$O$_5$ (2.0 equiv, 4.92 mmol, 935 mg) and NMP (15 mL). The resulting solution was stirred at 100° C. for 7 hrs and cooled to rt, then diluted with water and extracted with ethyl acetate. The ethyl acetate solution was concentrated. The remaining residue was purified by Flash-Prep-HPLC with a C$_{18}$ reverse phase column eluting with water (0.1% NH$_4$HCO$_3$+0.05% NH$_4$OH) and ACN with gradient from 25.0% ACN to 50.0% in 10 min to afford 600 mg (47.9%) of the title compound as a red solid. MS (M+H)$^+$=510.3.

Step 33-3, preparation of 3-{4-[(3S)-3-amino-3-methylpyrrolidin-1-yl]-5-{7-methyl-1H-imidazo[4,5-b]pyridin-2-yl}pyridin-3-yl}benzonitrile: to a DCM (1.0 mL) solution of tert-butyl N-[(3S)-1-[3-(3-cyanophenyl)-5-{7-methyl-1H-imidazo[4,5-b]pyridin-2-yl}pyridin-4-yl]-3-methylpyrrolidin-3-yl]carbamate (1.0 equiv, 0.10 mmol, 50 mg) was added TFA (0.2 mL). The resulting mixture was stirred at rt for 3 hrs. The reaction solution was concentrated and the remaining residue was purified by Pre-HPLC using SunFire Prep C$_{18}$ OBD (19×150 mm, 5 μm) with mobile phases of water (A, 0.05% TFA) and ACN (B) at flow rate of 20 ml/min. The fractions containing product were eluted out within the gradient of 13.0% ACN to 40.0% ACN in 6 min resulting in 26.8 mg (52.2%) of the TFA salt of the title compound as an orange solid after freeze-drying. MS (M+H)$^+$=410.2.

Example 34. 2-{4-[(3S)-3-amino-3-methylpyrrolidin-1-yl]-5-(3-cyano-4-fluorophenyl)pyridin-3-yl}-1H-imidazo[4,5-b]pyridine-7-carbonitrile (Compound 2-176)

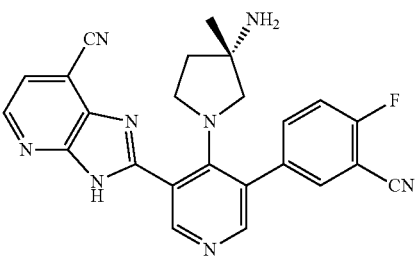 [SMILES: C[C@]1(N)CCN(c2c(-c3ccc(F)c(C#N)c3)cncc2-c2nc3c(C#N)ccnc3[nH]2)C1]

Step 34-1, preparation of 2-amino-3-nitropyridine-4-carbonitrile: to a 50 mL flask was added 4-chloro-3-nitropyridine-2-amine (1.0 equiv, 2.88 mmol, 500 mg), 1,1'-bis(diphenylphosphino)ferrocene (0.2 equiv, 0.58 mmol, 320 mg), Zn(CN)$_2$ (2.0 equiv, 5.76 mmol, 680 mg), Pd$_2$(dba)$_3$·CHCl$_3$ (0.10 equiv, 0.29 mmol, 299 mg) and DMF (10 mL). The reaction system was purged with nitrogen and heated at 120° C. for 2 h. The reaction solution was quenched with water (10 mL) and extracted with ethyl acetate (3×10 mL). The organic layers were combined, dried over anhydrous sodium sulfate, filtered and concentrated. The remaining residue was purified by silica gel chromatography eluting with ethyl acetate/petroleum ether (1:3) to afford 200 mg (42.3%) of the desired product as an orange solid. MS (M+H)$^+$=165.1.

Step 34-2, preparation of 2,3-diaminopyridine-4-carboxamide: to a propan-2-ol (5.0 mL) solution of 2-amino-3-nitropyridine-4-carbonitrile (1.0 equiv, 0.91 mmol, 150 mg) was added Fe (5.0 equiv, 4.57 mmol, 255 mg), NH$_4$Cl (5.0 equiv, 4.57 mmol, 244 mg) and water (1.0 mL). The resulting mixture was heated at 80° C. for 1 h. The reaction mixture was concentrated and applied onto silica gel column eluting with ethyl acetate/petroleum ether (1:3) to afford 100 mg (81.6%) of 2,3-diaminopyridine-4-carboxamide as a light yellow solid. MS (M+H)$^+$=153.2.

Step 34-3, preparation of tert-butyl N-[(3S)-1-(3-{7-carbamoyl-1H-imidazo[4,5-b]pyridin-2-yl}-5-(3-cyano-4-fluorophenyl)pyridin-4-yl)-3-methylpyrrolidin-3-yl]carbamate: from tert-butyl N-[(3S)-1-[3-(3-cyano-4-fluorophenyl)-5-formylpyridin-4-yl]-3-methylpyrrolidin-3-yl]carbamate (1.0 equiv, 0.12 mmol, 50 mg, "Example 31, step 31-1") and 2,3-diaminopyridine-4-carboxamide (2.0 equiv, 0.24 mmol, 36 mg), the title compound (35 mg, 53.4%) was prepared using a similar method to the one described in "Example 31, Step 31-2". MS (M+H)$^+$=557.3.

Step 34-4, preparation of tert-butyl N-[(3S)-1-(3-{7-cyano-1H-imidazo[4,5-b]pyridin-2-yl}-5-(3-cyano-4-fluorophenyl)pyridin-4-yl)-3-methylpyrrolidin-3-yl]carbamate: to a DCM solution (1.0 mL) of tert-butyl N-[(3S)-1-(3-{7-carbamoyl-1H-imidazo[4,5-b]pyridin-2-yl}-5-(3-cyano-4-fluorophenyl)pyridin-4-yl)-3-methylpyrrolidin-3-yl]carbamate (1.0 equiv, 0.06 mmol, 35 mg) was added TEA (4.5 equiv, 0.28 mmol, 29 mg) and trifluoroacetic anhydride (2.0 equiv, 0.12 mmol, 26 mg). The resulting mixture was stirred at ambient temperature for 1 h. The reaction solution was concentrated under vacuum and purified by silica gel chromatography to afford 25 mg of the desired product as a light yellow solid. MS (M+H)$^+$=539.3. In addition, 10 mg of side product N-[(3S)-1-(3-{7-cyano-1H-imidazo[4,5-b]pyridin- 2-yl}-5-(3-cyano-4-fluorophenyl)pyridin-4-yl)-3-methylpyrrolidin-3-yl]-2,2,2-trifluoroacetamide was also obtained as a light yellow solid. MS (M+H)⁺=535.2.

Step 34-5, preparation of 2-{4-[(3S)-3-amino-3-methylpyrrolidin-1-yl]-5-(3-cyano-4-fluorophenyl)pyridin-3-yl}-1H-imidazo[4,5-b]pyridine-7-carbonitrile: from tert-butyl N-[(3S)-1-(3-{7-cyano-1H-imidazo[4,5-b]pyridin-2-yl}-5-(3-cyano-4-fluorophenyl)pyridin-4-yl)-3-methylpyrrolidin-3-yl]carbamate (1.0 equiv, 0.046 mmol, 25 mg), the title compound (7.6 mg) was prepared as a TFA salt using a similar method to the one described in "Example 31, Step 31-3". MS (M+H)⁺=439.2.

Example 35. 2-{4-[(3S)-3-mino-3-methylpyrrolidin-1-yl]-5-(3-cyano-4-methoxyphenyl)pyridin-3-yl}-1H-imidazo[4,5-b]pyridine-7-carbonitrile (Compound 2-179)

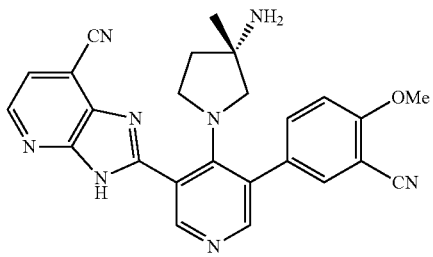 [SMILES: COc1ccc(-c2cncc(-c3nc4c(C#N)ccnc4[nH]3)c2N2CC[C@](C)(N)C2)cc1C#N]

Step 35-1, preparation of 2-{4-[(3S)-3-mino-3-methylpyrrolidin-1-yl]-5-(3-cyano-4-methoxyphenyl)pyridin-3-yl}-1H-imidazo[4,5-b]pyridine-7-carbonitrile: to an 8 mL vial was placed N-[(3S)-1-(3-{7-cyano-1H-imidazo[4,5-b]pyridin-2-yl}-5-(3-cyano-4-fluorophenyl)pyridin-4-yl)-3-methylpyrrolidin-3-yl]-2,2,2-trifluoroacetamide (1.0 equiv, 0.018 mmol, 10 mg, "side product from Example 34, step 34-4"), NaOH (4.2 equiv, 0.075 mmol, 3.0 mg), MeOH (3.0 mL) and H₂O (0.3 mL). The resulting solution was stirred at 50° C. for 5 h. The crude product was concentrated and purified by Prep-HPLC using Xbridge Prep C₁₈ OBD column (19×150 mm, 5 μm) with mobile phase of water (A, 0.05% TFA) and ACN (B) at flow rate of 20 mL/min. Fractions containing desired product were eluted out using gradient as follows: 0-35% B in 6 min, hold at 95% for 1 min, down to 19% in 1 min, hold at 19% for 1 min. This resulted in 0.8 mg (3.2%) of 2-{4-[(3S)-3-mino-3-methylpyrrolidin-1-yl]-5-(3-cyano-4-methoxyphenyl)pyridin-3-yl}-1H-imidazo[4,5-b]pyridine-7-carbonitrile as an orange solid. (M+H)⁺=451.3.

Example 36. 3-{4-[(3S)-3-amino-3-methylpyrrolidin-1-yl]-5-{7-methyl-1H-imidazo[4,5-b]pyridin-2-yl}pyridin-3-yl}-5-fluorobenzamide (Compound 2-169)

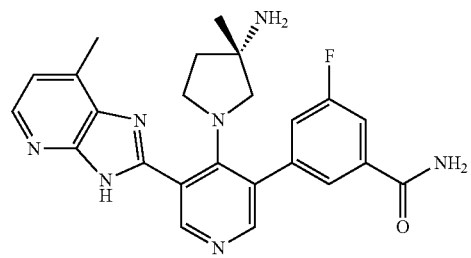 [SMILES: Cc1ccnc2[nH]c(-c3cncc(-c4cc(F)cc(C(N)=O)c4)c3N3CC[C@](C)(N)C3)nc12]

Step 36-1, preparation of 3-{4-[(3S)-3-amino-3-methylpyrrolidin-1-yl]-5-{7-methyl-1H-imidazo[4,5-b]pyridin-2-yl}pyridin-3-yl}-5-fluorobenzamide: to a 50 mL round-bottom flask was placed 3-{4-[(3S)-3-amino-3-methylpyrrolidin-1-yl]-5-{7-methyl-1H-imidazo[4,5-b]pyridin-2-yl}pyridin-3-yl}-5-fluorobenzonitrile (1.0 equiv, 0.06 mmol, 30 mg, "compound 2-202") and HCl/EA (1.0 M, 10 equiv, 0.6 mL). The resulting solution was stirred at room temperature for 3 h. The resulting mixture was concentrated and purified by Prep-HPLC using Xbridge Prep C₁₈ OBD column (19×150 mm, 5 μm) with mobile phase of water (A, 0.05% ammonia) and ACN (B) at flow rate of 20 mL/min. Fractions containing desired product were eluted out with gradient of 15% to 35% B in 8 min. Pure fractions was concentrated and combined with water (10 ml). Concentrated HCl (0.1 ml) was added and the resulting mixture was lyophilized under vacuum. This resulted in 13.2 mg (43.3%) of the HCl salt of 3-{4-[(3S)-3-amino-3-methylpyrrolidin-1-yl]-5-{7-methyl-1H-imidazo[4,5-b]pyridin-2-yl}pyridin-3-yl}-5-fluorobenzamide as a red solid. (M+H)⁺=446.2.

Example 37. 3-{4-[(3S)-3-amino-3-methylpyrrolidin-1-yl]-5-{5,7-dimethyl-1H-imidazo[4,5-b]pyridin-2-yl}pyridin-3-yl}benzonitrile (Compound 2-169)

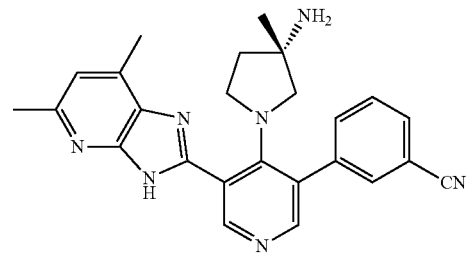 [SMILES: Cc1cc(C)c2nc(-c3cncc(-c4cccc(C#N)c4)c3N3CC[C@](C)(N)C3)[nH]c2n1]

Step 37-1, preparation of 5-bromo-4,6-dimethylpyridin-2-amine: to a 100 mL 3-necked round-bottom flask was placed 4,6-dimethylpyridin-2-amine (1.0 equiv, 19.6 mmol, 2.4 g) and DCM (20 mL). The reaction system was cooled down to −50° C. in a liquid nitrogen bath, and 1,3-dibromo-5,5-dimethylimidazolidine-2,4-dione (1.0 equiv, 19.6 mmol, 5.6 g) was added. The resulting solution was stirred at −50° C. for 30 min and gradually warmed to 25° C. in 30 min. The reaction mixture was quenched with saturated NaHCO₃ (20 mL) and extracted with dichloromethane (2×20 mL). The organic layers were combined and concentrated under vacuum to afford 3.2 g (81.0%) of 5-bromo-4,6-dimethylpyridin-2-amine as an off-white solid. (M+H)$^+$=200.8, 202.8.

Step 37-2, preparation of 5-bromo-4,6-dimethyl-3-nitropyridin-2-amine: to a 50 mL round-bottom flask was added H$_2$SO$_4$ (2.0 mL) and the reaction system was cooled down to −10° C. At the same temperature, 5-bromo-4,6-dimethylpyridin-2-amine (1.0 equiv, 2.49 mmol, 0.50 g) was added portion-wise over the period of 5 min, followed by the addition of KNO$_3$ (1.4 equiv, 3.48 mmol, 0.4 g) portion-wise over the period of 10 min. The resulting solution was stirred at room temperature for 1 h. The reaction mixture was quenched with water/ice (30 mL) and saturated aqueous NaHCO$_3$ was added until pH>7. Solid product precipitated out and the resulting suspension was filtered. Solids were collected and dried in oven under reduced pressure. This resulted in 0.45 g (73.5%) of 5-bromo-4,6-dimethyl-3-nitropyridin-2-amine as a yellow solid. (M+H)$^+$=245.9, 247.9.

Step 37-3, preparation of 4,6-dimethylpyridine-2,3-diamine: to a 50 mL round-bottom flask was placed 5-bromo-4,6-dimethyl-3-nitropyridin-2-amine (1.0 equiv, 2.64 mmol, 0.65 g), HCOONH$_4$ (4.8 equiv, 12.7 mmol, 0.80 g), MeOH (10 mL), and Pd/C (10 wt. %, 0.02 equiv, 0.06 mmol, 65 mg). The resulting solution was stirred at 70° C. for 2 h. The reaction mixture was cooled down and filtered. Filtrate was concentrated under vacuum to afford 0.32 g (88.3%) of 4,6-dimethylpyridine-2,3-diamine as an off-white solid. (M+H)$^+$=138.0.

Step 37-4, preparation of tert-butyl N-[(3S)-1-[3-(3-cyano-4-fluorophenyl)-5-{5,7-dimethyl-1H-imidazo[4,5-b]pyridin-2-yl}pyridin-4-yl]-3-methylpyrrolidin-3-yl]carbamate: from tert-butyl N-[(3S)-1-[3-(3-cyanophenyl)-5-formylpyridin-4-yl]-3-methylpyrrolidin-3-yl]carbamate (1.0 equiv, 0.28 mmol, 112 mg) and 4,6-dimethylpyridine-2,3-diamine (1.2 equiv, 0.33 mmol, 45 mg), the title compound was prepared in DMSO (2.0 mL) using a similar method to the one described in "Step 33-2, Example 33". The crude reaction solution was used for next step without further treatment. MS (M+H)$^+$=524.1.

Step 37-5, preparation of 3-{4-[(3S)-3-amino-3-methylpyrrolidin-1-yl]-5-{5,7-dimethyl-1H-imidazo[4,5-b]pyridin-2-yl}pyridin-3-yl}benzonitrile: to the crude DMSO solution of tert-butyl N-[(3S)-1-[3-(3-cyano-4-fluorophenyl)-5-{5,7-dimethyl-1H-imidazo[4,5-b]pyridin-2-yl}pyridin-4-yl]-3-methylpyrrolidin-3-yl]carbamate was added TFA (2.0 mL). The resulting mixture was stirred at 35° C. for 2 h. The reaction solution was filtered and filtrate was purified by Prep-HPLC using SunFire Prep C$_{18}$ OBD column (19×150 mm, 5 μm) with mobile phases of water (A, 0.05% TFA) and ACN (B) at flow rate of 20 mL/min. Fractions containing desired product were eluted out with gradient from 30.0% to 60.0% in 6 min. This resulted in 32 mg (77.9%) of the TFA salt of 3-{4-[(3S)-3-amino-3-methylpyrrolidin-1-yl]-5-{5,7-dimethyl-1H-imidazo[4,5-b]pyridin-2-yl}pyridin-3-yl}benzonitrile as an off-white solid. MS (M+H)$^+$=424.2.

The following compounds were prepared similarly to Example 37 with appropriate substituting reagents and substrates at different steps and they may require additional functional group modifications via well-known chemistry with appropriate reagents. The cyclization reaction of aldehydes with 1,2-diaminobenzenes can be carried out by heating in wet DMF, NMP, DMSO or other solvents with or without Na$_2$S$_2$O$_5$ under atmospheric oxygen. Different salt such as HCl or formic acid or TFA salt maybe obtained.

| Compound no. | MS (M + H)$^+$ |
|---|---|
| 2-174 | 442.2 |

Example A-1: Parenteral Pharmaceutical Composition

To prepare a parenteral pharmaceutical composition suitable for administration by injection (subcutaneous, intravenous), 1-100 mg of a water-soluble salt of a compound Formula (I), or a pharmaceutically acceptable salt or solvate thereof, is dissolved in sterile water and then mixed with 10 mL of 0.9% sterile saline. A suitable buffer is optionally added as well as optional acid or base to adjust the pH. The mixture is incorporated into a dosage unit form suitable for administration by injection Example A-2: Oral Solution To prepare a pharmaceutical composition for oral delivery, a sufficient amount of a compound of Formula (I), or a pharmaceutically acceptable salt thereof, is added to water (with optional solubilizer(s), optional buffer(s) and taste masking excipients) to provide a 20 mg/mL solution.

Example A-3: Oral Tablet

A tablet is prepared by mixing 20-50% by weight of a compound of Formula (I), or a pharmaceutically acceptable salt thereof, 20-50% by weight of microcrystalline cellulose, 1-10% by weight of low-substituted hydroxypropyl cellulose, and 1-10% by weight of magnesium stearate or other appropriate excipients. Tablets are prepared by direct compression. The total weight of the compressed tablets is maintained at 100 -500 mg.

Example A-4: Oral Capsule

To prepare a pharmaceutical composition for oral delivery, 10-500 mg of a compound of Formula (I), or a pharmaceutically acceptable salt thereof, is mixed with starch or other suitable powder blend. The mixture is incorporated into an oral dosage unit such as a hard gelatin capsule, which is suitable for oral administration.

In another embodiment, 10-500 mg of a compound of Formula (I), or a pharmaceutically acceptable salt thereof, is placed into Size 4 capsule, or size 1 capsule (hypromellose or hard gelatin) and the capsule is closed.

Example A-5: Topical Gel Composition

To prepare a pharmaceutical topical gel composition, a compound of Formula (I), or a pharmaceutically acceptable salt thereof, is mixed with hydroxypropyl cellulose, propylene glycol, isopropyl myristate and purified alcohol USP. The resulting gel mixture is then incorporated into containers, such as tubes, which are suitable for topical administration.

Example B-1: SSTR assays

Membrane Preparation:
Crude membrane fractions are prepared from Chinese hamster ovary (CHO) cells stably expressing one of the five human or rodent somatostatin receptor subtypes. The cells are grown to 85-100% confluence on standard tissue culture dishes in DM-MEM growth media (Gibco) with following additives: 10% fetal bovine serum (Gibco), 100 U/mL penicillin (Gibco), 100 ug/mL streptomycin (Gibco), 10 mM HEPES (Gibco), 0.5 mg/mL G-418 (Gibco). To prepare membranes, cells are washed once with 1× Dulbecco's phosphate buffered saline (Gibco) containing 10 mM HEPES (Gibco) then once with sodium free binding buffer (50 mM Tris Base, 5 mM $MgCl_2$-$6H_2O$ and 1 mM EGTA adjusted to pH 7.8). The cells are then scraped into binding buffer containing a protease inhibitor cocktail (100 ug/mL pepstatin A (Sigma), 50 ug/mL leupeptin (Sigma), 25 ug/mL aprotinin (Sigma) and 10 mg/mL Bacitracin (USB Corporation)). The cells are centrifuged at 43,500× g, homogenized, and the resulting membranes are collected by centrifugation at 67,000× g. The membranes are then resuspended in binding buffer containing the protease inhibitor cocktail using a glass dounce homogenizer.

Functional Assays

General overview: All five SSTR subtypes are Gi coupled G-protein coupled receptors (GPCRs) that lead to decreases in intracellular cyclic AMP (cAMP) when activated by an agonist. Therefore, measurement of intracellular cAMP levels can be used to assess whether compounds of the invention are agonists of SSTR subtypes (John Kelly, Troy Stevens, W. Joseph Thompson, and Roland Seifert, *Current Protocols in Pharmacology*, 2005, 2.2.1-2.2). One example of an intracellular cAMP assay is described below.

cAMP Assay Protocol for SST2R:

Four days prior to the assay, 5,000 Chinese hamster ovary cells (CHO-K1, ATCC #CCL-61) stably expressing the human somatostatin receptor subtype 2 are plated in each well of a 96-well tissue culture-treated plate in Ham's F12 growth media (ThermoFisher #10-080-CM) supplemented with 10% donor bovine serum (Gemini Bio-Products #100-506), 100 U/mL penicillin; 100 ug/mL streptomycin; 2 mM L-glutamine (Gemini Bio-Products #400-110) and 0.2 mg/mL hygromycin B (GoldBio #31282-04-9). The cells are cultured at 37° C., 5% $CO_2$ and 95% humidity. On the day of the assay, the media is aspirated and the cells are treated with 50 µL of 1.6 µM NKH477 (Sigma #N3290) plus various dilutions of compounds of the invention in assay buffer [1× Hank's Balanced Salt Solution (ThermoFisher #SH3058802), 0.5 mM HEPES pH 7.4, 0.1% bovine serum albumin, 0.2 mM 3-Isobutyl-1-methylxanthine (IBMX, VWR #200002-790)]. The cells are incubated for 20 minutes at 37° C. (the final concentration of the compounds of the invention are typically 0-10,000 nM). The cells are treated with 50 µL of lysis buffer (HRTF cAMP kit, Cisbio). The lysate is transferred to 384-well plates and cAMP detection and visualization antibodies are added and incubated for 1-24 hours at room temperature. The time-resolved fluorescent signal is read with a Tecan M1000Pro multiplate reader. The intracellular cAMP concentrations are calculated by regression to a standard curve and are plotted vs. the concentration of the compounds of the invention and the $EC_{50}$ of the compounds are calculated using standard methods. All data manipulations are in GraphPad Prism v6 or v7.

cAMP Assay Protocol for SST3R:

Four days prior to the assay, 2,000 Chinese hamster ovary cells (CHO-K1, ATCC #CCL-61) stably expressing the human somatostatin receptor subtype 3 are plated in each well of a 96-well tissue culture-treated plate in Ham's F12 growth media (ThermoFisher #10-080-CM) supplemented with 10% donor bovine serum (Gemini Bio-Products #100-506), 100 U/mL penicillin; 100 ug/mL streptomycin; 2 mM L-glutamine (Gemini Bio-Products #400-110) and 0.25 mg/mL G418 Sulfate (GoldBio #108321-42-2). The cells are cultured at 37° C., 5% $CO_2$ and 95% humidity. On the day of the assay, the media is aspirated and the cells are treated with 50 µL of 1.6 µM NKH477 (Sigma #N3290) plus various dilutions of compounds of the invention in assay buffer [1× Hank's Balanced Salt Solution (ThermoFisher #SH3058802), 0.5 mM HEPES pH 7.4, 0.1% bovine serum albumin, 0.2 mM 3-Isobutyl-1-methylxanthine (IBMX, VWR #200002-790)]. The cells are incubated for 20 minutes at 37° C. (the final concentration of the compounds of the invention are typically 0-10,000 nM). The cells are treated with 50 µL of lysis buffer (HRTF cAMP kit, Cisbio) for 30 minutes and then the lysate is diluted to 250 µL with assay buffer. The lysate is transferred to 384-well plates and cAMP detection and visualization antibodies are added and incubated for 1-24 hours at room temperature. The time-resolved fluorescent signal is read with a Tecan M1000Pro multiplate reader. The intracellular cAMP concentrations are calculated by regression to a standard curve and are plotted vs. the concentration of the compounds of the invention and the $EC_{50}$ of the compounds are calculated using standard methods. All data manipulations are in GraphPad Prism v6 or v7.

cAMP Assay Protocol hSST4R:

Four days prior to the assay, 2,000 Chinese hamster ovary cells (CHO-K1, ATCC #CCL-61) stably expressing the human somatostatin receptor subtype 4 are plated in each well of a 96-well tissue culture-treated plate in Ham's F12 growth media (ThermoFisher #10-080-CM) supplemented with 10% donor bovine serum (Gemini Bio-Products #100-506), 100 U/mL penicillin; 100 ug/mL streptomycin; 2 mM L-glutamine (Gemini Bio-Products #400-110) and 0.25 mg/mL G418 Sulfate (GoldBio #108321-42-2). The cells are cultured at 37° C., 5% $CO_2$ and 95% humidity. On the day of the assay, the media is aspirated and the cells are treated with 50 µL of 1.6 µM NKH477 (Sigma #N3290) plus various dilutions of compounds of the invention in assay buffer [1× Hank's Balanced Salt Solution (ThermoFisher #SH3058802), 0.5 mM HEPES pH 7.4, 0.1% bovine serum albumin, 0.2 mM 3-Isobutyl-1-methylxanthine (IBMX, VWR #200002-790)]. The cells are incubated for 20 minutes at 37° C. (the final concentration of the compounds of the invention are typically 0-10,000 nM). The cells are treated with 50 µL of lysis buffer (HRTF cAMP kit, Cisbio) for 30 minutes and then the lysate is diluted to 250 µL with assay buffer. The lysate is transferred to 384-well plates and cAMP detection and visualization antibodies are added and incubated for 1-24 hours at room temperature. The time-resolved fluorescent signal is read with a Tecan M1000Pro multiplate reader. The intracellular cAMP concentrations are calculated by regression to a standard curve and are plotted vs. the concentration of the compounds of the invention and the $EC_{50}$ of the compounds are calculated using standard methods. All data manipulations are in GraphPad Prism v6 or v7.

cAMP Assay Protocol for SST5R:

Four days prior to the assay, 2,000 Chinese hamster ovary cells (CHO-K1, ATCC #CCL-61) stably expressing the human somatostatin receptor subtype 5 are plated in each well of a 96-well tissue culture-treated plate in Ham's F12 growth media (ThermoFisher #10-080-CM) supplemented with 10% donor bovine serum (Gemini Bio-Products #100-506), 100 U/mL penicillin; 100 µg/mL streptomycin; 2 mM L-glutamine (Gemini Bio-Products #400-110) and 0.25 mg/mL G418 Sulfate (GoldBio #108321-42-2). The cells are cultured at 37° C., 5% $CO_2$ and 95% humidity. On the day of the assay, the media is aspirated and the cells are treated with 50 µL of 1.6 µM NKH477 (Sigma #N3290) plus various dilutions of compounds of the invention in assay buffer [1× Hank's Balanced Salt Solution (ThermoFisher #SH3058802), 0.5 mM HEPES pH 7.4, 0.1% bovine serum albumin, 0.2 mM 3-Isobutyl-1-methylxanthine (IBMX, VWR #200002-790)]. The cells are incubated for 20 minutes at 37° C. (the final concentration of the compounds of the invention are typically 0-10,000 nM). The cells are treated with 50 μL of lysis buffer (HRTF cAMP kit, Cisbio) for 30 minutes and then the lysate is diluted to 250 μL with assay buffer. The lysate is transferred to 384-well plates and cAMP detection and visualization antibodies are added and incubated for 1-24 hours at room temperature. The time-resolved fluorescent signal is read with a Tecan M1000Pro multiplate reader. The intracellular cAMP concentrations are calculated by regression to a standard curve and are plotted vs. the concentration of the compounds of the invention and the $EC_{50}$ of the compounds are calculated using standard methods. All data manipulations are in GraphPad Prism v6 or v7.

Illustrative biological activity of compounds is demonstrated in the following Tables, by evaluating the inhibition of cAMP activities via human SST receptors.

Table A demonstrates illustrative biological activity of compounds by evaluating the inhibition of cAMP activities via human SST5 receptor, where a means $EC_{50}$ is <10 nM; b means $EC_{50}$ is between 10 to 100 nM; c means $EC_{50}$ is between 100 to 1000 nM; d means $EC_{50}$ is >1000 nM.

TABLE A

Representative SST5 Activity

| Compound No. | SST5 potency |
|---|---|
| 1-1 | a |
| 1-2 | a |
| 1-3 | a |
| 1-4 | b |
| 1-5 | b |
| 1-6 | a |
| 1-7 | a |
| 1-8 | c |
| 1-9 | a |
| 1-10 | a |
| 1-11 | b |
| 1-12 | c |
| 1-13 | b |
| 1-14 | b |
| 1-15 | b |
| 1-16 | c |
| 1-17 | c |
| 1-18 | b |
| 1-19 | b |
| 1-20 | a |
| 1-21 | a |
| 1-22 | c |
| 1-23 | c |
| 1-24 | b |
| 1-25 | b |
| 1-26 | c |
| 1-27 | b |
| 1-28 | a |
| 1-29 | a |
| 1-30 | b |
| 1-31 | b |
| 1-32 | c |
| 1-33 | c |
| 1-34 | a |
| 1-35 | d |
| 1-36 | b |
| 1-37 | a |
| 1-38 | d |
| 1-39 | a |
| 1-40 | b |
| 1-41 | c |
| 1-42 | a |
| 1-43 | b |
| 1-44 | c |
| 1-45 | b |
| 1-46 | b |
| 1-47 | a |
| 1-48 | a |
| 1-49 | a |
| 1-50 | a |
| 1-51 | a |
| 1-52 | b |
| 1-53 | a |
| 1-54 | a |
| 1-55 | b |
| 1-56 | d |
| 1-57 | b |
| 1-58 | a |
| 1-59 | a |
| 1-60 | a |
| 1-61 | a |
| 1-62 | a |
| 1-63 | a |
| 1-64 | a |
| 1-65 | a |
| 1-66 | b |
| 1-67 | c |
| 1-68 | a |
| 1-69 | a |
| 1-70 | a |
| 1-71 | a |
| 1-72 | b |
| 1-73 | a |
| 1-74 | a |
| 1-75 | b |
| 1-76 | a |
| 2-1 | b |
| 2-2 | c |
| 2-3 | a |
| 2-4 | a |
| 2-5 | b |
| 2-6 | a |
| 2-7 | a |
| 2-8 | a |
| 2-9 | b |
| 2-10 | a |
| 2-11 | |
| 2-12 | b |
| 2-13 | a |
| 2-14 | c |
| 2-15 | b |
| 2-16 | b |
| 2-17 | b |
| 2-18 | a |
| 2-19 | b |
| 2-20 | a |
| 2-21 | a |
| 2-22 | a |
| 2-23 | a |
| 2-24 | b |
| 2-25 | b |
| 2-26 | a |
| 2-27 | a |
| 2-28 | a |
| 2-29 | a |
| 2-30 | c |
| 2-31 | c |
| 2-32 | a |
| 2-33 | c |
| 2-34 | a |
| 2-35 | b |
| 2-36 | c |
| 2-37 | a |
| 2-38 | a |
| 2-39 | a |
| 2-40 | b |
| 2-41 | b |
| 2-42 | c |
| 2-43 | b |

TABLE A-continued

Representative SST5 Activity

| Compound No. | SST5 potency |
|---|---|
| 2-44 | a |
| 2-45 | c |
| 2-46 | c |
| 2-47 | a |
| 2-48 | b |
| 2-49 | a |
| 2-50 | b |
| 2-51 | a |
| 2-52 | a |
| 2-53 | b |
| 2-54 | a |
| 2-55 | a |
| 2-56 | c |
| 2-57 | a |
| 2-58 | b |
| 2-59 | b |
| 2-60 | a |
| 2-61 | b |
| 2-62 | a |
| 2-63 | a |
| 2-64 | d |
| 2-65 | a |
| 2-66 | c |
| 2-76 | b |
| 2-68 | b |
| 2-69 | d |
| 2-70 | c |
| 2-71 | b |
| 2-72 | a |
| 2-73 | d |
| 2-74 | a |
| 2-75 | a |
| 2-76 | a |
| 2-77 | a |
| 2-78 | c |
| 2-79 | a |
| 2-80 | a |
| 2-81 | b |
| 2-82 | d |
| 2-83 | c |
| 2-84 | a |
| 2-85 | a |
| 2-86 | a |
| 2-87 | a |
| 2-88 | d |
| 2-89 | b |
| 2-90 | d |
| 2-91 | c |
| 2-92 | b |
| 2-93 | c |
| 2-94 | b |
| 2-95 | b |
| 2-96 | a |
| 2-97 | a |
| 2-98 | a |
| 2-99 | a |
| 2-100 | a |
| 2-101 | a |
| 2-102 | a |
| 2-103 | b |
| 2-104 | b |
| 2-105 | b |
| 2-106 | a |
| 2-107 | d |
| 2-108 | a |
| 2-109 | a |
| 2-110 | b |
| 2-111 | b |
| 2-112 | c |
| 2-113 | c |
| 2-114 | a |
| 2-115 | b |
| 2-116 | a |
| 2-117 | b |
| 2-118 | a |
| 2-119 | a |
| 2-120 | a |
| 2-121 | a |
| 2-122 | a |
| 2-123 | a |
| 2-124 | a |
| 2-125 | a |
| 2-126 | d |
| 2-127 | a |
| 2-128 | a |
| 2-129 | b |
| 2-130 | c |
| 2-131 | b |
| 2-132 | a |
| 2-133 | a |
| 2-134 | a |
| 2-135 | a |
| 2-136 | b |
| 2-137 | b |
| 2-138 | a |
| 2-139 | a |
| 2-140 | a |
| 2-141 | a |
| 2-142 | a |
| 2-143 | a |
| 2-144 | a |
| 2-145 | a |
| 2-146 | a |
| 2-147 | a |
| 2-148 | a |
| 2-149 | a |
| 2-150 | a |
| 2-151 | a |
| 2-152 | a |
| 2-153 | a |
| 2-154 | a |
| 2-155 | a |
| 2-156 | a |
| 2-157 | a |
| 2-158 | a |
| 2-159 | a |
| 2-160 | a |
| 2-161 | a |
| 2-162 | a |
| 2-163 | a |
| 2-164 | a |
| 2-165 | a |
| 2-166 | a |
| 2-167 | a |
| 2-168 | a |
| 2-169 | a |
| 2-170 | a |
| 2-171 | a |
| 2-172 | a |
| 2-173 | a |
| 2-174 | a |
| 2-175 | a |
| 2-176 | a |
| 2-177 | a |
| 2-178 | a |
| 2-179 | b |
| 2-180 | a |
| 2-181 | b |
| 2-182 | a |
| 2-183 | a |
| 2-184 | a |
| 2-185 | a |
| 2-186 | a |
| 2-187 | a |
| 2-188 | a |
| 2-189 | a |
| 2-190 | a |
| 2-191 | a |

TABLE A-continued

Representative SST5 Activity

| Compound No. | SST5 potency |
|---|---|
| 2-192 | a |
| 2-193 | a |
| 2-194 | a |
| 2-195 | a |
| 2-196 | b |
| 2-197 | a |
| 2-198 | a |
| 2-199 | c |
| 2-200 | a |
| 2-201 | a |
| 2-202 | a |

Table B demonstrates illustrative biological selectivity of exemplary compounds for the SST5 receptor over SST2 receptor, by evaluating the inhibition of cAMP activities via human SST5 receptor and human SST2 receptor, where a means $EC_{50}$ is <10 nM; b means $EC_{50}$ is between 10 to 100 nM; c means $EC_{50}$ is between 100 to 1000 nM; d means $EC_{50}$ is >1000 nM. +=10 to 99; ++=100 to 499; +++=≥500.

TABLE B

Illustrative Selectivity Data Demonstrating Preference for SST5 vs SST2

| Compound No. | SST5 potency | SST2 potency | Fold selectivity for SST5 vs SST2 |
|---|---|---|---|
| 1-1 | a | d | ++ |
| 1-2 | a | d | +++ |
| 1-3 | a | c | ++ |
| 1-4 | b | d | ++ |
| 1-5 | b | d | +++ |
| 1-6 | a | d | +++ |
| 1-7 | a | d | +++ |
| 1-9 | a | d | +++ |
| 1-10 | a | d | +++ |
| 1-37 | a | d | +++ |
| 1-39 | a | d | +++ |
| 1-42 | a | c | +++ |
| 1-51 | a | d | +++ |
| 1-64 | a | d | +++ |
| 1-65 | a | c | +++ |
| 1-68 | a | d | +++ |
| 1-69 | a | d | +++ |
| 1-70 | a | d | +++ |
| 1-71 | a | d | +++ |
| 2-1 | b | c | + |
| 2-3 | a | c | +++ |
| 2-4 | a | b | ++ |
| 2-6 | a | c | +++ |
| 2-7 | a | c | +++ |
| 2-8 | a | d | +++ |
| 2-10 | a | c | +++ |
| 2-11 | | | +++ |
| 2-13 | a | c | +++ |
| 2-18 | a | d | +++ |
| 2-20 | a | c | +++ |
| 2-21 | a | d | +++ |
| 2-22 | a | c | ++ |
| 2-23 | a | c | +++ |
| 2-26 | a | c | ++ |
| 2-27 | a | c | ++ |
| 2-28 | a | b | ++ |
| 2-29 | a | c | + |
| 2-34 | a | c | +++ |
| 2-37 | a | c | +++ |
| 2-38 | a | c | +++ |
| 2-39 | a | c | ++ |
| 2-43 | b | d | +++ |
| 2-44 | a | c | +++ |
| 2-49 | a | c | ++ |
| 2-51 | a | c | +++ |
| 2-52 | a | c | +++ |
| 2-54 | a | c | +++ |
| 2-57 | a | c | +++ |
| 2-60 | a | c | ++ |
| 2-62 | a | c | +++ |
| 2-63 | a | c | +++ |
| 2-65 | a | c | ++ |
| 2-76 | a | c | +++ |
| 2-79 | a | c | ++ |
| 2-80 | a | c | +++ |
| 2-86 | a | c | ++ |

TABLE B-continued

Illustrative Selectivity Data Demonstrating Preference for SST5 vs SST2

| Compound No. | SST5 potency | SST2 potency | Fold selectivity for SST5 vs SST2 |
|---|---|---|---|
| 2-101 | a | c | +++ |
| 2-106 | a | c | +++ |
| 2-108 | a | c | ++ |
| 2-109 | a | c | ++ |
| 2-116 | a | d | +++ |
| 2-119 | a |   | ++ |
| 2-120 | a | d | ++ |
| 2-121 | a | c | +++ |
| 2-122 | a | c | ++ |
| 2-123 | a | b | +++ |
| 2-124 | a | c | +++ |
| 2-125 | a | c | +++ |
| 2-127 | a | c | ++ |
| 2-128 | a | c | +++ |
| 2-131 | b | d | +++ |
| 2-132 | a | d | +++ |
| 2-135 | a | b | ++ |
| 2-139 | a | b | ++ |
| 2-140 | a | b | ++ |
| 2-141 | a | c | ++ |
| 2-142 | a | d | +++ |
| 2-143 | a | c | +++ |
| 2-144 | a | d | +++ |
| 2-145 | a | c | +++ |
| 2-146 | a | c | ++ |
| 2-147 | a | c | +++ |
| 2-148 | a | c | +++ |
| 2-149 | a | c | ++ |
| 2-154 | a | b | ++ |
| 2-155 | a | c | ++ |
| 2-157 | a | b | +++ |
| 2-162 | a | c | +++ |
| 2-163 | a | c | +++ |
| 2-165 | a | c | ++ |
| 2-166 | a | c | +++ |
| 2-167 | a | d | +++ |
| 2-170 | a | d | +++ |
| 2-171 | a | c | +++ |
| 2-172 | a | d | +++ |
| 2-175 | a | c | +++ |
| 2-177 | a | c | +++ |
| 2-178 | a | d | ++ |
| 2-180 | a | b | ++ |
| 2-181 | b | d | ++ |
| 2-182 | a | c | ++ |
| 2-183 | a | c | ++ |
| 2-184 | a | c | ++ |
| 2-185 | a | c | ++ |
| 2-186 | a | c | +++ |
| 2-187 | a | c | ++ |
| 2-188 | a | c | ++ |
| 2-189 | a | b | ++ |
| 2-190 | a | b | + |
| 2-191 | a | c | +++ |
| 2-192 | a | b | ++ |
| 2-193 | a | c | ++ |
| 2-194 | a | c | + |
| 2-195 | a | d | +++ |
| 2-196 | b | c | + |
| 2-197 | a | c | ++ |
| 2-198 | a | d | ++ |
| 2-199 | c | d | + |
| 2-200 | a | c | +++ |
| 2-201 | a | b | + |
| 2-202 | a | c | +++ |
| 1-(3-(4-methyl-1H-benzo[d]imidazol-2-yl)-5-(m-tolyl)pyridin-4-yl)piperidin-4-amine | d | a | 0.002 |
| 1-[3-(7-chloro-1H-1,3-benzodiazol-2-yl)-5-(3-fluoro-5-methylphenyl)pyridin-4-yl]piperidin-4-amine | c | a | 0.0008 |
| 1-[3-(3-chlorophenyl)-5-{7-methyl-1H-imidazo[4,5-b]pyridin-2-yl}pyridin-4-yl]piperidin-4-amine | d | b | 0.009 |

TABLE B-continued

Illustrative Selectivity Data Demonstrating Preference for SST5 vs SST2

| Compound No. | SST5 potency | SST2 potency | Fold selectivity for SST5 vs SST2 |
|---|---|---|---|
| 1-[3-(6-chloro-4-methoxy-1H-1,3-benzodiazol-2-yl)-5-(3-fluoro-5-methylphenyl)pyridin-4-yl]piperidin-4-amine | | | 0.00004 |

Table C demonstrates illustrative biological selectivity of exemplary compounds for the SST5 receptor over SST3 receptor, by evaluating the inhibition of cAMP activities via human SST5 receptor and human SST3 receptor.

TABLE C

| Compound No. | Fold selectivity for SST5 vs SST3 |
|---|---|
| 1-51 | 200 |
| 1-65 | >1000 |
| 2-34 | 98 |
| 2-63 | 43 |
| 2-101 | 42 |
| 2-154 | 118 |
| 2-162 | 517 |
| 2-171 | 183 |
| 2-178 | 147 |
| 2-182 | 6.3 |
| 2-183 | 6.7 |
| 2-184 | 7.0 |
| 2-185 | 6.1 |
| 2-186 | 158 |
| 2-187 | 93 |
| 2-188 | 16 |
| 2-189 | 27 |
| 2-190 | 16 |
| 2-191 | 24 |
| 2-192 | 18 |
| 2-200 | 159 |
| 2-201 | 5.1 |

Table D demonstrates illustrative biological selectivity of exemplary compounds for the SST5 receptor over SST4 receptor, by evaluating the inhibition of cAMP activities via human SST5 receptor and human SST4 receptor.

TABLE D

| Compound No. | Fold selectivity for SST5 vs SST4 |
|---|---|
| 1-41 | 8.8 |
| 1-51 | 812 |
| 1-65 | 384 |
| 2-34 | 14 |
| 2-63 | 18 |
| 2-101 | 11 |
| 2-145 | 63 |
| 2-162 | 109 |
| 2-164 | 323 |
| 2-165 | 56 |
| 2-171 | 18 |
| 2-182 | 0.94 |
| 2-183 | 4.0 |
| 2-184 | 1.4 |
| 2-185 | 1.2 |
| 2-200 | 136 |
| 2-201 | 1.0 |

Example B-2: Liver Microsomal Stability Assay Protocol

The in vitro stabilities of compounds of interest were determined for various species using pooled male and female human, pooled male Sprague-Dawley rat, pooled male Cynomolgus monkey, and pooled male Beagle dog liver microsomes at microsomal protein concentrations of 0.5 mg/mL. Incubations were carried out in a potassium phosphate buffer (50 mM). The NADPH-generating system was composed of NADP+ (1 mM), magnesium chloride (3 mM), EDTA (1 mM), glucose-6-phosphate (5 mM) and glucose-6-phosphate dehydrogenase (1 Unit/mL) for all experiments. Compounds of interest in DMSO/acetonitrile were added to achieve a final incubation concentration of 1 µM (final DMSO content was 0.1% v/v and final acetonitrile content was 0.9%). The final incubation volume was 400 µL. Incubations were conducted at 37° C. for 0, 5, 10, 20, 40 and 60 minutes in a shaking water bath and terminated by removing 50 µL of incubation mixture and adding to 100 µL of ice cold acetonitrile containing internal standard. Following precipitation by centrifugation at 3500 rpm and 4° C. for 30 minutes, compounds of interest and internal standard were analyzed in the resultant supernatant using a multiple reaction monitoring (MRM) LC-MS/MS method. MS conditions were optimized for each analyte. Depletion rates of compounds of interest were measured and half-life, scaled intrinsic clearance, and predicted scaled systemic clearance calculations were made using this data.

Example B-3: Cytochrome P450 (CYP) 2D6 Enzyme Time Dependent Inhibition (TDI) Assay Protocol The inhibition of Cytochrome P450 (CYP) 2D6 enzyme mediated Dextromethorphan O-demethylation (Dextrorphan) were determined using pooled male and female human liver microsomes at microsomal protein concentrations of 0.1 mg/mL. The NADPH-generating system mix was composed of potassium phosphate buffer pH 7.4 (50 mM), NADP+ (1 mM), magnesium chloride (3 mM), EDTA (1 mM), glucose-6-phosphate (5 mM), glucose-6-phosphate dehydrogenase (1 Unit/mL), human liver microsomes (0.1 mg/mL) and water. Compounds of interest in DMSO serial diluted to six different concentrations (final DMSO content of 0.1% v/v) were added to the NADPH-generating system. CYP 2D6 substrate Dextromethorphan was added at a final incubation concentration of 5 µM. The final incubation volume was 200 µL. Incubations were conducted at 37° C. for 10 minutes in a shaking water bath to evaluate the drug candidates as direct time dependent inhibitors of CYP 2D6. In a separate test plate, drug candidates were pre-incubated at 37° C. for 30 minutes in a shaking water bath in NADPH-generating system mix in the absence of Dextromethorphan substrate to allow for the formation of metabolites. This plate was removed from the water bath and placed on ice for 5 minutes. Dextromethorphan substrate was then added and the plate was incubated at 37° C. for 10 minutes in a shaking water bath to determine if any metabolites formed during the 30 minute pre-incubation inhibit the CYP 2D6 enzyme. All incubations were terminated by removing 50 μL of incubation mixture and adding to 200 μL of ice cold acetonitrile containing internal standard. Following precipitation by centrifugation at 3500 rpm and 4° C. for 30 minutes, the resultant supernatant were analyzed by using a multiple reaction monitoring (MRM) LC-MS/MS method detecting for internal standard and the CYP 2D6 enzyme mediated Dextromethorphan O-demethylation metabolite Dextrorphan and $IC_{50}$ values were determined.

Table E illustrates representative human liver microsomal stability and time dependent CYP2D6 inhibition (TDI) of exemplary compounds.

TABLE E

| Compound No. | HLM Stability t½ (min) | CYP2D6 inhibition, IC50 (μM) | |
|---|---|---|---|
| | | t = 0 min | t = 30 min |
| 2-182 | 53 | 7.6 | 6.5 |
| 2-183 | 77 | 6.4 | 3.5 |
| 2-184 | 58 | 4.2 | 2.5 |
| 2-185 | 77 | 9.5 | 2.3 |
| 2-201 | 173 | 4.7 | 1.8 |
| 2-34 | >693 | >10 | >10 |
| 2-178 | 231 | >10 | 9.7 |
| 2-186 | 347 | 5.4 | 1.1 |
| 2-187 | 41 | >10 | 2.9 |
| 2-162 | >693 | >10 | >10 |
| 2-188 | 33 | >10 | 8.7 |
| 2-190 | 139 | >10 | >10 |
| 2-189 | >693 | >10 | >10 |
| 2-191 | 139 | 5.7 | 5.1 |
| 2-192 | 99 | 4.2 | 4.7 |
| 2-154 | >693 | >10 | >10 |

Example B-4: Genetic Models of Hyperinsulinism in Rodents

Representative assays evaluating the effect of a selective somatostatin subtype (sst5) agonist described herein in genetic models of hyperinsulinism in rodents, specifically the SUR1$^{-/-}$ mouse model, are described. The SUR1$^{-/-}$ mouse reproduces the key pathophysiological features of $K_{ATP}$ congenital hyperinsulinism (HI), the most common and severe genetic form of hyperinsulinism. SUR1$^{-/-}$ mice are both significantly more hypoglycemic when fasted and significantly more hyperglycemic when glucose-loaded compared with control wild-type. Evaluation of the effect of oral administration of a somatostatin subtype (sst5) agonist described herein on plasma glucose levels after a fast is described below.

In Vivo Experiments:

SUR1$^{-/-}$ mice and wild type mice are administered a somatostatin subtype (sst5) agonist described herein at a dose of 30 mg/Kg/day for 1 week. Fasting plasma glucose, insulin, and betahydroxybutyrate concentrations are measured after a 16 hr fast at baseline and after 1 week of treatment. Glucose and an insulin tolerance tests are performed during the treatment period.

Sample size: Average fasting plasma glucose levels in SUR1$^{-/-}$ mice are 59.4+/−5.0 mg/dL. With 5 mice per group there is greater than 90% power to detect a difference of 20% (equivalent to bringing the levels to normal range) on fasting plasma glucose levels in treated versus control-treated SUR1$^{-/-}$ mice (using alpha 0.05).

Treatment groups: (1) a compound described herein; (2) selective somatostatin 2 agonist; and (3) Placebo.

Genotype groups: (1) SUR1$^{-/-}$ mice; and (2) Wild type mice

Experimental Procedures:

Fasting Evaluation: Fasting plasma glucose are measured after a 16 hour fast. Plasma glucose and betahydroxybutyrate levels are checked by a hand held glucose meter (Nova Stat Strip glucose meters) in blood obtained from a tail nick (only one nick will be necessary) and 15 microliters of blood are collected to measure insulin levels.

Intraperitoneal glucose tolerance test: After an overnight fast, mice are given an i.p. dose of glucose (2 g/kg). Plasma glucose and insulin concentrations are measured at baseline and every 30 min for 2 hrs. Fifteen microliters of blood/time point is obtained and measured for insulin levels.

Insulin tolerance test: After a 6 hr fast, mice are given an i.p. injection of insulin (1 unit/kg). Glucose concentration is measured at baseline and every 10 min for 30 minutes or until the mice reach a hypoglycemic state, then every 30 min for 2 hrs.

In Vitro Experiments:

The direct effects of a somatostatin subtype (sst5) agonist described herein or selective somatostatin 2 agonist on insulin secretion are tested in isolated pancreatic islets from wild type and SUR1$^{-/-}$ mice. The direct effects of the compounds are also tested in islets isolated from patients with $K_{ATP}$HI who undergo pancreatectomy and those from healthy human volunteers.

Batch incubation: 5 islets for each well with 4 replicates of each condition in 96-well plate format are used for the study. Islets are exposed to 4 concentrations of glucose (0, 5, 10 and 25 mM) or mixture of amino acids (0, 2, 4 and 10 mM) in the absence or presents of 4 concentrations of 2 compounds (a somatostatin subtype (sst5) agonist described herein, somatostatin 2 agonist). The effects of compounds and the effective doses on insulin secretion are obtained after those experiments.

Cytosolic calcium measurements: Cytosolic calcium ([Ca$^{2+}$]i) dynamics are assessed using Fura-2 as calcium indicator; islets isolated from wild type or SUR1$^{-/-}$ mice are exposed to glucose and amino acids. The effects of the compounds on [Ca$^{2+}$]i dynamics are directly evaluated.

Islets perifusion: After batch incubations and calcium measurements, the effective concentration of compounds are determined. The effects of those compounds with effective dose on insulin secretion dynamics are evaluated in perifused islets.

$K_{ATP}$HI human islets: Compounds are also tested with $K_{ATP}$H human islets. Islets are isolated from surgical specimens from patients with $K_{ATP}$H who underwent pancreatectomy. $K_{ATP}$H are perifused in response to amino acid and glucose stimulation in the absence or presence of the compounds. [Ca$^{2+}$]i dynamics are also tested.

The examples and embodiments described herein are for illustrative purposes only and various modifications or changes suggested to persons skilled in the art are to be included within the spirit and purview of this application and scope of the appended claims.

What is claimed is:

1. A compound of Formula (II), or a pharmaceutically acceptable salt, solvate, diastereomeric mixture, or individual enantiomers thereof:

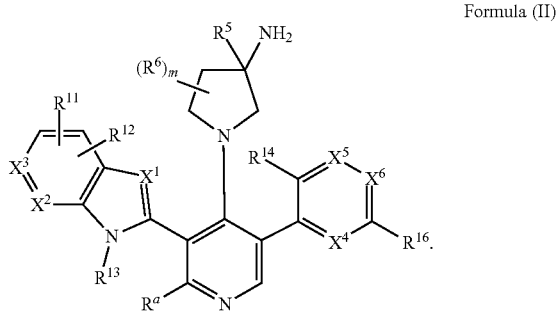

Formula (II)

wherein:

$R^3$ and $R^4$ are independently H or substituted or unsubstituted $C_1$-$C_6$alkyl;

$R^5$ is H, —OH, substituted or unsubstituted $C_1$-$C_6$alkyl, substituted or unsubstituted $C_1$-$C_6$alkoxy, or substituted or unsubstituted $C_1$-$C_6$heteroalkyl;

each $R^6$ is independently H, halogen, —OR$^{17}$, —N(R$^{17}$)$_2$, —CN, —CO$_2$R$^{17}$, —C(=O)N(R$^{17}$)$_2$, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted monocyclic carbocycle, or substituted or unsubstituted monocyclic heterocycle;

$R^a$ is H or —NR$^7$R$^8$;

$R^7$ is H, substituted or unsubstituted $C_1$-$C_4$alkyl, substituted or unsubstituted $C_1$-$C_4$fluoroalkyl, substituted or unsubstituted $C_1$-$C_4$heteroalkyl, or substituted or unsubstituted $C_3$-$C_6$cycloalkyl;

$R^8$ is H, substituted or unsubstituted $C_1$-$C_4$alkyl, substituted or unsubstituted $C_1$-$C_4$fluoroalkyl, substituted or unsubstituted $C_1$-$C_4$heteroalkyl, or substituted or unsubstituted $C_3$-$C_6$cycloalkyl;

$X^1$ is N or C—R$^9$;

$R^9$ is H, F, Cl, Br, —CN, —N(R$^{17}$)$_2$, substituted or unsubstituted $C_1$-$C_4$alkyl, substituted or unsubstituted $C_1$-$C_4$alkoxy, substituted or unsubstituted $C_1$-$C_4$fluoroalkyl, substituted or unsubstituted $C_1$-$C_4$fluoroalkoxy, substituted or unsubstituted $C_1$-$C_4$heteroalkyl, or substituted $C_3$-$C_6$cycloalkyl;

$X^2$ is C—R$^{10}$ or N;

$X^3$ is C—R$^{11}$ or N;

$R^{10}$, each $R^{11}$ and $R^{12}$ are each independently H, halogen, substituted or unsubstituted $C_1$-$C_4$alkyl, substituted or unsubstituted $C_1$-$C_4$alkenyl, substituted or unsubstituted $C_1$-$C_4$alkynyl, substituted or unsubstituted $C_1$-$C_4$fluoroalkyl, substituted or unsubstituted $C_1$-$C_6$heteroalkyl, substituted or unsubstituted monocyclic carbocycle, substituted or unsubstituted monocyclic heterocycle, —CN, —OR$^{17}$, —CO$_2$R$^{17}$, —C(=O)N(R$^{17}$)$_2$, —N(R$^{17}$)$_2$, —NR$^{17}$C(=O)R$^{18}$, —NR$^{17}$C(=O)OR$^{18}$, —NR$^{17}$C(=O)N(R$^{17}$)$_2$, —C(R$^{17}$)=N—OR$^{17}$, —SR$^{17}$, —S(=O)R$^{17}$, —SO$_2$R$^{17}$, or —SO$_2$N(R$^{17}$)$_2$;

$R^{13}$ is substituted or unsubstituted $C_1$-$C_4$alkyl, substituted or unsubstituted $C_1$-$C_4$fluoroalkyl, substituted or unsubstituted $C_1$-$C_4$heteroalkyl, or substituted or unsubstituted $C_3$-$C_6$cycloalkyl;

$X^4$ and $X^6$ are independently CR$^{14}$ or N;

each $R^{14}$ is independently H, halogen, substituted or unsubstituted $C_1$-$C_4$alkyl, substituted or unsubstituted $C_1$-$C_4$fluoroalkyl, substituted or unsubstituted $C_1$-$C_6$heteroalkyl, substituted or unsubstituted monocyclic carbocycle, substituted or unsubstituted monocyclic heterocycle, —CN, —OR$^{17}$, —CO$_2$R$^{17}$, —C(=O)N(R$^{17}$)$_2$, —N(R$^{17}$)$_2$, —NR$^{17}$C(=O)R$^{18}$, —NR$^{17}$C(=O)OR$^{18}$, —NR$^{17}$C(=O)N(R$^{17}$)$_2$, —C(R$^{17}$)=N—OR$^{17}$, —SR$^{17}$, —S(=O)R$^{17}$, —SO$_2$R$^{17}$, or —SO$_2$N(R$^{17}$)$_2$;

$X^5$ is CR$^{15}$ or N;

$R^{15}$ and $R^{16}$ are independently H, halogen, substituted or unsubstituted $C_1$-$C_4$alkyl, substituted or unsubstituted $C_1$-$C_4$fluoroalkyl, substituted or unsubstituted $C_1$-$C_6$heteroalkyl, substituted or unsubstituted monocyclic carbocycle, substituted or unsubstituted monocyclic heterocycle, —CN, —OR$^{17}$, —CO$_2$R$^{17}$, —C(=O)N(R$^{17}$)$_2$, —N(R$^{17}$)$_2$, —NR$^{17}$C(=O)R$^{18}$, —NR$^{17}$C(=O)OR$^{18}$, —NR$^{17}$C(=O)N(R$^{17}$)$_2$, —C(R$^{17}$)=N—OR$^{17}$, —SR$^{17}$, —S(=O)R$^{17}$, —SO$_2$R$^{17}$, or —SO$_2$N(R$^{17}$)$_2$;

each $R^{17}$ is independently selected from H, substituted or unsubstituted $C_1$-$C_6$alkyl, substituted or unsubstituted $C_1$-$C_6$heteroalkyl, substituted or unsubstituted $C_3$-$C_7$cycloalkyl, substituted or unsubstituted monocyclic $C_2$-$C_6$heterocycloalkyl, substituted or unsubstituted phenyl, and substituted or unsubstituted monocyclic heteroaryl;

or two $R^{17}$ on the same N atom are taken together with the N atom to which they are attached to form a substituted or unsubstituted N-containing heterocycle;

each $R^{18}$ is independently selected from substituted or unsubstituted $C_1$-$C_6$alkyl, substituted or unsubstituted $C_1$-$C_6$heteroalkyl, substituted or unsubstituted $C_3$-$C_7$cycloalkyl, substituted or unsubstituted monocyclic $C_2$-$C_6$heterocycloalkyl, substituted or unsubstituted phenyl, and substituted or unsubstituted monocyclic heteroaryl; and m is 0, 1, or 2;

wherein any substituted group is substituted with one or two substituents that are independently selected from halogen, —CN, —NH$_2$, —OH, —NH(CH$_3$), —N(CH$_3$)$_2$, —CH$_3$, —CH$_2$CH$_3$, —CF$_3$, —OCH$_3$, and —OCF$_3$.

2. The compound of claim 1, or a pharmaceutically acceptable salt, solvate, diastereomeric mixture, or individual enantiomers thereof, wherein:

$R^a$ is H or —NR$^7$R$^8$;

$R^5$ is H, —OH, or $C_1$-$C_4$alkyl;

each $R^6$ is independently H, halogen, —OR$^{17}$, —N(R$^{17}$)$_2$, —CN, —CO$_2$R$^{17}$, —C(=O)N(R$^{17}$)$_2$, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted phenyl, or substituted or unsubstituted monocyclic 5-membered or 6-membered heterocycle;

$R^7$ is H, $C_1$-$C_4$alkyl, $C_1$-$C_4$fluoroalkyl, $C_1$-$C_4$heteroalkyl, or $C_3$-$C_6$cycloalkyl; and $R^8$ is H, $C_1$-$C_4$alkyl, $C_1$-$C_4$fluoroalkyl, $C_1$-$C_4$heteroalkyl, or $C_3$-$C_6$cycloalkyl.

3. The compound of claim 1, or a pharmaceutically acceptable salt, solvate, diastereomeric mixture, or individual enantiomers thereof, wherein:

$R^5$ is H, —OH, —CH$_3$ or —CH$_2$CH$_3$;

each $R^6$ is independently H, F, —OH, —OCH$_3$, —OCH$_2$CH$_3$, —OCF$_3$, —NH$_2$, —NHCH$_3$, —N(CH$_3$)$_2$, —CN, —C(=O)OCH$_3$, —C(=O)NH$_2$, —C(=O)NHCH$_3$, —C(=O)N(CH$_3$)$_2$, —CH$_3$, —CH$_2$CH$_3$, —CH$_2$OH, —CH$_2$OCH$_3$, —CH$_2$CN, or —CF$_3$; and $R^a$ is H.

4. A compound of Formula (III), or a pharmaceutically acceptable salt, pharmaceutically acceptable solvate, diastereomeric mixture, or individual enantiomers thereof:

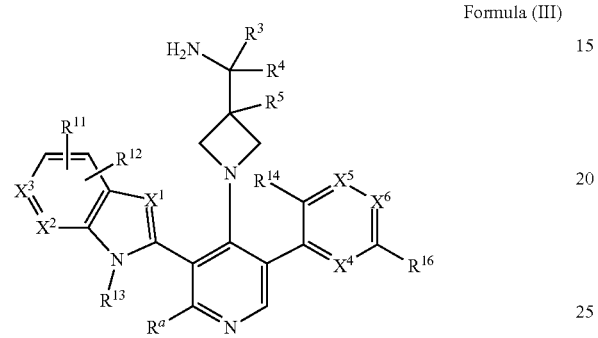

Formula (III)

wherein:

$R^3$ and $R^4$ are independently H or substituted or unsubstituted C$_1$-C$_6$alkyl;

$R^5$ is H, —OH, substituted or unsubstituted C$_1$-C$_6$alkyl, substituted or unsubstituted C$_1$-C$_6$alkoxy, or substituted or unsubstituted C$_1$C$_6$heteroalkyl;

$R^a$ is H or —NR$^7$R$^8$;

$R^7$ is H, substituted or unsubstituted C$_1$-C$_4$alkyl, substituted or unsubstituted C$_1$-C$_4$fluoroalkyl, substituted or unsubstituted C$_1$-C$_4$heteroalkyl, or substituted or unsubstituted C$_3$-C$_6$cycloalkyl;

$R^8$ is H, substituted or unsubstituted C$_1$-C$_4$alkyl, substituted or unsubstituted C$_1$-C$_4$fluoroalkyl, substituted or unsubstituted C$_1$-C$_4$heteroalkyl, or substituted or unsubstituted C$_3$-C$_6$cycloalkyl;

$X^1$ is N or C—R$^9$;

$R^9$ is H, F, Cl, Br, —CN, —N(R$^{17}$)$_2$, substituted or unsubstituted C$_1$-C$_4$alkyl, substituted or unsubstituted C$_1$-C$_4$alkoxy, substituted or unsubstituted C$_1$-C$_4$fluoroalkyl, substituted or unsubstituted C$_1$-C$_4$fluoroalkoxy, substituted or unsubstituted C$_1$-C$_4$heteroalkyl, or substituted C$_3$-C$_6$cycloalkyl;

$X^2$ is C—R$^{10}$ or N;

$X^3$ is C—R$^{11}$ or N;

$R^{10}$, each $R^{11}$ and $R^{12}$ are each independently H, halogen, substituted or unsubstituted C$_1$-C$_4$alkyl, substituted or unsubstituted C$_1$-C$_4$alkenyl, substituted or unsubstituted C$_1$-C$_4$alkynyl, substituted or unsubstituted C$_1$-C$_4$fluoroalkyl, substituted or unsubstituted C$_1$-C$_6$heteroalkyl, substituted or unsubstituted monocyclic carbocycle, substituted or unsubstituted monocyclic heterocycle, —CN, —OR$^{17}$, —CO$_2$R$^{17}$, —C(=O)N(R$^{17}$)$_2$, —N(R$^{17}$)$_2$, —NR$^{17}$C(=O)R$^{18}$, —NR$^{17}$C(=O)OR$^{18}$, —NR$^{17}$C(=O)N(R$^{17}$)$_2$, —C(R$^{17}$)=N—OR$^{17}$, —SR$^{17}$, —S(=O)R$^{17}$, —SO$_2$R$^{17}$, or —SO$_2$N(R$^{17}$)$_2$;

$R^{13}$ is H, substituted or unsubstituted C$_1$-C$_4$alkyl, substituted or unsubstituted C$_1$-C$_4$fluoroalkyl, substituted or unsubstituted C$_1$-C$_4$heteroalkyl, or substituted or unsubstituted C$_3$-C$_6$cycloalkyl;

$X^4$ and $X^6$ are independently CR$^{14}$ or N;

each $R^{14}$ is independently H, halogen, substituted or unsubstituted C$_1$-C$_4$alkyl, substituted or unsubstituted C$_1$-C$_4$fluoroalkyl, substituted or unsubstituted C$_1$-C$_6$heteroalkyl, substituted or unsubstituted monocyclic carbocycle, substituted or unsubstituted monocyclic heterocycle, —CN, —OR$^{17}$, —CO$_2$R$^{17}$, —C(=O)N(R$^{17}$)$_2$, —N(R$^{17}$)$_2$, —NR$^{17}$C(=O)R$^{18}$, —NR$^{17}$C(=O)OR$^{18}$, —NR$^{17}$C(=O)N(R$^{17}$)$_2$, —C(R$^{17}$)=N—OR$^{17}$, —SR$^{17}$, —S(=O)R$^{17}$, —SO$_2$R$^{17}$, or —SO$_2$N(R$^{17}$)$_2$;

$X^5$ is CR$^{15}$ or N;

$R^{15}$ and $R^{16}$ are independently H, halogen, substituted or unsubstituted C$_1$-C$_4$alkyl, substituted or unsubstituted C$_1$-C$_4$fluoroalkyl, substituted or unsubstituted C$_1$-C$_6$heteroalkyl, substituted or unsubstituted monocyclic carbocycle, substituted or unsubstituted monocyclic heterocycle, —CN, —OR$^{17}$, —CO$_2$R$^{17}$, —C(=O)N(R$^{17}$)$_2$, —N(R$^{17}$)$_2$, —NR$^{17}$C(=O)R$^{18}$, —NR$^{17}$C(=O)OR$^{18}$, —NR$^{17}$C(=O)N(R$^{17}$)$_2$, —C(R$^{17}$)=N—OR$^{17}$, —SR$^{17}$, —S(=O)R$^{17}$, —SO$_2$R$^{17}$, or —SO$_2$N(R$^{17}$)$_2$;

each $R^{17}$ is independently selected from H, substituted or unsubstituted C$_1$-C$_6$alkyl, substituted or unsubstituted C$_1$-C$_6$heteroalkyl, substituted or unsubstituted C$_3$-C$_7$cycloalkyl, substituted or unsubstituted monocyclic C$_2$-C$_6$heterocycloalkyl, substituted or unsubstituted phenyl, and substituted or unsubstituted monocyclic heteroaryl;

or two $R^{17}$ on the same N atom are taken together with the N atom to which they are attached to form a substituted or unsubstituted N-containing heterocycle;

each $R^{18}$ is independently selected from substituted or unsubstituted C$_1$-C$_6$alkyl, substituted or unsubstituted C$_1$-C$_6$heteroalkyl, substituted or unsubstituted C$_3$-C$_7$cycloalkyl, substituted or unsubstituted monocyclic C$_2$-C$_6$heterocycloalkyl, substituted or unsubstituted phenyl, and substituted or unsubstituted monocyclic heteroaryl.

5. The compound of claim 1, or a pharmaceutically acceptable salt, solvate, diastereomeric mixture, or individual enantiomers thereof, wherein:

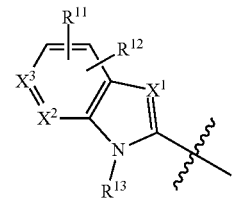

is

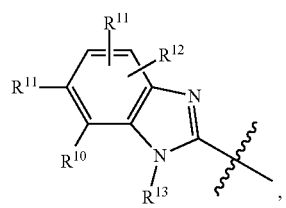

,

-continued

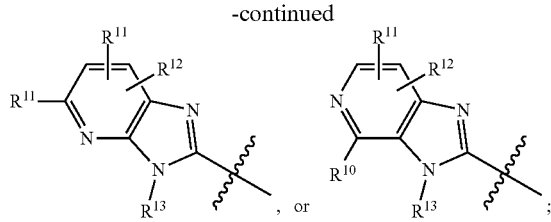

and

R[13] is H, or $C_1$-$C_4$alkyl.

6. The compound of claim 1, or a pharmaceutically acceptable salt, solvate, diastereomeric mixture, or individual enantiomers thereof, wherein:

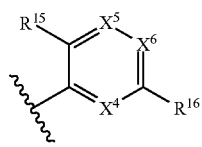

is

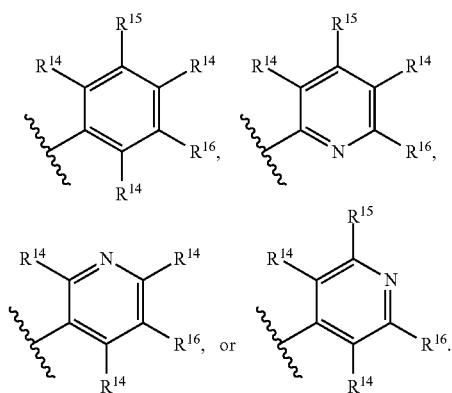

7. The compound of claims 4, or a pharmaceutically acceptable salt, solvate, diastereomeric mixture, or individual enantiomers thereof, wherein:

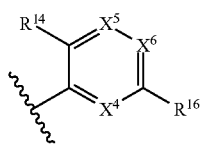

is

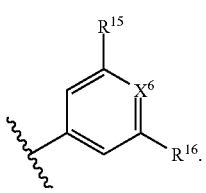

8. The compound of claim 1, or a pharmaceutically acceptable salt, solvate, diastereomeric mixture, or individual enantiomers thereof, wherein the compound has the structure of Formula (IV), or a pharmaceutically acceptable salt, pharmaceutically acceptable solvate, diastereomeric mixture, or individual enantiomers thereof:

Formula (IV)

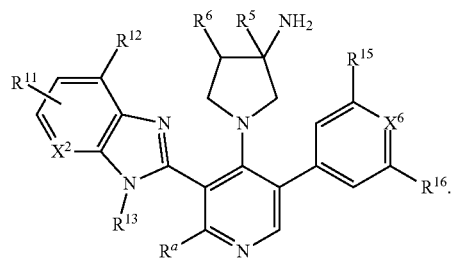

9. The compound of claim 1, wherein the compound has the structure of Formula (IVc), (IVd), (IVe), or (IVf), or a pharmaceutically acceptable salt, pharmaceutically acceptable solvate, diastereomeric mixture, or individual enantiomers thereof:

Formula (IVc)

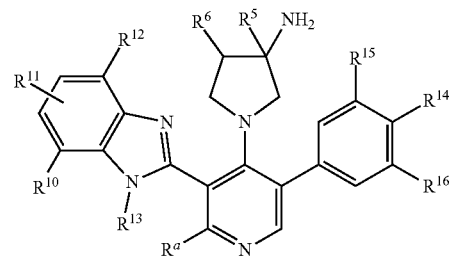

Formula (IVd)

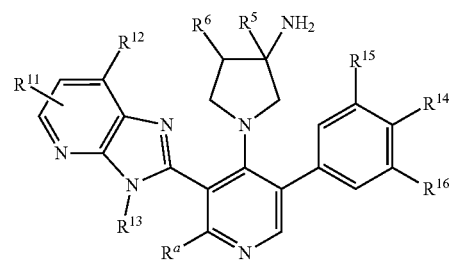

Formula (IVe)

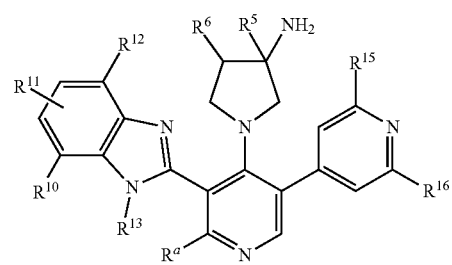

Formula (IVf)

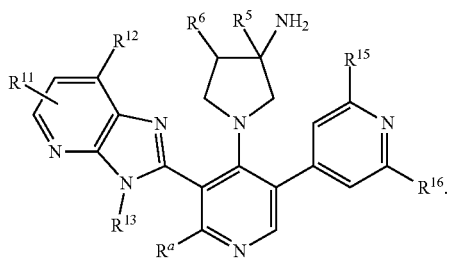

10. The compound of claim 9, or a pharmaceutically acceptable salt, solvate, diastereomeric mixture, or individual enantiomers thereof, wherein:
   $R^5$ is H, —OH, or $C_1$-$C_4$alkyl.
   each $R^6$ is independently H, halogen, —$OR^{17}$, —$N(R^{17})_2$, —CN, —$CO_2R^{17}$, —C(=O)N($R^{17}$)$_2$, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted phenyl, or substituted or unsubstituted monocyclic 5-membered or 6-membered heterocycle;
   $R^a$ is H or —$NR^7R^8$;
   $R^7$ is H, $C_1$-$C_4$alkyl, $C_1$-$C_4$fluoroalkyl, $C_1$-$C_4$heteroalkyl, or $C_3$-$C_6$cycloalkyl; and
   $R^8$ is H, $C_1$-$C_4$alkyl, $C_1$-$C_4$fluoroalkyl, $C_1$-$C_4$heteroalkyl, or $C_3$-$C_6$cycloalkyl.

11. The compound of any claim 9, or a pharmaceutically acceptable salt, solvate, diastereomeric mixture, or individual enantiomers thereof, wherein:
   $R^a$ is H;
   $R^5$ is H, —OH, —$CH_3$ or —$CH_2CH_3$; and
   each $R^6$ is independently H, F, —OH, —$OCH_3$, —$OCH_2CH_3$, —$OCF_3$, —$NH_2$, —$NHCH_3$, —$N(CH_3)_2$, —CN, —C(=O)$OCH_3$, —C(=O)$NH_2$, —C(=O)$NHCH_3$, —C(=O)N($CH_3$)$_2$, —$CH_3$, —$CH_2CH_3$, —$CH_2OH$, —$CH_2OCH_3$, —$CH_2CN$, or —$CF_3$.

12. The compound of claim 4, wherein the compound has the structure of Formula (V), or a pharmaceutically acceptable salt, pharmaceutically acceptable solvate, diastereomeric mixture, or individual enantiomers thereof:

Formula (V)

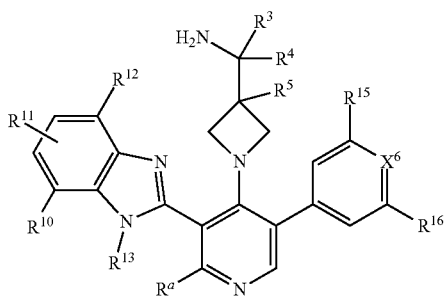

wherein:
   $R^3$ and $R^4$ are independently H, —$CH_3$, or —$CH_2CH_3$;
   $R^5$ is H, —OH, or $C_1$-$C_4$alkyl;
   $R^a$ is H or —$NR^7R^8$;
   $R^7$ is H, $C_1$-$C_4$alkyl, $C_1$-$C_4$fluoroalkyl, $C_1$-$C_4$heteroalkyl, or $C_3$-$C_6$cycloalkyl; and
   $R^8$ is H, $C_1$-$C_4$alkyl, $C_1$-$C_4$fluoroalkyl, $C_1$-$C_4$heteroalkyl, or $C_3$-$C_6$cycloalkyl.

13. The compound of claim 1, or a pharmaceutically acceptable salt, solvate, diastereomeric mixture, or individual enantiomers thereof, wherein:
   $R^{10}$ and $R^{12}$ are each independently H, halogen, substituted or unsubstituted $C_1$-$C_4$alkyl, substituted or unsubstituted $C_1$-$C_4$fluoroalkyl, substituted or unsubstituted $C_2$-$C_4$alkenyl, substituted or unsubstituted $C_2$-$C_4$alkynyl, substituted or unsubstituted $C_1$-$C_6$heteroalkyl, substituted or unsubstituted monocyclic $C_3$-$C_5$heterocycloalkyl, substituted or unsubstituted monocyclic $C_1$-$C_5$heteroaryl, —CN, —$CO_2R^{17}$, —C(=O)N($R^{17}$)$_2$, —N($R^{17}$)$_2$, —$NR^{17}$C(=O)$R^{18}$, —C($R^{17}$)=N—$OR^{17}$, —$SR^{17}$, —S(=O)$R^{18}$, —$SO_2R^{18}$, or —$SO_2N(R^{17})_2$; and
   each is independently H, halogen, substituted or unsubstituted $C_1$-$C_4$alkyl, substituted or unsubstituted $C_1$-$C_4$fluoroalkyl, substituted or unsubstituted $C_2$-$C_4$alkenyl, substituted or unsubstituted $C_2$-$C_4$alkynyl, substituted or unsubstituted $C_1$-$C_6$heteroalkyl, —CN, —OH, —O-(substituted or unsubstituted $C_1$-$C_4$alkyl), or —O-(substituted or unsubstituted $C_1$-$C_4$fluoroalkyl).

14. The compound of claim 1, or a pharmaceutically acceptable salt, solvate, diastereomeric mixture, or individual enantiomers thereof, wherein:
   $R^{10}$ and $R^{12}$ are each independently H, F, Cl, —$CH_3$, —$CF_3$, —C≡CH, —CN, —OH, —$OCH_3$, —$OCF_3$, azetidinyl, pyrrolidinyl, —CN, —OH, —$OCH_3$, —$OCH_2CH_3$, —$OCH_2CH_2OH$, —$OCH_2CN$, —$CO_2H$, —$CO_2CH_3$, —C(=O)$NH_2$, —C(=O)$NHCH_3$, —C(=O)N($CH_3$)$_2$, —$NH_2$, —$NHCH_3$, —N($CH_3$)$_2$, —NHC(=O)$CH_3$, —$NCH_3$C(=O)$CH_3$, —CH=N—OH, —CH=N—$OCH_3$, —$SO_2CH_3$, or —$SO_2NH_2$; and
   each $R^{11}$ is independently H, F, Cl, Br, —CN, —$CH_3$, —$CF_3$, —CN, —OH, —$OCH_3$, or —$OCF_3$.

15. The compound of claim 1, or a pharmaceutically acceptable salt, solvate, diastereomeric mixture, or individual enantiomers thereof, wherein:
   each $R^{14}$ is independently H, halogen, substituted or unsubstituted $C_1$-$C_4$alkyl, substituted or unsubstituted $C_1$-$C_4$fluoroalkyl, substituted or unsubstituted $C_1$-$C_4$heteroalkyl, —CN, —OH, —O-(substituted or unsubstituted $C_1$-$C_4$alkyl), or —O-(substituted or unsubstituted $C_1$-$C_4$fluoroalkyl);
   $R^{15}$ is H, halogen, substituted or unsubstituted $C_1$-$C_4$alkyl, substituted or unsubstituted $C_1$-$C_4$fluoroalkyl, substituted or unsubstituted $C_1$-$C_4$heteroalkyl, —CN, —OH, —O-(substituted or unsubstituted $C_1$-$C_4$alkyl), or -O-(substituted or unsubstituted $C_1$-$C_4$fluoroalkyl); and
   $R^{16}$ H, halogen, substituted or unsubstituted $C_1$-$C_4$alkyl, substituted or unsubstituted $C_1$-$C_4$fluoroalkyl, substituted or unsubstituted $C_1$-$C_4$heteroalkyl, substituted or unsubstituted phenyl, substituted or unsubstituted $C_3$-$C_6$cycloalkyl, substituted or unsubstituted monocyclic $C_3$-$C_5$heterocycloalkyl, substituted or unsubstituted monocyclic $C_1$-$C_5$heteroaryl, —CN, —$OR^{17}$, —$CO_2R^{17}$, —C(=O)N($R^{17}$)$_2$, —N($R^{17}$)$_2$, —$NR^{17}$C(=O)$R^{18}$, —$NR^{17}$C(=O)$OR^{18}$, —$NR^{17}$C(=O)N($R^{17}$)$_2$, —C($R^{17}$)=N—$OR^{17}$, —$SR^{17}$, —S(=O)$R^{17}$, —$SO_2R^{17}$, or —$SO_2N(R^{17})_2$.

16. The compound of claim 1, or a pharmaceutically acceptable salt, solvate, diastereomeric mixture, or individual enantiomers thereof, wherein:
   each $R^{14}$ is independently H, F, Cl, Br, —$CH_3$, —$CF_3$, —CN, —OH, —$OCH_3$, or —$OCF_3$;

R[15] is H, F, Cl, Br, —CH₃, —CF₃, —CN, —OH, —OCH₃, or —OCF₃; and
R[16] is H, F, Cl, Br, —CH₃, —CF₃, —CN, —OH, —OCH₃, —OCF₃, or —NH₂.

17. The compound of claim 1, wherein the compound is:
1-[3-(4,6-difluoro-1H-1,3-benzodiazol-2-yl)-5-(3-fluoro-5-methylphenyl)pyridin-4-yl]pyrrolidin-3-amine;
(3R)-1-[3-(3-chloro-5-fluorophenyl)-5-(4-fluoro-1H-1,3-benzodiazol-2-yl)pyridin-4-yl]pyrrolidin-3-amine;
(3S)-1-[3-(3-chloro-5-fluorophenyl)-5-(4-fluoro-1H-1,3-benzodiazol-2-yl)pyridin-4-yl]pyrrolidin-3-amine;
1-[3-(3-chloro-5-fluorophenyl)-5-(4-fluoro-1H-1,3-benzodiazol-2-yl)pyridin-4-yl]-3-methylpyrrolidin-3-amine;
3-{4-[(3S)-3-aminopyrrolidin-1-yl]-5-(4-fluoro-1H-1,3-benzodiazol-2-yl)pyridin-3-yl}-5-chlorobenzonitrile;
3-[4-(3-amino-3-methylpyrrolidin-1-yl)-5-(4-fluoro-1H-1,3-benzodiazol-2-yl)pyridin-3-yl]-5-fluorobenzonitrile;
3-{4-[(3S)-3-aminopyrrolidin-1-yl]-5-(4-fluoro-1H-1,3-benzodiazol-2-yl)pyridin-3-yl}benzonitrile;
3{4-[(3S)-3-aminopyrrolidin-1-yl]-5-(4-fluoro-1H-1,3-benzodiazol-2-yl)pyridin-3-yl}fluorobenzonitrile;
(3S)-1-[3-(4-fluoro-1H-1,3-benzodiazol-2-yl)-5-{3-fluoro-5-[(methoxyimino)methyl]phenyl}pyridin-4-yl]pyrrolidin-3-amine;
1-[3-(4-fluoro-1H-1,3-benzodiazol-2-yl)-5-[3-(trifluoromethoxy)phenyl]pyridin-4-yl]-3-methylpyrrolidin-3-amine;
1-[3-(4-fluoro-1H-1,3-benzodiazol-2-yl)-5-(3-methoxyphenyl)pyridin-4-yl]-3-methylpyrrolidin-3-amine;
(3S)-1-[3-(4-fluoro-1H-1,3-benzodiazol-2-yl)-5-{3-[(methoxyimino)methyl]phenyl}pyridin-4-yl]pyrrolidin-3-amine;
3-[4-(3-amino-3-methylpyrrolidin-1-yl)-5-(4-fluoro-1H-1,3-benzodiazol-2-yl)pyridin-3-yl]benzonitrile;
4'-(3-amino-3-methylpyrrolidin-1-yl)-5'-(4-fluoro-1H-1,3-benzodiazol-2-yl)-N,N-dimethyl-[3,3'-bipyridin]-6-amine;
4-(3-amino-3-methylpyrrolidin-1-yl)-5-(4-fluoro-1H-1,3-benzodiazol-2-yl)-[3,4'-bipyridin]-2'-amine;
1-[3 -(4-fluoro-1H-1,3-benzodiazol-2-yl)-5-[3-(1H-pyrazol-1-yl)phenyl]pyridin-4-yl]-3-methylpyrrolidin-3-amine;
3-{3-[4-(3 -amino-3-methylpyrrolidin-1-yl)-5-(4-fluoro-1H-1,3-benzodiazol-2-yl)pyridin-3-yl]phenyl}-1,3-oxazolidin-2-one;
3-[4-(3-amino-3-methylpyrrolidin-1-yl)-5-(4-fluoro-1H-1,3-benzodiazol-2-yl)pyridin-3-yl]benzamide;
3-[4-(3-amino-3-methylpyrrolidin-1-yl)-5-(4-fluoro-1H-1,3-benzodiazol-2-yl)pyridin-3-yl]-N-methylbenzamide;
3-[4-(3-amino-3-methylpyrrolidin-1-yl)-5-(4-fluoro-1H-1,3-benzodiazol-2-yl)pyridin-3-yl]-5-fluorobenzamide;
1-[3-(4-fluoro-1H-1,3-benzodiazol-2-yl)-5-(3-methanesulfonylphenyl)pyridin-4-yl]-3-methylpyrrolidin-3-amine;
1-[3-(2,3-dihydro-1-benzofuran-6-yl)-5-(4-fluoro-1H-1,3-benzodiazol-2-yl)pyridin-4-yl]-3-methylpyrrolidin-3-amine;
5-{4-[(3S)-3-aminopyrrolidin-1-yl]-5-(4-fluoro-1H-1,3-benzodiazol-2-yl)pyridin-3-yl}-2-fluorobenzonitrile;
3-{4-[(3S)-3-aminopyrrolidin-1-yl]-5-(4-fluoro-1H-1,3-benzodiazol-2-yl)pyridin-3-yl}-2-fluorobenzonitrile;
3-{4-[(3S)-3-aminopyrrolidin-1-yl]-5-(4-fluoro-1H-1,3-benzodiazol-2-yl)pyridin-3-yl}-5-fluorophenol;
5-{4-[(3S)-3-aminopyrrolidin-1-yl]-5-(4-fluoro-1H-1,3-benzodiazol-2-yl)pyridin-3-yl}thiophene-2-carbonitrile;
2-{3-[4-(3-amino-3-methylpyrrolidin-1-yl)-5-(4-fluoro-1H-1,3-benzodiazol-2-yl)pyridin-3-yl]-5-fluorophenoxy}acetonitrile;
1-[3-(3-chlorophenyl)-5-(4-fluoro-1H-1,3-benzodiazol-2-yl)pyridin-4-yl]-3-methylpyrrolidin-3-amine;
1-[3-(4-fluoro-1H-1,3-benzodiazol-2-yl)-5-(1H-indol-6-yl)pyridin-4-yl]-3-methylpyrrolidin-3-amine;
1-[3-(4-fluoro-1H-1,3-benzodiazol-2-yl)-5-(1H-indol-5-yl)pyridin-4-yl]-3-methylpyrrolidin-3-amine;
3-[4-(3-amino-3-methylpyrrolidin-1-yl)-5-(4-fluoro-1H-1,3-benzodiazol-2-yl)pyridin-3-yl]-N,N-dimethylbenzamide;
3-{4-[(3S)-3-aminopyrrolidin-1-yl]-5-(4-fluoro-1H-1,3-benzodiazol-2-yl)pyridin-3-yl}-2,6-difluorobenzonitrile;
3-{4-[3-amino-4-(trifluoromethyl)pyrrolidin-1-yl]-5-(4-fluoro-1H-1,3-benzodiazol-2-yl)pyridin-3-yl}benzonitrile;
3-{4-[(3S)-3-aminopyrrolidin-1-yl]-5-(4-methyl-1H-1,3-benzodiazol-2-yl)pyridin-3-yl}-5-fluorobenzonitrile;
4-{4-[(3S)-3-aminopyrrolidin-1-yl]-5-(4-fluoro-1H-1,3-benzodiazol-2-yl)pyridin-3-yl}-2-fluorobenzonitrile;
5-{4-[(3S)-3-aminopyrrolidin-1-yl]-5-(4-fluoro-1H-1,3-benzodiazol-2-yl)pyridin-3-yl}-2-hydroxybenzonitrile;
5-{4-[(3S)-3-aminopyrrolidin-1-yl]-5-(4-methyl-1H-1,3-benzodiazol-2-yl)pyridin-3-yl}-2-fluorobenzonitrile;
3-{4-[(3S)-3-aminopyrrolidin-1-yl]-5-(4,7-difluoro-1H-1,3-benzodiazol-2-yl)pyridin-3-yl}-5-fluorobenzonitrile;
5-{4-[(3S)-3-aminopyrrolidin-1-yl]-5-(4-fluoro-1H-1,3-benzodiazol-2-yl)pyridin-3-yl}-2-chlorobenzonitrile;
2-{4-[(3S)-3-aminopyrrolidin-1-yl]-5-(4,7-difluoro-1H-1,3-benzodiazol-2-yl)pyridin-3-yl}-6-fluorobenzonitrile;
3-{4-[(3S)-3-aminopyrrolidin-1-yl]-5-(4,5,6,7-tetrafluoro-1H-1,3-benzodiazol-2-yl)pyridin-3-yl}benzonitrile;
4-{4-[(3S)-3-aminopyrrolidin-1-yl]-5-(4-fluoro-1H-1,3-benzodiazol-2-yl)pyridin-3-yl}benzonitrile;
3-{4-[(3S)-3-aminopyrrolidin-1-yl]-5-(4,7-difluoro-1H-1,3-benzodiazol-2-yl)pyridin-3-yl}benzamide;
5-{4-[(3S)-3-aminopyrrolidin-1-yl]-5-(4,7-difluoro-1H-1,3-benzodiazol-2-yl)pyridin-3-yl}-2-fluorobenzonitrile;
3-{4-[trans-3-amino-4-methoxypyrrolidin-1-yl]-5-(4-fluoro-1H-1,3-benzodiazol-2-yl)pyridin-3-yl}benzonitrile;
3-{4-[cis-3-amino-4-methoxypyrrolidin-1-yl]-5-(4-fluoro-1H-1,3-benzodiazol-2-yl)pyridin-3-yl}benzonitrile;
2-{4-[(3S)-3-aminopyrrolidin-1-yl]-5-(4-fluoro-1H-1,3-benzodiazol-2-yl)pyridin-3-yl}-6-chlorobenzonitrile;
5-{4-[(3S)-3-aminopyrrolidin-1-yl]-5-(4,7-difluoro-1H-1,3-benzodiazol-2-yl)pyridin-3-yl}-2-(trifluoromethyl)benzonitrile;
5-{4-[(3S)-3-aminopyrrolidin-1-yl]-5-(4,7-difluoro-1H-1,3-benzodiazol-2-yl)pyridin-3-yl}-2-methylbenzonitrile;
5-{4-[(3S)-3-aminopyrrolidin-1-yl]-5-{7-methyl-1H-imidazo[4,5-b]pyridin-2-yl}pyridin-3-yl}-2-fluorobenzonitrile;
5-{4-[(3S)-3-aminopyrrolidin-1-yl]-5-(4-chloro-1H-1,3-benzodiazol-2-yl)pyridin-3-yl}-2-fluorobenzonitrile;

5-{4-[(3S)-3-aminopyrrolidin-1-yl]-5-(4,5-difluoro-1H-1,3-benzodiazol-2-yl)pyridin-3-yl}-2-fluorobenzonitrile;

1-[3-(4-fluoro-1H-1,3-benzodiazol-2-yl)-5-[3-(1H-imidazol-1-yl)phenyl]pyridin-4-yl]-3-methylpyrrolidin-3-amine;

3-{4-[3-amino-3-(hydroxymethyl)pyrrolidin-1-yl]-5-(4-fluoro-1H-1,3-benzodiazol-2-yl)pyridin-3-yl}benzonitrile;

3-{4-[trans-3-amino-4-fluoropyrrolidin-1-yl]-5-(4-fluoro-1H-1,3-benzodiazol-2-yl)pyridin-3-yl}benzonitrile;

3-{4-[trans-3-amino-4-phenylpyrrolidin-1-yl]-5-(4-fluoro-1H-1,3-benzodiazol-2-yl)pyridin-3-yl}benzonitrile;

3-{4-[(3S)-3-aminopyrrolidin-1-yl]-5-(4-bromo-1H-1,3-benzodiazol-2-yl)pyridin-3-yl}benzonitrile;

(3S)-1-[3-(4-fluoro-1H-1,3-benzodiazol-2-yl)-5-(3-methanesulfonylphenyl)pyridin-4-yl]pyrrolidin-3-amine;

(3S)-1-[3-(2,3-dihydro-1-benzofuran-6-yl)-5-(4-fluoro-1H-1,3-benzodiazol-2-yl)pyridin-4-yl]pyrrolidin-3-amine;

5-{4-[(3S)-3-aminopyrrolidin-1-yl]-5-[4-(trifluoromethyl)-1H-1,3-benzodiazol-2-yl]pyridin-3-yl}-2-fluorobenzonitrile;

5-{4-[(3S)-3-aminopyrrolidin-1-yl]-5-(4,7-difluoro-1H-1,3-benzodiazol-2-yl)pyridin-3-yl}-2-fluorobenzamide;

3-{4-[(3S)-3-aminopyrrolidin-1-yl]-5-(4-chloro-1H-1,3-benzodiazol-2-yl)pyridin-3-yl}-5-fluorobenzonitrile;

3-{4-[(3S)-3-aminopyrrolidin-1-yl]-5-(7-fluoro-4-methyl-1H-1,3-benzodiazol-2-yl)pyridin-3-yl}-5-fluorobenzonitrile;

3-{4-[3-amino-3-(trifluoromethyl)pyrrolidin-1-yl]-5-(4-fluoro-1H-1,3-benzodiazol-2-yl)pyridin-3-yl}benzamide;

3-{4-[(3S)-3-aminopyrrolidin-1-yl]-5-(4-methyl-1H-1,3-benzodiazol-2-yl)pyridin-3-yl}-5-fluorobenzamide;

3-{4-[(2R,4S)-4-amino-2-(hydroxymethyl)pyrrolidin-1-yl]-5-(4-fluoro-1H-1,3-benzodiazol-2-yl)pyridin-3-yl}-5-fluorobenzonitrile;

4-[(3S)-3-aminopyrrolidin-1-yl]-5-(4-fluoro-1H-1,3-benzodiazol-2-yl)-N-methyl-[3,4'-bipyridin]-2'-amine;

3-{4-[cis-3-amino-4-hydroxypyrrolidin-1-yl]-5-(4-fluoro-1H-1,3-benzodiazol-2-yl)pyridin-3-yl}benzonitrile;

trans-4-amino-1-[3-(3-cyanophenyl)-5-(4-fluoro-1H-1,3-benzodiazol-2-yl)pyridin-4-yl]pyrrolidine-3-carboxamide;

3-{4-[cis-3-amino-4-fluoropyrrolidin-1-yl]-5-(4-fluoro-1H-1,3-benzodiazol-2-yl)pyridin-3-yl}benzonitrile;

5-{4-[(3S)-3-aminopyrrolidin-1-yl]-5-(4-fluoro-1H-1,3-benzodiazol-2-yl)pyridin-3-yl}-2-fluorobenzamide;

3-{4-[(3S)-3-aminopyrrolidin-1-yl]-5-(4-fluoro-1H-1,3-benzodiazol-2-yl)pyridin-3-yl}-5-fluorobenzamide;

5-{4-[(3S)-3-aminopyrrolidin-1-yl]-5-(4-fluoro-1H-1,3-benzodiazol-2-yl)pyridin-3-yl}-2-methoxybenzamide;

3-{4-[(3S)-3-aminopyrrolidin-1-yl]-5-(4-fluoro-1-methyl-1H-1,3-benzodiazol-2-yl)pyridin-3-yl}benzonitrile;

3-{4-[(3S)-3-aminopyrrolidin-1-yl]-5-(7-fluoro-1-methyl-1H-1,3-benzodiazol-2-yl)pyridin-3-yl}benzonitrile;

3-{4-[(3S)-3-aminopyrrolidin-1-yl]-5-(4-chloro-1-methyl-1H-1,3-benzodiazol-2-yl)pyridin-3-yl}benzonitrile;

3-{4-[(3S)-3-aminopyrrolidin-1-yl]-5-(4-chloro-1-methyl-1H-1,3-benzodiazol-2-yl)pyridin-3-yl}benzonitrile;

3-{4-[3-amino-3-(trifluoromethyl)pyrrolidin-1-yl]-5-(4-fluoro-1H-1,3-benzodiazol-2-yl)pyridin-3-yl}-5-fluorobenzonitrile;

3-{4-[(3S)-3-aminopyrrolidin-1-yl]-5-(6-fluoro-4-methyl-1H-1,3-benzodiazol-2-yl)pyridin-3-yl}-5-fluorobenzonitrile;

3-{4-[(3S)-3-aminopyrrolidin-1-yl]-5-(4-methyl-1H-1,3-benzodiazol-2-yl)pyridin-3-yl}benzonitrile;

3-{4-[trans-3-amino-4-hydroxypyrrolidin-1-yl]-5-(4-fluoro-1H-1,3-benzodiazol-2-yl)pyridin-3-yl}benzonitrile;

2-{4-[(3S)-3-aminopyrrolidin-1-yl]-5-(3-cyanophenyl)pyridin-3-yl}-1H-1,3-benzodiazole-4-carboxylic acid;

2-{4-[(3S)-3-aminopyrrolidin-1-yl]-5-(3-cyanophenyl)pyridin-3-yl}-1H-1,3-benzodiazole-4-carboxamide;

3-{4-[(3S)-3-aminopyrrolidin-1-yl]-5-(4-ethynyl-1H-1,3-benzodiazol-2-yl)pyridin-3-yl}benzonitrile;

3-{4-[(3S)-3-aminopyrrolidin-1-yl]-5-(4-fluoro-1H-1,3-benzodiazol-2-yl)pyridin-3-yl}benzamide;

3-{4-[(3S)-3-aminopyrrolidin-1-yl]-5-(5-fluoro-4-methyl-1H-1,3-benzodiazol-2-yl)pyridin-3-yl}-5-fluorobenzonitrile;

3-{4-[(3S)-3-aminopyrrolidin-1-yl]-5-(4,6-difluoro-1H-1,3-benzodiazol-2-yl)pyridin-3-yl}-5-fluorobenzonitrile;

3-{4-[(2S,4S)-4-amino-2-(hydroxymethyl)pyrrolidin-1-yl]-5-(4-fluoro-1H-1,3-benzodiazol-2-yl)pyridin-3-yl}-5-fluorobenzonitrile;

3-{4-[trans-3-amino-4-(hydroxymethyl)pyrrolidin-1-yl]-5-(4-fluoro-1H-1,3-benzodiazol-2-yl)pyridin-3-yl}benzonitrile;

2-{4-[(3S)-3-aminopyrrolidin-1-yl]-5-(3-cyanophenyl)pyridin-3-yl}-N-methyl-1H-1,3-benzodiazole-4-carboxamide;

3-{4-[(3S)-3-aminopyrrolidin-1-yl]-5-[4-(hydroxymethyl)-1H-1,3-benzodiazol-2-yl]pyridin-3-yl}benzonitrile;

(3S)-1-[3-(4-fluoro-1H-1,3-benzodiazol-2-yl)-5-(3-fluoro-5-methanesulfonylphenyl)pyridin-4-yl]pyrrolidin-3-amine;

(3S)-1-[3-(4,6-difluoro-1H-1,3-benzodiazol-2-yl)-5-(3-methanesulfonylphenyl)pyridin-4-yl]pyrrolidin-3-amine;

(3S)-1-[3-(3-chloro-5-fluorophenyl)-5-(6-fluoro-1H-1,3-benzodiazol-2-yl)pyridin-4-yl]pyrrolidin-3-amine;

(3S)-1-[3-(5-chloro-1H-1,3-benzodiazol-2-yl)-5-(3-chloro-5-fluorophenyl)pyridin-4-yl]pyrrolidin-3-amine;

3-{4-[(3S)-3-aminopyrrolidin-1-yl]-5-(7-fluoro-4-methyl-1H-1,3-benzodiazol-2-yl)pyridin-3-yl}-5-fluorobenzamide;

3-{4-[(3S)-3-aminopyrrolidin-1-yl]-5-(4-methyl-1H-1,3-benzodiazol-2-yl)pyridin-3-yl}benzamide;

5-{4-[(3S)-3-aminopyrrolidin-1-yl]-5-(4-methyl-1H-1,3-benzodiazol-2-yl)pyridin-3-yl}-2-chlorobenzonitrile;

3-{4-[(3S)-3-aminopyrrolidin-1-yl]-5-(4,5-difluoro-1H-1,3-benzodiazol-2-yl)pyridin-3-yl}-5-fluorobenzonitrile;

3-{4-[(3S)-3-aminopyrrolidin-1-yl]-5-(4-ethyl-1H-1,3-benzodiazol-2-yl)pyridin-3-yl}benzonitrile;

3-{4-[(3S)-3-aminopyrrolidin-1-yl]-5-(7-fluoro-4-methyl-1H-1,3-benzodiazol-2-yl)pyridin-3-yl}benzonitrile;

(3S)-1-[3-(3-chloro-5-fluorophenyl)-5-(5-methyl-1H-1,3-benzodiazol-2-yl)pyridin-4-yl]pyrrolidin-3-amine;

2-{4-[(3S)-3-aminopyrrolidin-1-yl]-5-(3-chloro-5-fluorophenyl)pyridin-3-yl}-1H-1,3-benzodiazole-5-carbonitrile;

(3S)-1-[3-(3-chloro-5-fluorophenyl)-5-(5-methoxy-1H-1,3-benzodiazol-2-yl)pyridin-4-yl]pyrrolidin-3-amine;

4-(3-amino-3-methylpyrrolidin-1-yl)-5-(4-methyl-1H-1,3-benzodiazol-2-yl)-[3,4'-bipyridine]-2'-carboxamide;

4-[(3S)-3-aminopyrrolidin-1-yl]-5-(7-fluoro-4-methyl-1H-1,3-benzodiazol-2-yl)-[3,4'-bipyridine]-2'-carbonitrile;

4-[(3S)-3-aminopyrrolidin-1-yl]-5-(7-fluoro-4-methyl-1H-1,3-benzodiazol-2-yl)-[3,4'-bipyridine]-2'-carboxamide;

3-[4-(3-amino-3-methylpyrrolidin-1-yl)-5-{7-methyl-1H-imidazo[4,5-b]pyridin-2-yl}pyridin-3-yl]-5-fluorobenzonitrile;

3-{4-[(3S)-3-aminopyrrolidin-1-yl]-5-(1H-1,3-benzodiazol-2-yl)pyridin-3-yl}-5-fluorobenzonitrile;

3-{4-[(3S)-3-aminopyrrolidin-1-yl]-5-(1-methyl-1H-1,3-benzodiazol-2-yl)pyridin-3-yl}-5-fluorobenzonitrile;

3-{4-[(3S)-3-aminopyrrolidin-1-yl]-5-(1-propyl-1H-1,3-benzodiazol-2-yl)pyridin-3-yl}-5-fluorobenzonitrile;

3-{4-[(3S)-3-aminopyrrolidin-1-yl]-5-[1-(2-methoxyethyl)-1H-1,3-benzodiazol-2-yl]pyridin-3-yl}-5-fluorobenzonitrile;

3-{4-[(3S)-3-aminopyrrolidin-1-yl]-5-[1-(cyanomethyl)-1H-1,3-benzodiazol-2-yl]pyridin-3-yl}-5-fluorobenzonitrile;

3-{4-[(3S)-3-aminopyrrolidin-1-yl]-5-(1,4-dimethyl-1H-1,3-benzodiazol-2-yl)pyridin-3-yl}-5-fluorobenzonitrile;

3-{4-[(3S)-3-aminopyrrolidin-1-yl]-5-(1,7-dimethyl-1H-1,3-benzodiazol-2-yl)pyridin-3-yl}-5-fluorobenzonitrile;

3-{4-[(3S)-3-aminopyrrolidin-1-yl]-5-(4-chloro-1-methyl-1H-1,3-benzodiazol-2-yl)pyridin-3-yl}-5-fluorobenzonitrile;

3-{4-[(3S)-3-aminopyrrolidin-1-yl]-5-(7-chloro-1-methyl-1H-1,3-benzodiazol-2-yl)pyridin-3-yl}-5-fluorobenzonitrile;

3-[4-(3-amino-3-methylpyrrolidin-1-yl)-5-(4-methyl-1H-1,3-benzodiazol-2-yl)pyridin-3-yl]-5-fluorobenzamide;

5-[4-(3-amino-3-methylpyrrolidin-1-yl)-5-{7-methyl-1H-imidazo[4,5-b]pyridin-2-yl}pyridin-3-yl]-2-fluorobenzonitrile;

5-[4-(3-amino-3-methylpyrrolidin-1-yl)-5-(4-fluoro-1H-1,3-benzodiazol-2-yl)pyridin-3-yl]-2-fluorobenzamide;

4-(3-amino-3-methylpyrrolidin-1-yl)-5-(4-fluoro-1H-1,3-benzodiazol-2-yl)-[3,4'-bipyridine]-2'-carbonitrile;

3-[4-(3-amino-3-methylpyrrolidin-1-yl)-5-{7-methyl-1H-imidazo[4,5-b]pyridin-2-yl}pyridin-3-yl]benzonitrile;

4-(3-amino-3-methylpyrrolidin-1-yl)-5-(4-methyl-1H-1,3-benzodiazol-2-yl)-[3,4'-bipyridine]-2'-carbonitrile;

5-[4-(3-amino-3-methylpyrrolidin-1-yl)-5-(4-methyl-1H-1,3-benzodiazol-2-yl)pyridin-3-yl]-2-fluorobenzamide;

5-[4-(3-amino-3-methylpyrrolidin-1-yl)-5-(7-fluoro-4-methyl-1H-1,3-benzodiazol-2-yl)pyridin-3-yl]-2-fluorobenzamide;

5-[4-(3-amino-3-methylpyrrolidin-1-yl)-5-(4-methyl-1H-1,3-benzodiazol-2-yl)pyridin-3-yl]-2,3-difluorobenzoic acid;

5-[4-(3-amino-3-methylpyrrolidin-1-yl)-5-(4-methyl-1H-1,3-benzodiazol-2-yl)pyridin-3-yl]-2,3-difluorobenzamide;

4-[(3S)-3-aminopyrrolidin-1-yl]-5-(4-methyl-1H-1,3-benzodiazol-2-yl)-[3,4'-bipyridine]-2'-carbonitrile;

3-{4-[(3S)-3-aminopyrrolidin-1-yl]-5-(4-methyl-1H-indol-2-yl)pyridin-3-yl}-5-fluorobenzonitrile;

4-[(3S)-3-aminopyrrolidin-1-yl]-5-(4-fluoro-1H-1,3-benzodiazol-2-yl)-6'-methyl-[3,4'-bipyridin]-2'-amine;

5-{4-[(3S)-3-aminopyrrolidin-1-yl]-5-(4-chloro-1-methyl-1H-1,3-benzodiazol-2-yl)pyridin-3-yl}-2-fluorobenzonitrile;

5-{4-[(3S)-3-aminopyrrolidin-1-yl]-5-(1,4-dimethyl-1H-1,3-benzodiazol-2-yl)pyridin-3-yl}-2-fluorobenzonitrile;

5-{4-[(3S)-3-aminopyrrolidin-1-yl]-5-(7-chloro-1-methyl-1H-1,3-benzodiazol-2-yl)pyridin-3-yl}-2-fluorobenzonitrile;

5-{4-[(3S)-3-aminopyrrolidin-1-yl]-5-(1,7-dimethyl-1H-1,3-benzodiazol-2-yl)pyridin-3-yl}-2-fluorobenzonitrile;

3-{4-[(3S)-3-amino-3-(hydroxymethyl)pyrrolidin-1-yl]-5-(4-methyl-1H-1,3-benzodiazol-2-yl)pyridin-3-yl}-5-fluorobenzonitrile;

3-{4-[(3R)-3-amino-3-(hydroxymethyl)pyrrolidin-1-yl]-5-(4-methyl-1H-1,3-benzodiazol-2-yl)pyridin-3-yl}-5-fluorobenzonitrile;

3-{4-[(3S)-3-aminopyrrolidin-1-yl]-5-(7-methyl-1H-indol-2-yl)pyridin-3-yl}-5-fluorobenzonitrile;

3-[4-(3-amino-3-methylpyrrolidin-1-yl)-5-(4-methyl-1H-1,3-benzodiazol-2-yl)pyridin-3-yl]-2-fluorobenzamide;

5-{4-[(3S)-3-aminopyrrolidin-1-yl]-5-(4-methyl-1H-1,3-benzodiazol-2-yl)pyridin-3-yl}-2,3-difluorobenzonitrile;

5-[4-(3-amino-3-methylpyrrolidin-1-yl)-5-{7-methyl-1H-imidazo[4,5-b]pyridin-2-yl}pyridin-3-yl]-2,3-difluorobenzonitrile;

(3S)-1-{3-[4-fluoro-3-(trifluoromethoxy)phenyl]-5-(4-methyl-1H-1,3-benzodiazol-2-yl)pyridin-4-yl}pyrrolidin-3-amine;

5-{4-[(3S)-3-aminopyrrolidin-1-yl]-5-(1-ethyl-4-fluoro-1H-1,3-benzodiazol-2-yl)pyridin-3-yl}-2-fluorobenzonitrile;

3-{4-[(3S)-3-aminopyrrolidin-1-yl]-5-(1-ethyl-4-fluoro-1H-1,3-benzodiazol-2-yl)pyridin-3-yl}benzonitrile;

3-{4-[(3S)-3-aminopyrrolidin-1-yl]-5-(1-ethyl-4-fluoro-1H-1,3-benzodiazol-2-yl)pyridin-3-yl}-5-fluorobenzonitrile;

4-[(3S)-3-amino-3-methylpyrrolidin-1-yl]-5-(4-methyl-1H-1,3-benzodiazol-2-yl)-[3,4'-bipyridine]-2'-carbonitrile;

(3S)-1-[3-(4-methyl-1H-1,3-benzodiazol-2-yl)-5-(3-methylphenyl)pyridin-4-yl]pyrrolidin-3-amine;

2-[4-(3-amino-3-methylpyrrolidin-1-yl)-5-(3-cyano-4-fluorophenyl)pyridin-3-yl]-1H-1,3-benzodiazole-4-carbonitrile;

4-(3-amino-3-methylpyrrolidin-1-yl)-5-[4-(trifluoromethyl)-1H-1,3-benzodiazol-2-yl]-[3,4'-bipyridine]-2'-carbonitrile;

5-[4-(3-amino-3-methylpyrrolidin-1-yl)-5-{7-methyl-3H-imidazo[4,5-c]pyridin-2-yl}pyridin-3-yl]-2-fluorobenzamide;

4-[(3S)-3-amino-3-methylpyrrolidin-1-yl]-5-(4-fluoro-1-methyl-1H-1,3-benzodiazol-2-yl)-[3,4'-bipyridine]-2'-carbonitrile;

4-[(3S)-3-amino-3-methylpyrrolidin-1-yl]-5-(4-chloro-1-methyl-1H-1,3-benzodiazol-2-yl)-[3,4'-bipyridine]-2'-carbonitrile;
4-[(3S)-3-amino-3-methylpyrrolidin-1-yl]-5-(1,4-dimethyl-1H-1,3-benzodiazol-2-yl)-[3,4'-bipyridine]-2'-carbonitrile;
3-{4-[(3S)-3-amino-3-methylpyrrolidin-1-yl]-5-(4-fluoro-1-methyl-1H-1,3-benzodiazol-2-yl)pyridin-3-yl}benzonitrile;
5-{4-[(3S)-3-amino-3-methylpyrrolidin-1-yl]-5-{7-methyl-1H-imidazo[4,5-b]pyridin-2-yl}pyridin-3-yl}-2-fluorobenzonitrile;
3-{4-[(3S)-3-amino-3-methylpyrrolidin-1-yl]-5-{7-methyl-1H-imidazo[4,5-b]pyridin-2-yl}pyridin-3-yl}benzonitrile;
4-[(3S)-3-amino-3-methylpyrrolidin-1-yl]-5-(4-methyl-1H-1,3-benzodiazol-2-yl)-[3,4'-bipyridine]-2'-carboxamide;
4-(3-amino-3-methylpyrrolidin-1-yl)-5-(4-chloro-1H-1,3-benzodiazol-2-yl)-[3,4'-bipyridine]-2'-carbonitrile;
2-{4-[(3S)-3-aminopyrrolidin-1-yl]-5-(3-cyano-4-fluorophenyl)pyridin-3-yl}-1H-1,3-benzodiazole-4-carbonitrile;
5-[4-(3-amino-3-methylpyrrolidin-1-yl)-5-{4-methyl-3H-imidazo[4,5-c]pyridin-2-yl}pyridin-3-yl]-2-fluorobenzonitrile;
4-(3-amino-3-methylpyrrolidin-1-yl)-5-(4-cyano-1H-1,3-benzodiazol-2-yl)-[3,4'-bipyridine]-2'-carbonitrile;
4-[(3S)-3-aminopyrrolidin-1-yl]-5-(4-chloro-1H-1,3-benzodiazol-2-yl)-[3,4'-bipyridine]-2'-carbonitrile;
4-[(3S)-3-amino-3-methylpyrrolidin-1-yl]-5-(4-fluoro-1H-1,3-benzodiazol-2-yl)-[3,4'-bipyridine]-2'-carbonitrile;
4-[(3S)-3-amino-3-methylpyrrolidin-1-yl]-5-(4-chloro-1H-1,3-benzodiazol-2-yl)-[3,4'-bipyridine]-2'-carbonitrile;
4-[(3S)-3-amino-3-methylpyrrolidin-1-yl]-5-(5-fluoro-4-methyl-1H-1,3-benzodiazol-2-yl)-[3,4'-bipyridine]-2'-carbonitrile;
5-{4-[(3S)-3-amino-3-methylpyrrolidin-1-yl]-5-{7-methyl-1H-imidazo[4,5-b]pyridin-2-yl}pyridin-3-yl}-2,3-difluorobenzonitrile;
4-[(3S)-3-amino-3-methylpyrrolidin-1-yl]-5-(6-fluoro-4-methyl-1H-1,3-benzodiazol-2-yl)-[3,4'-bipyridine]-2'-carbonitrile;
5-{4-[(3S)-3-amino-3-methylpyrrolidin-1-yl]-5-{1H-imidazo[4,5-b]pyridin-2-yl}pyridin-3-yl}-2-fluorobenzonitrile;
5-{4-[(3S)-3-amino-3-methylpyrrolidin-1-yl]-5-{6-fluoro-1H-imidazo[4,5-b]pyridin-2-yl}pyridin-3-yl}-2-fluorobenzonitrile;
3-{4-[(3S)-3-amino-3-methylpyrrolidin-1-yl]-5-{7-methyl-1H-imidazo[4,5-b]pyridin-2-yl}pyridin-3-yl}-5-fluorobenzamide;
5-{4-[(3S)-3-amino-3-methylpyrrolidin-1-yl]-5-{6-methyl-1H-imidazo[4,5-b]pyridin-2-yl}pyridin-3-yl}-2-fluorobenzonitrile;
2-{4-[(3S)-3-amino-3-methylpyrrolidin-1-yl]-5-(3-cyano-4-fluorophenyl)pyridin-3-yl}-1H-1,3-benzodiazole-7-carbonitrile;
5-{4-[(3S)-3-amino-3-methylpyrrolidin-1-yl]-5-{7-methoxy-1H-imidazo[4,5-b]pyridin-2-yl}pyridin-3-yl}-2-fluorobenzonitrile;
3-{4-[(3S)-3-amino-3-methylpyrrolidin-1-yl]-5-{5,7-dimethyl-1H-imidazo[4,5-b]pyridin-2-yl}pyridin-3-yl}benzonitrile;
5-{4-[(3S)-3-amino-3-methylpyrrolidin-1-yl]-5-{5,7-dimethyl-1H-imidazo[4,5-b]pyridin-2-yl}pyridin-3-yl}-2-fluorobenzonitrile;
4-[(3S)-3-amino-3-methylpyrrolidin-1-yl]-5-[7-(trifluoromethyl)-1H-1,3-benzodiazol-2-yl]-[3,4'-bipyridine]-2'-carbonitrile;
2-{4-[(3S)-3-amino-3-methylpyrrolidin-1-yl]-5-(3-cyano-4-fluorophenyl)pyridin-3-yl}-1H-imidazo[4,5-b]pyridine-7-carbonitrile;
2-{4-[(3S)-3-amino-3-methylpyrrolidin-1-yl]-5-(3-cyanophenyl)pyridin-3-yl}-1H-1,3-benzodiazole-7-carbonitrile;
(3S)-1-[5-(4-fluoro-1H-1,3-benzodiazol-2-yl)-2'-methyl-[3,4'-bipyridin]-4-yl]-3-methylpyrrolidin-3-amine;
2-{4-[(3S)-3-amino-3-methylpyrrolidin-1-yl]-5-(3-cyano-4-methoxyphenyl)pyridin-3-yl}-1H-imidazo[4,5-b]pyridine-7-carbonitrile;
(3S)-1-[3-(3-chlorophenyl)-5-{7-methyl-1H-imidazo[4,5-b]pyridin-2-yl}pyridin-4-yl]-3-methylpyrrolidin-3-amine;
(3S)-1-[5-(4-fluoro-1H-1,3-benzodiazol-2-yl)-2'-methyl-[3,4'-bipyridin]-4-yl]pyrrolidin-3-amine;
(3S)-1-[3-(3-fluoro-5-methylphenyl)-5-(4-methyl-1H-1,3-benzodiazol-2-yl)pyridin-4-yl]pyrrolidin-3-amine;
(3S)-1-[3-(3-chloro-5-fluorophenyl)-5-(4-methyl-1H-1,3-benzodiazol-2-yl)pyridin-4-yl]pyrrolidin-3-amine;
(3S)-1-[3-(3-fluoro-5-methoxyphenyl)-5-(4-methyl-1H-1,3-benzodiazol-2-yl)pyridin-4-yl]pyrrolidin-3-amine;
(3S)-1-{3-[3-fluoro-5-(trifluoromethyl)phenyl]-5-(4-methyl-1H-1,3-benzodiazol-2-yl)pyridin-4-yl}pyrrolidin-3-amine;
(3S)-1-[5-(4-fluoro-1H-1,3-benzodiazol-2-yl)-2'-(trifluoromethyl)-[3,4'-bipyridin]-4-yl]-3-methylpyrrolidin-3-amine;
(3S)-1-[5-(4-fluoro-1H-1,3-benzodiazol-2-yl)-2'-methoxy-[3,4'-bipyridin]-4-yl]-3-methylpyrrolidin-3-amine;
(3S)-1-[3-(4-fluoro-3-methylphenyl)-5-{7-methyl-1H-imidazo[4,5-b]pyridin-2-yl}pyridin-4-yl]-3-methylpyrrolidin-3-amine;
(3S)-1-[3-(4-fluoro-3-methoxyphenyl)-5-{7-methyl-1H-imidazo[4,5-b]pyridin-2-yl}pyridin-4-yl]-3-methylpyrrolidin-3-amine;
(3S)-1-[3-(3,4-difluorophenyl)-5-{7-methyl-1H-imidazo[4,5-b]pyridin-2-yl}pyridin-4-yl]-3-methylpyrrolidin-3-amine;
(3S)-1-{3-[4-fluoro-3-(trifluoromethyl)phenyl]-5-{7-methyl-1H-imidazo[4,5-b]pyridin-2-yl}pyridin-4-yl}-3-methylpyrrolidin-3-amine;
(3S)-1-[3-(3-chloro-4-fluorophenyl)-5-{7-methyl-1H-imidazo[4,5-b]pyridin-2-yl}pyridin-4-yl]-3-methylpyrrolidin-3-amine;
(3S)-1-[3-(4-fluoro-1H-1,3-benzodiazol-2-yl)-5-(3-fluoro-5-methylphenyl)pyridin-4-yl]pyrrolidin-3-amine;
1-[3-(4,6-difluoro-1H-1,3-benzodiazol-2-yl)-5-(3-fluoro-5-methylphenyl)pyridin-4-yl]pyrrolidin-3-amine;
3-{4-[(3S)-3-aminopyrrolidin-1-yl]-5-(4,6-difluoro-1H-1,3-benzodiazol-2-yl)pyridin-3-yl}-5-fluorobenzonitrile;
(3S)-1-[3-(6-chloro-1H-1,3-benzodiazol-2-yl)-5-(3-fluoro-5-methylphenyl)pyridin-4-yl]pyrrolidin-3-amine;
(3S)-1-[3-(7-chloro-1H-1,3-benzodiazol-2-yl)-5-(3-fluoro-5-methylphenyl)pyridin-4-yl]pyrrolidin-3-amine;

3-{4-[(3S)-3-aminopyrrolidin-1-yl]-5-(6-chloro-1H-1,3-benzodiazol-2-yl)pyridin-3-yl}-5-fluorobenzonitrile;

(3R)-1-[3-(4-methyl-1H-1,3-benzodiazol-2-yl)-5-(3-methylphenyl)pyridin-4-yl]pyrrolidin-3-amine;

3-{4-[(3S)-3-amino-3-methylpyrrolidin-1-yl]-5-(4-fluoro-1H-1,3-benzodiazol-2-yl)pyridin-3-yl}benzonitrile;

(3S)-1-[3-(3,5-difluorophenyl)-5-(4-methyl-1H-1,3-benzodiazol-2-yl)pyridin-4-yl]pyrrolidin-3-amine; or 3-{4-[(3S)-3-amino-3-methylpyrrolidin-1-yl]-5-{7-methyl-1H-imidazo[4,5-b]pyridin-2-yl}pyridin-3-yl}-5-fluorobenzonitrile;

or a pharmaceutically acceptable salt, or solvate thereof.

18. The compound of claim 4, wherein the compound is:

1-{1-[3-(5-fluoro-1H-1,3-benzodiazol-2-yl)-5-(3-fluoro-5-methylphenyl)pyridin-4-yl]azetidin-3-yl}methanamine;

1-{1-[3-(4-fluoro-1H-1,3-benzodiazol-2-yl)-5-(3-fluoro-5-methylphenyl)pyridin-4-yl]azetidin-3-yl}methanamine;

1-{1-[3-(4-chloro-1H-1,3-benzodiazol-2-yl)-5-(3-fluoro-5-methylphenyl)pyridin-4-yl]azetidin-3-yl}methanamine;

1-{1-[3-(5-chloro-1H-1,3-benzodiazol-2-yl)-5-(3-fluoro-5-methylphenyl)pyridin-4-yl]azetidin-3-yl}methanamine;

2-{4-[3-(aminomethyl)azetidin-1-yl]-5-(3-fluoro-5-methylphenyl)pyridin-3-yl}-1H-1,3-benzodiazole-4-carbonitrile;

1-{1-[3-(4,5-difluoro-1H-1,3-benzodiazol-2-yl)-5-(3-fluoro-5-methylphenyl)pyridin-4-yl]azetidin-3-yl}methanamine;

1-{1-[3-(4,6-difluoro-1H-1,3-benzodiazol-2-yl)-5-(3-fluoro-5-methylphenyl)pyridin-4-yl]azetidin-3-yl}methanamine;

2-{4-[3-(aminomethyl)azetidin-1-yl]-5-(3-fluoro-5-methylphenyl)pyridin-3-yl}-1H-1,3-benzodiazole-5-carbonitrile;

1-{1-[3-(3-fluoro-5-methylphenyl)-5-(4-methyl-1H-1,3-benzodiazol-2-yl)pyridin-4-yl]azetidin-3-yl}methanamine;

1-{1-[3-(3-fluoro-5-methylphenyl)-5-(5-methyl-1H-1,3-benzodiazol-2-yl)pyridin-4-yl]azetidin-3-yl}methanamine;

1-{1-[3-(3-fluoro-5-methylphenyl)-5-(4-methoxy-1H-1,3-benzodiazol-2-yl)pyridin-4-yl]azetidin-3-yl}methanamine;

1-{1-[3-(3-fluoro-5-methylphenyl)-5-(5-methoxy-1H-1,3-benzodiazol-2-yl)pyridin-4-yl]azetidin-3-yl}methanamine;

1-{1-[3-(5,6-difluoro-1H-1,3-benzodiazol-2-yl)-5-(3-fluoro-5-methylphenyl)pyridin-4-yl]azetidin-3-yl}methanamine;

1-{1-[3-(5-chloro-6-fluoro-1H-1,3-benzodiazol-2-yl)-5-(3-fluoro-5-methylphenyl)pyridin-4-yl]azetidin-3-yl}methanamine;

1-{1-[3-(6-fluoro-4-methoxy-1H-1,3-benzodiazol-2-yl)-5-(3-fluoro-5-methylphenyl)pyridin-4-yl]azetidin-3-yl}methanamine;

2-{4-[3-(aminomethyl)azetidin-1-yl]-5-(3-fluoro-5-methylphenyl)pyridin-3-yl}-4-fluoro-1H-1,3-benzodiazole-6-carbonitrile;

2-{4-[3-(aminomethyl)azetidin-1-yl]-5-(3-fluoro-5-methylphenyl)pyridin-3-yl}-6-fluoro-1H-1,3-benzodiazole-5-carbonitrile;

1-{1-[3-(6-chloro-4-fluoro-1H-1,3-benzodiazol-2-yl)-5-(3-fluoro-5-methylphenyl)pyridin-4-yl]azetidin-3-yl}methanamine;

1-{1-[3-(4,6-difluoro-1H-1,3-benzodiazol-2-yl)-5-(3,5-dimethylphenyl)pyridin-4-yl]azetidin-3-yl}methanamine;

1-{1-[3-(3-chloro-5-methylphenyl)-5-(4,6-difluoro-1H-1,3-benzodiazol-2-yl)pyridin-4-yl]azetidin-3-yl}methanamine;

1-{1-[3-(4,6-difluoro-1H-1,3-benzodiazol-2-yl)-5-(3,5-difluorophenyl)pyridin-4-yl]azetidin-3-yl}methanamine;

1-{1-[3-(3-fluoro-5-methylphenyl)-5-{3H-imidazo[4,5-c]pyridin-2-yl}pyridin-4-yl]azetidin-3-yl}methanamine;

1-{1-[3-(3-fluoro-5-methylphenyl)-5-{1H-imidazo[4,5-b]pyridin-2-yl}pyridin-4-yl]azetidin-3-yl}methanamine;

1-{1-[3-(4-fluoro-1-methyl-1H-1,3-benzodiazol-2-yl)-5-(3-fluoro-5-methylphenyl)pyridin-4-yl]azetidin-3-yl}methanamine;

1-{1-[3-(7-fluoro-1-methyl-1H-1,3-benzodiazol-2-yl)-5-(3-fluoro-5-methylphenyl)pyridin-4-yl]azetidin-3-yl}methanamine;

3-(aminomethyl)-1-[3-(4,6-difluoro-1H-1,3-benzodiazol-2-yl)-5-(3-fluoro-5-methylphenyl)pyridin-4-yl]azetidin-3-ol;

1-{1-[3-(4,6-difluoro-1H-1,3-benzodiazol-2-yl)-5-phenylpyridin-4-yl]azetidin-3-yl}methanamine;

1-{1-[3-(4,6-difluoro-1H-1,3-benzodiazol-2-yl)-5-(3-fluorophenyl)pyridin-4-yl]azetidin-3-yl}methanamine;

1-{1-[3-(4,6-difluoro-1H-1,3-benzodiazol-2-yl)-5-(3-methylphenyl)pyridin-4-yl]azetidin-3-yl}methanamine;

1-{1-[3-(4,6-difluoro-1H-1,3-benzodiazol-2-yl)-5-(2-methylphenyl)pyridin-4-yl]azetidin-3-yl}methanamine;

1-{1-[3-(4,6-difluoro-1H-1,3-benzodiazol-2-yl)-5-(4-methylphenyl)pyridin-4-yl]azetidin-3-yl}methanamine;

1-{1-[5-(4,6-difluoro-1H-1,3-benzodiazol-2-yl)-5'-methyl-[3,3'-bipyridin]-4-yl]azetidin-3-yl}methanamine;

1-{1-[3-(4,6-difluoro-1H-1,3-benzodiazol-2-yl)-5-[3-methyl-5-(trifluoromethyl)phenyl]pyridin-4-yl]azetidin-3-yl}methanamine;

3-{4-[3-(aminomethyl)azetidin-1-yl]-5-(4,6-difluoro-1H-1,3-benzodiazol-2-yl)pyridin-3-yl}-5-fluorobenzonitrile;

1-{1-[3-(4,6-difluoro-1H-1,3-benzodiazol-2-yl)-5-(1H-indol-6-yl)pyridin-4-yl]azetidin-3-yl}methanamine;

1-{1-[3-(4,6-difluoro-1H-1,3-benzodiazol-2-yl)-5-(1H-indol-7-yl)pyridin-4-yl]azetidin-3-yl}methanamine;

1-{1-[3-(4,7-difluoro-1H-1,3-benzodiazol-2-yl)-5-(3-fluoro-5-methylphenyl)pyridin-4-yl]azetidin-3-yl}methanamine;

1-{1-[3-(4,6-difluoro-1H-1,3-benzodiazol-2-yl)-5-(1-methyl-1H-pyrazol-4-yl)pyridin-4-yl]azetidin-3-yl}methanamine;

1-{1-[3-(3-chloro-5-fluorophenyl)-5-(4,6-difluoro-1H-1,3-benzodiazol-2-yl)pyridin-4-yl]azetidin-3-yl}methanamine;

1-{1-[3-chloro-5-(trifluoromethyl)phenyl]-5-(4,6-difluoro-1H-1,3-benzodiazol-2-yl)pyridin-4-yl}azetidin-3-yl}methanamine;

1-{1-[3-(4,6-difluoro-1H-1,3-benzodiazol-2-yl)-5-(naphthalen-2-yl)pyridin-4-yl]azetidin-3-yl}methanamine;

1-{1-[3-(4,6-difluoro-1H-1,3-benzodiazol-2-yl)-5-(3-fluoro-5-methylphenyl)pyridin-4-yl]azetidin-3-yl}ethan-1-amine;
1-{1-[3-(4,6-difluoro-1H-1,3-benzodiazol-2-yl)-5-(4-fluorophenyl)pyridin-4-yl]azetidin-3-yl}methanamine;
1-{1-[3-(4,6-difluoro-1H-1,3-benzodiazol-2-yl)-5-(2-fluorophenyl)pyridin-4-yl]azetidin-3-yl}methanamine;
1-{1-[3-(4,6-difluoro-1H-1,3-benzodiazol-2-yl)-5-(2-fluoro-5-methylphenyl)pyridin-4-yl]azetidin-3-yl}methanamine;
1-{1-[3-(4,6-difluoro-1H-1,3-benzodiazol-2-yl)-5-(5-fluoro-2-methylphenyl)pyridin-4-yl]azetidin-3-yl}methanamine;
1-{1-[3-(4,6-difluoro-1H-1,3-benzodiazol-2-yl)-5-(4-fluoro-3-methylphenyl)pyridin-4-yl]azetidin-3-yl}methanamine;
1-{1-[3-(4,6-difluoro-1H-1,3-benzodiazol-2-yl)-5-(3,4,5-trifluorophenyl)pyridin-4-yl]azetidin-3-yl}methanamine;
2-amino-2-{1-[3-(4,6-difluoro-1H-1,3-benzodiazol-2-yl)-5-(3-fluoro-5-methylphenyl)pyridin-4-yl]azetidin-3-yl}ethan-1-ol;
1-{1-[3-(4,6-difluoro-1H-1,3-benzodiazol-2-yl)-5-(3-fluoro-5-methylphenyl)pyridin-4-yl]-3-methylazetidin-3-yl}methanamine;
1-{1-[3-(4,6-difluoro-1H-1,3-benzodiazol-2-yl)-5-(3-fluoro-5-methylphenyl)pyridin-4-yl]azetidin-3-yl}propan-1-amine;
1-{1-[3-(4,6-difluoro-1H-1,3-benzodiazol-2-yl)-5-(naphthalen-1-yl)pyridin-4-yl]azetidin-3-yl}methanamine;
1-{1-[3-(3-chlorophenyl)-5-(4,6-difluoro-1H-1,3-benzodiazol-2-yl)pyridin-4-yl]azetidin-3-yl}methanamine;
3-{4-[3-(aminomethyl)azetidin-1-yl]-5-(4,6-difluoro-1H-1,3-benzodiazol-2-yl)pyridin-3-yl}benzonitrile;
1-{1-[3-(4,6-difluoro-1H-1,3-benzodiazol-2-yl)-5-(3-fluoro-4-methylphenyl)pyridin-4-yl]azetidin-3-yl}methanamine;
1-{1-[3-(3-fluoro-5-methylphenyl)-5-(1H-imidazol-2-yl)pyridin-4-yl]azetidin-3-yl}methanamine;
1-{1-[3-(3-chloro-2-fluorophenyl)-5-(4,6-difluoro-1H-1,3-benzodiazol-2-yl)pyridin-4-yl]azetidin-3-yl}methanamine
1-{1-[3-(4,6-difluoro-1H-1,3-benzodiazol-2-yl)-5-(3-fluoro-5-methoxyphenyl)pyridin-4-yl]azetidin-3-yl}methanamine;
1-{1-[3-(3-chloro-5-methoxyphenyl)-5-(4,6-difluoro-1H-1,3-benzodiazol-2-yl)pyridin-4-yl]azetidin-3-yl}methanamine;
1-{1-[3-(3,5-dichlorophenyl)-5-(4,6-difluoro-1H-1,3-benzodiazol-2-yl)pyridin-4-yl]azetidin-3-yl}methanamine;
1-{1-[3-(3-chloro-5-fluorophenyl)-5-(4,6-difluoro-1H-1,3-benzodiazol-2-yl)pyridin-4-yl]azetidin-3-yl}ethan-1-amine;
1-{1-[3-(3-chloro-5-fluorophenyl)-5-(4,6-difluoro-1H-1,3-benzodiazol-2-yl)pyridin-4-yl]-3-fluoroazetidin-3-yl}methanamine;
1-{1-[3-(4,6-difluoro-1H-1,3-benzodiazol-2-yl)-5-[3-fluoro-5-(trifluoromethyl)phenyl]pyridin-4-yl]azetidin-3-yl}ethan-1-amine;
3-{4-[3-(1-aminoethyl)azetidin-1-yl]-5-(4,6-difluoro-1H-1,3-benzodiazol-2-yl)pyridin-3-yl}-5-fluorobenzonitrile;
5-{4-[3-(1-aminoethyl)azetidin-1-yl]-5-(4,6-difluoro-1H-1,3-benzodiazol-2-yl)pyridin-3-yl}-2-fluorobenzonitrile;
1-{1-[3-(3-chloro-2-methylphenyl)-5-(4,6-difluoro-1H-1,3-benzodiazol-2-yl)pyridin-4-yl]azetidin-3-yl}methanamine;
1-{1-[3-(4,6-difluoro-1H-1,3-benzodiazol-2-yl)-5-(2-fluoro-3-methylphenyl)pyridin-4-yl]azetidin-3-yl}methanamine;
1-{1-[3-(4,6-difluoro-1H-1,3-benzodiazol-2-yl)-5-(3-fluorophenyl)pyridin-4-yl]-3-methylazetidin-3-yl}ethan-1-amine;
1-{1-[3-(4,6-difluoro-1H-1,3-benzodiazol-2-yl)-5-[3-(trifluoromethyl)phenyl]pyridin-4-yl]-3-methylazetidin-3-yl}ethan-1-amine;
3-{4-[3-(1-aminoethyl)-3-methylazetidin-1-yl]-5-(4,6-difluoro-1H-1,3-benzodiazol-2-yl)pyridin-3-yl}benzonitrile;
1-{1-[3-(4,6-difluoro-1H-1,3-benzodiazol-2-yl)-5-[3-fluoro-5-(trifluoromethyl)phenyl]pyridin-4-yl]azetidin-3-yl}ethan-1-amine;
1-{1-[3-(4,6-difluoro-1H-1,3-benzodiazol-2-yl)-5-(4-ethoxy-3-fluorophenyl)pyridin-4-yl]azetidin-3-yl}ethan-1-amine;
1-{1-[3-(4,6-difluoro-1H-1,3-benzodiazol-2-yl)-5-(3-fluoro-2-methoxyphenyl)pyridin-4-yl]azetidin-3-yl}ethan-1-amine;
1-{1-[3-(2-chloro-3-fluorophenyl)-5-(4,6-difluoro-1H-1,3-benzodiazol-2-yl)pyridin-4-yl]azetidin-3-yl}ethan-1-amine;
2-{4-[3-(1-aminoethyl)azetidin-1-yl]-5-(4,6-difluoro-1H-1,3-benzodiazol-2-yl)pyridin-3-yl}-6-fluorophenol; or
1-{1-[3-(4,6-difluoro-1H-1,3-benzodiazol-2-yl)-5-(2-fluoro-3-methylphenyl)pyridin-4-yl]azetidin-3-yl}ethan-1-amine;

or a pharmaceutically acceptable salt, or solvate thereof.

19. A pharmaceutical composition comprising a compound claim 1, or a pharmaceutically acceptable salt, solvate, diastereomeric mixture, or individual enantiomers thereof, and at least one pharmaceutically acceptable excipient.

20. A method of treating a disease or condition in a mammal comprising administering a compound of claim 1, or a pharmaceutically acceptable salt, solvate, diastereomeric mixture, or individual enantiomers thereof, to the mammal in need thereof; wherein the disease or condition is hyperinsulinemic hypoglycemia, hypoglycemia due to endogenous insulin, drug induced hyperinsulinism, or hypoglycemia due to exogenous (injected) insulin.

21. A method for treating a disease or condition in a mammal that comprising administering a small molecule somatostatin receptor subtype 5 (SSTR5) agonist to the mammal in need thereof, wherein the small molecule SSTR5 agonist is at least 10 times more selective for modulating or binding to SSTR5 than for somatostatin receptor subtype 2 (SSTR2); wherein the disease or condition is hyperinsulinemic hypoglycemia, hypoglycemia due to endogenous insulin, drug induced hyperinsulinism, or hypoglycemia due to exogenous (injected) insulin.

* * * * *